US011970729B2

(12) United States Patent
Rothberg et al.

(10) Patent No.: US 11,970,729 B2
(45) Date of Patent: Apr. 30, 2024

(54) METHODS FOR NUCLEIC ACID SEQUENCING

(71) Applicant: Quantum-Si Incorporated, Guilford, CT (US)

(72) Inventors: Jonathan M. Rothberg, Guilford, CT (US); Jeremy Lackey, Foster City, CA (US); Brian Reed, Madison, CT (US); Xinghua Shi, Madison, CT (US); Haidong Huang, Madison, CT (US)

(73) Assignee: Quantum-Si Incorporated, Branford, CT (US)

( * ) Notice: Subject to any disclaimer, the term of this patent is extended or adjusted under 35 U.S.C. 154(b) by 362 days.

(21) Appl. No.: 17/314,626

(22) Filed: May 7, 2021

(65) Prior Publication Data

US 2022/0073973 A1  Mar. 10, 2022

Related U.S. Application Data

(60) Continuation of application No. 16/212,724, filed on Dec. 7, 2018, now Pat. No. 11,001,875, which is a
(Continued)

(51) Int. Cl.
*C12Q 1/6818* (2018.01)
*C12Q 1/6869* (2018.01)
(Continued)

(52) U.S. Cl.
CPC ......... *C12Q 1/6818* (2013.01); *C12Q 1/6869* (2013.01); *C12Q 1/6874* (2013.01);
(Continued)

(58) Field of Classification Search
CPC .. C12Q 1/6818; C12Q 1/6869; C12Q 1/6874; C12Q 2563/103; G01N 2021/6419;
(Continued)

(56) References Cited

U.S. PATENT DOCUMENTS 5,198,543 A  3/1993 Blanco et al.
5,302,509 A  4/1994 Cheeseman
(Continued)

FOREIGN PATENT DOCUMENTS

CN  1226928 A  8/1999
CN  1358868 A  7/2002
(Continued)

OTHER PUBLICATIONS

Invitation to Pay Additional Fees for International Application No. PCT/US2014/066014 dated Jan. 28, 2015.
(Continued)

*Primary Examiner* — Hina F Ayub
(74) *Attorney, Agent, or Firm* — Wolf, Greenfield & Sacks, P.C.

(57) ABSTRACT

Methods of sequencing molecules based on luminescence lifetimes and/or intensities are provided. In some aspects, methods of sequencing nucleic acids involve determining the luminescence lifetimes, and optionally luminescence intensities, of a series of luminescently labeled nucleotides incorporated during a nucleic acid sequencing reaction.

23 Claims, 43 Drawing Sheets

Specification includes a Sequence Listing.

Related U.S. Application Data division of application No. 15/161,125, filed on May 20, 2016, now Pat. No. 10,174,363, which is a continuation-in-part of application No. 14/821,688, filed on Aug. 7, 2015, now Pat. No. 9,885,657.

(60) Provisional application No. 62/164,464, filed on May 20, 2015, provisional application No. 62/164,482, filed on May 20, 2015, provisional application No. 62/164,485, filed on May 20, 2015, provisional application No. 62/164,506, filed on May 20, 2015.

(51) Int. Cl.
*C12Q 1/6874* (2018.01)
*G01N 21/64* (2006.01)

(52) U.S. Cl.
CPC ..... *G01N 21/6408* (2013.01); *G01N 21/6428* (2013.01); *G01N 21/6454* (2013.01); *G01N 21/648* (2013.01); *G01N 2021/6419* (2013.01); *G01N 2021/6421* (2013.01); *G01N 2021/6439* (2013.01); *G01N 2201/06113* (2013.01); *G01N 2201/0697* (2013.01)

(58) Field of Classification Search
CPC ... G01N 2021/6421; G01N 2021/6439; G01N 21/6408; G01N 21/6428; G01N 21/6454; G01N 21/648; G01N 2201/06113; G01N 2201/0697
See application file for complete search history.

(56) References Cited

U.S. PATENT DOCUMENTS

| | | |
|---|---|---|
| 5,311,013 A | 5/1994 | Gutcheck et al. |
| 5,471,515 A | 11/1995 | Fossum et al. |
| 5,674,743 A | 10/1997 | Ulmer |
| 5,707,804 A | 1/1998 | Mathies et al. |
| 5,822,472 A | 10/1998 | Danielzik et al. |
| 5,851,840 A | 12/1998 | Sluka et al. |
| 5,912,155 A | 6/1999 | Chatterjee et al. |
| 6,137,117 A | 10/2000 | Feldstein et al. |
| 6,153,442 A | 11/2000 | Pirio et al. |
| 6,198,869 B1 | 3/2001 | Kraus et al. |
| 6,210,896 B1 | 4/2001 | Chan |
| 6,232,103 B1 | 5/2001 | Short |
| 6,248,518 B1 | 6/2001 | Parkhurst et al. |
| 6,255,083 B1 | 7/2001 | Williams |
| 6,261,797 B1 | 7/2001 | Sorge et al. |
| 6,265,193 B1 | 7/2001 | Brandis et al. |
| 6,280,939 B1 | 8/2001 | Allen |
| 6,327,410 B1 | 12/2001 | Walt et al. |
| 6,355,420 B1 | 3/2002 | Chan |
| 6,399,320 B1 | 6/2002 | Markau et al. |
| 6,399,335 B1 | 6/2002 | Kao et al. |
| 6,437,345 B1 | 8/2002 | Bruno-Raimondi et al. |
| 6,607,883 B1 | 8/2003 | Frey et al. |
| 6,716,394 B2 | 4/2004 | Jensen et al. |
| 6,762,048 B2 | 7/2004 | Williams |
| 6,787,308 B2 | 9/2004 | Balasubramanian et al. |
| 6,825,921 B1 | 11/2004 | Modlin et al. |
| 6,846,638 B2 | 1/2005 | Shipwash |
| 6,869,764 B2 | 3/2005 | Williams et al. |
| 6,936,702 B2 | 8/2005 | Williams et al. |
| 7,033,762 B2 | 4/2006 | Nelson et al. |
| 7,041,812 B2 | 5/2006 | Kumar et al. |
| 7,052,847 B2 | 5/2006 | Korlach et al. |
| 7,056,661 B2 | 6/2006 | Korlach et al. |
| 7,057,026 B2 | 6/2006 | Barnes et al. |
| 7,153,672 B1 | 12/2006 | Eickbush et al. |
| 7,158,224 B2 | 1/2007 | Montagu |
| 7,170,050 B2 | 1/2007 | Turner et al. |
| 7,179,654 B2 | 2/2007 | Verdonk et al. |
| 7,229,799 B2 | 6/2007 | Williams |
| 7,270,951 B1 | 9/2007 | Stemple et al. |
| 7,345,764 B2 | 3/2008 | Bulovic et al. |
| 7,361,466 B2 | 4/2008 | Korlach et al. |
| 7,393,640 B2 | 7/2008 | Kumar et al. |
| 7,405,281 B2 | 7/2008 | Xu et al. |
| 7,462,452 B2 | 12/2008 | Williams et al. |
| 7,595,883 B1 | 9/2009 | El Gamal et al. |
| 7,630,073 B2 | 12/2009 | Lundquist et al. |
| 7,738,086 B2 | 6/2010 | Shepard et al. |
| 7,745,116 B2 | 6/2010 | Williams |
| 7,820,983 B2 | 10/2010 | Lundquist et al. |
| 7,871,777 B2 | 1/2011 | Schneider et al. |
| 7,873,085 B2 | 1/2011 | Babushkin et al. |
| 7,875,440 B2 | 1/2011 | Williams et al. |
| 7,968,702 B2 | 6/2011 | Wegener et al. |
| 7,973,146 B2 | 7/2011 | Shen et al. |
| 7,981,604 B2 | 7/2011 | Quake |
| 8,034,623 B2 | 10/2011 | Oh et al. |
| 8,058,030 B2 | 11/2011 | Smith et al. |
| 8,084,734 B2 | 12/2011 | Vertes et al. |
| 8,133,672 B2 | 3/2012 | Bjornson et al. |
| 8,153,375 B2 | 4/2012 | Travers et al. |
| 8,174,696 B2 | 5/2012 | Ebbesen et al. |
| 8,192,961 B2 | 6/2012 | Williams |
| 8,252,910 B2 | 8/2012 | Korlach et al. |
| 8,257,954 B2 | 9/2012 | Clark et al. |
| 8,274,034 B2 | 9/2012 | Vogel et al. |
| 8,274,040 B2 | 9/2012 | Zhong et al. |
| 8,278,728 B2 | 10/2012 | Murshid |
| 8,309,330 B2 | 11/2012 | Travers et al. |
| 8,323,939 B2 | 12/2012 | Hanzel et al. |
| 8,343,746 B2 | 1/2013 | Rank et al. |
| 8,354,252 B2 | 1/2013 | Wegener et al. |
| 8,420,366 B2 | 4/2013 | Clark et al. |
| 8,455,193 B2 | 6/2013 | Travers et al. |
| 8,465,699 B2 | 6/2013 | Fehr et al. |
| 8,481,264 B2 | 7/2013 | Bjornson et al. |
| 8,501,406 B1 | 8/2013 | Gray et al. |
| 8,501,922 B2 | 8/2013 | Otto et al. |
| 8,502,169 B2 | 8/2013 | Rigneault et al. |
| 8,530,154 B2 | 9/2013 | Williams |
| 8,580,539 B2 | 11/2013 | Korlach |
| 8,581,179 B2 | 11/2013 | Franzen |
| 8,846,881 B2 | 9/2014 | Korlach et al. |
| 8,865,077 B2 | 10/2014 | Chiou et al. |
| 8,906,614 B2 | 12/2014 | Wegener et al. |
| 8,921,086 B2 | 12/2014 | Hanzel et al. |
| 8,927,212 B2 | 1/2015 | Kong et al. |
| 8,980,584 B2 | 3/2015 | Williams |
| 9,062,091 B2 | 6/2015 | Bjornson et al. |
| 9,127,259 B2 | 9/2015 | Bjornson et al. |
| 9,404,146 B2 | 8/2016 | Travers et al. |
| 9,435,810 B2 | 9/2016 | Havranek et al. |
| 9,464,107 B2 | 10/2016 | Wegener et al. |
| 9,542,527 B2 | 1/2017 | Travers et al. |
| 9,551,031 B2 | 1/2017 | Korlach et al. |
| 9,551,660 B2 | 1/2017 | Kong et al. |
| 9,566,335 B1 | 2/2017 | Emili et al. |
| 9,582,640 B2 | 2/2017 | Travers et al. |
| 9,600,626 B2 | 3/2017 | Travers et al. |
| 9,678,080 B2 | 6/2017 | Bjornson et al. |
| 9,719,073 B2 | 8/2017 | Emig et al. |
| 9,845,501 B2 | 12/2017 | Williams |
| 9,879,319 B2 | 1/2018 | Korlach et al. |
| 9,910,956 B2 | 3/2018 | Travers et al. |
| 9,957,291 B2 | 5/2018 | Sebo et al. |
| 10,023,605 B2 | 7/2018 | Bjornson et al. |
| 10,066,258 B2 | 9/2018 | Kong et al. |
| 10,150,872 B2 | 12/2018 | Zheng et al. |
| 10,161,002 B2 | 12/2018 | Korlach et al. |
| 10,174,363 B2 | 1/2019 | Rothberg et al. |
| 10,481,162 B2 | 11/2019 | Emili et al. |
| 10,544,449 B2 | 1/2020 | Shen et al. |
| 10,545,153 B2 | 1/2020 | Marcotte et al. |
| 10,570,445 B2 | 2/2020 | Kong et al. |
| 10,676,788 B2 | 6/2020 | Shen et al. |
| 10,745,750 B2 | 8/2020 | Korlach et al. |
| 10,787,573 B2 | 9/2020 | Zheng et al. |
| 11,001,875 B2 | 5/2021 | Rothberg et al. |

(56) References Cited

U.S. PATENT DOCUMENTS

| | | |
|---|---|---|
| 2002/0031836 A1 | 3/2002 | Feldstein |
| 2003/0092005 A1 | 5/2003 | Levene et al. |
| 2004/0018504 A1* | 1/2004 | Bjorn .................... G01N 33/68 435/6.16 |
| 2004/0067503 A1 | 4/2004 | Tan et al. |
| 2004/0169842 A1 | 9/2004 | Dosluoglu et al. |
| 2004/0259091 A1 | 12/2004 | Yasuda et al. |
| 2005/0042633 A1 | 2/2005 | Williams |
| 2005/0147979 A1 | 7/2005 | Koo et al. |
| 2005/0186601 A1 | 8/2005 | Szasz |
| 2005/0214812 A1 | 9/2005 | Li et al. |
| 2005/0266456 A1 | 12/2005 | Williams et al. |
| 2006/0024676 A1 | 2/2006 | Uhlmann et al. |
| 2006/0083945 A1 | 4/2006 | Morishita et al. |
| 2007/0072196 A1 | 3/2007 | Xu et al. |
| 2007/0219367 A1 | 9/2007 | Shchepinov et al. |
| 2007/0250274 A1 | 10/2007 | Volkov et al. |
| 2007/0281288 A1 | 12/2007 | Belkin et al. |
| 2008/0050747 A1 | 2/2008 | Korlach et al. |
| 2009/0191563 A1 | 6/2009 | Steemer et al. |
| 2009/0263802 A1 | 10/2009 | Drmanac |
| 2010/0009872 A1 | 1/2010 | Eid et al. |
| 2010/0029494 A1 | 2/2010 | Cherkasov et al. |
| 2010/0035254 A1 | 2/2010 | Williams |
| 2010/0173394 A1 | 7/2010 | Colston et al. |
| 2010/0203515 A1 | 8/2010 | Rigler |
| 2010/0255487 A1 | 10/2010 | Beechem et al. |
| 2010/0323406 A1 | 12/2010 | Vatta et al. |
| 2011/0003343 A1 | 1/2011 | Nikiforov et al. |
| 2011/0122402 A1 | 5/2011 | Westphal |
| 2011/0136201 A1 | 6/2011 | Mao et al. |
| 2011/0165652 A1 | 7/2011 | Hardin et al. |
| 2011/0189702 A1 | 8/2011 | Sun |
| 2011/0200989 A1 | 8/2011 | Janaway et al. |
| 2011/0236983 A1 | 9/2011 | Beechem et al. |
| 2011/0281740 A1 | 11/2011 | Beechem et al. |
| 2011/0281776 A1 | 11/2011 | Eshoo et al. |
| 2011/0300534 A1 | 12/2011 | Chiou et al. |
| 2012/0094332 A1 | 4/2012 | Lee et al. |
| 2012/0322692 A1 | 12/2012 | Pham et al. |
| 2013/0005047 A1 | 1/2013 | Mayer et al. |
| 2013/0023039 A1 | 1/2013 | Zaccarin et al. |
| 2013/0071849 A1 | 3/2013 | Kong et al. |
| 2013/0084562 A1 | 4/2013 | Fletcher et al. |
| 2013/0217007 A1 | 8/2013 | Kamtekar et al. |
| 2013/0316912 A1 | 11/2013 | Bjornson et al. |
| 2014/0087474 A1 | 3/2014 | Huber et al. |
| 2015/0117156 A1 | 4/2015 | Xu et al. |
| 2015/0141267 A1 | 5/2015 | Rothberg et al. |
| 2015/0141268 A1 | 5/2015 | Rothberg et al. |
| 2016/0041095 A1 | 2/2016 | Rothberg et al. |
| 2016/0084761 A1 | 3/2016 | Rothberg et al. |
| 2016/0133668 A1 | 5/2016 | Rothberg et al. |
| 2017/0107562 A1 | 4/2017 | Rothberg et al. |
| 2017/0136433 A1 | 5/2017 | Sun et al. |
| 2017/0315058 A1 | 11/2017 | Zhou et al. |
| 2018/0211003 A1 | 7/2018 | Travers et al. |
| 2018/0299460 A1 | 10/2018 | Emili |
| 2018/0346507 A1 | 12/2018 | Sebo et al. |
| 2019/0010183 A1 | 1/2019 | Bjornson et al. |
| 2019/0136232 A1 | 5/2019 | Kellis et al. |
| 2019/0249153 A1 | 8/2019 | Kamtekar et al. |
| 2019/0330688 A1 | 10/2019 | Rothberg et al. |
| 2020/0141944 A1 | 5/2020 | Emili et al. |
| 2020/0148727 A1 | 5/2020 | Tullman et al. |

FOREIGN PATENT DOCUMENTS

| | | |
|---|---|---|
| CN | 104419765 A | 3/2015 |
| EP | 0710668 A2 | 5/1996 |
| EP | 1681356 A1 | 7/2006 |
| EP | 2182523 A1 | 5/2010 |
| EP | 2339632 A1 | 6/2011 |
| EP | 2391639 | 12/2011 |
| EP | 2134871 B1 | 3/2012 |
| JP | 2007-033159 A | 2/2007 |
| JP | 2010-066212 A | 3/2010 |
| WO | WO 91/06678 A1 | 5/1991 |
| WO | WO 93/06482 A1 | 4/1993 |
| WO | WO 2005/044836 A2 | 5/2005 |
| WO | WO 2005/073407 A1 | 8/2005 |
| WO | WO 2007/015168 A2 | 2/2007 |
| WO | WO 2007/070572 A2 | 6/2007 |
| WO | WO 2010/065322 A1 | 6/2010 |
| WO | WO 2010/115016 A2 | 10/2010 |
| WO | WO 2013/171197 A1 | 11/2013 |
| WO | WO 2019/040825 A1 | 2/2019 |

OTHER PUBLICATIONS

International Search Report and Written Opinion for International Application No. PCT/US2014/066014 dated Apr. 7, 2015.
International Preliminary Report on Patentability for International Application No. PCT/US2014/066014 dated May 26, 2016.
Invitation to Pay Additional Fees for International Application No. PCT/US2015/044360 dated Nov. 20, 2015.
International Search Report and Written Opinion for International Application No. PCT/US2015/044360 dated Feb. 3, 2016.
Invitation to Pay Additional Fees for International Application No. PCT/US2015/044378 dated Oct. 30, 2015.
International Search Report and Written Opinion for International Application No. PCT/US2015/044378 dated Jan. 15, 2016.
Invitation to Pay Additional Fees for International Application No. PCT/US2015/044379 dated Nov. 2, 2015.
International Search Report and Written Opinion for International Application No. PCT/US2015/044379 dated Jan. 15, 2016.
Invitation to Pay Additional Fees for International Application No. PCT/US2014/066013 dated Jan. 28, 2015.
International Search Report and Written Opinion for International Application No. PCT/US2014/066013 dated Apr. 7, 2015.
International Preliminary Report on Patentability for International Application No. PCT/US2014/066013 dated May 26, 2016.
Invitation to Pay Additional Fees for International Application No. PCT/US2014/066010 dated Jan. 28, 2015.
International Search Report and Written Opinion for International Application No. PCT/US2014/066010 dated Apr. 7, 2015.
International Preliminary Report on Patentability for International Application No. PCT/US2014/066010 dated May 26, 2016.
European Communication for European Application No. 16729108.7 dated Nov. 19, 2018.
International Search Report and Written Opinion for International Application No. PCT/US2016/033616 dated Oct. 7, 2016.
International Preliminary Report on Patentability for International Application No. PCT/US2016/033616 dated Nov. 30, 2017.
[No Author Listed] 5.2 Megapixels, 1-inch, 250fps, global-shutter CMOS image sensor, Anafocus, Oct. 2012, 4 pages, Sevilla, Spain.
[No Author Listed] Description of our technology, CrackerBio, 4 pages, Taiwan.
[No Author Listed] Detect Cancer with our 4 Picos ICCD camera, Stanford Computer Optics, 2013, 2 pages, http://www.stanfordcomputeroptics.com/applications/life-science/time-resolved-flim.html [last accessed May 9, 2014].
[No Author Listed] ICCD camera applications in the field of Life Science, Stanford Computer Optics, 2013, 2 pages, http://www.stanfordcomputeroptics.com/applications/life-science.html [last accessed May 9, 2014].
[No Author Listed] OLED-on-CMOS for Sensors and Microdisplays, IPMS Fraunhofer Institut Photonische Mikrosysteme, 2 pages, Dresden, Germany.
Achermann, Exciton—Plasmon Interactions in Metal—Semiconductor Nanostructures, The Journal Physical Chemistry Letters, Sep. 13, 2010, 1(19):2837-43.
Akselrod et al, Twenty-fold enhancement of molecular fluorescence by coupling to a J-aggregate critically coupled resonator. ACS Nano. Jan. 24, 2012;6(1):467-71. doi: 10.1021/nn203789t. Epub Dec. 1, 2011.

(56) References Cited

OTHER PUBLICATIONS

Algar et al., Interfacial Chemistry and the Design of Solid-Phase Nucleic Acid Hybridization Assays Using Immobilized Quantum Dots as Donors in Fluorescence Resonance Energy Transfer, Sensors, Jun. 2011, 11(6):6214-36.
Aouani et al., Bright unidirectional fluorescence emission of molecules in a nanoaperture with plasmonic corrugations. Nano Lett. Feb. 9, 2011;11(2):637-44. doi: 10.1021/nl103738d. Epub Jan. 19, 2011.
Aouani et al., Plasmonic Antennas for Directional Sorting of Fluorescence Emission, Nano Letters, May 18, 2011, 11(6):2400-6.
Aouani et al., Saturated excitation of fluorescence to quantify excitation enhancement in aperture antennas, Optics Express, Jul. 30, 2012, 20(16):18085-90.
Aouani et al., Supporting Information for Bright unidirectional fluorescence emission of molecules in a nanoaperture with plasmonic corrugations. Nano Lett. Feb. 9, 2011;11(2):19 pages.
Aouani et al., Supporting Information for Plasmonic Antennas for Directional Sorting of Fluorescence Emission, Nano Letters, May 18, 2011, 11(6):9 pages.
Bergman et al., Surface Plasmon Amplification by Stimulated Emission of Radiation: Quantum Generation of Coherent Surface Plasmons in Nanosystems, Physical Review Letters, Jan. 17, 2013, 90(2):027402-1-4.
Bogaerts et al., High speed 36 Gbps 12Mpixel global pipelined shutter CMOS image sensor with CDS, 2011 International Image Sensor Workshop, Jun. 8-11, 2011, 4 pages, Hokkaido, Japan.
Carretero-Palacious et al., Mechanisms for extraordinary optical transmission through bull's eye structures, Optics Express, May 23, 2011, 19(11):10429-42.
Chanyawadee et al., Nonradiative exciton energy transfer in hybrid organic-inorganic heterostructures, Phys. Rev. B., May 14, 2008, 77(19): 193402-1-4.
Daldosso et al., Fabrication and optical characterization of thin two-dimensional Si3N4 waveguides, Materials Science in Semiconductor Processing, Oct. 18, 2004, 7(4-6): 453-8.
Davies et al., Plasmonic Nanogap Tilings: Light-Concentrating Surfaces for Low-Loss Photonic Integration, ACS Nano, Jul. 4, 2013, 7(8):7093-100, arXiv: 1305.2839v2, http://arxiv.org/abs/1305.2839v2.
Deshpande et al., Electrically driven polarized single-photon emission from an InGaN quantum dot in a GaN nanowire, Nature Communcations, Apr. 9, 2013, 8 pages.
Deutsch et al., Luminescence upconversion in colloidal double quantum dots, Nature Nanotechnology Letter, Sep. 2013, 8(9):649-53.
Edel et al., Accurate Single Molecule FRET Efficiency Determination for Surface Immobilized DNA Using Maximum Likelihood Calculated Lifetimes, J. Phys. Chem, Mar. 22, 2007, 111(11):2986-90.
Eggeling et al., Data registration and selective single-molecule analysis using multi-parameter fluorescence detection. J Biotechnol. Apr. 13, 2001;86(3):163-80.
Eggeling et al., Monitoring conformational dynamics of a single molecule by selective fluorescence spectroscopy. Proc. Natl. Acad. Sci. 1998;95:1556-61.
Eid et al., Real-time DNA sequencing from single polymerase molecules. Science. Jan. 2, 2009;323(5910):133-8. doi:10.1126/science.1162986. Epub Nov. 20, 2008.
Eid et al., Supporting Online Material for Real-time DNA sequencing from single polymerase molecules. Science. Jan. 2, 2009;323(5910):21 pages.
Feldman et al., Wafer-Level Camera Technologies Shrink Camera Phone Handsets, Photonics.com, Aug. 1, 2007, 3 pages, http://www.photonics.com/Article.aspx?AID=30459 . [last accessed Dec. 17, 2013].
Fu et al., A microfabricated fluorescence-activated cell sorter. Nature Biotechnology. Nov. 1999; 17(11): 1109-1111.
Gorin et al., Fabrication of silicon nitride waveguides for visible-light using PECVD: a study of the effect of plasma frequency on optical properties, Optics Express, Sep. 1, 2008, 16(18):13509-16.
Gryczynski et al., Two-photon excitation by the evanescent wave from total internal reflection. Anal Biochem., Apr. 5, 1997;247(1):69-76.
Haase et al., Upconverting Nanoparticles, Angewandte Chemie International Edition, Jun. 20, 2011, 50(26):5808-29.
Hallman et al., 3 nJ, 100 ps laser pulses generated with an asymmetric waveguide laser diode for a single-photon avalanche diode time-of-flight (SPAD TOF) rangefinder application, Measurement Science and Technology, Jan. 5, 2012, 23(2): 8 pages.
Hansard et al., Time-of-Flight Cameras: Principles, Methods and Applications, Nov. 2012, 102 pages, Springer-Verlag, London, UK.
He et al., DNA Sequencing by Capillary Electrophoresis with Four-Decay Fluorescence Detection, Anal. Chem., Dec. 15, 2000, 72(24):5865-73.
Herold et al., OLED-on-CMOS Integration for Augmented-Reality Systems, IEEE 2008 International Students and Young Scientists Workshop Photonics and Microsystems, Jun. 20-22, 2008, 19-22, Wroclaw—Szlarska Poreba, Poland.
Heucke et al., Placing Individual Molecules in the Center of Nanoapertures, Nano Letters, Feb. 12, 2014, 14(2):391-5.
Inoue et al., CMOS active pixel image sensor with in-pixel CDS for high-speed cameras, Proc. SPIE, Sensors and Camera Systems for Scientific, Industrial, and Digital Photography Applications V, 250, Jun. 7, 2004, 5301(4):8 pages.
Ishii et al., Self-matched high-voltage rectangular wave pulse generator, Rev. Sci. Instrum, Nov. 1985, 56(11):2116-8.
Jun et al., Plasmonic beaming and active control over fluorescent emission, Nature Communications, Apr. 19, 2011, 6 pages.
Juodawlkis et al., High-Power, Low-Noise Slab-Coupled Optical Waveguide (SCOW) Amplifiers and Lasers, IEEE Optical Society of America Optical Fiber Communication Conference and Exposition and the National FiberOptic Engineers Conference, Mar. 6-10, 2011, 3 pages, Los Angeles, CA.
Juodawlkis et al., High-Power, Ultralow-Noise Semiconductor External Cavity Lasers Based on Low-Confinement Optical Waveguide Gain Media, Proc. of SPIE Novel In-Plane Semiconductor Lasers IX, Feb. 12, 2010, vol. 7616:76160X-1-9.
Kano et al., Two-photon-excited fluorescence enhanced by a surface plasmon. Opt Lett. Nov. 15, 1996;21(22):1848-50.
Karow, PacBio Aims to Boost Throughput of SMRT Technology with Microchip Co-development Deal, In Sequence and Clinical Sequencing News, Jul. 24, 2012, 3 pages, Genome Web.
Klein et al., Controlling plasmonic hot spots by interfering Airy beams, Optics Letters, Aug. 15, 2012, 37(16): 3402-4.
Korlach et al., Real-time DNA sequencing from single polymerase molecules. Methods Enzymol. May 2010;472:431-55. doi: 10.1016/S0076-6879(10)72001-2.
Koushik et al., Cerulean, Venus, and VenusY67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.
Kreye et al, P-200: Evaluation of different OLED-Stacks for Active-Matrix OLED Microdisplays on CMOS-Substrates, SID 06 Digest, Jun. 2006, 37(1); 979-81.
Kumar et al., Terminal phosphate labeled nucleotides: synthesis, applications, and linker effect on incorporation by DNA polymerases. Nucleosides Nucleotides Nucleic Acids. Nov. 2005;24(5-7):401-8.
Lenne et al., Fluorescence fluctuations analysis in nanoapertures: physical concepts and biological applications, Histochem Cell Biol, Sep. 2008, 130:795-805.
Leslie et al., Convex Lens-Induced Confinement for Imaging Single Molecules, Anal. Chem., Jul. 15, 2010, 82(14):6224-9.
Levy et al., An 852×600 Pixel OLED-on-Silicon Color Microdisplay Using CMOS Subthreshold-Voltage-Scaling Current Drivers, IEEE Journal of Solid-State Circuits, Dec. 2002, 37(12): 1879-89.
Lezec et al., Beaming Light from a Subwavelength Aperture, Science, Aug. 2, 2002, 297(5582):820-2.

(56) References Cited

OTHER PUBLICATIONS

Li et al., Employing ~100% Excitons in OLEDs by Utilizing a Fluorescent Molecule with Hybridized Local and Charge-Transfer Excited State, Advanced Functional Materials, Mar. 19, 2014, 24(11):1609-14.
Lin et al., Cosine-Gauss Plasmon Beam: A Localized Long-Range Nondiffracting Surface Wave, Physical Review Letters, Aug. 31, 2012, 109(9):093904-1-5.
McGinty et al., Wide-field fluorescence lifetime imaging of cancer, Biomedical Optics Express, Sep. 1, 2010, 1(2): 627-40.
Misra et al., White organic LEDs and their recent advancements, Semiconductor Science and Technology, Apr. 25, 2006, 21(7):R35-47.
Mitchell et al., Nanosecond Fluorescence Lifetime Imaging with gated CCD detection and pulsed laser excitation, Photonic Research Systems Ltd., May 1, 2013, 13 pages, Newhaven East Sussex UK.
Murshid et al., Array of concentric CMOS photodiodes for detection and de-multiplexing of spatially modulated optical channels, Optics & Laser Technology, Sep. 2009, 41(6):764-9.
Murshid et al., CMOS Detectors: Concentric photodiode array enables spatial-domain multiplexing, Laser Focus World, Apr. 1, 2009, 10 pages, http://www.laserfocusworld.com/articles/print/volume45/issue-4/features/cmos-detectors-concentric-photodiode-array-enables-spatial-domain-multiplexing.html, [last accessed Dec. 12, 2013].
Murshid et al., Concentric octagonal CMOS photodiodes for direct detection of spatially multiplexed optical fiber channels, Optical Society of America, Oct. 2008, 1 page.
Nozik, Multiple exciton generation in semiconductor quantum dots, Chemical Physics Letters, May 20, 2008, 457(1-3):3-11.
Park et al., A dual-modality optical coherence tomography and fluorescence lifetime imaging microscopy system for simultaneous morphological and biochemical tissue characterization, Biochemical Optics Express, Aug. 2, 2010, 1(1):186-200.
Pfeifer et al., Improved optical outcoupling of OLED microdisplays by nanostructured substrates, IEEE Semiconductor Conference Dresden, Sep. 27-18, 2011, 4 pages, Dresden, Germany.
Poddubny et al., Photonic quasicrystalline and aperiodic structures, Physica E: Low-dimensional Systems and Nanostructures, May 2010, 42(7): 1871-95.
Pons et al., Solution-phase single quantum dot fluorescence resonance energy transfer. J Am Chem Soc., Nov. 29, 2006;128(47):15324-31.
Pudavar, Fluorescence Lifetime Imaging (FILM), Leica Microsystems Inc., Oct. 25, 2009, 60 pages, Exton, PA.
Punj et al., Plasmonic antennas and zero-mode waveguides to enhance single molecule fluorescence detection and fluorescence correlation spectroscopy toward physiological concentrations. Wiley Interdiscip Rev Nanomed Nanobiotechnol. May-Jun. 2014;6(3):268-82. doi: 10.1002/wnan.1261. Epub Feb. 24, 2014.
Ramuz et al., Coupling light from an organic light emitting diode (OLED) into a single-mode waveguide: Toward monolithically integrated optical sensors, Journal of Applied Physics, Apr. 2009, 105(8):084508-1-7.
Ran et al., Design of a 16 gray scales 320×240 pixels OLED-on-silicon driving circuit, Journal of Semiconductors, Jan. 2009, 30(1):015010-1-4.
Reckziegel et al., Optical sensors based on monlithic integrated organic light-emitting diodes (OLEDs), Proceedings of SPIE Optical Sensors, Apr. 28, 2008, vol. 7003: 8 pages.
Richter et al., Bidirectional OLED microdisplay: Combining display and image sensor functionality into a monolithic CMOS chip, 2011 IEEE International Solid-State Circuits Conference Digest of Technical Papers (ISSCC), Feb. 20-24, 2011, 3 pages, San Francisco, CA.
Richter et al., OLED-on-CMOS based bidirectional microdisplay for near-to-eye and sensor applications, IEEE Semiconductor Conference Dresden, Sep. 27-28, 2011, 3 pages, Dresden, Germany.
Rigneault et al., Enhancement of Single-Molecule Fluorescence Detection in Subwavelength Apertures, Physical Review Letters, Sep. 9, 2005, 95(11): 117401-1-4.
Romero-Garcia et al., Silicon nitride back-end optics for biosensor applications, Proc. of SPIE Integrated Optics: Physics and Simulations, May 7, 2013, vol. 8781: 87810W-1-11.
Romero-Garcia et al., Visible wavelength silicon nitride focusing grating coupler with AlCu/TiN reflector. Optics Letters. Jul. 15, 2013, 38(14):2521-3.
Rui et al., Demonstration of beam steering via dipole-coupled plasmonic spiral antenna, Scientific Reports, Jul. 19, 2013, 7 pages.
Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 28, 2007. PMID: 17520113.
Sakadzic et al., Multi-photon microscopy with a low-cost and highly efficient Cr:LiCAF laser, Optics Express, Dec. 8, 2008, 16(25):20848-63.
Salthouse et al., Development of a Time Domain Fluorimeter for Fluorescent Lifetime Multiplexing Analysis, IEEE Biomed Circuits Syst., Sep. 1, 2008, 2(3): 204-11.
Sato et al., Polyproline-rod approach to isolating protein targets of bioactive small molecules: isolation of a new target of indomethacin. J Am Chem Soc. Jan. 31, 2007;129(4):873-80. doi: 10.1021/ja0655643. PMID: 17243824.
Sauer et al., Time-Resolved Identification of Individual Mononucleotide Molecules in Aqueous Solution with Pulsed Semiconductor Lasers. Bioimaging, Institute of Physics. 1998;6(1):14-24.
Schalberger et al., 60.4: Distinguished Paper: A Fully Integrated 1" AMOLED Display Using Current Feedback Based on a Five Mask LTPS CMOS Process, SID 10 Digest, May 2010, 41(1): 905-8.
Schmidt, Direct Encapsulation of OLED on CMOS, Bio and Nano Packaging Techniques for Electron Devices, Jul. 17, 2012, Chapter 29, 581-99, Springer-Verlag Berling Heidelberg.
Siegfried et al., Gap Plasmons and Near-Field Enhancement in Closely Packed Sub-10 nm Gap Resonators, Nano Lett., Oct. 10, 2013, 13(11):5449-53.
Sorokina et al., Fluorescent Lifetime Trajectories of a Single Fluorophore Reveal Reaction Intermediates During Transcription Initiation, J. Am. Chem. Soc., Jul. 22, 2009, 131(28):9630- 31.
Sorokina et al., Supporting Information for Fluorescent Lifetime Trajectories of a Single Fluorophore Reveal Reaction Intermediates During Transcription Initiation, J. Am. Chem. Soc., Jul. 22, 2009, 131(28):4 pages.
Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.
Sun et al., Fluorescence lifetime imaging microscopy (FLIM) for image guided surgery, Stanford Computer Optics, 2013, 2 pages, http://www.stanfordcomputeroptics.com/applications/life-science/flim-guided-surgery.html, [last accessed May 9, 2014].
Taitt et al., Evanescent wave fluorescence biosensors. Biosens Bioelectron. Jun. 2005;20(12):2470-87. Epub Dec. 8, 2004.
Takkellapati et al., Synthesis of aminomethyl- and bis-aminomethyl-fluorescein energy transfer terminators. Nucleosides Nucleotides Nucleic Acids. Dec. 2007;26(10-12):1467-70.
Toerker et al., Integration of Top-Emitting Organic Light Emitting Diodes on CMOS Substrates, Proc. of SPIE Organic Optoelectronics and Photonics III, Apr. 16, 2008, vol. 6999, 4 pages.
Toma et al., Compact surface plasmon-enhanced fluorescence biochip, Opt. Express Apr. 22, 2013, 21(8): 10121-10132.
Toma et al., Surface plasmon-coupled emission on plasmonic Bragg gratings, Optics Express, Jun. 18, 2012, 20(13): 14042-53.
Tuske et al., The J-helix of *Escherichia coli* DNA Polymerase I (Klenow Fragment) Regulates Polymerase and 3'- 5'-Exonuclease Functions. The Journal of Biological Chemistry. 2000;275(31):23759-68.
Uhring et al., 200 ps FWHM and 100 MHz Repetition Rate Ultrafast Gated Camera for Optical Medical Functional Imaging, Proc. of SPIE Optical Sensing and Detection II, May 9, 2012, vol. 8439, 10 pages.

(56) References Cited

OTHER PUBLICATIONS

Unfricht et al., Grating-coupled surface plasmon resonance: a cell and protein microarray platform. Proteomics. Nov. 2005;5(17):4432-42.

Vogel et al., OLED-on-CMOS Integration for Optoelectronic Sensor Applications, Proc. of SPIE Silicon Photonics II, Mar. 1, 2007, vol. 6477:8 pages.

Vogel et al., Optoelectronic Sensors based on OLED-on-CMOS, 2008 2nd European Conference & Exhibition on Integration Issues of Minaturized Systems—MOMS, MOEMS, ICS, and Electronic Components (SSI), Apr. 9-10, 2008, 3 pages, Barcelona, Spain.

Von Ketteler et al., Fluorescence Lifetime-Based Glucose Sensing using NADH, Proc. of SPIE Optical Diagnostics and Sensing XII: Toward Point-of-Care Diagnostics; and Design and Performance Validation of Phantoms Used in Conjunction with Optical Measurement of Tissue IV, Feb. 1, 2012, vol. 8229, 8 pages.

Walpole, Slab-coupled optical waveguide lasers: a review, Proc. SPIE Novel In-Plane Semiconductor Lasers III, May 11, 2004, vol. 5365, 124-32.

Wenger et al., Emission and excitation contributions to enhanced single molecule fluorescence by gold nanometric apertures, Optics Express, Mar. 3, 2008, 16(5):3008-20.

Wenger et al., Enhanced fluorescence from metal nanoapertures: physical characterizations and biophotonic applications, Proc. SPIE Plasmonics in Biology and Medicine VII, Feb. 16, 2010, 8 pages.

Wenger, Aperture optical antennas, Optical Antennas, Feb. 2013, 25pages, Cambridge University Press, Cambridge, UK.

Whitney et al., Floral Iridescence, Produced by Diffractive Optics, Acts as a Cue for Animal Pollinators. Science. 2009;323(5910):130-3.

Widengren et al., Single-molecule detection and identification of multiple species by multiparameter fluorescence detection. Anal Chem. Mar. 15, 2006;78(6):2039-50.

Williams et al., An artificial processivity clamp made with streptavidin facilitates oriented attachment of polymerase-DNA complexes to surfaces. Nucleic Acids Res. Oct. 2008;36(18):e121. doi: 10.1093/nar/gkn531. Epub Aug. 22, 2008. PMID: 18723573; PMCID: PMC2566871.

Willoughby, Elastically Averaged Precision Alignment, Massachusetts Institute of Technology, Jun. 2005, 158 pages, Cambridge, MA.

Xiao et al., New Technology of Modern Examination of Traditional Chinese Medicine. Yangcheng Evening News Publishing Company. Oct. 2002:204.

Xiong et al., Aluminum nitrade as a new material for chip-scale optomechanics and nonlinear optics, New Journal of Physics, Sep. 17, 2012, 14: 21 pages.

Yan-Yan et al., OLED-on-silicon chip with new pixel circuit, J. Cent. South Univ., May 2012 19(5):1276-82.

Ying et al., Optical Detection and Application of Single Molecules. University Chemistry. Oct. 31, 1999; 1-6.

Yu et al., Light Propagation with Phase Discontinuities: Generalized Laws of Reflection and Refraction, Science, Oct. 21, 2011, 334 (6054):333-7.

Yuk et al. Analysis of immunoarrays using a gold grating-based dual mode surface plasmon-coupled emission (SPCE) sensor chip. Analyst. Jun. 7, 2012;137(11):2574-81. doi: 10.1039/c2an35143a. Epub Apr. 13, 2012.

Zhang et al., Continuous metal plasmonic frequency selective surfaces, Optics Express, Nov. 7, 2011, 19(23):23279-85.

Zhao et al., Plasmonic demultiplexer and guiding. ACS Nano. Nov. 23, 2010;4(11):6433-8. doi: 10.1021/nn101334a. Epub Oct. 6, 2010.

Zhu et al., Zero-Mode Waveguides for Single-Molecule Analysis, Annu. Rev. Biophys., Jun. 2012, 41:269-93.

Zong et al., Equivalent Circuit Model of Top-emitting OLED for the Designing of OLED-on-Silicon Microdisplay, Advanced Materials Research, Nov. 2011, 383-90:7037-42.

\* cited by examiner 3-1
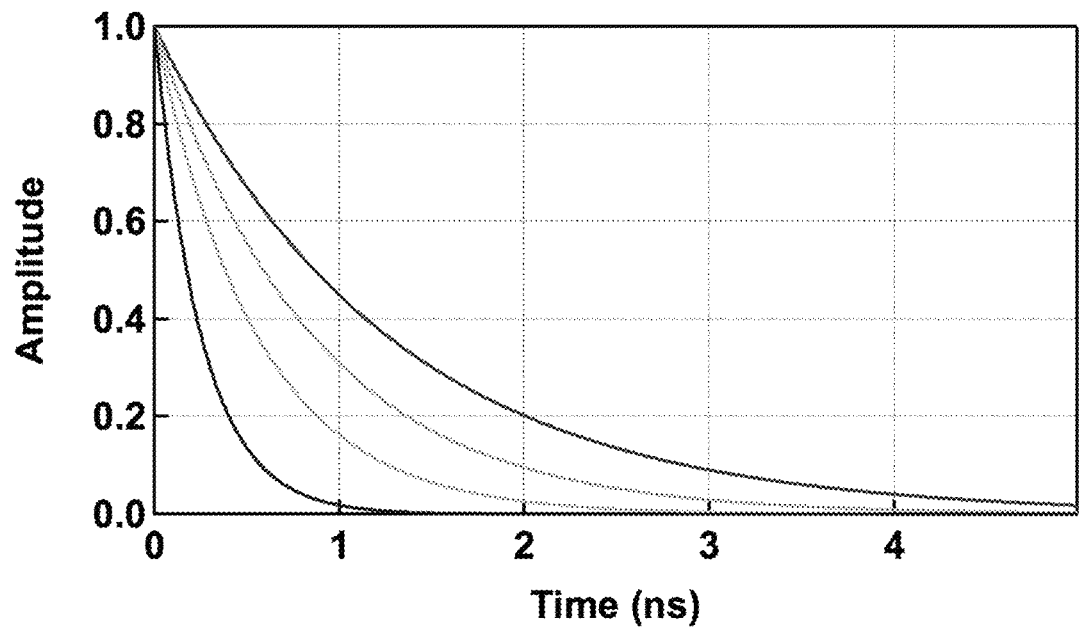
3-2
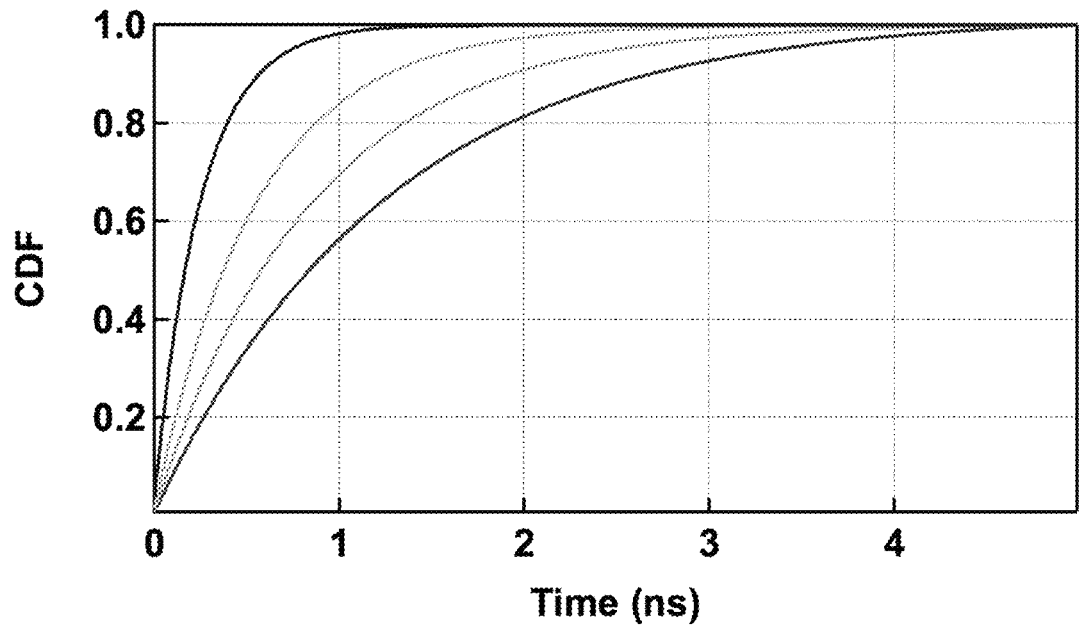
FIG. 3

5-1

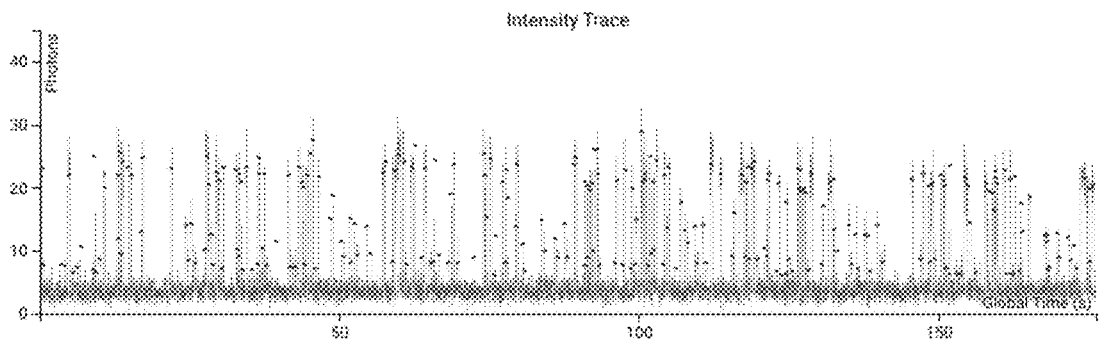

5-2

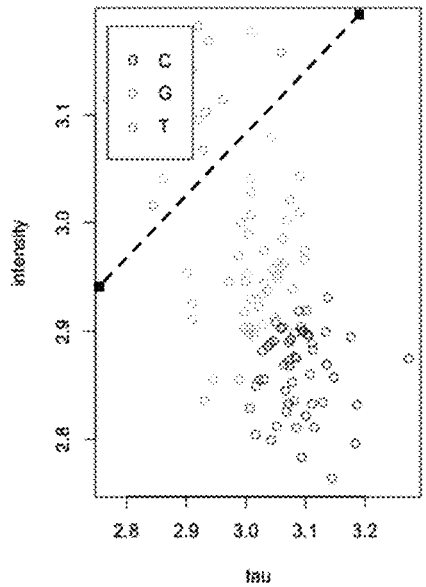

5-3

```
P1    1 AACCCACC-CC-CCAAA-CACA-ACATAATCTCTAATCA-CAACAACCAACACCAACACCACCAAA-CA-A-ACATATCT    72
        ||||||||  || |||||  ||||  ||||| |||||  |||  ||||||||| |||  ||| |||||||||| ||  | ||||||||
S1  110 AACCCACCACCACCAAAACACACACATA-TCTCTC-TCAACAACAAC-AAC-CCACCACCACCAAAACACACATATCT    185

P1   73 CTCTCAACAA--ACA--CAACCACC-CCAACACAAACACATACCTCTC-CAACAACAACAAACCAC-AC-ACTAAAACAC    144
        ||||||||||   |||    |||||||| ||||  ||| ||||||||| ||||||||||||||| |||| || ||||||||
S1  186 CTCTCAACAACAACAACCCACCACCACCAAAACACACACATATCTCTCTCAACAACAACAACCCACCACCACCAAAACAC    265

P1  145 ACACATACATCTCTCAACAACAACAACCCAACACCACCAAAAACACA-ATATCTCTTCTCA-CAACAACAAACCCCAAT    222
        |||||||  |||||||||||||||||||||||||||||||||| ||||| |||||| |||||||||| ||| |||||| ||
S1  266 ACACATATCTCTCTCAACAACAACAACCCACCACCACCAAAACACACACATATCTCT-CTCAACAACAACAACCCACCAC    344

P1  223 CA-AAAAAAACACACATATTCTCTCTCAACAA    253  SEQ ID NO: 1
        ||  ||||  |||||||| ||||| |||||||||
S1  345 CACCAAAACACACACATAT-CTCTCTCAACAA    375  SEQ ID NO: 2
```

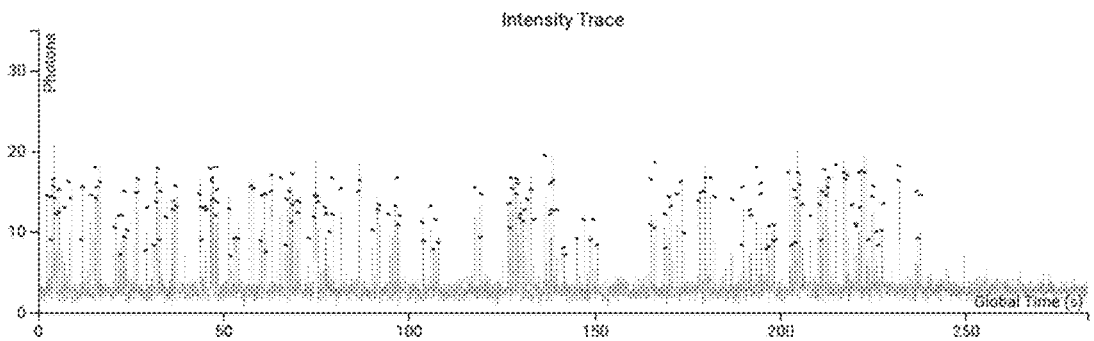

6-2

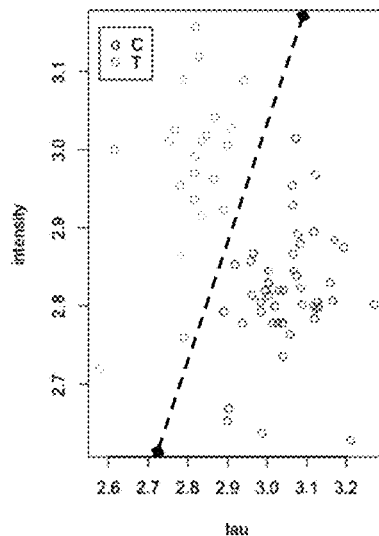

6-3

```
P1     1 ACACCAACAATAAAAAAAAAAA-ACCTCTC-CAA--AC-ACAACACAAA------AAAAAAAAAAAAATA-CTC-C-CAAC    66
         | | || || |||||||||||| | ||||| ||| || |||||| |||       |||||||||||||||| ||| | ||||
S1    69 AAAAAAAAAAAAAAAAAAAAAAATATCTCTCTCAACAACAACAACAAAAAAAAAAAAAAAAAAAAATATCTCTCTCAAC     148

P1    67 AACAAACAAAAAAAAAAAAAAAAAAAAAAAAAATATCTCTCA-CAACAACAAC----------AAAAAAAAAAAAAATA    137
         ||||| ||| |||||||||||||||||||||||| || ||||| ||||||||           |||||||||||||||||
S1   149 AACAA-CAACAAAAAAAAAAAAAAAAAAAAAAAAATATCTCTCTCAACAACAACAACAAAAAAAAAAAAAAAAAAAATA    227

P1   138 TCCCTCTCAACA-CA-CAACAATAAAAAAAAAA----------TCTC-CTCA-CAACAA-AACAAAAAAAAAAAAAA    202
         || ||||||| || || ||||| |||||||||||          |||| |||| |||||| ||||||||||||||||
S1   228 TCTCTCTCAACAACAACAACAAAAAAAAAAAAAAAAAAAAATATCTCTCTCAACAACAACAAAAAAAAAAAAAAAA    307

P1   203 AAA------AT-T-TCTCTAAACA-C                       229 SEQ ID NO: 3
         |||      || | ||||| |||| |
S1   308 AAAAAAAAATATCTCTCTCAACAAC                        331 SEQ ID NO: 4
```

FIG. 6

13-3
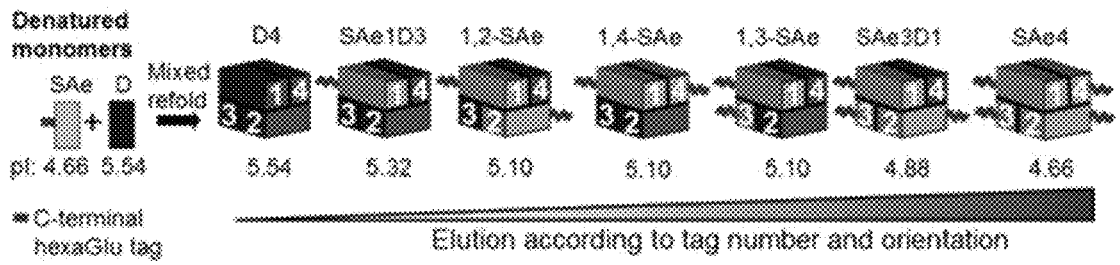
>Streptavidin-E6 (SAe) SEQ ID NO: 6
MAEAGITGTWYNQLGSTFIVTAGADGALTGTYESAVGNAESRYVLTGRYDSAPATDGSGTALGWTVAWK
NNYRNAHSATTWSGQYVGGAEARINTQWLLTSGTTEANAWKSTLVGHDTFTKVKPSAASEEEEEE
>Dead (D) SEQ ID NO: 7
MAEAGITGTWYAQLGDTFIVTAGADGALTGTYEAAVGNAESRYVLTGRYDSAPATDGSGTALGWTVAWK
NNYRNAHSATTWSGQYVGGAEARINTQWLLTSGTTEANAWKSTLVGHDTFTKVKPSAAS
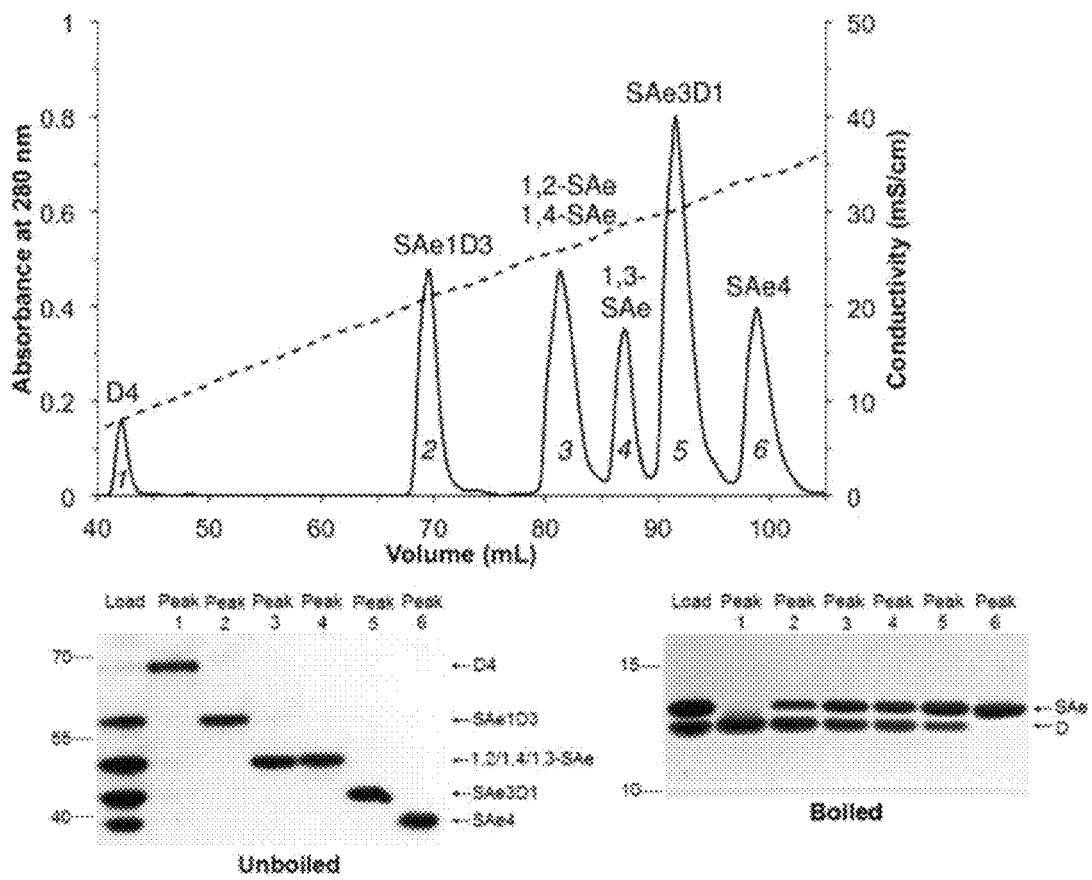
FIG. 13 (CONT)

18-2
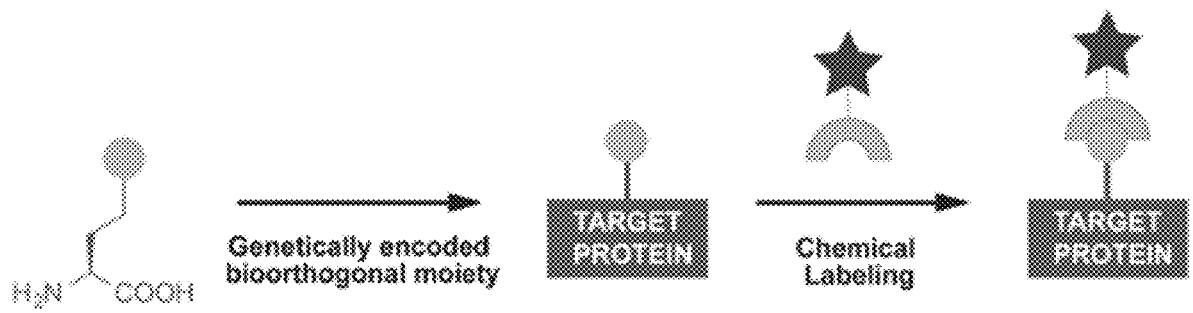
18-3
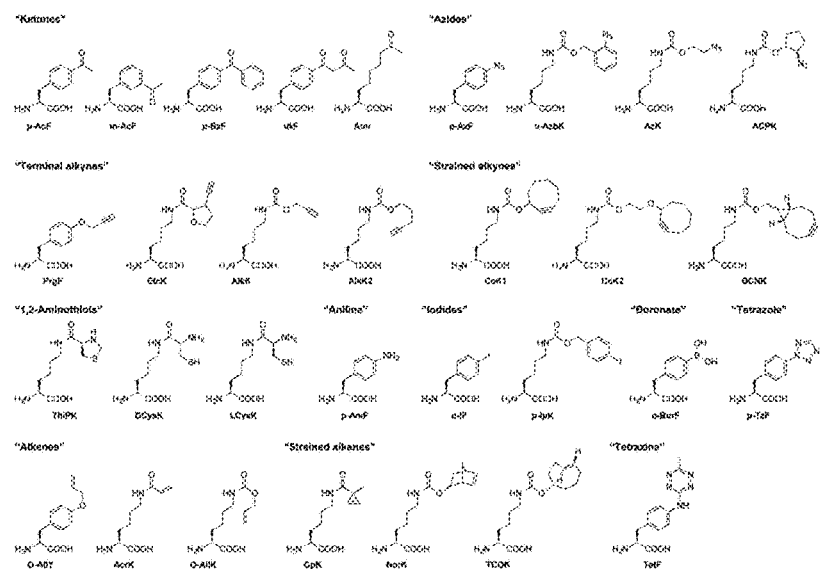
FIG. 18 (CONT)

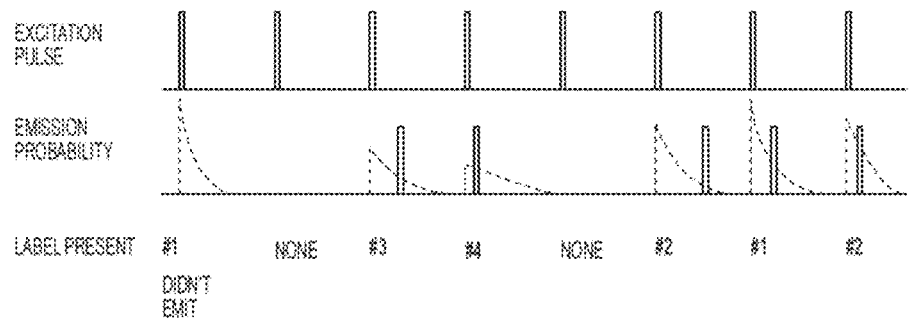
FIG. 31A
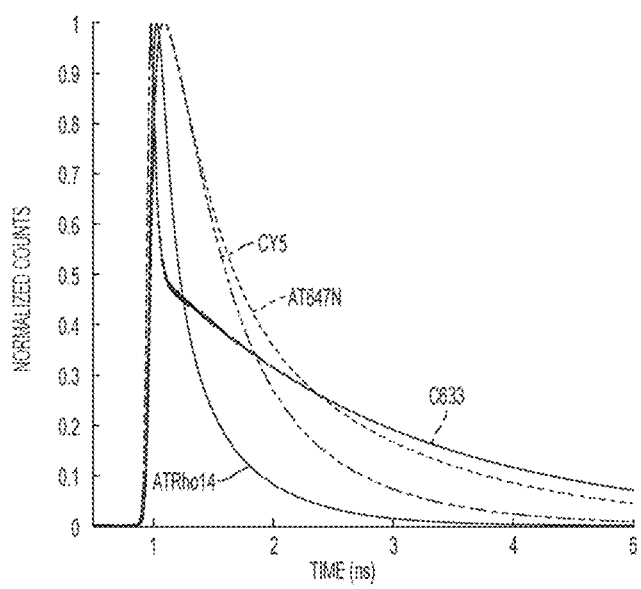
FIG. 31B
FIG. 31C

```
                         SEQUENCE LISTING

<160> NUMBER OF SEQ ID NOS: 17

<210> SEQ ID NO 1
<211> LENGTH: 253
<212> TYPE: DNA
<213> ORGANISM: Artificial Sequence
<220> FEATURE:
<223> OTHER INFORMATION: Synthetic Polynucleotide

<400> SEQUENCE: 1
aacccacccc ccaaacacaa cataatctct aatcacaaca accaacacca acaccaccaa    60
acaaacatat ctctctcaac aaacacaacc accccaacac aaacacatac ctctccaaca   120
acaacaaacc acacactaaa acacacacat acatctctca acaacaacaa cccaacacca   180
ccaaaaaaca caatatctct tctcacaaca acaaacccca atcaaaaaaa acacacatat   240
tctctctcaa caa                                                     253

<210> SEQ ID NO 2
<211> LENGTH: 266
<212> TYPE: DNA
<213> ORGANISM: Artificial Sequence
<220> FEATURE:
<223> OTHER INFORMATION: Synthetic Polynucleotide

<400> SEQUENCE: 2
aacccaccac caccaaaaca cacacatatc tctctcaaca acaacaaccc accaccacca    60
aaacacacac atatctctct caacaacaac aacccaccac caccaaaaca cacacatatc   120
tctctcaaca acaacaaccc accaccacca aaacacacac atatctctct caacaacaac   180
aacccaccac caccaaaaca cacacatatc tctctcaaca acaacaaccc accaccacca   240
aaacacacac atatctctct caacaa                                       266

<210> SEQ ID NO 3
<211> LENGTH: 219
<212> TYPE: DNA
<213> ORGANISM: Artificial Sequence
<220> FEATURE:
<223> OTHER INFORMATION: Synthetic Polynucleotide

<400> SEQUENCE: 3
acaccaacaa taaaaaaaaa aaacctctcc aaacacaaca caaaaaaaaa aaaaaatact    60
cccaacaaca aacaaaaaaa aaaaaaaaaa aaaaaaaaaa atatctctca caacaacaac   120
aaaaaaaaaa aaaaatatcc ctctcaacac acaacaataa aaaaaaaaaa tctcctcaca   180
acaaaacaaa aaaaaaaaaa aaaaatttc tctaaacac                          219
```

<210> SEQ ID NO 4
<211> LENGTH: 263
<212> TYPE: DNA
<213> ORGANISM: Artificial Sequence
<220> FEATURE:
<223> OTHER INFORMATION: Synthetic Polynucleotide

<400> SEQUENCE: 4

```
aaaaaaaaaa aaaaaaaaaa aatatctctc tcaacaacaa caacaaaaaa aaaaaaaaaa      60
aaaaaaatat ctctctcaac aacaacaaca aaaaaaaaaa aaaaaaaaaa aatatctctc     120
tcaacaacaa caacaaaaaa aaaaaaaaaa aaaaaaatat ctctctcaac aacaacaaca     180
aaaaaaaaaa aaaaaaaaaa aatatctctc tcaacaacaa caacaaaaaa aaaaaaaaaa     240
aaaaaaatat ctctctcaac aac                                            263
```

<210> SEQ ID NO 5
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 5

```
tccgtacgac                                                             10
```

<210> SEQ ID NO 6
<211> LENGTH: 134
<212> TYPE: PRT
<213> ORGANISM: Artificial Sequence
<220> FEATURE:
<223> OTHER INFORMATION: Synthetic Polypeptide

<400> SEQUENCE: 6

```
Met Ala Glu Ala Gly Ile Thr Gly Thr Trp Tyr Asn Gln Leu Gly Ser
  1               5                  10                  15

Thr Phe Ile Val Thr Ala Gly Ala Asp Gly Ala Leu Thr Gly Thr Tyr
             20                  25                  30

Glu Ser Ala Val Gly Asn Ala Glu Ser Arg Tyr Val Leu Thr Gly Arg
         35                  40                  45

Tyr Asp Ser Ala Pro Ala Thr Asp Gly Ser Gly Thr Ala Leu Gly Trp
     50                  55                  60

Thr Val Ala Trp Lys Asn Asn Tyr Arg Asn Ala His Ser Ala Thr Thr
 65                  70                  75                  80

Trp Ser Gly Gln Tyr Val Gly Gly Ala Glu Ala Arg Ile Asn Thr Gln
                 85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala Ser
        115                 120                 125

Glu Glu Glu Glu Glu Glu
    130
```

<210> SEQ ID NO 7
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 7

```
Met Ala Glu Ala Gly Ile Thr Gly Thr Trp Tyr Ala Gln Leu Gly Asp
```

```
                1               5                   10                  15
            Thr Phe Ile Val Thr Ala Gly Ala Asp Gly Ala Leu Thr Gly Thr Tyr
                            20                  25                  30
            Glu Ala Ala Val Gly Asn Ala Glu Ser Arg Tyr Val Leu Thr Gly Arg
                            35                  40                  45
            Tyr Asp Ser Ala Pro Ala Thr Asp Gly Ser Gly Thr Ala Leu Gly Trp
                            50                  55                  60
            Thr Val Ala Trp Lys Asn Asn Tyr Arg Asn Ala His Ser Ala Thr Thr
             65                 70                  75                  80
            Trp Ser Gly Gln Tyr Val Gly Ala Glu Ala Arg Ile Asn Thr Gln
                            85                  90                  95
            Trp Leu Leu Thr Ser Gly Thr Thr Glu Ala Asn Ala Trp Lys Ser Thr
                            100                 105                 110
            Leu Val Gly His Asp Thr Phe Thr Lys Val Lys Pro Ser Ala Ala Ser
                            115                 120                 125
```

<210> SEQ ID NO 8
<211> LENGTH: 196
<212> TYPE: DNA
<213> ORGANISM: Artificial Sequence
<220> FEATURE:
<223> OTHER INFORMATION: Synthetic Polynucleotide

<400> SEQUENCE: 8

```
aaaatataat aataattaaa aaaaaataaa aaaattaaaa aattttttta aaaaaaaaaa     60
taaaaaaata aaaaaatttt taaaaaaaaa aaatattttta aaaattaaa aaaaaaaatt    120
aaaaaaaaaa aaaaaaaaaa atatttaaaa aaaaaaaaaa ataaaaatta aaaaaaaaat    180
aaaaaatatt ttattt                                                    196
```

<210> SEQ ID NO 9
<211> LENGTH: 194
<212> TYPE: DNA
<213> ORGANISM: Artificial Sequence
<220> FEATURE:
<223> OTHER INFORMATION: Synthetic Polynucleotide

<400> SEQUENCE: 9

```
aaaaaaaaaa aatattttaa aaaaaaaaaa aaaaaaatat tttaaaaaaa aaaaaaaaaa     60
aatatttta aaaaaaaaaa aaaaaaatat tttaaaaaaa aaaaaaaaaa aatatttaa    120
aaaaaaaaaa aaaaaaatat tttaaaaaaa aaaaaaaaaa aatatttaa aaaaaaaaaa    180
aaaaaaatat ttta                                                      194
```

<210> SEQ ID NO 10
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 10

```
Leu Cys Thr Pro Ser Arg Gly Ser Leu Phe Thr Gly Arg
 1               5                   10
```

<210> SEQ ID NO 11
<211> LENGTH: 11
<212> TYPE: PRT
<213> ORGANISM: Artificial Sequence
<220> FEATURE:
<223> OTHER INFORMATION: Synthetic Polypeptide

```
<400> SEQUENCE: 11

Asp Ser Leu Glu Phe Ile Ala Ser Lys Leu Ala
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 12

Val Leu Asp Ser Leu Glu Phe Ile Ala Ser Lys Leu Ala
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 13

Gly Ser Gln Asp Val Leu Asp Ser Leu Glu Phe Ile Ala Ser Lys Leu
1               5                   10                  15

Ala

<210> SEQ ID NO 14
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 14

Leu Pro Xaa Thr Gly
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 15

Cys Val Ile Ala
1

<210> SEQ ID NO 16
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 16

Gly Leu Asn Asp Ile Phe Glu Ala Gln Lys Ile Glu Trp His Glu
1               5                   10                  15

<210> SEQ ID NO 17
```

```
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 17

Gly Phe Glu Ile Asp Lys Val Trp Tyr Asp Leu Asp Ala
1               5                   10
```

METHODS FOR NUCLEIC ACID SEQUENCING

RELATED APPLICATIONS

This application is a continuation of U.S. patent application Ser. No. 16/212,724, titled "METHODS FOR NUCLEIC ACID SEQUENCING," filed Dec. 7, 2018, which is a divisional application of U.S. patent application Ser. No. 15/161,125, titled "METHODS FOR NUCLEIC ACID SEQUENCING," filed May 20, 2016, now U.S. Pat. No. 10,174,363, which claims priority under 35 U.S.C. § 119(e) to U.S. Provisional Patent Application No. 62/164,482, titled "METHODS FOR NUCLEIC ACID SEQUENCING," filed May 20, 2015, U.S. Provisional Patent Application No. 62/164,506, titled "INTEGRATED DEVICE FOR TEMPORAL BINNING OF RECEIVED PHOTONS," filed May 20, 2015, U.S. Provisional Patent Application No. 62/164,464, titled "INTEGRATED DEVICE WITH EXTERNAL LIGHT SOURCE FOR PROBING, DETECTING, AND ANALYZING MOLECULES," filed May 20, 2015, and U.S. Provisional Patent Application No. 62/164,485, titled "PULSED LASER," filed May 20, 2015, each of which is hereby incorporated by reference in its entirety.

U.S. patent application Ser. No. 15/161,125, titled "METHODS FOR NUCLEIC ACID SEQUENCING," filed May 20, 2016, also is a continuation-in-part of and claims priority under 35 U.S.C. § 120 to U.S. patent application Ser. No. 14/821,688, titled "INTEGRATED DEVICE WITH EXTERNAL LIGHT SOURCE FOR PROBING, DETECTING, AND ANALYZING MOLECULES," filed Aug. 7, 2015, now U.S. Pat. No. 9,885,657, which is hereby incorporated by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on May 7, 2021, is named R070870020US02-SEQ-GIC.txt, and is 7,858 bytes in size.

FIELD OF THE APPLICATION

The present application is directed generally to methods, compositions, and devices for performing rapid, massively parallel, quantitative analysis of biological and/or chemical samples, and methods of fabricating said devices.

BACKGROUND

Detection and analysis of biological samples may be performed using biological assays ("bioassays"). Bioassays conventionally involve large, expensive laboratory equipment requiring research scientists trained to operate the equipment and perform the bioassays. Moreover, bioassays are conventionally performed in bulk such that a large amount of a particular type of sample is necessary for detection and quantitation.

Some bioassays are performed by tagging samples with luminescent markers that emit light of a particular wavelength. The markers are illuminated with a light source to cause luminescence, and the luminescent light is detected with a photodetector to quantify the amount of luminescent light emitted by the markers. Bioassays using luminescent markers conventionally involve expensive laser light sources to illuminate samples and complicated luminescent detection optics and electronics to collect the luminescence from the illuminated samples.

SUMMARY

According to an aspect of the present application, a single molecule can be identified (e.g., distinguished from other possible molecules in a reaction sample) based on one or more properties of a series of photons that are emitted from the molecule when it is exposed to a plurality of separate light pulses. In some embodiments, the emitted photons can be used to identify/distinguish the molecule based on a different luminescent lifetime. In some embodiments, luminescent lifetime can be calculated. In some embodiments, the actual lifetime does not need to be calculated. For example, one or more properties suggestive of luminescent lifetime can be used (e.g., local time of emission, time distribution of detected emissions). In some embodiments, the emitted photons can be used to determine the luminescent intensity of the molecule, and the luminescent intensity can be used to identify the molecule. In some embodiments, the emitted photons can be used to determine the luminescent lifetime and luminescent intensity of the molecule, and the luminescent lifetime or luminescent intensity can be used to identify the molecule. In some embodiments, the identity of the molecule can be based on a combination of both luminescent lifetime and luminescent intensity.

In some embodiments, a molecule can be labeled with a luminescent label. In some embodiments, the luminescent label is a fluorophore. In some embodiments, the luminescent label can be identified or distinguished based on a property of the luminescent label. Properties of a luminescent label (e.g., a fluorophore) include, but are not limited to luminescent lifetimes, absorption spectra, emission spectra, luminescence quantum yield, and luminescent intensity. In some embodiments, luminescent labels are identified or distinguished based on luminescent lifetime. In some embodiments, luminescent labels are identified or distinguished based on luminescent intensity. In some embodiments, luminescent labels are identified or distinguished based on the wavelength of the delivered excitation energy necessary to observe an emitted photon. In some embodiments, luminescent labels are identified or distinguished based on the wavelength of an emitted photon. In some embodiments, luminescent labels are identified or distinguished based on both luminescent lifetime and the wavelength of the delivered excitation energy necessary to observe an emitted photon. In some embodiments, luminescent labels are identified or distinguished based on both a luminescent intensity and the wavelength of the delivered excitation energy necessary to observe an emitted photon. In some embodiments, luminescent labels are identified or distinguished based on luminescent lifetime, luminescent intensity, and the wavelength of the delivered excitation energy necessary to observe an emitted photon. In some embodiments, luminescent labels are identified or distinguished based on both luminescent lifetime and the wavelength of an emitted photon. In some embodiments, luminescent labels are identified or distinguished based on both a luminescent intensity and the wavelength of an emitted photon. In some embodiments, luminescent labels are identified or distinguished based on luminescent lifetime, luminescent intensity, and the wavelength of an emitted photon.

In certain embodiments, different types of molecules in a reaction mixture or experiment are labeled with different luminescent markers. In some embodiments, the different markers have different luminescent properties which can be distinguished. In some embodiments, the different markers are distinguished by having different luminescent lifetimes, different luminescent intensities, different wavelengths of emitted photons, or a combination thereof. The presence of a plurality of types of molecules with different luminescent markers may allow for different steps of a complex reaction to be monitored, or for different components of a complex reaction product to be identified. In some embodiments, the order in which the different types of molecules react or interact can be determined.

In some embodiments, different nucleotides can be luminescently labeled with a different number of the same luminescent molecule (e.g., one or more of the same fluorescent dye). In some embodiments, changing the number of luminescent molecules in a luminescent label can allow different nucleotides to be distinguished based on different intensities. In some embodiments, different nucleotides can each be labeled with a different type of luminescent molecule and/or a different number of each luminescent molecule. In some embodiments, different types of luminescent molecules allow different nucleotides to be distinguished based on different intensities and/or different lifetimes.

In certain embodiments, the luminescent properties of a plurality of types of molecules with different luminescent markers are used to identify the sequence of a biomolecule, such as a nucleic acid or protein. In some embodiments, the luminescent properties of a plurality of types of molecules with different luminescent markers are used to identify single molecules as they are incorporated during the synthesis of a biomolecule. In some embodiments, the luminescent properties of a plurality of types of nucleotides with different luminescent markers are used to identify single nucleotides as they are incorporated during a sequencing reaction. This may allow for determination of the sequence of a nucleic acid template. In some embodiments, the luminescently labeled nucleotides are incorporated into a nucleic acid strand complementary to nucleic acid template. In some embodiments, the complementary strand comprises a primer.

In certain embodiments, the plurality of types of nucleotides with different luminescent markers comprises four types of luminescently labeled nucleotides. In some embodiments, the four luminescently labeled nucleotides absorb and/or emit photons within one spectral range. In some embodiments, three of the luminescently labeled nucleotides emit within a first spectral range, and a fourth luminescently labeled nucleotide absorbs and/or emits photons within a second spectral range. In some embodiments, two of the luminescently labeled nucleotides emit within a first spectral range, and the a third and fourth luminescently labeled nucleotide emit luminescence within a second spectral range. In some embodiments, two of the luminescently labeled nucleotides emit within a first spectral range, a third nucleotide ab absorbs and/or emits photons within a second spectral range, and a fourth nucleotide absorbs and/or emits photons within a third spectral range. In some embodiments, each of the four luminescently labeled nucleotides absorbs and/or emits photons within a different spectral range. In some embodiments, each type of luminescently labeled nucleotide that absorbs and/or emits photons within the same spectral range has a different luminescent lifetime or luminescent intensity, or both.

In some embodiments, four different types of nucleotides (e.g., adenine, guanine, cytosine, thymine/uracil) in a reaction mixture can each be labeled with one or more luminescent molecules. In some embodiments, each type of nucleotide can be connected to more than one of the same luminescent molecule (e.g., two or more of the same fluorescent dye connected to a nucleotide). In some embodiments, each luminescent molecule can be connected to more than one nucleotide (e.g., two or more of the same nucleotide). In some embodiments, more than one nucleotide can be connected to more than one luminescent molecule. In some embodiments, a protecting molecule serves as an anchor for attaching one or more nucleotides (e.g., of the same type) and one or more luminescent molecules (e.g., of the same type). In some embodiments, all four nucleotides are labeled with luminescent molecules that absorb and emit within the same spectral range (e.g., 520-570 nm).

In some embodiments, the luminescent labels among a set of four nucleotides can be selected from dyes comprising an aromatic or heteroaromatic compound and can be a pyrene, anthracene, naphthalene, acridine, stilbene, indole, benzindole, oxazole, carbazole, thiazole, benzothiazole, phenanthridine, phenoxazine, porphyrin, quinoline, ethidium, benzamide, cyanine, carbocyanine, salicylate, anthranilate, coumarin, fluoroscein, rhodamine, or other like compound. Exemplary dyes include xanthene dyes, such as fluorescein or rhodamine dyes, naphthalene dyes, coumarin dyes, acridine dyes, cyanine dyes, benzoxazole dyes, stilbene dyes, pyrene dyes, phthalocyanine dyes, phycobiliprotein dyes, squaraine dyes, and the like.

In some embodiments, the luminescent labels among a set of four nucleotides comprise Alexa Fluor® 546, Cy®3B, Alexa Fluor® 555 and Alexa Fluor® 555, and the FRET pair Alexa Fluor® 555 and Cy®3.5. In some embodiments, the luminescent labels among a set of four nucleotides comprise Alexa Fluor® 555, Cy®3.5, Alexa Fluor® 546, and DyLight® 554-R1. In some embodiments, the luminescent labels among a set of four nucleotides comprise Alexa Fluor® 555, Cy®3.5, ATTO Rho6G, and DyLight® 554-R1. In some embodiments, the luminescent labels among a set of four nucleotides comprise Alexa Fluor® 555, Cy®3B, ATTO Rho6G, and DyLight® 554-R1. In some embodiments, the luminescent labels among a set of four nucleotides comprise Alexa Fluor® 555, Cy®3B, ATTO 542, and DyLight® 554-R1. In some embodiments, the luminescent labels among a set of four nucleotides comprise Alexa Fluor® 555, Cy®3B, ATTO 542, and Alexa Fluor® 546. In some embodiments, the luminescent labels among a set of four nucleotides comprise Cy®3.5, Cy®3B, ATTO Rho6G, and DyLight® 554-R1.

In certain embodiments, at least one type, at least two types, at least three types, or at least four of the types of luminescently labeled nucleotides comprise a luminescent dye selected from the group consisting of 6-TAMRA, 5/6-Carboxyrhodamine 6G, Alexa Fluor® 546, Alexa Fluor® 555, Alexa Fluor® 568, Alexa Fluor® 610, Alexa Fluor® 647, Aberrior Star 635, ATTO 425, ATTO 465, ATTO 488, ATTO 495, ATTO 514, ATTO 520, ATTO Rho6G, ATTO 542, ATTO 647N, ATTO Rho14, Chromis 630, Chromis 654A, Chromeo™ 642, CF™514, CF™532, CF™543, CF™546, CF™546, CF™555, CF™568, CF™633, CF™640R, CF™660C, CF™660R, CF™680R, Cy®3, Cy®3B, Cy®3.5, Cy®5, Cy®5.5, Dyomics-530, Dyomics-547P1, Dyomics-549P1, Dyomics-550, Dyomics-554, Dyomics-555, Dyomics-556, Dyomics-560, Dyomics-650, Dyomics-680, DyLight® 554-R1, DyLight® 530-R2, DyLight® 594, DyLight® 635-B2, DyLight® 650, DyLight® 655-B4, DyLight® 675-B2, DyLight® 675-B4, DyLight® 680, HiLyte™ Fluor 532, HiLyte™ Fluor 555, HiLyte™ Fluor 594, LightCycler® 640R, Seta™ 555, Seta™ 670, Seta™700, Seta™u 647, and Seta™u 665, or are of formulae (Dye 101), (Dye 102), (Dye 103), (Dye 104), (Dye 105), or (Dye 106), as described herein.

In some embodiments, at least one type, at least two types, at least three types, or at least four of the types of luminescently labeled nucleotides each comprise a luminescent dye selected from the group consisting of Alexa Fluor® 546, Alexa Fluor® 555, Cy®3B, Cy®3.5, DyLight® 554-R1, Alexa Fluor® 546, Atto Rho6G, ATTO 425, ATTO 465, ATTO 488, ATTO 495, ATTO 514, ATTO 520, ATTO Rho6G, and ATTO 542.

In some embodiments, a first type of luminescently labeled nucleotide comprises Alexa Fluor® 546, a second type of luminescently labeled nucleotide comprises Cy®3B, a third type of luminescently labeled nucleotide comprises two Alexa Fluor® 555, and a fourth type of luminescently labeled nucleotide comprises Alexa Fluor® 555 and Cy®3.5.

In some embodiments, a first type of luminescently labeled nucleotide comprises Alexa Fluor® 555, a second type of luminescently labeled nucleotide comprises Cy®3.5, a third type of luminescently labeled nucleotide comprises Alexa Fluor® 546, and a fourth type of luminescently labeled nucleotide comprises DyLight® 554-R1.

In some embodiments, a first type of luminescently labeled nucleotide comprises Alexa Fluor® 555, a second type of luminescently labeled nucleotide comprises Cy®3.5, a third type of luminescently labeled nucleotide comprises ATTO Rho6G, and a fourth type of luminescently labeled nucleotide comprises DyLight® 554-R1.

In some embodiments, a first type of luminescently labeled nucleotide comprises Alexa Fluor® 555, a second type of luminescently labeled nucleotide comprises Cy®3B, a third type of luminescently labeled nucleotide comprises ATTO Rho6G, and a fourth type of luminescently labeled nucleotide comprises DyLight® 554-R1.

In some embodiments, a first type of luminescently labeled nucleotide comprises Alexa Fluor® 555, a second type of luminescently labeled nucleotide comprises Cy®3B, a third type of luminescently labeled nucleotide comprises ATTO 542, and a fourth type of luminescently labeled nucleotide comprises DyLight® 554-R1.

In some embodiments, a first type of luminescently labeled nucleotide comprises Alexa Fluor® 555, a second type of luminescently labeled nucleotide comprises Cy®3B, a third type of luminescently labeled nucleotide comprises ATTO 542, and a fourth type of luminescently labeled nucleotide comprises Alexa Fluor® 546.

In some embodiments, a first type of luminescently labeled nucleotide comprises Cy®3.5, a second type of luminescently labeled nucleotide comprises Cy®3B, a third type of luminescently labeled nucleotide comprises ATTO Rho6G, and a fourth type of luminescently labeled nucleotide comprises DyLight® 554-R1.

In some embodiments, at least one type, at least two types, at least three types, or at least four of the types of luminescently labeled nucleotides comprise a luminescent dye selected from the group consisting of Alexa Fluor® 532, Alexa Fluor® 546, Alexa Fluor® 555, Alexa Fluor® 594, Alexa Fluor® 610, CF™532, CF™543, CF™555, CF™594, Cy®3, DyLight® 530-R2, DyLight® 554-R1, DyLight® 590-R2, DyLight® 594, DyLight® 610-B1, or are of formulae (Dye 101), (Dye 102), (Dye 103), (Dye 104), (Dye 105), or (Dye 106).

In some embodiments, a first and second type of luminescently labeled nucleotide comprise a luminescent dye selected from the group consisting of Alexa Fluor® 532, Alexa Fluor® 546, Alexa Fluor® 555, CF™532, CF™543, CF™555, Cy®3, DyLight® 530-R2, DyLight® 554-R1, and a third and fourth type of luminescently labeled nucleotide comprise a luminescent dye selected from the group consisting of Alexa Fluor® 594, Alexa Fluor® 610, CF™594, DyLight® 590-R2, DyLight® 594, DyLight® 610-B1, or are of formulae (Dye 101), (Dye 102), (Dye 103), (Dye 104), (Dye 105), or (Dye 106).

In certain embodiments, at least one type, at least two types, at least three types, or at least four of the types of luminescently-labeled nucleotide molecules comprise a luminescent protein selected from the group consisting of TagBFP, mTagBFP2, Azurite, EBFP2, mKalama1, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, monomeric Azami Green, TagGFP2, mUKG, mWasabi, Clover, mNeonGreen, EYFP, Citrine, Venus, SYFP2, TagYFP, monomeric Kusabira-Orange, mKOK, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, NirFP, TagRFP657, IFP1.4, iRFP, mKeima Red, LSS-mKate1, LSS-mKate2, mBeRFP, PA-GFP, PAmCherry1, PATagRFP, Kaede (green), Kaede (red), KikGR1 (green), KikGR1 (red), PS-CFP2, mEos2 (green), mEos2 (red), PSmOrange, or Dronpa.

Aspects of the present application provide methods, and systems and devices useful to such methods, for delivering an excitation energy to a molecule to be identified and detecting emitted photons after the excitation. In certain embodiments, detecting comprises recording for each detected luminescence the time duration between the luminescence and the prior pulse of excitation energy. In certain embodiments, detecting comprises recording for each of a plurality of detected luminescences the time duration between the luminescence and the prior pulse of excitation energy. In certain embodiments, a plurality of pulses of excitation energy are delivered. The luminescent marker of the molecule to be identified may be excited by each pulse or a portion of the pulses. In certain embodiments, a plurality of luminescences are detected by one or more sensors. The luminescent marker of the molecule to be identified may emit luminescence after each excitation or a portion of the excitations. The fraction of excitation events that result in a luminescence is based on the luminescence quantum yield of the marker. In some embodiments, increasing the number of luminescent molecules that comprise a luminescent marker can increase the quantum yield (e.g., increase the number of luminescence emissions). Additionally not all luminescences emitted by a marker will be detected, for example, some luminescences will be directed away from the sensors. In certain embodiments, the excitation energy or energies are selected based on the luminescent properties of the luminescent markers, including the absorption spectra and wavelengths at which a marker emits photons after excitation in a given spectral range.

In certain embodiments, the frequency of pulsed excitation energies is selected based on the luminescent properties (e.g., luminescent lifetime) of the luminescently labeled molecule to be detected. In some embodiments, the gap between pulses is longer than the luminescent lifetime of one or more luminescently labeled molecules being excited. In some embodiments, the gap is between about two times and about ten times, between about ten times and about 100 times, or between about 100 times and about 1000 times longer than the luminescent lifetime of one or more luminescently labeled molecules being excited. In some embodiments, the gap is about 10 times longer than the luminescent lifetime of one or more luminescently labeled molecules being excited.

In certain embodiments, the frequency of pulsed excitation energies is selected based on the chemical process being monitored. For a sequencing reaction the number of pulses delivered to the target volume while a luminescently labeled nucleotide is being incorporated will in part determine the number of emitted photons detected. In some embodiments, the frequency is selected to allow for a sufficient number of photons to be detected during the incorporation of a luminescently labeled nucleotide, wherein a sufficient number is the number of photons necessary to distinguish the luminescently labeled nucleotide from amongst a plurality of types of luminescently labeled nucleotides. In some embodiments, the luminescently labeled nucleotide is distinguished based on the wavelength of the emitted photons. In some embodiments, the luminescently labeled nucleotide is distinguished based on the luminescent emission lifetime, e.g., the time between pulse excitation and emission detection. In some embodiments, the luminescently labeled nucleotide is distinguished based on the wavelength and the luminescent emission lifetime of the emitted photons. In some embodiments, the luminescently labeled nucleotide is distinguished based on the luminescent intensity of the emission signal (e.g., based on the frequency of emission or the total number of emission events within a time period). In some embodiments, the luminescently labeled nucleotide is distinguished based on the luminescent intensity of the emission signal and the luminescent lifetime. In some embodiments, the luminescently labeled nucleotide is distinguished based on the luminescent intensity and the wavelength. In some embodiments, the luminescently labeled nucleotide is distinguished based on the luminescent intensity, the wavelength, and the luminescent lifetime.

According to an aspect of the present application, a system comprising an excitation source module and an integrated device is provided. The excitation source module comprises an excitation source configured to emit a pulse of excitation energy having a first duration of time. The integrated device includes a target volume configured to receive a molecule which, when coupled to the pulse of excitation energy emits luminescence, a first energy path along which the pulse of excitation energy moves from an energy source coupling component to the target volume, a sensor that detects the luminescence over a second duration of time, wherein the second duration of time is greater than the first duration of time, a second energy path along which the luminescence moves from the target volume to the sensor, and a third energy path along which the pulse of excitation energy moves from the excitation source to the energy source coupling component.

According to another aspect of the present application, an integrated device comprising a target volume and a sensor is provided. The target volume is configured to receive a sample labeled with one of a plurality of luminescent markers, each of the plurality of luminescent markers having a different lifetime value. The sensor is configured to detect luminescence from one of the plurality of luminescent markers over a plurality of time durations. The plurality of time durations are selected to differentiate among the plurality of luminescent markers. According to another aspect of the present application, an integrated device comprising a target volume and a plurality of sensors is provided. The target volume is configured to receive a sample labeled with one of a plurality of luminescent markers. Each of the plurality of luminescent markers emit luminescence within one of a plurality of spectral ranges and a portion of the plurality of luminescent markers that emit luminescence at one of the plurality of spectral ranges each have different luminescent lifetimes. Each sensor of the plurality of sensors is configured to detect one of the plurality of spectral ranges over a plurality of time durations and the plurality of time durations are selected to differentiate among the portion of the plurality of luminescent markers.

According to another aspect of the present application, a system comprising a plurality of excitation sources and an integrated device is provided. The plurality of excitation sources emit a plurality of excitation energies. Each of the plurality of excitation sources emit pulses of one of the plurality of excitation energies. The integrated device includes a target volume configured to receive a sample labeled with one of a plurality of luminescent markers and a sensor configured to detect luminescence from one of the plurality of luminescent markers over a plurality of time durations after a pulse of one of the plurality of excitation energies. A portion of the plurality of luminescent markers that emit luminescence after being illuminated by one of the plurality of excitation energies each have different lifetime values. The accumulation of a plurality of data timing the duration between a pulse event and a luminescent emission differentiate among the plurality of luminescent markers.

According to another aspect of the present application, a method of sequencing a target nucleic acid is provided. In some embodiments, the method of sequencing a target nucleic acid comprises steps of: (i) providing a mixture comprising (a) said target nucleic acid, (b) a primer complementary to said target nucleic acid, (c) a nucleic acid polymerase, and (d) nucleotides for incorporation into a growing nucleic acid strand complementary to said target nucleic acid, wherein said nucleotides include different types of luminescently labeled nucleotides, wherein said luminescently labeled nucleotides yield detectable signals during sequential incorporation into said growing nucleic acid strand, which detectable signals for said different types of luminescently labeled nucleotides are differentiable from one another in a time domain (e.g., by determining timing and/or frequency of the detectable signals); (ii) subjecting said mixture of (i) to a polymerization reaction under conditions that are sufficient to yield said growing nucleic acid strand by extension of said primer; (iii) measuring said detectable signals from said luminescently labeled nucleotides during sequential incorporation into said growing nucleic acid strand; and (iv) determining the timing and/or frequency of said measured detectable signals from said luminescently labeled nucleotides upon sequential incorporation into said growing nucleic acid strand to identify a time sequence of incorporation of said luminescently labeled nucleotides into said growing nucleic acid strand, thereby determining a sequence of said target nucleic acid.

In some embodiments, the target nucleic acid or the nucleic acid polymerase is attached to a support. In some embodiments, the time sequence of incorporation is identified subsequent to subjecting the mixture of (i) to the polymerization reaction. In some embodiments, the detectable signals are optical signals. In some embodiments, the optical signals are luminescent signals. In some embodiments, determining the timing and/or frequency of the measured detectable signals comprises (i) receiving said detectable signals at one or more sensors; and (ii) selectively directing charge carriers of a plurality of charge carriers produced in response to said detectable signals received at said one or more sensors into at least one charge carrier storage region based upon times at which said charge carriers are produced.

In some embodiments, the timing and/or frequency of said measured detectable signals comprise measurements of decay lifetimes. In some embodiments, the timing and/or frequency of the measured detectable signals comprise measurements of arrival times of the detectable signals at one or more sensors that detect the detectable signals. In some embodiments, the method further comprises segregating charge carriers produced by the detectable signals into bins associated with the one or more sensors based on the arrival times of the detectable signals. In some embodiments, the timing and/or frequency of the measured detectable signals are non-spectral measurements.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

When describing embodiments in reference to the drawings, direction references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of an embodied device. A device may be embodied in other orientations.

As is apparent from the detailed description, the examples depicted in the figures (e.g., FIGS. 1-37) and further described for the purpose of illustration throughout the application describe non-limiting embodiments, and in some cases may simplify certain processes or omit features or steps for the purpose of clearer illustration.

Figure 1:
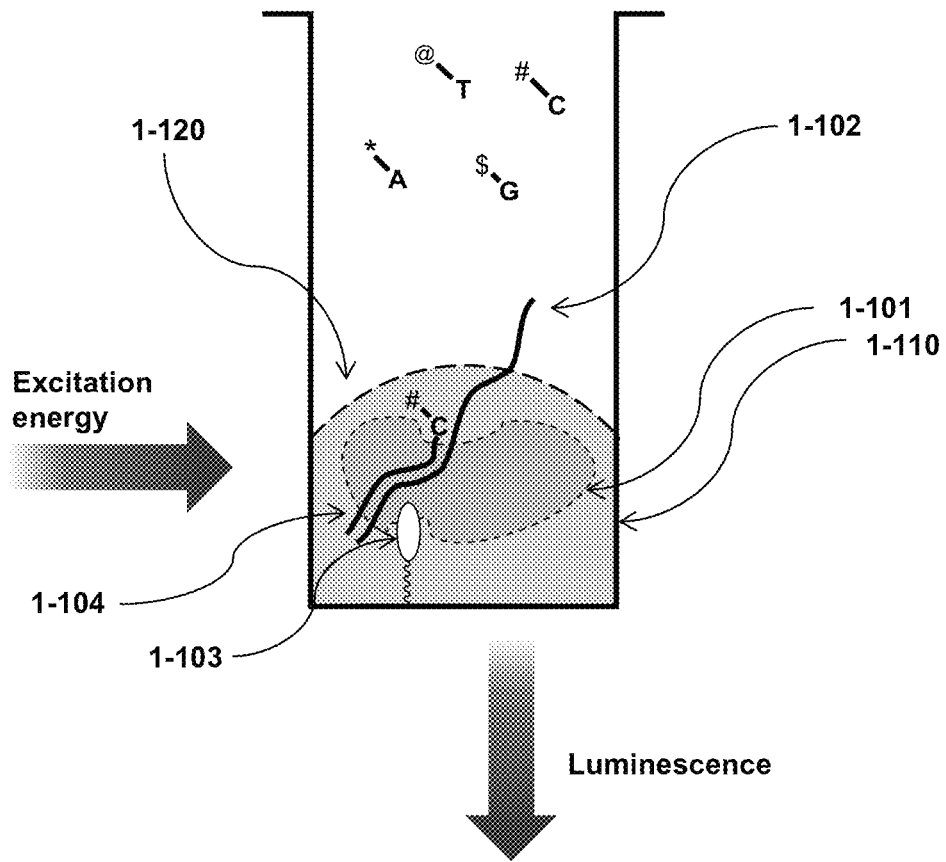

FIG. 1 shows a non-limiting schematic of a sample well (e.g., a sample well) containing various components for nucleic acid sequencing.

Figure 2:
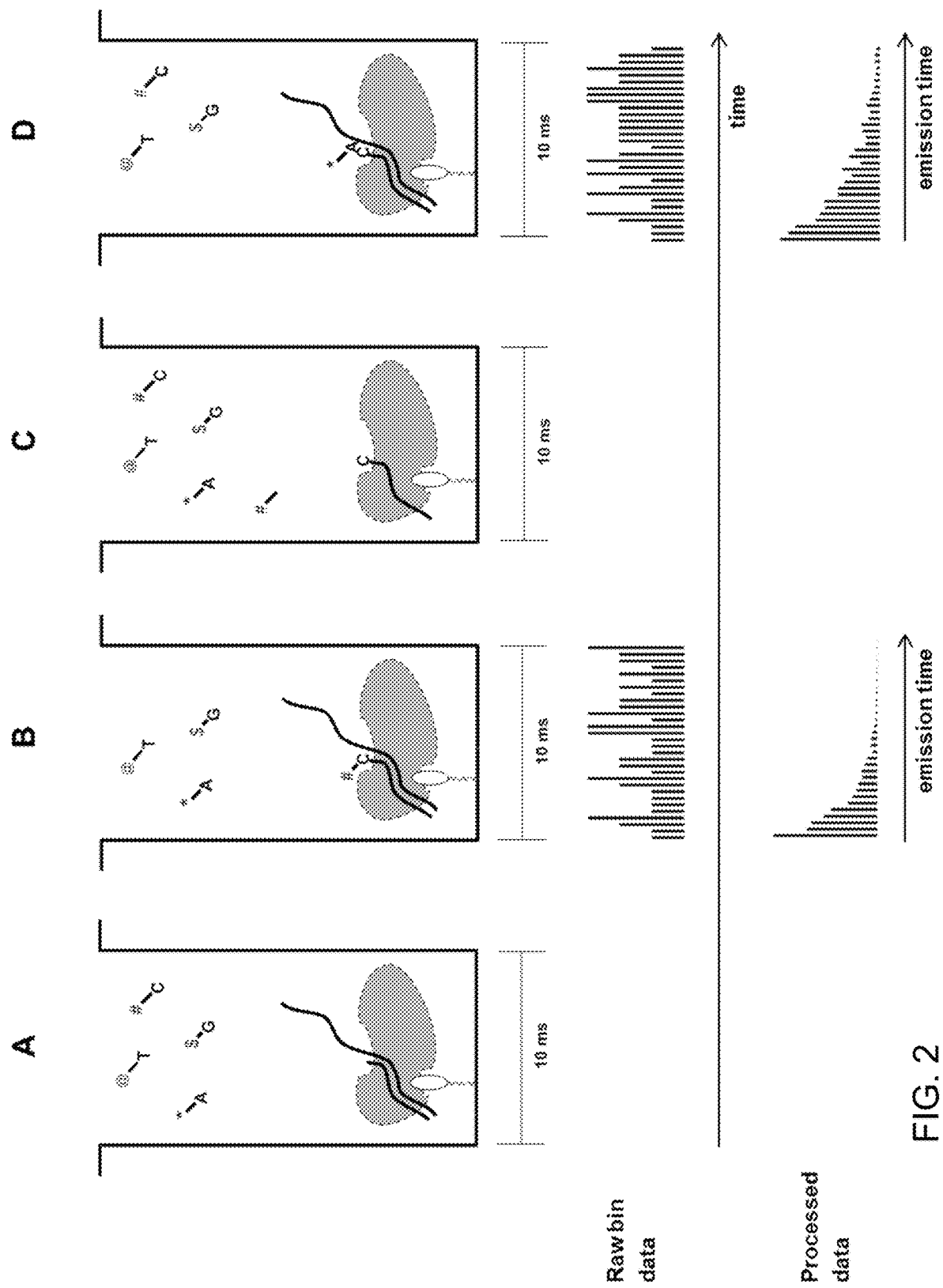

FIG. 2 shows a non-limiting, exemplary experiment of nucleic acid sequencing for four stages; (A) before incorporation of a luminescently labeled nucleotide; (B) a first incorporation event; (C) a period between the first and second incorporation events; and (D) a second incorporation event; along with corresponding examples of raw and processed data during stages (A)-(D).

FIG. 3 depicts a non-limiting signal vs. emission time for four luminescent molecules with different luminescent lifetimes and normalized cumulative distribution function for the probability of decay.

Figure 4:
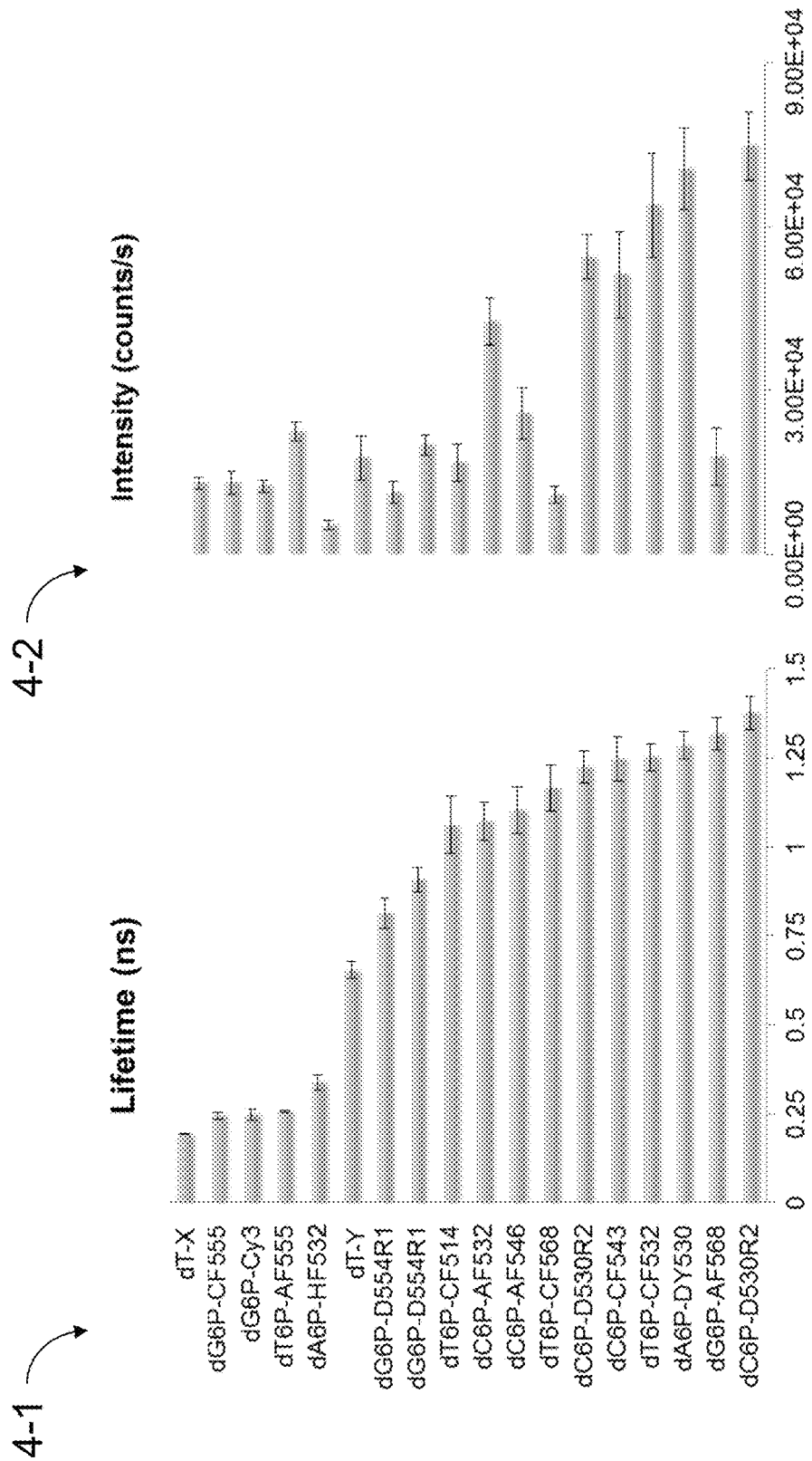

FIG. 4 shows a non-limiting chart of luminescent lifetimes and a chart for luminescent intensities for exemplary luminescently labeled nucleotides.

FIG. 5 depicts a non-limiting sequencing experiment with four luminescently labeled nucleotides: (A) trace of detected luminescences from green and red pulses; (B) reduction of data from green pulses based on luminescent lifetime and intensity of each nucleotide incorporation; and (C) alignment of the experimentally determined sequence with the template sequence.

FIG. 6 depicts a non-limiting sequencing experiment with four luminescently labeled nucleotides: (A) trace of detected luminescences from green pulses; (B) reduction of data from green pulses based on luminescent lifetime and intensity of each nucleotide incorporation; and (C) alignment of the experimentally determined sequence with the template sequence.

Figure 7:
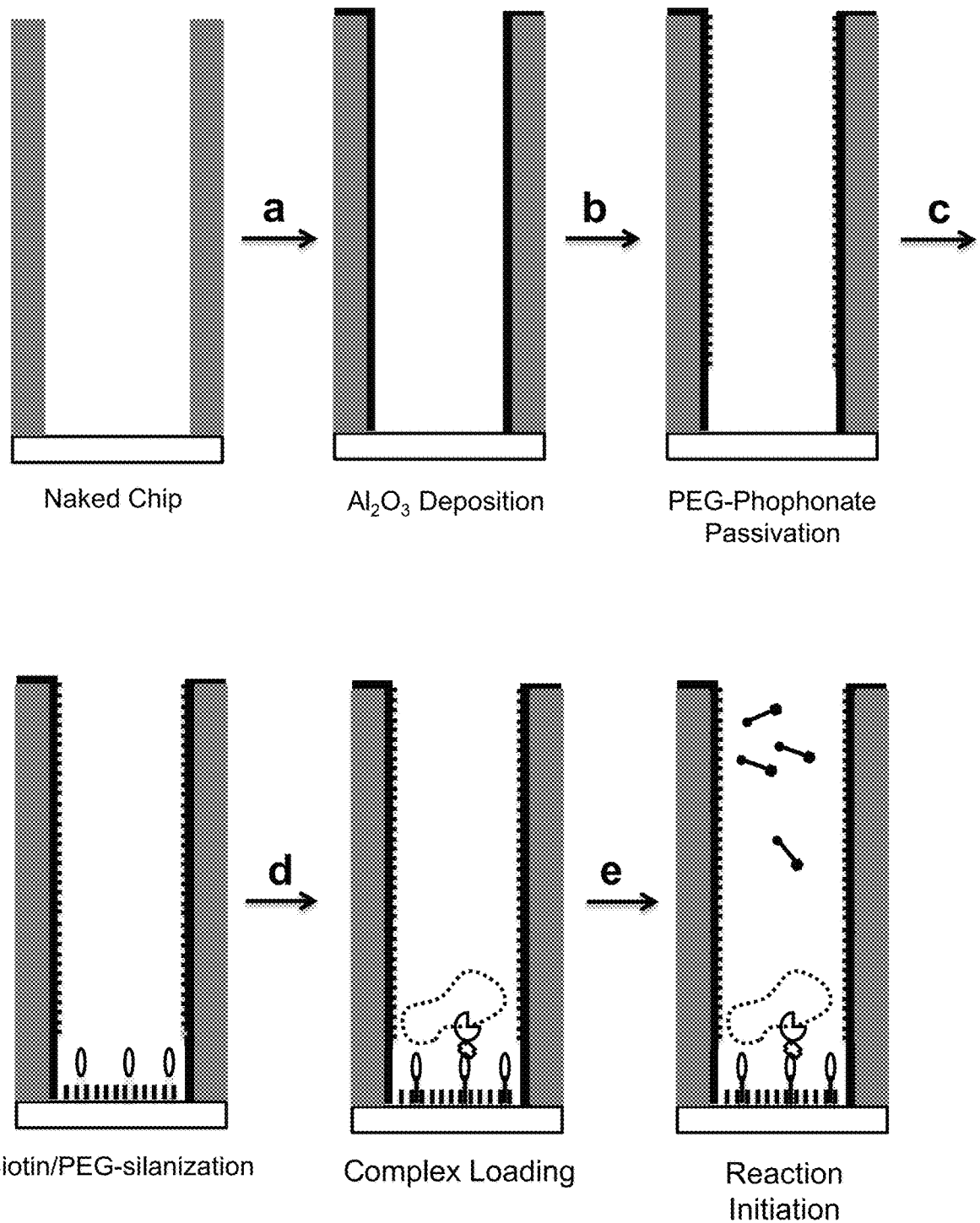

FIG. 7 shows a non-limiting, exemplary process for surface preparation, including the steps of (a) deposition, (b) passivation, (c) silanization, (d) complex loading, and (e) sequencing reaction initiation.

Figure 8:
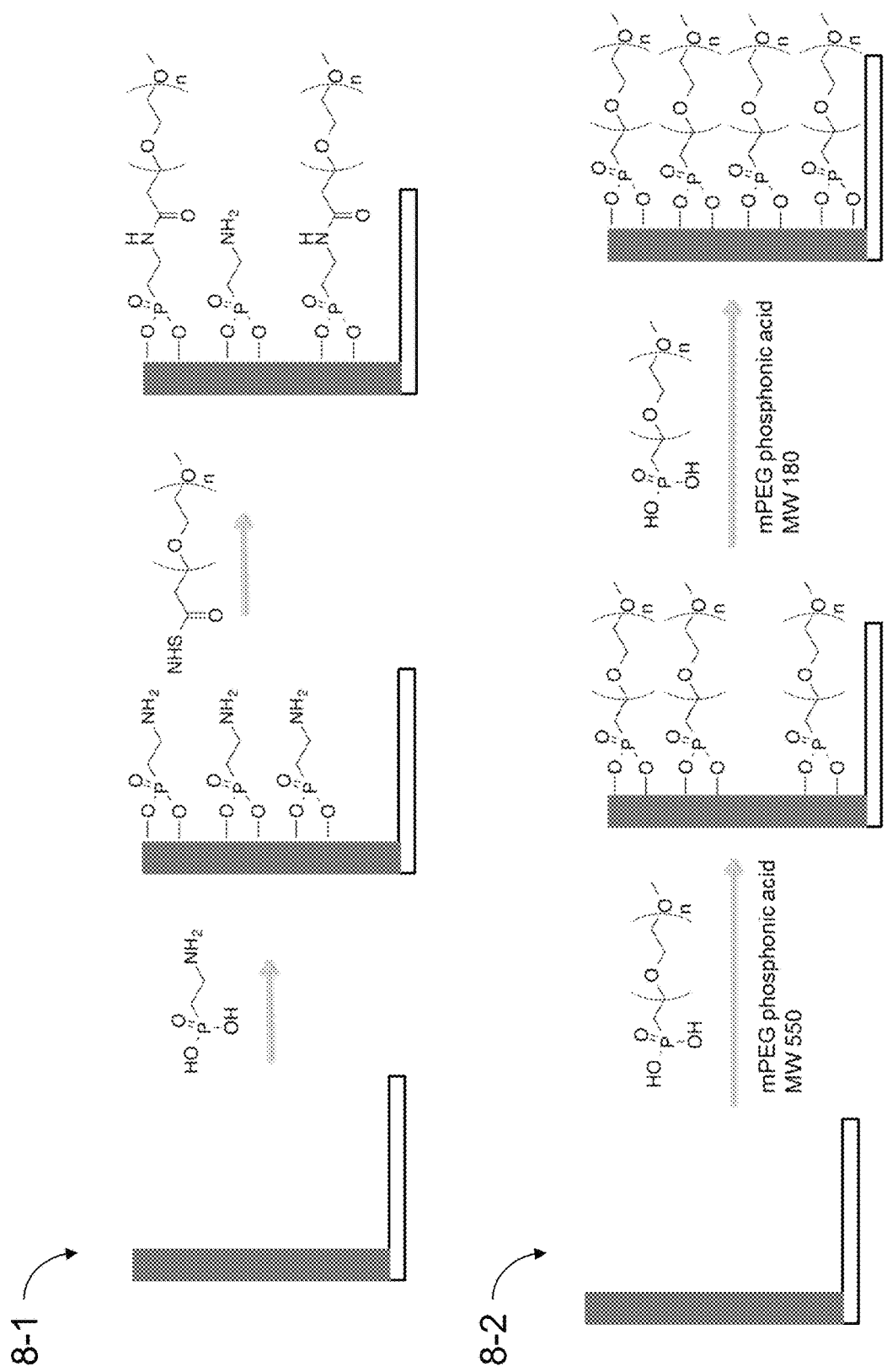

FIG. 8 shows two non-limiting methods for passivation of metal oxide surfaces with phosphonate-PEG groups.

Figure 9:
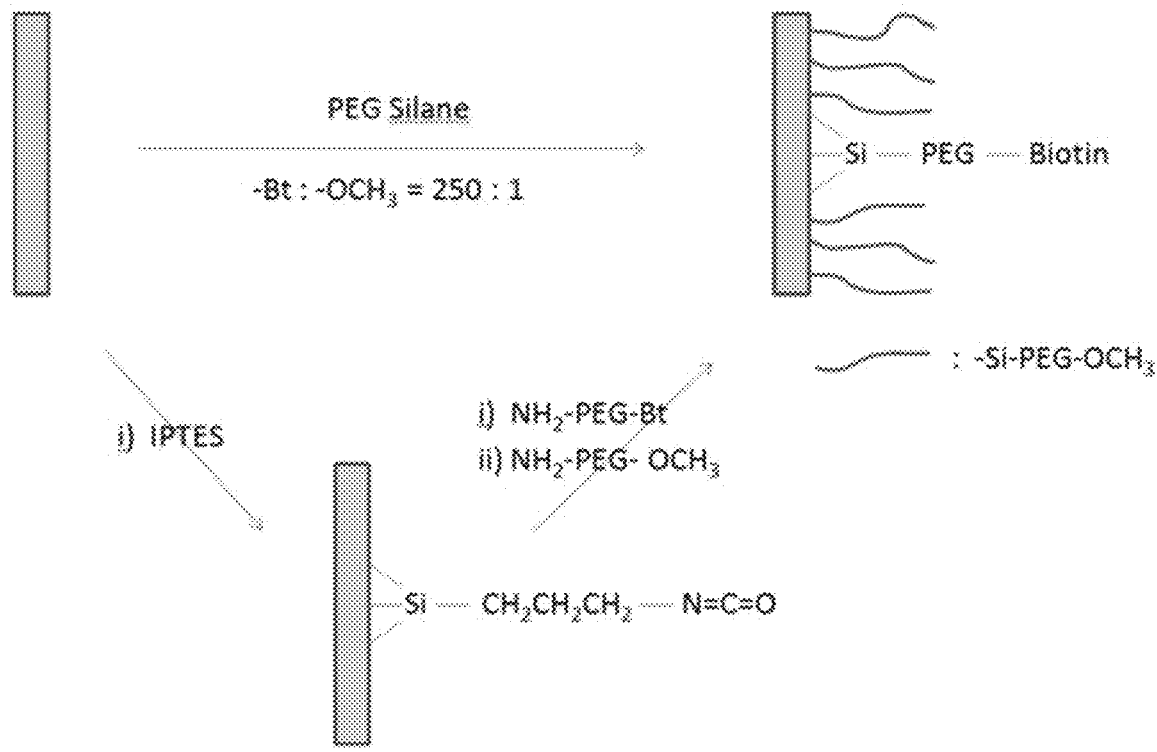

FIG. 9 shows two non-limiting methods for functionalization of glass with of silane-PEG-biotin and silane-PEG mixtures.

Figure 10:
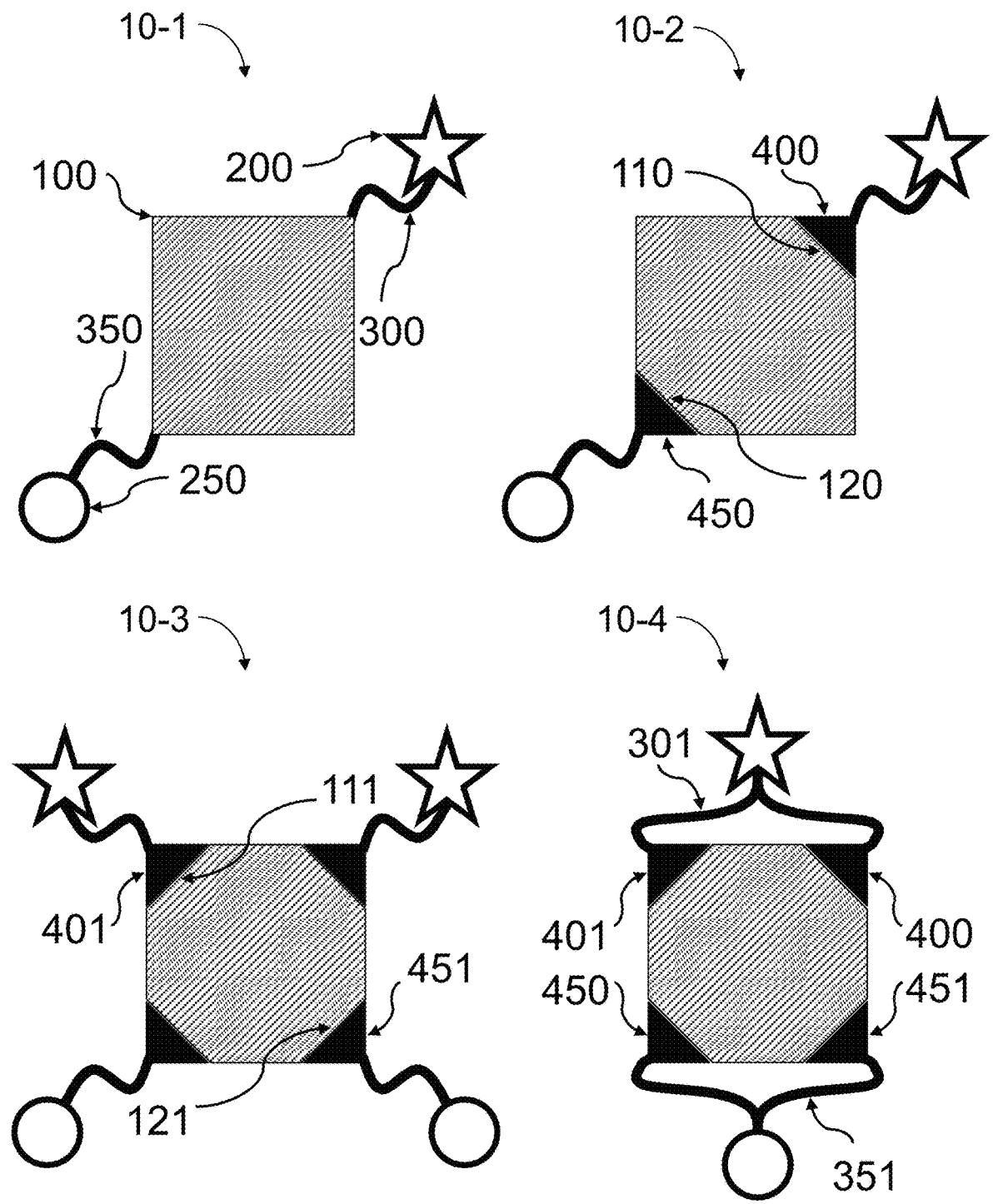

FIG. 10 depicts non-limiting examples of one or more luminescent molecules and one or more nucleotides connected via a protecting molecule.

Figure 11:
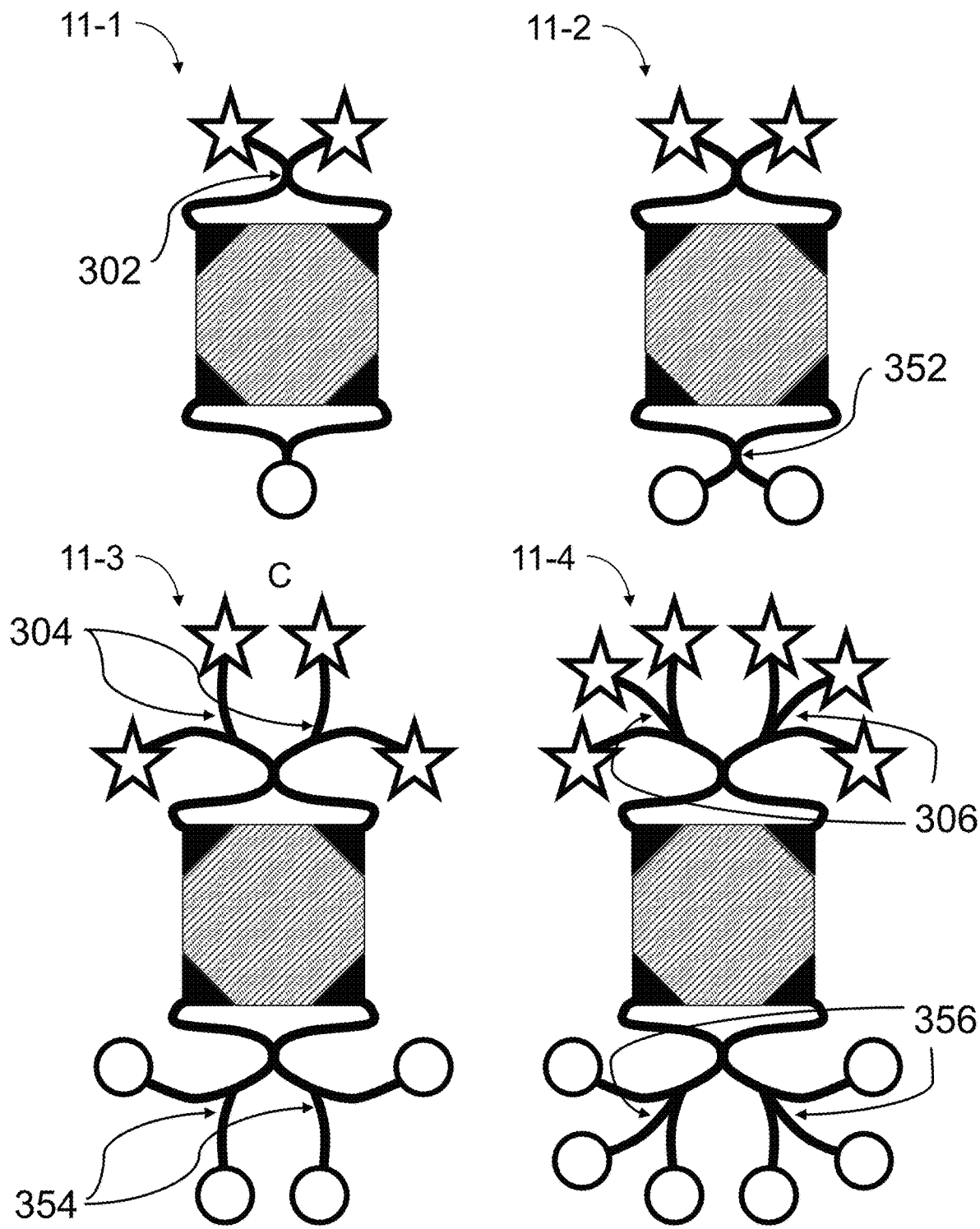

FIG. 11 depicts non-limiting examples of configurations involving one or more nucleotides and one or more luminescent molecules attached via split linkers to a protecting molecule.

Figure 12:
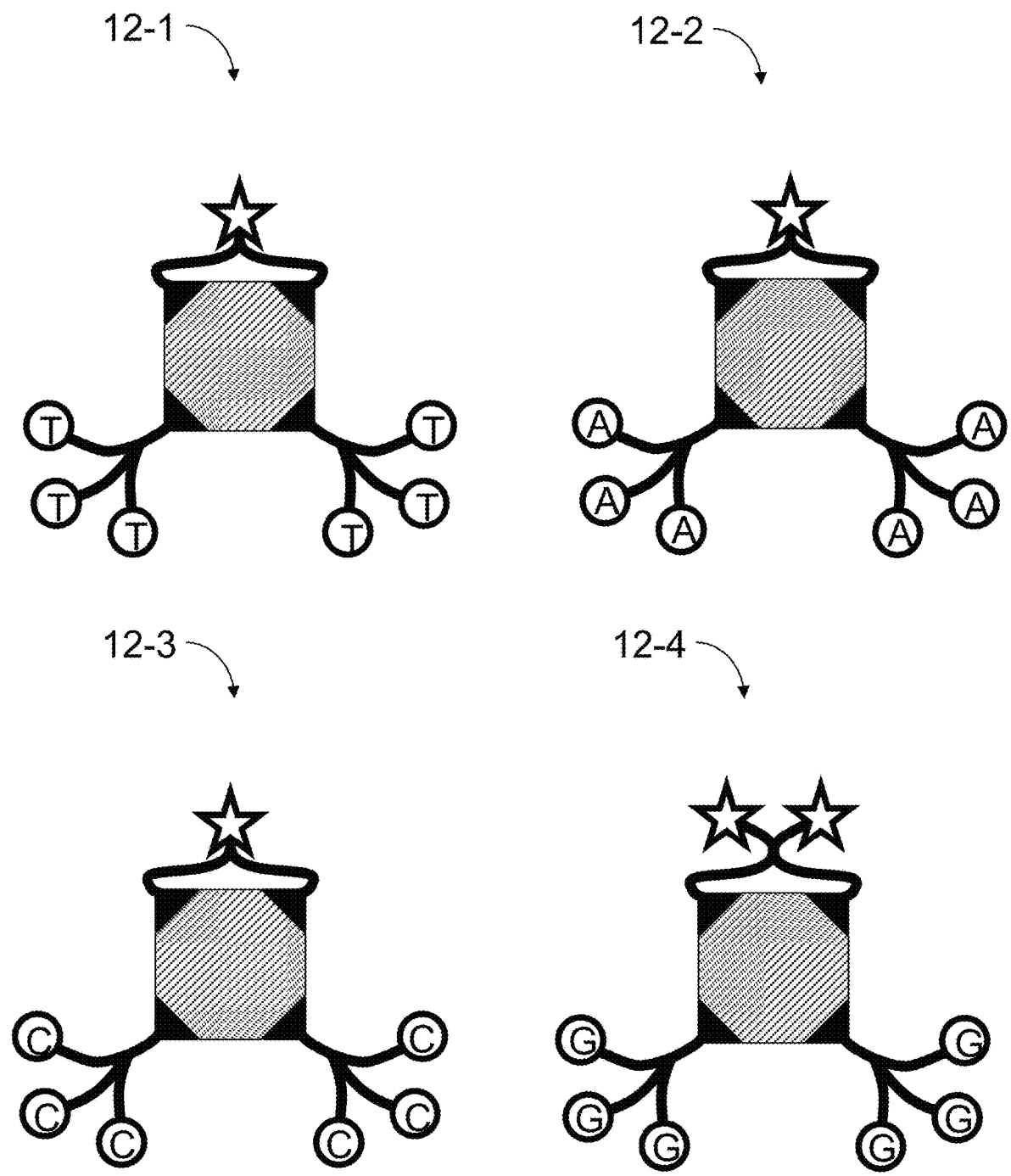
Figure 12:
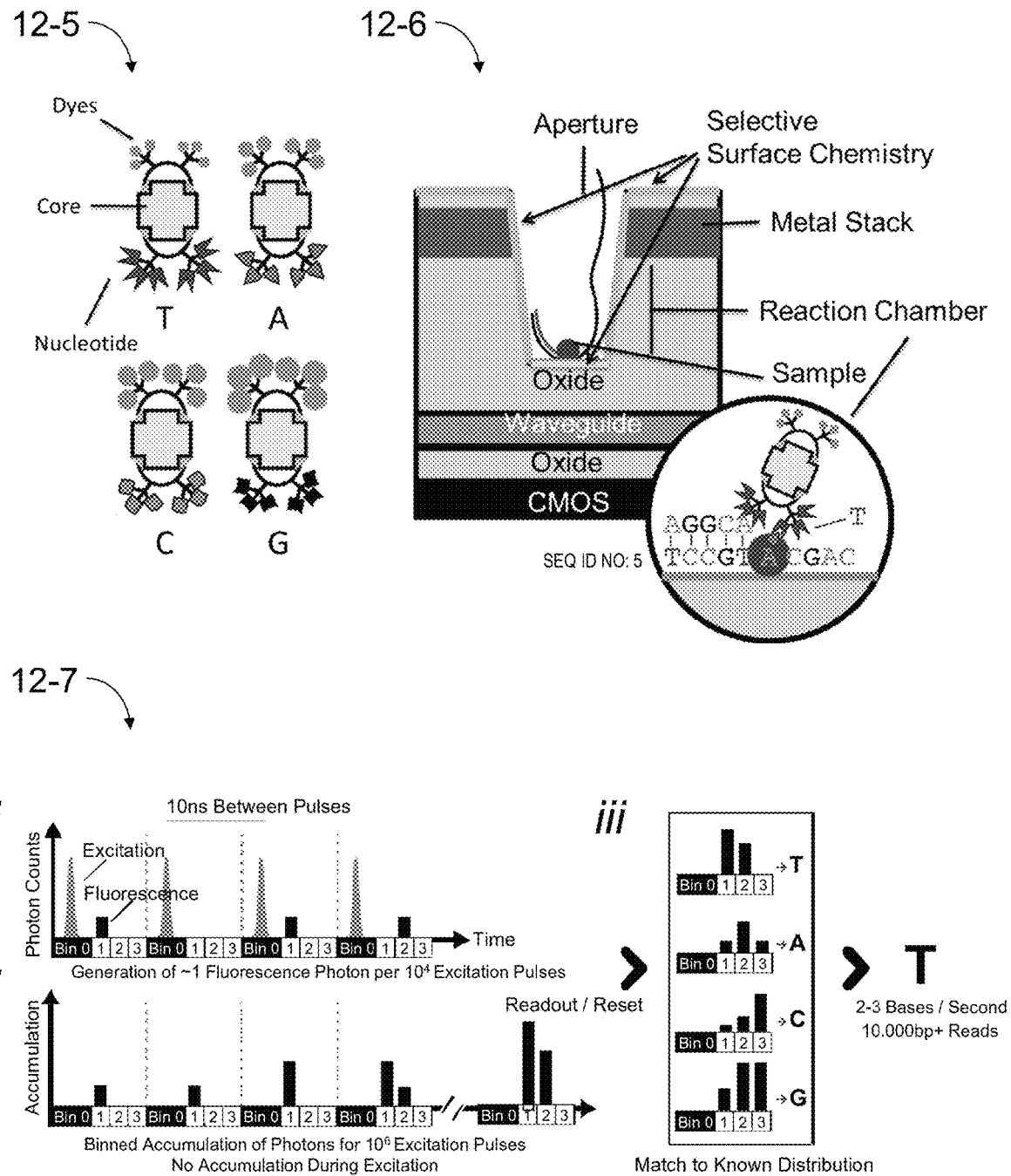

FIG. 12 depicts a non-limiting embodiment of configurations of luminescently-labeled nucleotide molecules that can be used in a sequencing reaction and an exemplary sequencing experiment, wherein the luminescent properties of a luminescently-labeled nucleotide are used to identify the base being incorporated into the sequencing reaction.

Figure 13:
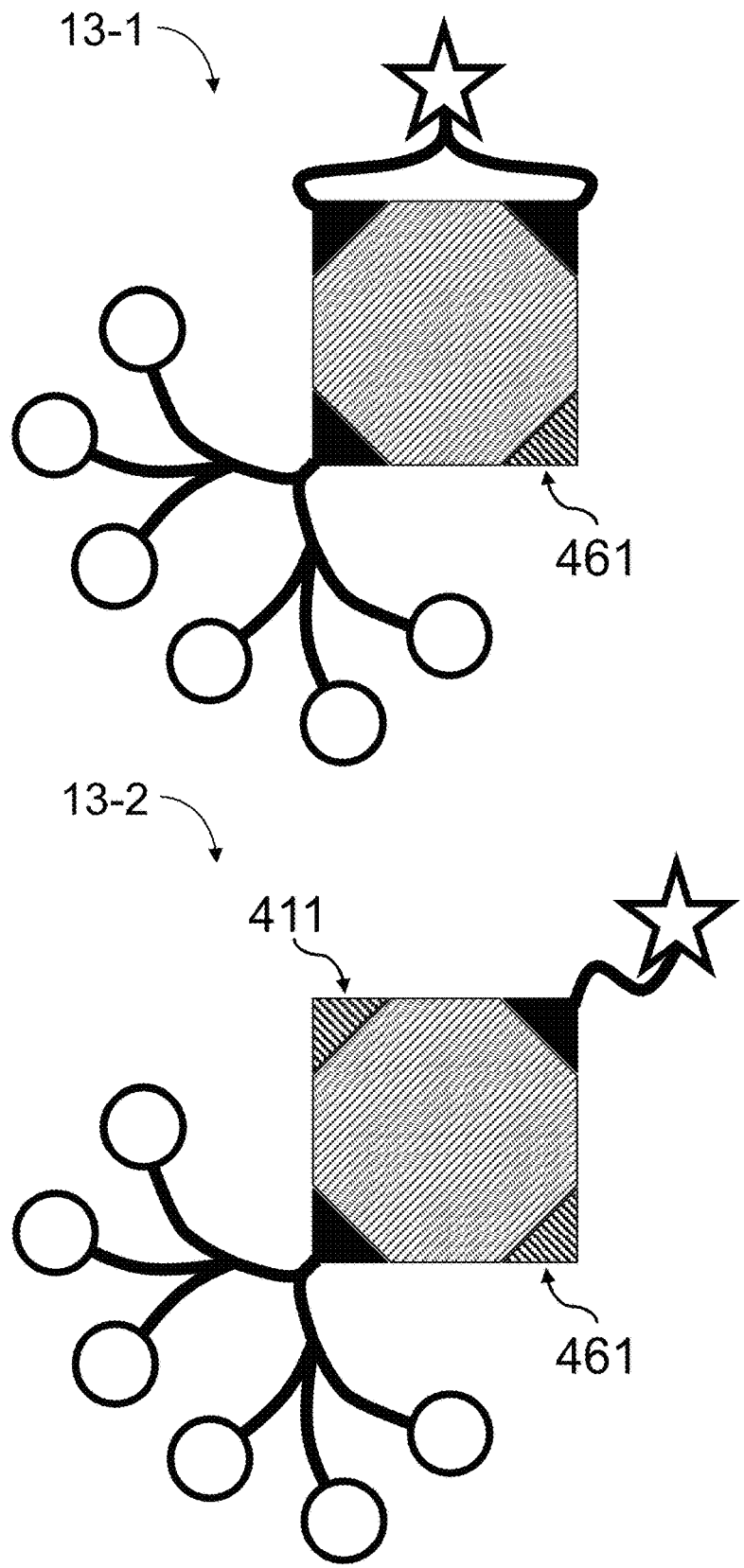

FIG. 13 depicts a non-limiting example of engineering non-functional binding sites into a protecting molecule to attach luminescent molecules and nucleotides at selected sites.

Figure 14:
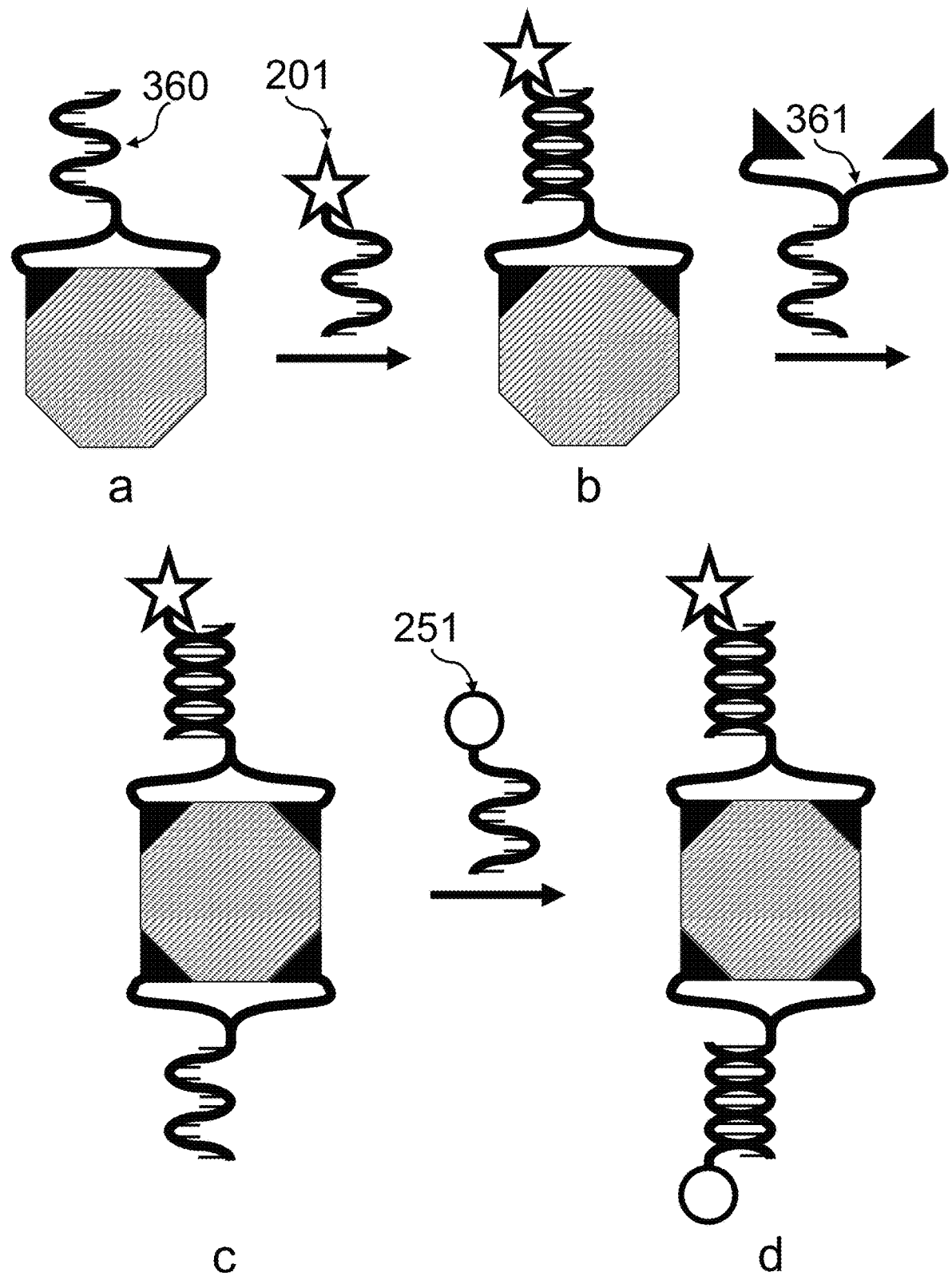

FIG. 14 depicts a non-limiting example in which a luminescent molecule and a nucleotide are connected via a protecting molecule, wherein the linkers attaching the luminescent molecule and the nucleotide to the protecting molecule comprise oligonucleotides.

Figure 15:
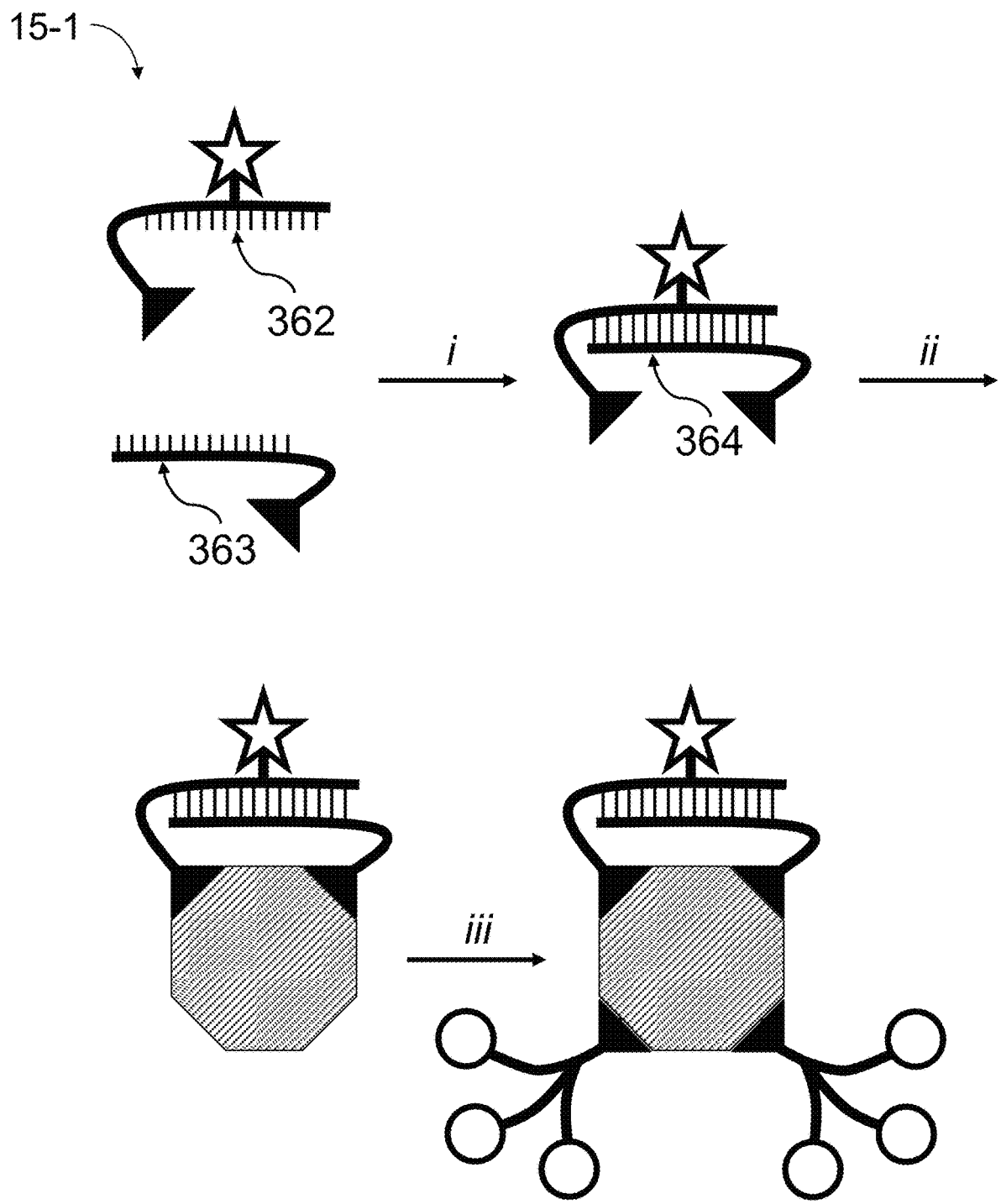
Figure 15:
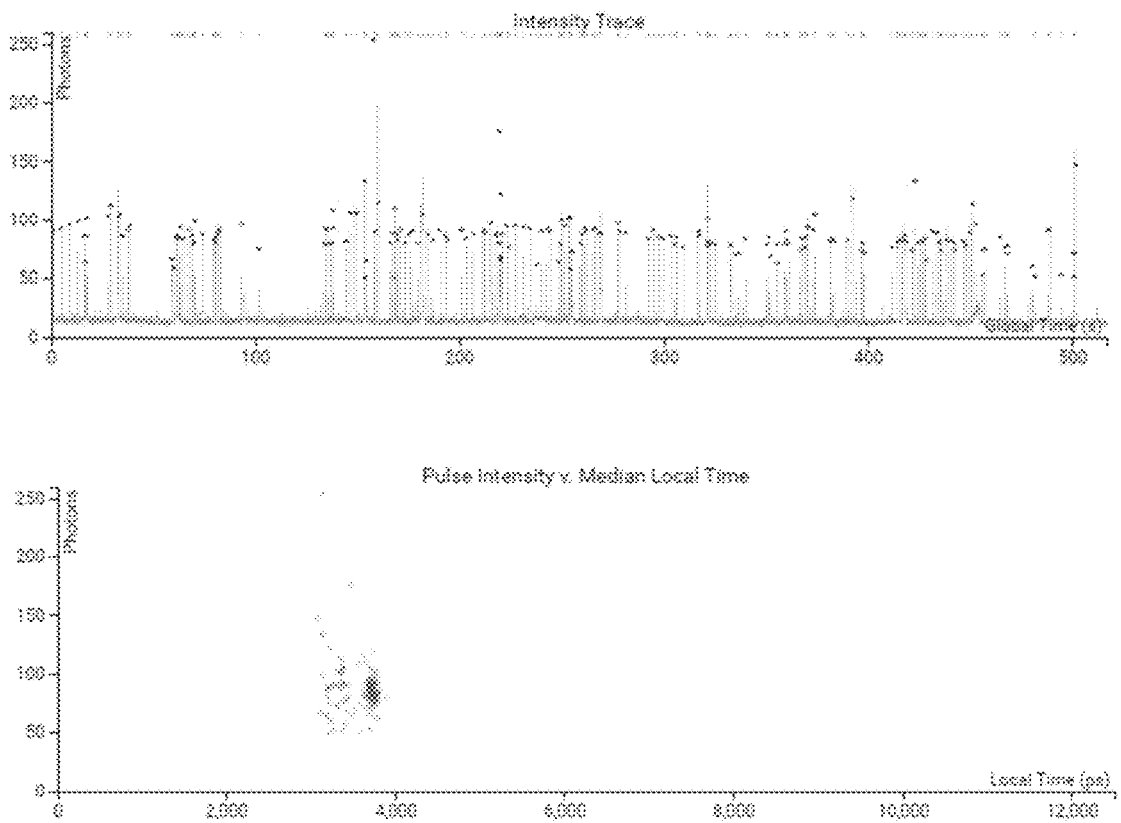

FIG. 15 depicts a non-limiting example in which a luminescent molecule is attached to a protecting molecule via annealed complementary oligonucleotides, wherein each oligonucleotide strand contains one non-covalent binding ligand compatible with a binding site on the protecting molecule.

Figure 16:
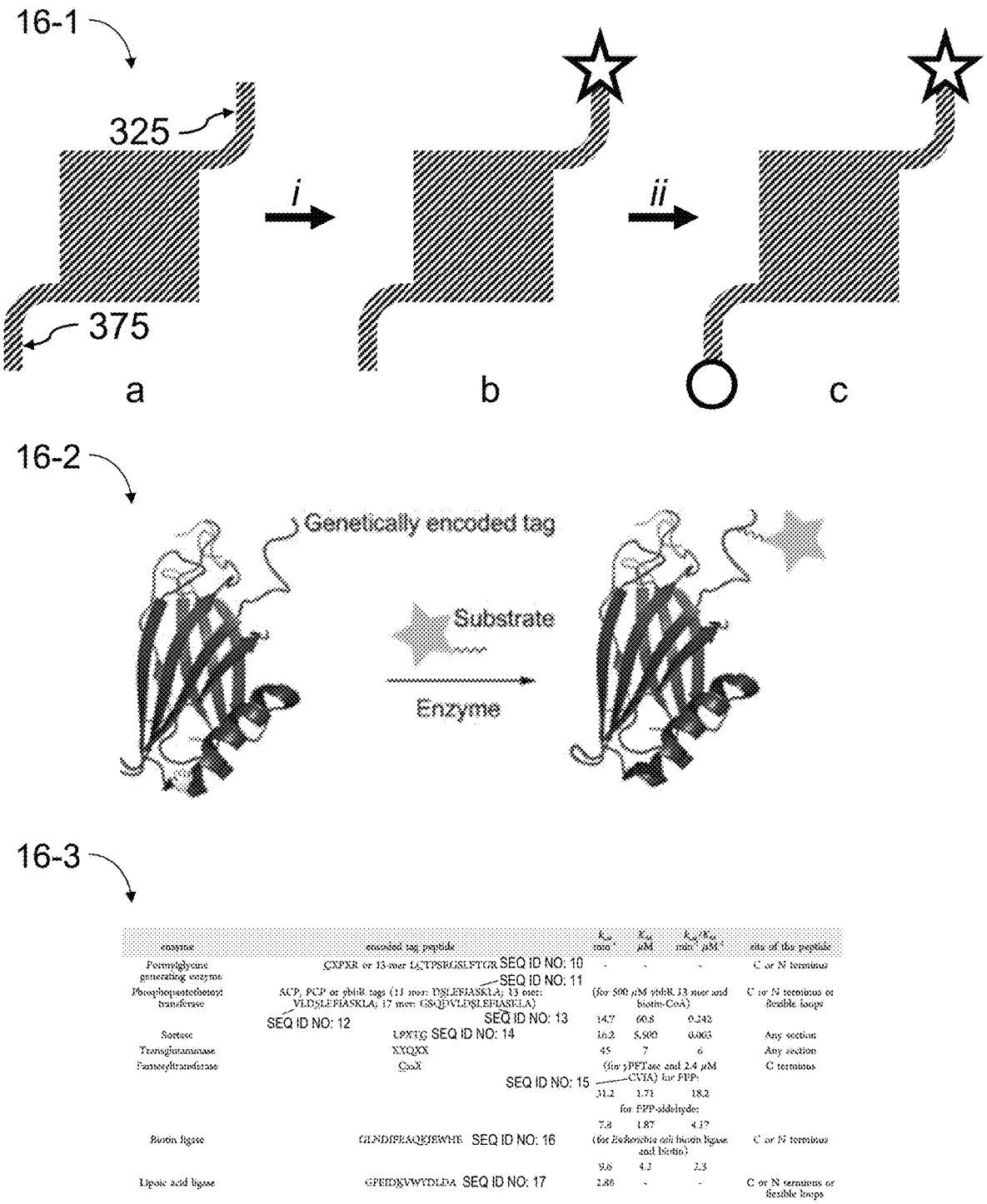

FIG. 16 depicts a non-limiting example of utilizing genetically encoded tags to attach a luminescent molecule and a nucleotide at independent sites of a protecting molecule.

Figure 17:
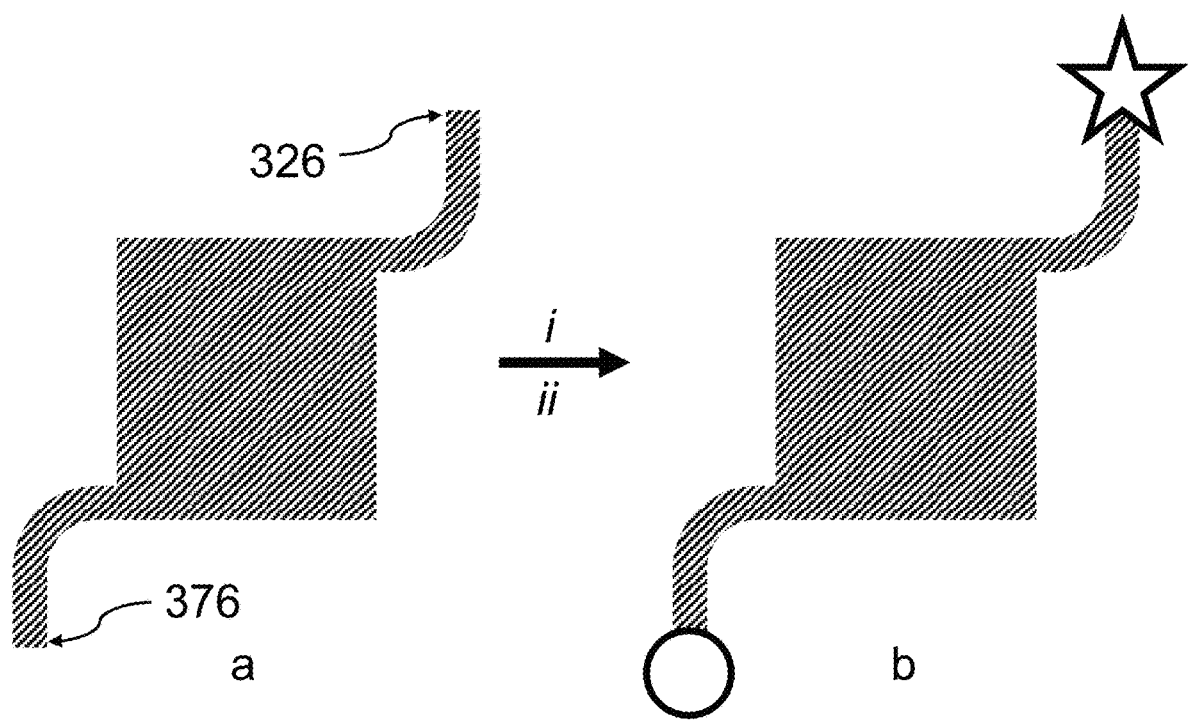
Figure 17:
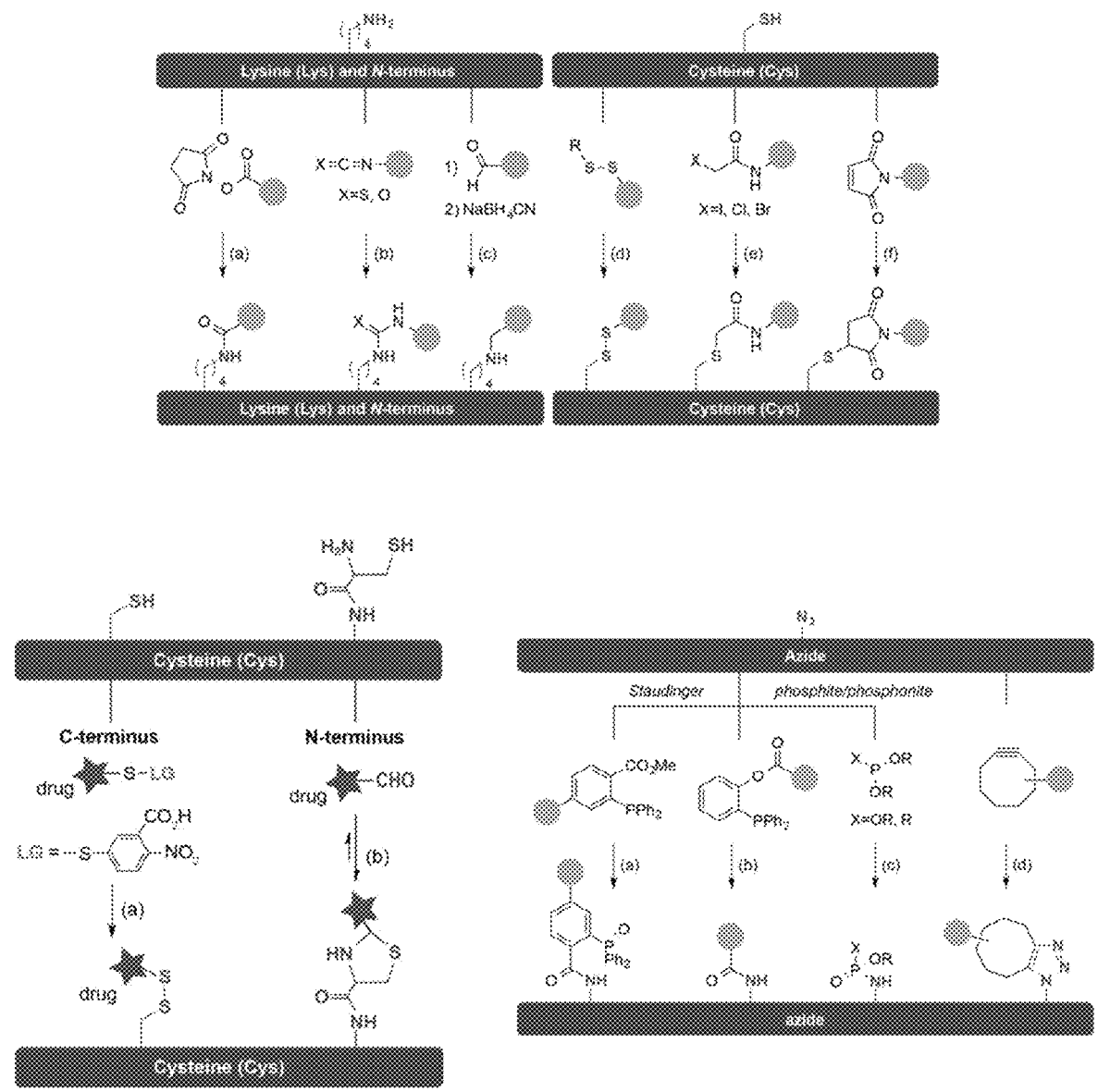

FIG. 17 depicts a non-limiting example of utilizing reactive groups at the terminal groups of a protein to attach a luminescent molecule and a nucleotide at independent sites of a protecting molecule.

Figure 18:
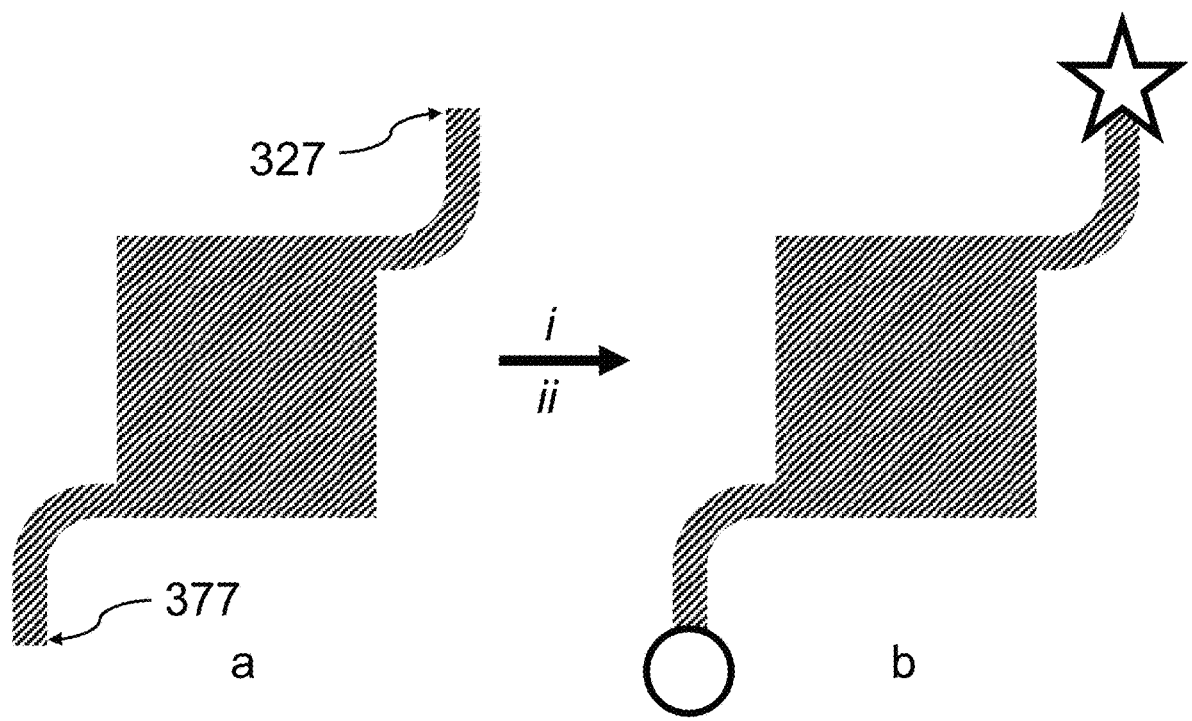

FIG. 18 depicts a non-limiting example of utilizing unnatural amino acids to attach a luminescent molecule and a nucleotide at independent sites of a protecting molecule.

Figure 19A:
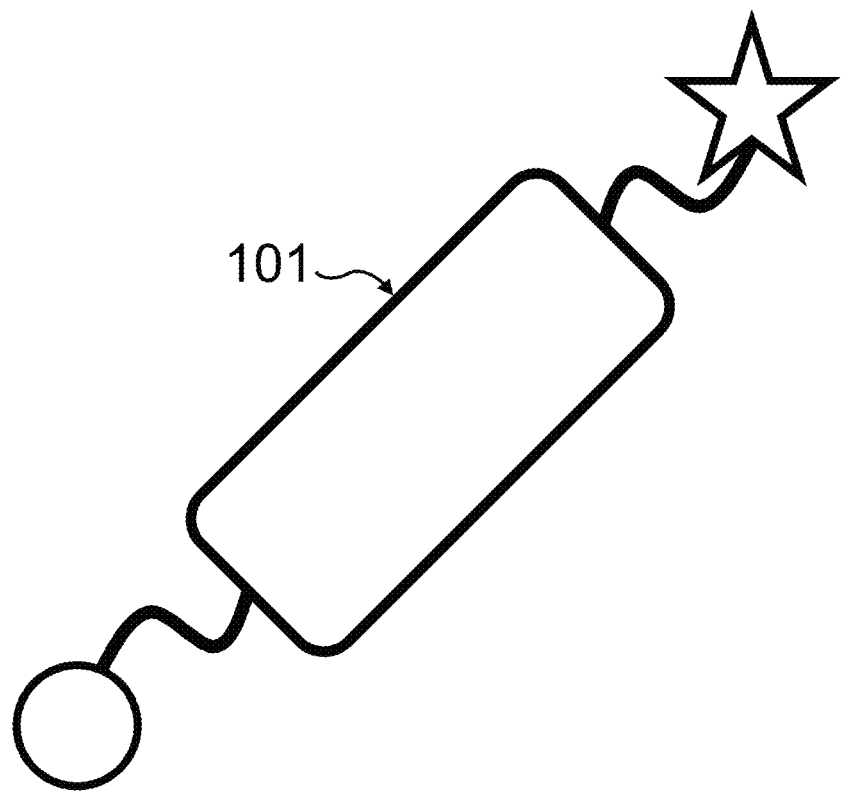
Figure 19B:
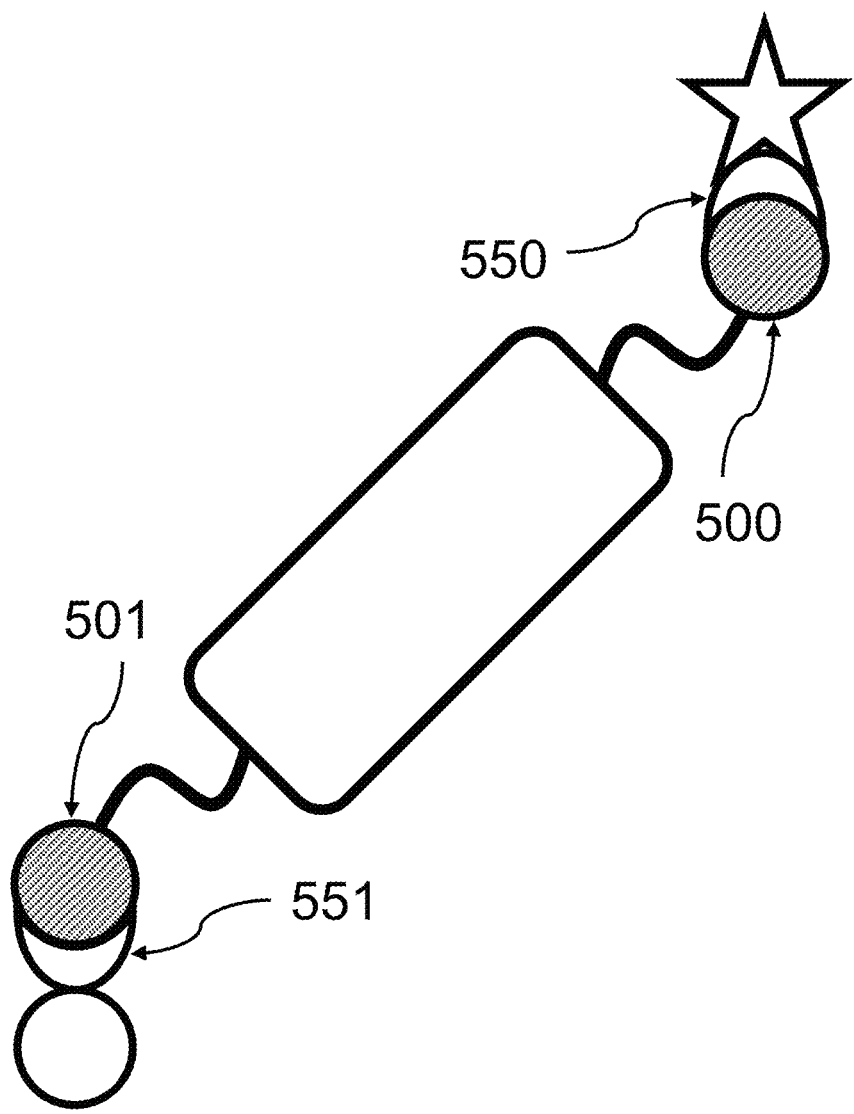

FIG. 19A and FIG. 19B depict non-limiting examples of a luminescent molecule and a nucleotide separated by a non-protein protecting molecule.

Figure 20:
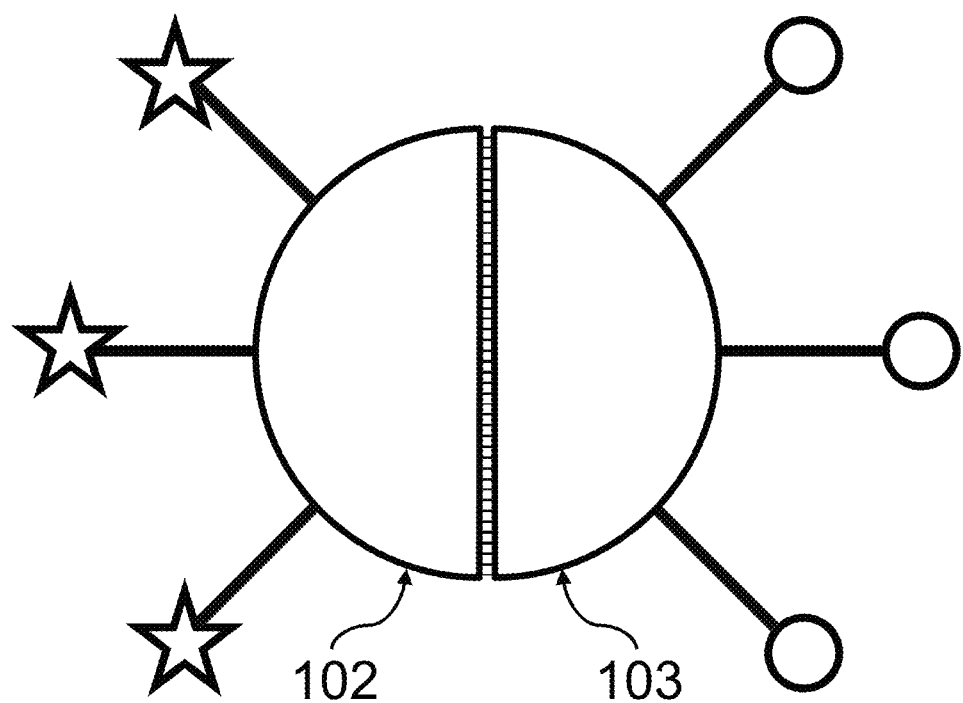

FIG. 20 depicts a non-limiting embodiment of a protecting molecule comprised of a protein-protein binding pair.

Figure 21:
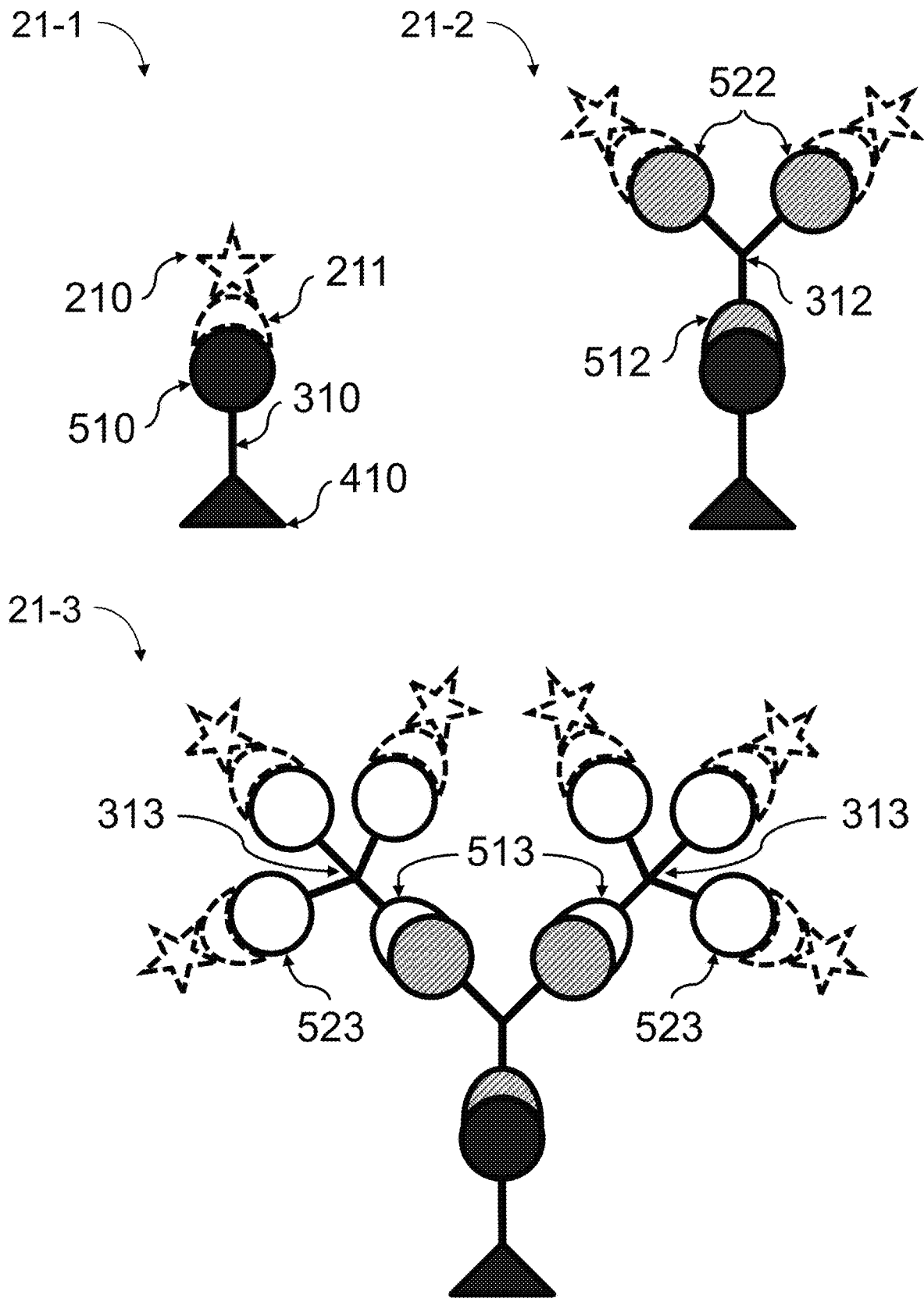

FIG. 21 depicts non-limiting examples of linker configurations.

Figure 22:
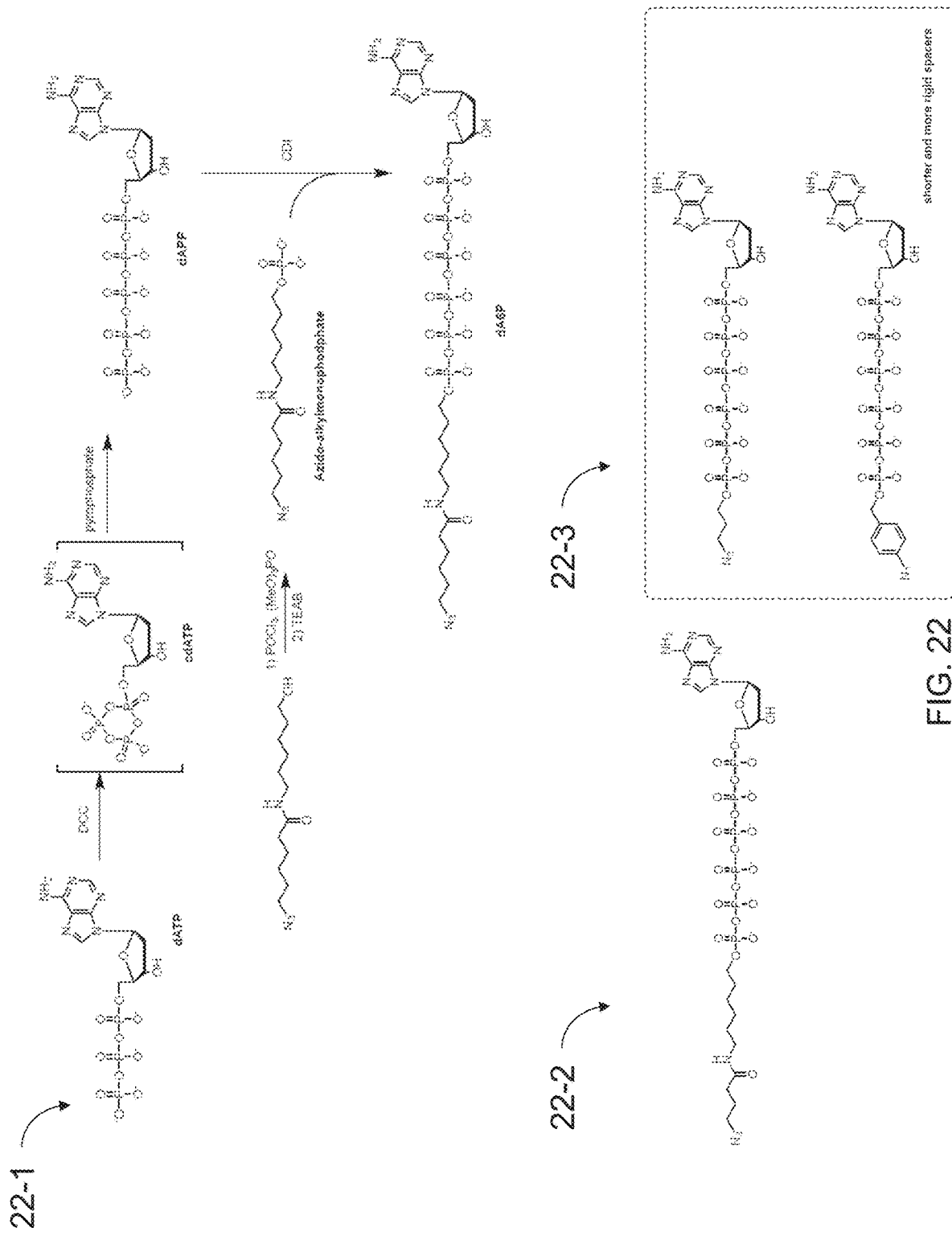

FIG. 22 depicts a non-limiting reaction scheme for nucleotide linker synthesis and exemplary structures.

Figure 23A:
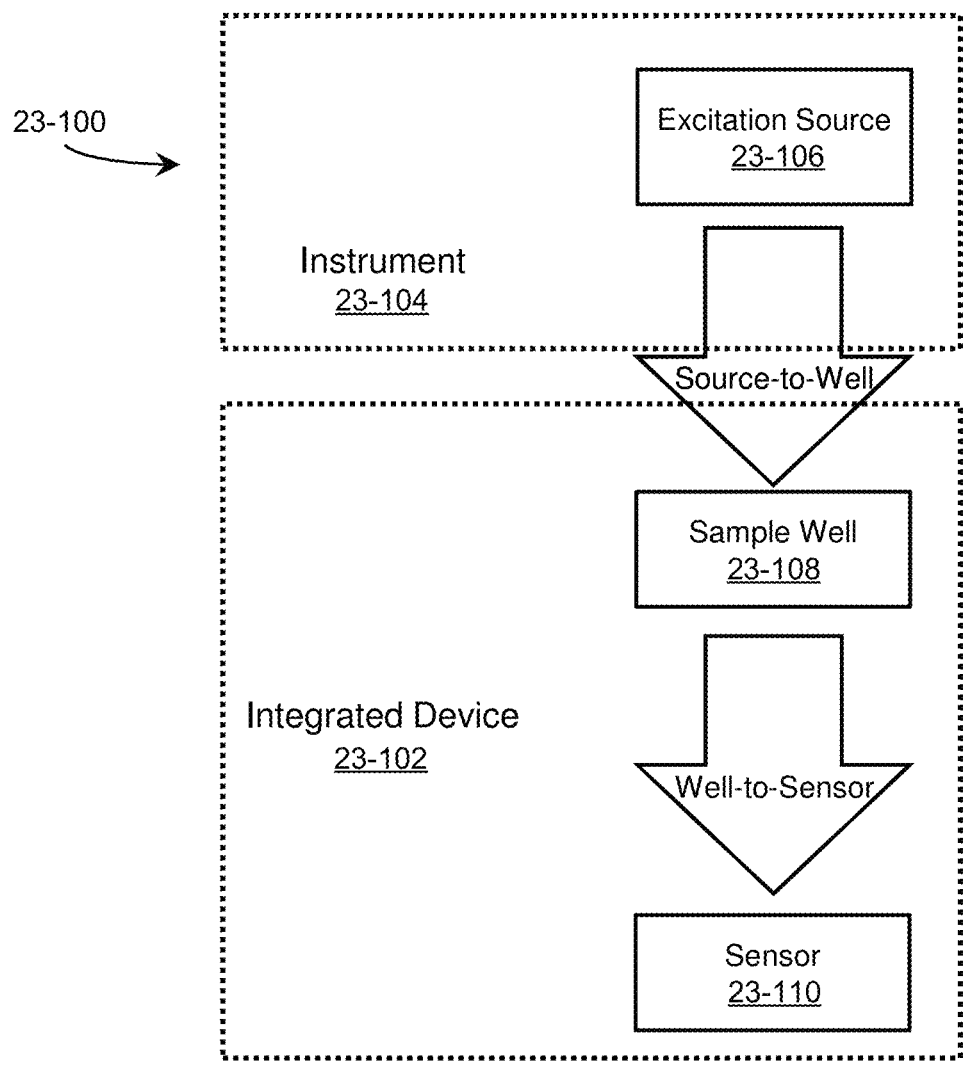

FIG. 23A is a block diagram representation of an apparatus that may be used for rapid, mobile analysis of biological and chemical specimens, according to some embodiments.

Figure 23B:
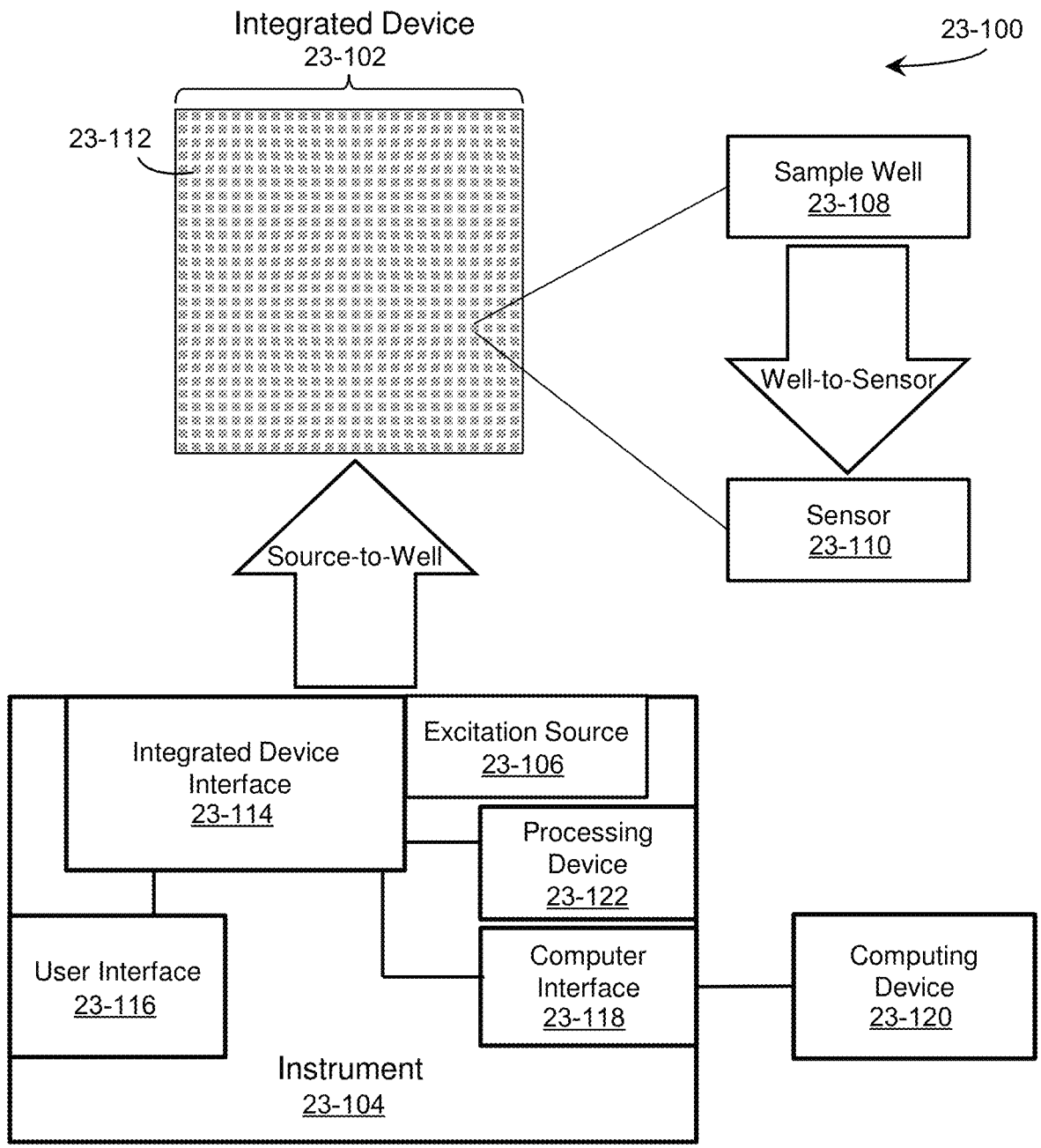

FIG. 23B is a block diagram of an integrated device and an instrument, according to some embodiments.

Figure 24A:
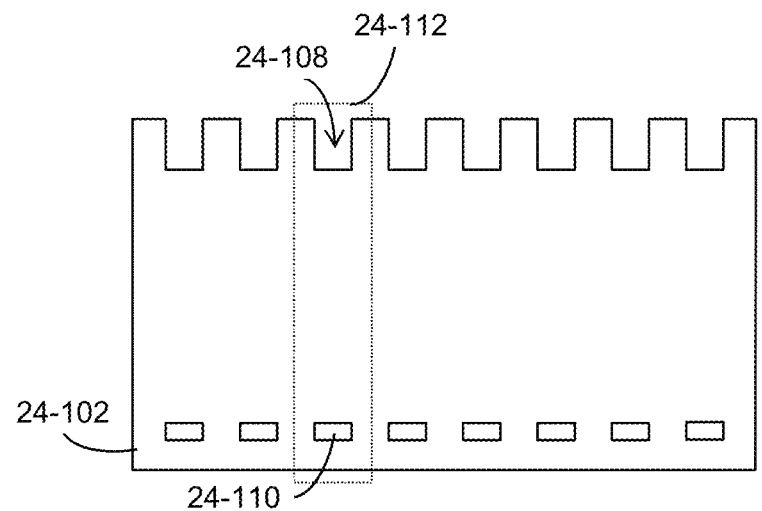

FIG. 24A depicts a row of pixels of an integrated device, according to some embodiments.

Figure 24B:
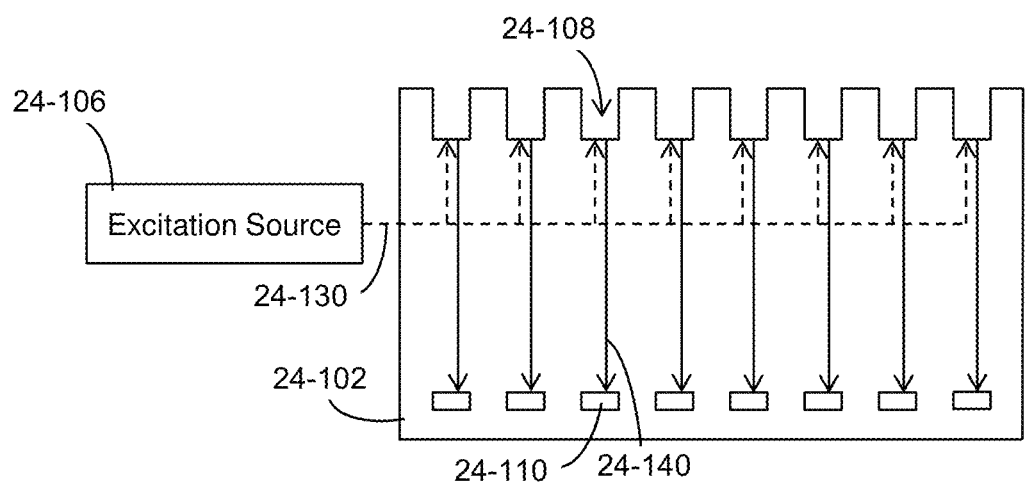

FIG. 24B depicts excitation energy coupling to sample wells in a row of pixels and emission energy from each sample well directed towards sensors, according to some embodiments.

Figure 25:
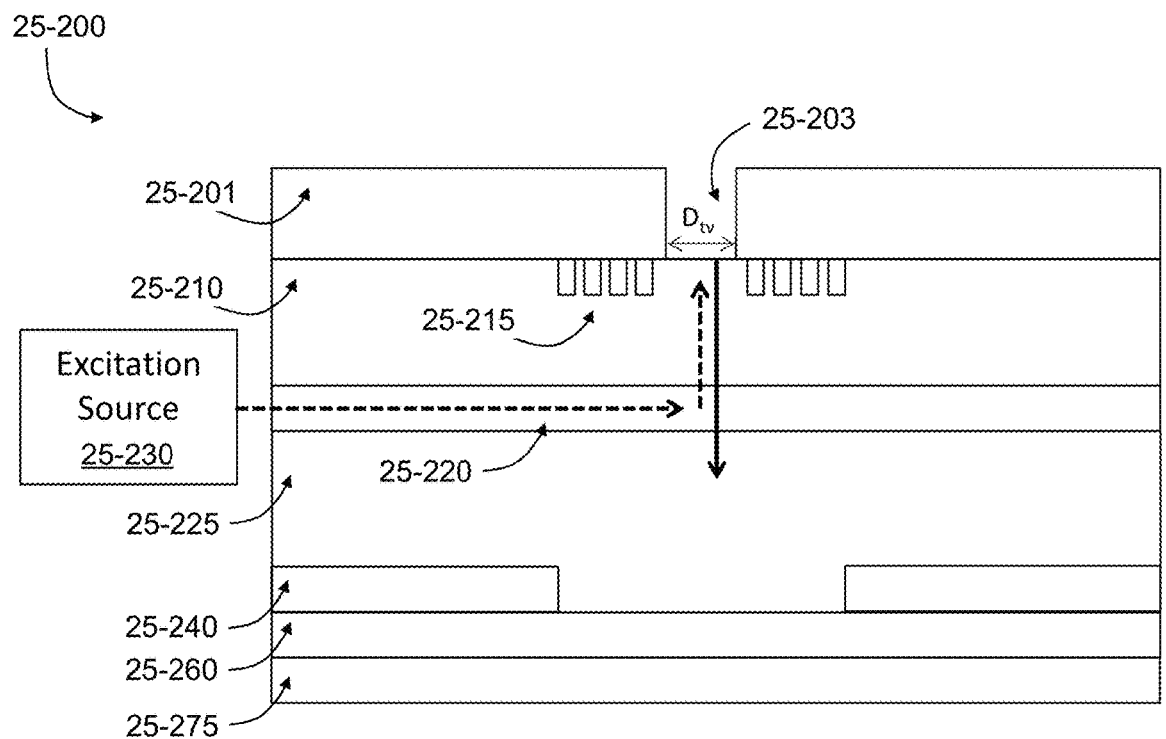

FIG. 25 depicts an integrated device and an excitation source, according to some embodiments.

Figure 26:
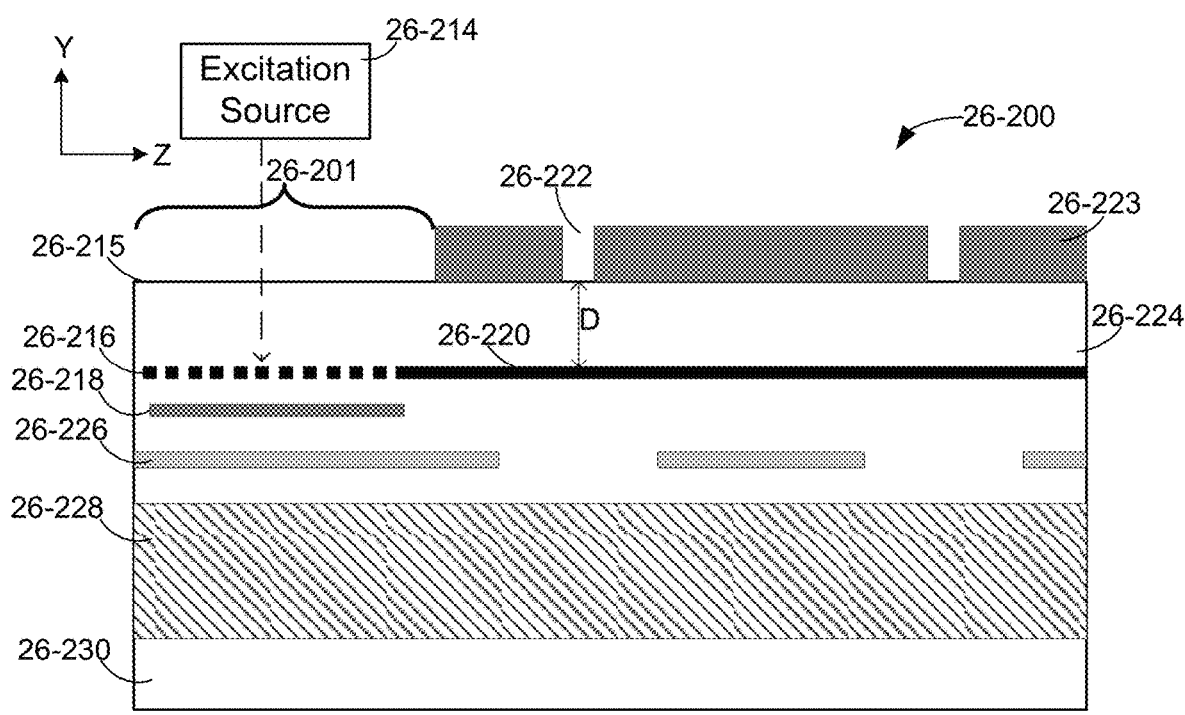

FIG. 26 depicts an integrated device and an excitation source, according to some embodiments.

Figure 27A:
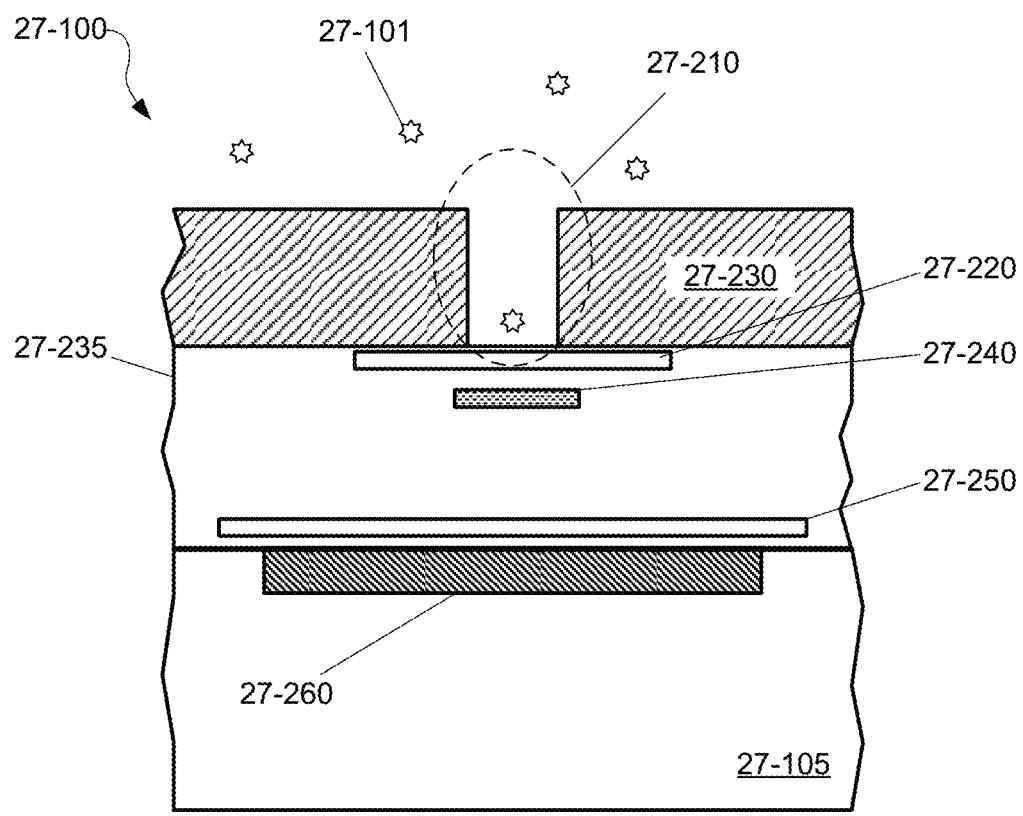

FIG. 27A depicts a sample well formed in a pixel region of an integrated device, according to one embodiment.

Figure 27B:
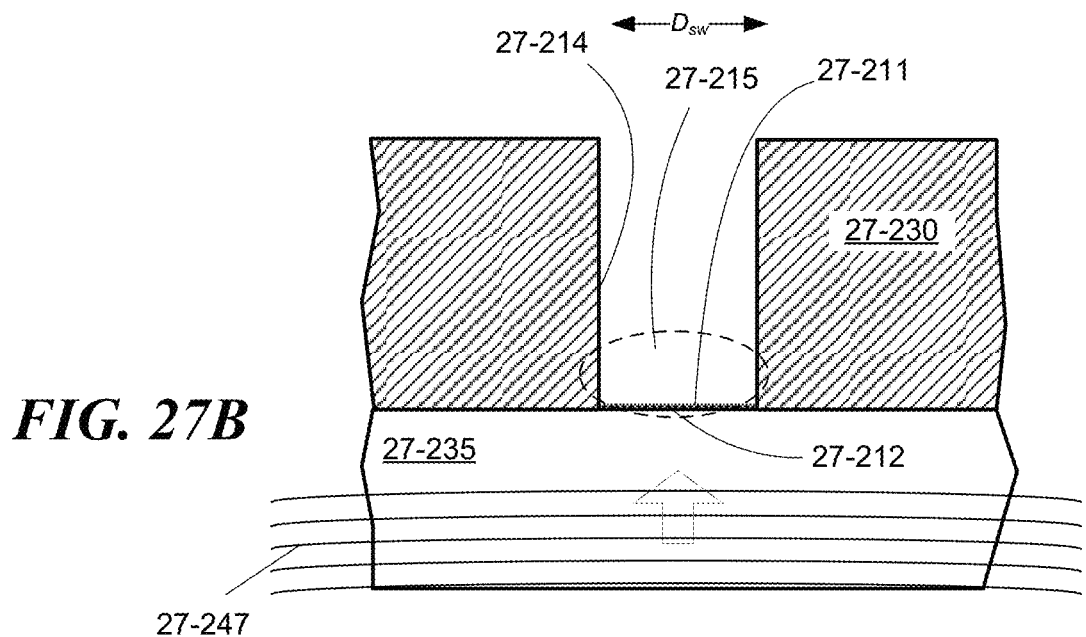

FIG. 27B depicts excitation energy incident on a sample well, according to some embodiments.

Figure 27C:
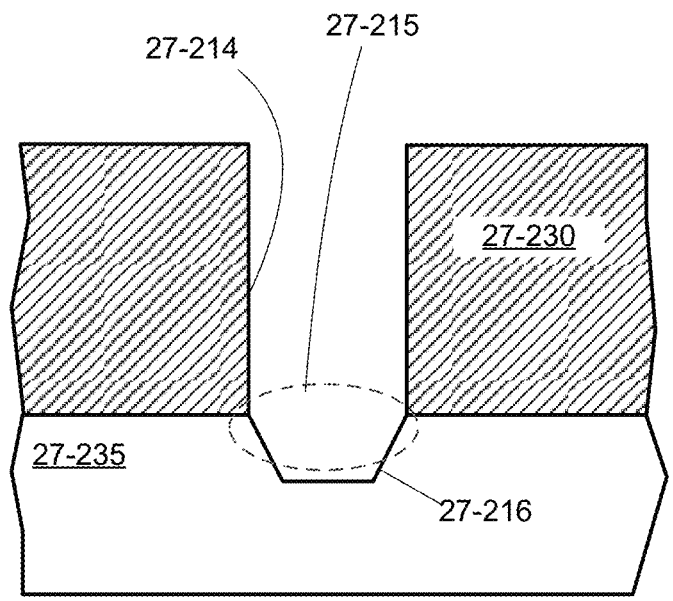

FIG. 27C depicts a sample well that includes a divot, which increases excitation energy at an excitation region associated with the sample well in some embodiments.

Figure 28:
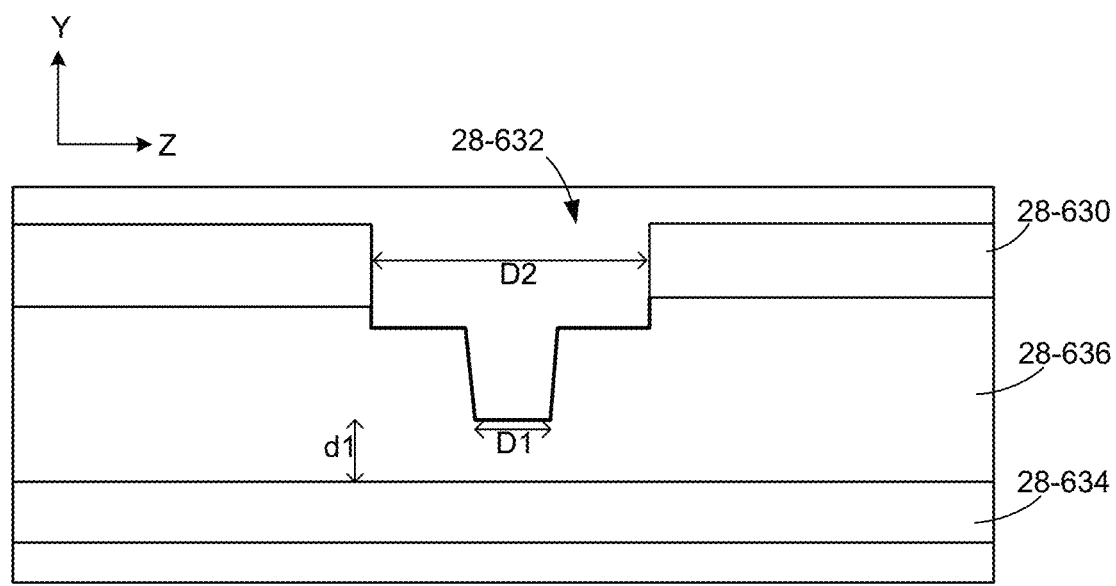

FIG. 28 depicts a sample well and divot, according to some embodiments.

Figure 29A:
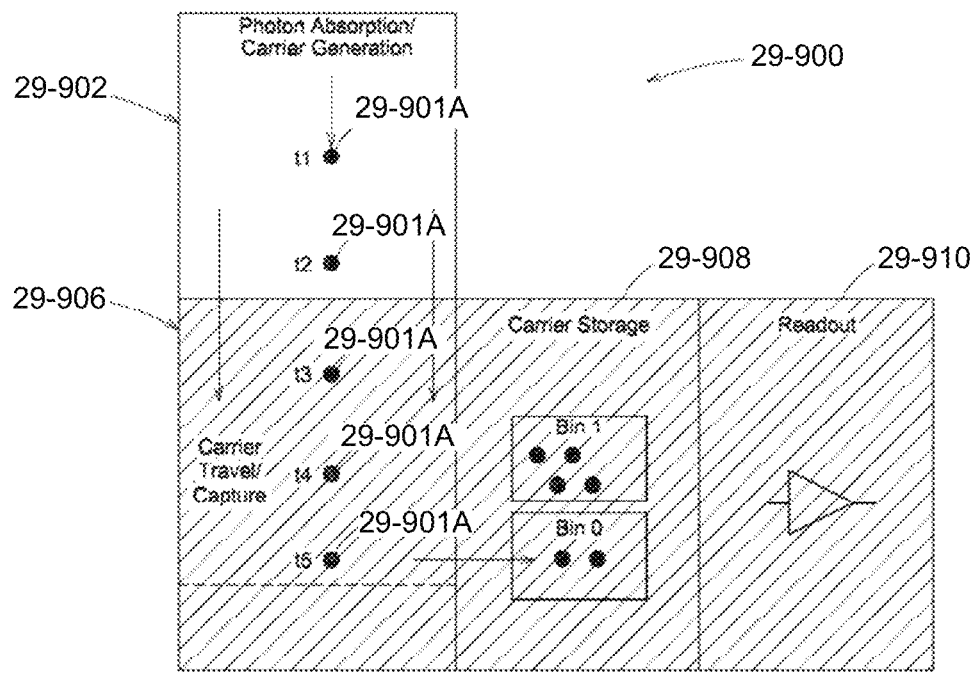
Figure 29B:
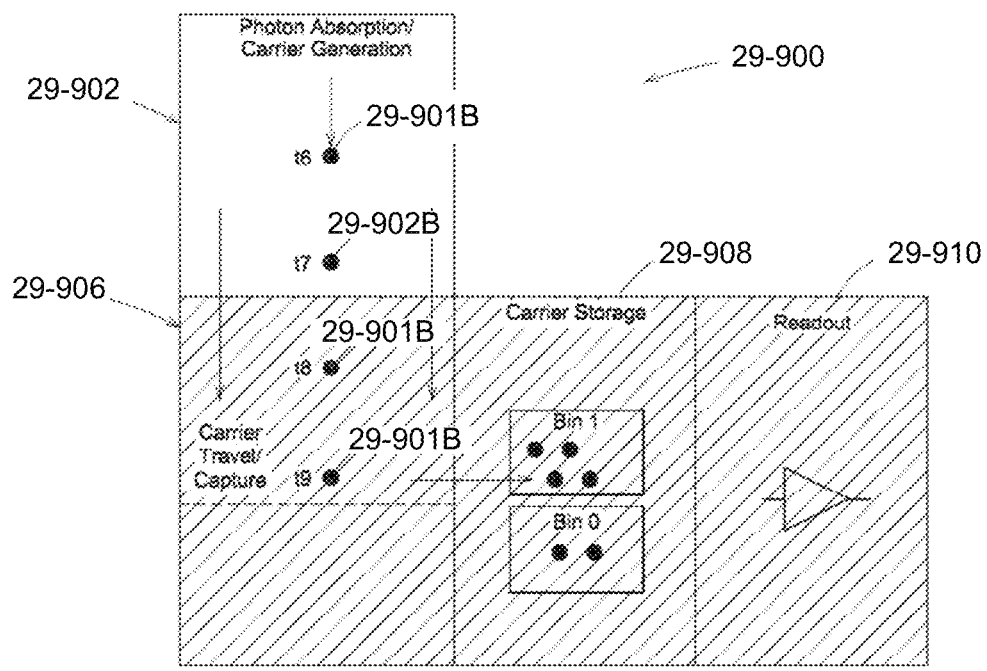

FIGS. 29A and 29B depict a sensor with time bins, according to some embodiments.

Figure 30A:
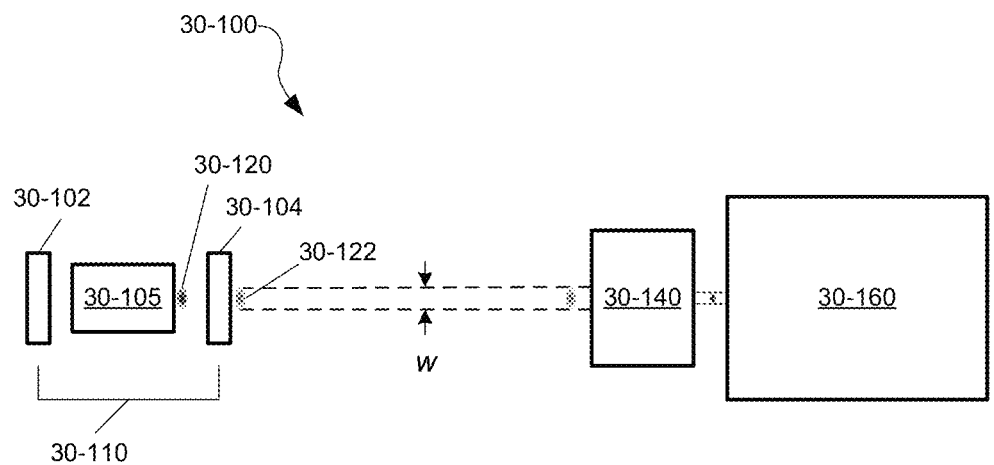

FIG. 30A depicts an exemplary system for providing light pulses, according to some embodiments.

Figure 30B:
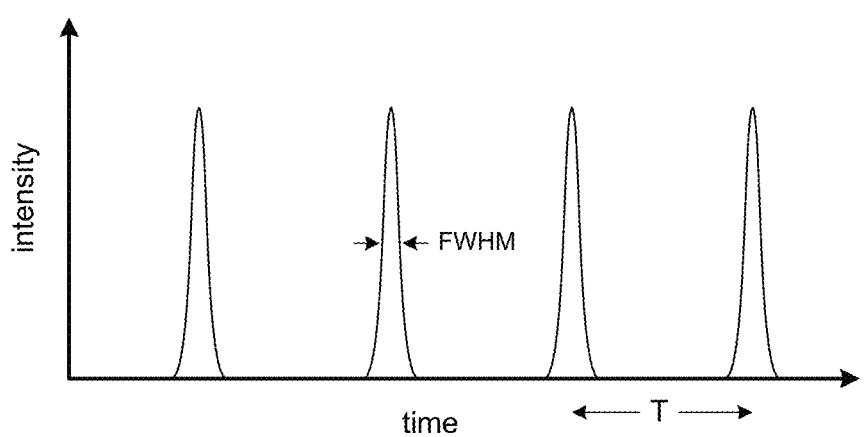

FIG. 30B depicts a plot of light intensity as a function of time.

FIG. 31A depicts a schematic for performing measurements, according to some embodiments.

FIG. 31B depicts a plot of light signal as a function of time, according to some embodiments.

FIG. 31C depicts a signal profile for markers across time bins, according to some embodiments.

Figures 32A, 32B:
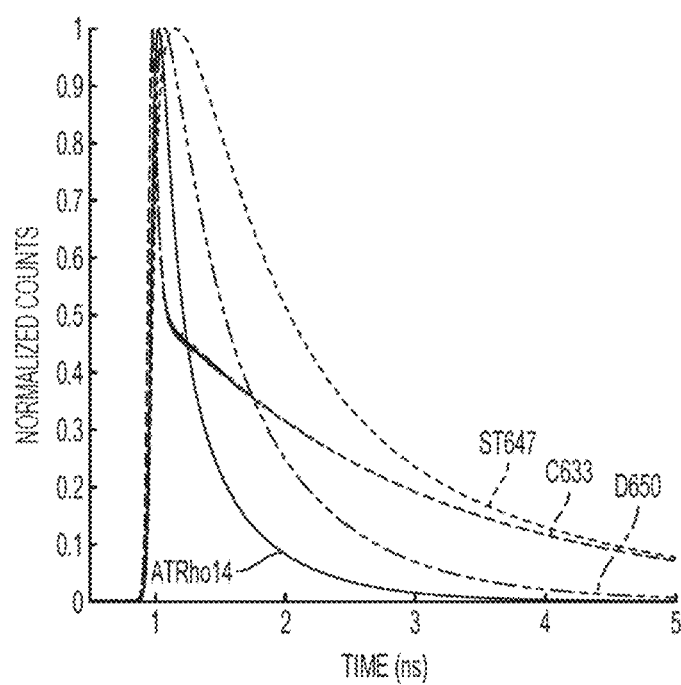

FIG. 32A depicts a plot of light signal as a function of time, according to some embodiments.

FIG. 32B depicts a signal profile for markers across time bins, according to some embodiments.

Figure 33A:
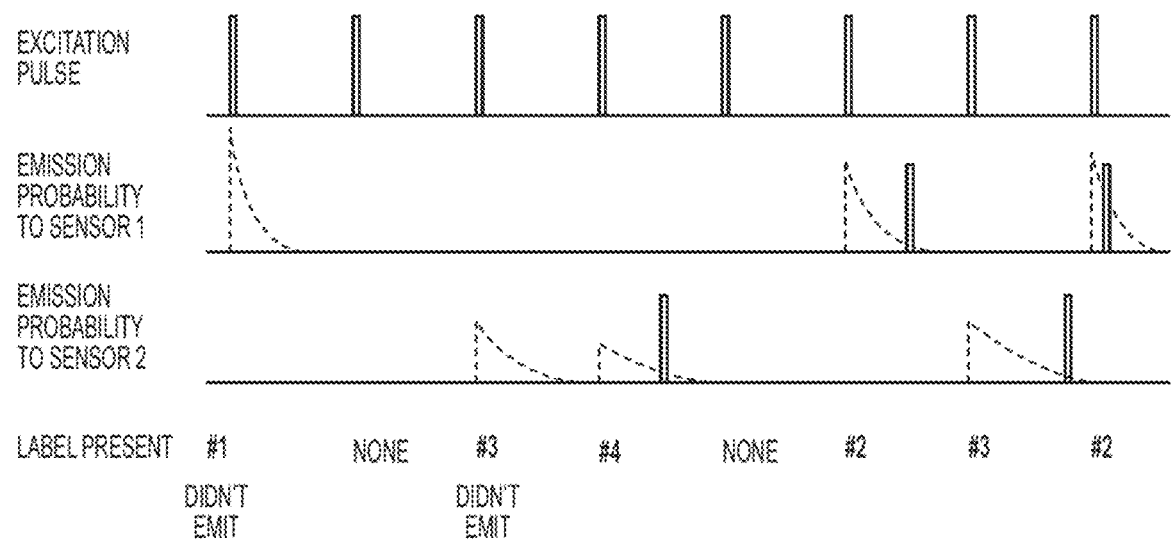

FIG. 33A depicts a schematic for performing measurements, according to some embodiments.

Figure 33B:
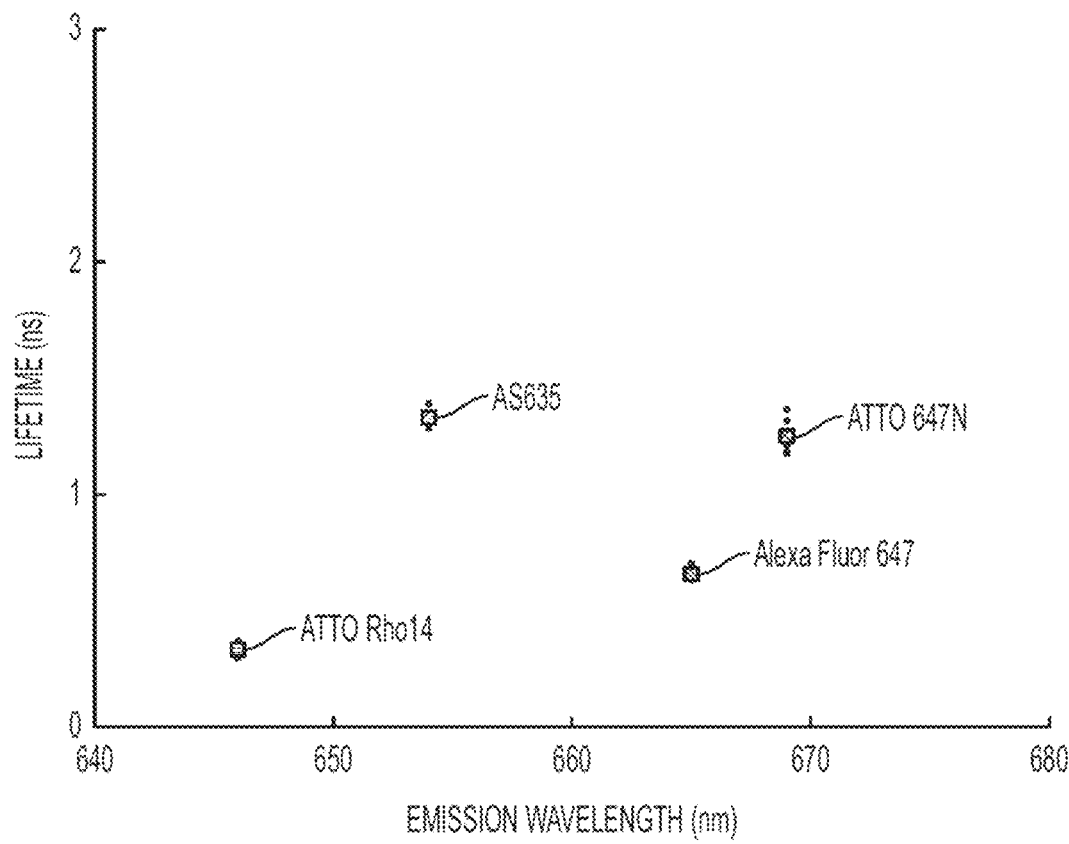

FIG. 33B depicts a plot of lifetime as a function of emission wavelength, according to some embodiments.

Figure 34A:
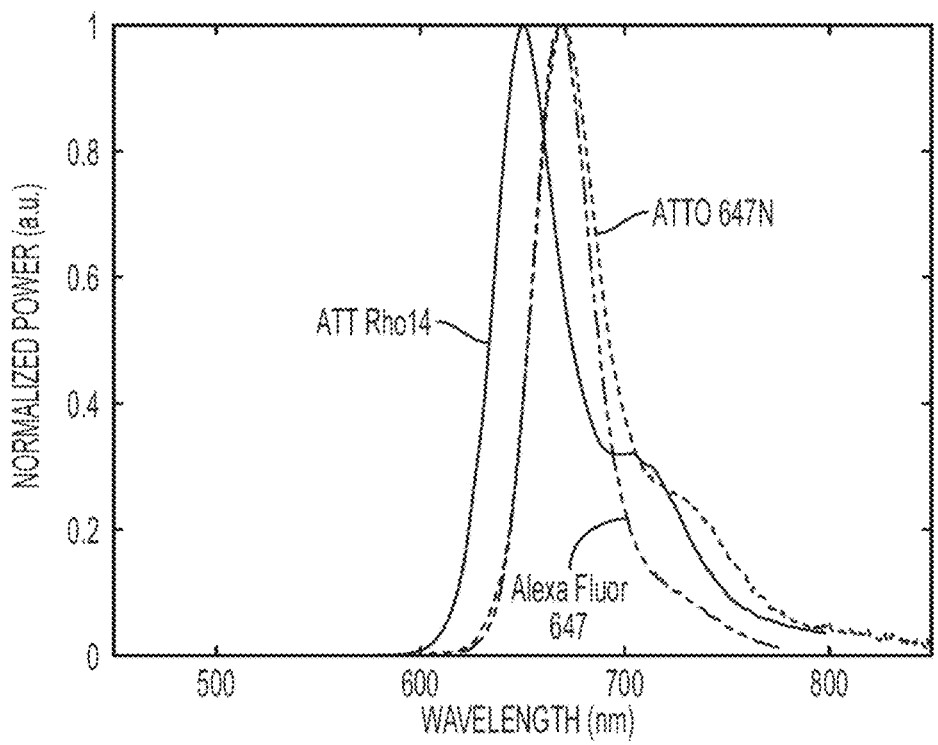

FIG. 34A depicts a plot of light signal as a function of wavelength, according to some embodiments.

Figure 34B:
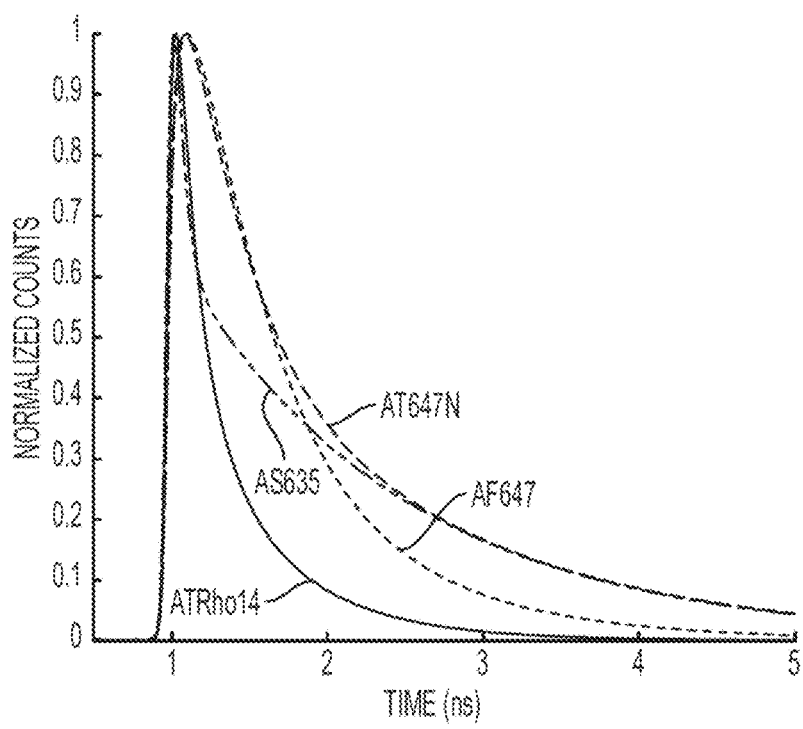

FIG. 34B depicts a plot of light signal as a function of time, according to some embodiments.

Figure 35A:
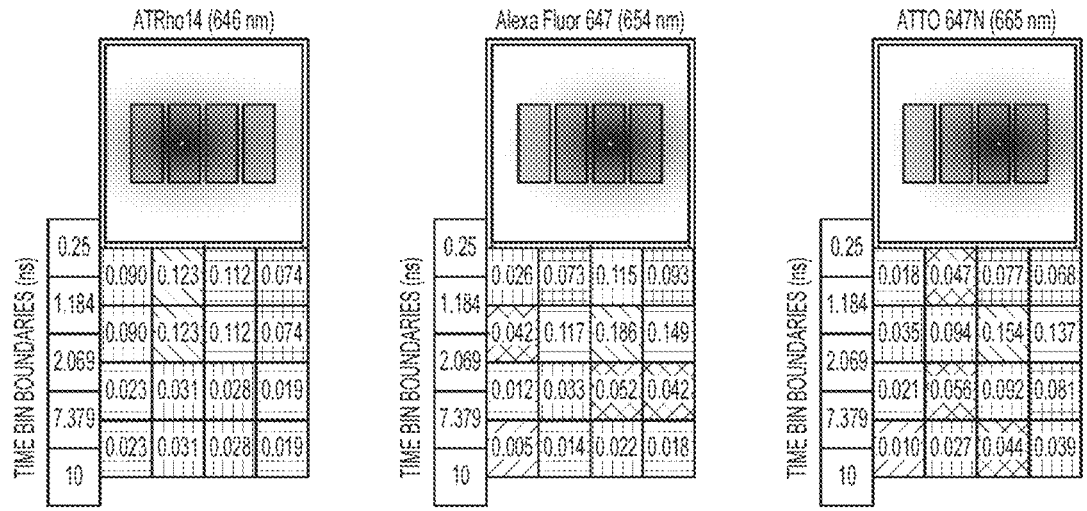

FIG. 35A depicts a signal profile for markers across time bins for multiple sensors, according to some embodiments.

Figure 35B:
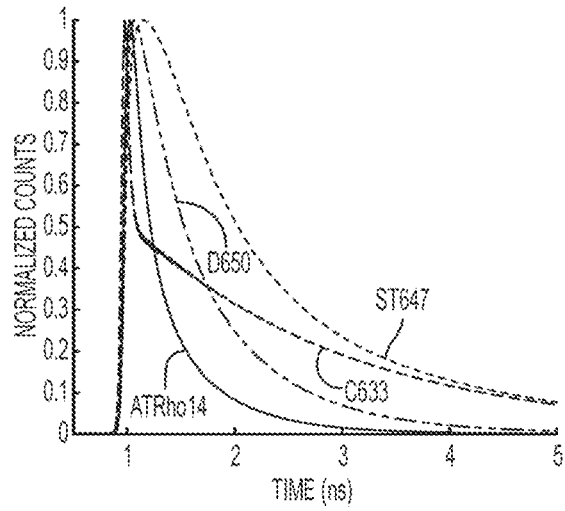

FIG. 35B depicts a plot of light signal as a function of time, according to some embodiments.

Figure 35C:
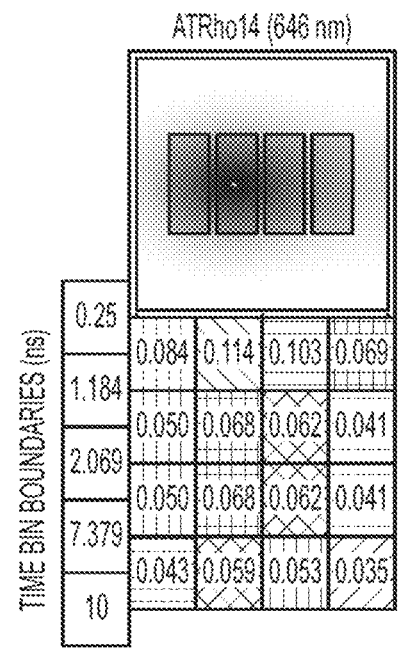

FIG. 35C depicts a signal profile for a marker across time bins for multiple sensors, according to some embodiments.

Figure 36A:
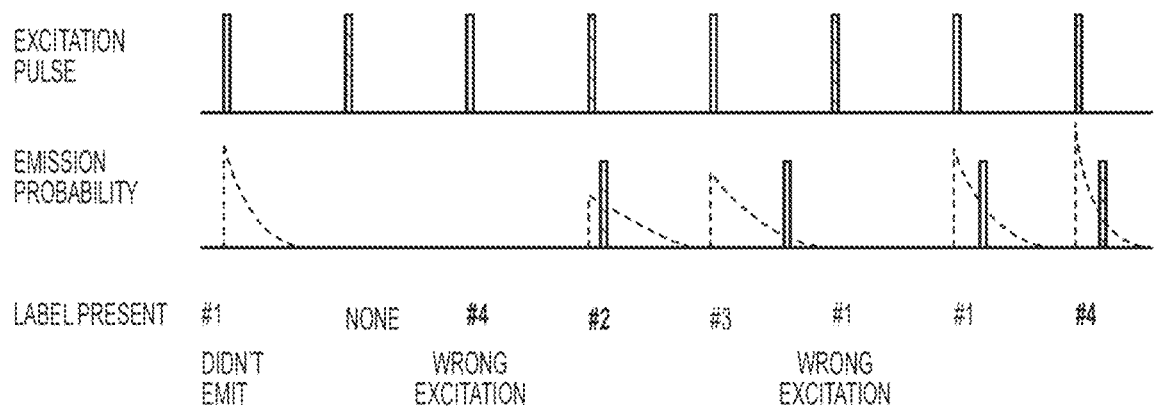

FIG. 36A depicts a schematic for performing measurements, according to some embodiments.

Figure 36B:
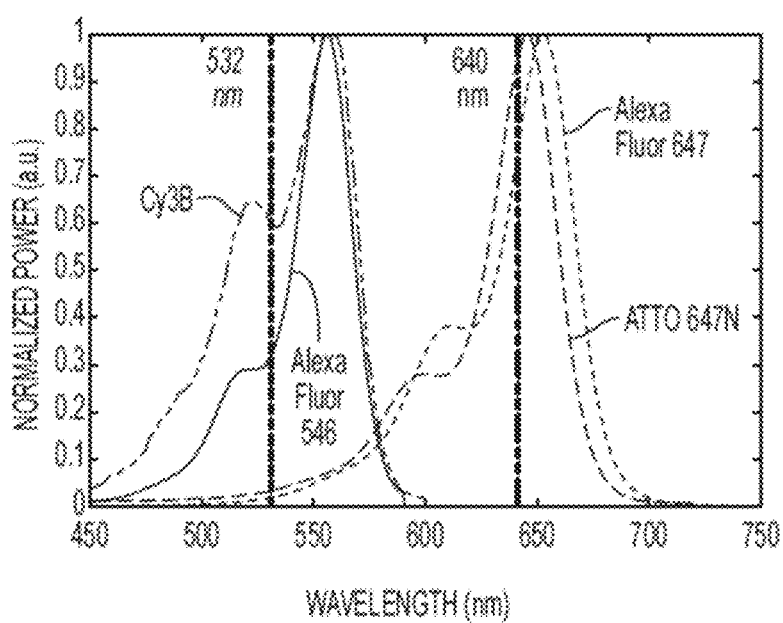

FIG. 36B depicts a plot of light signal as a function of wavelength, according to some embodiments.

Figure 37A:
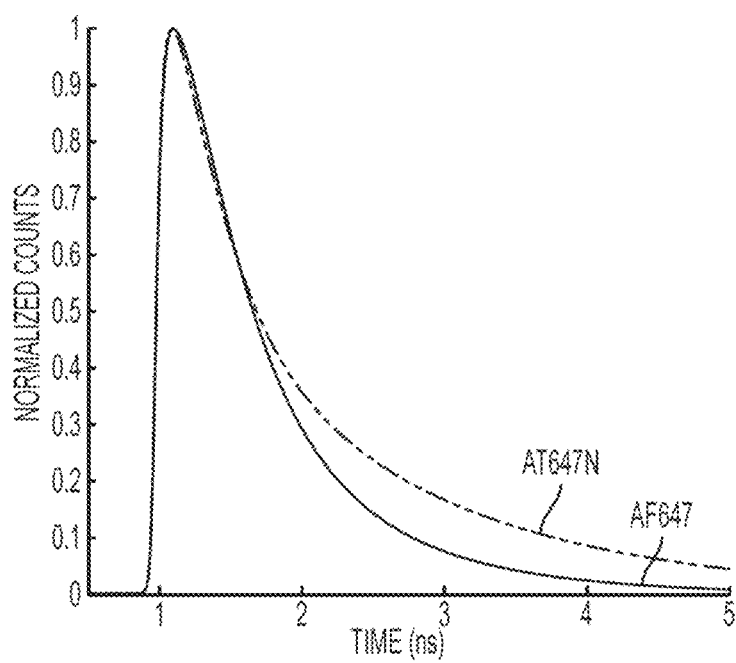

FIG. 37A depicts a plot of light signal as a function of time, according to some embodiments.

Figure 37B:
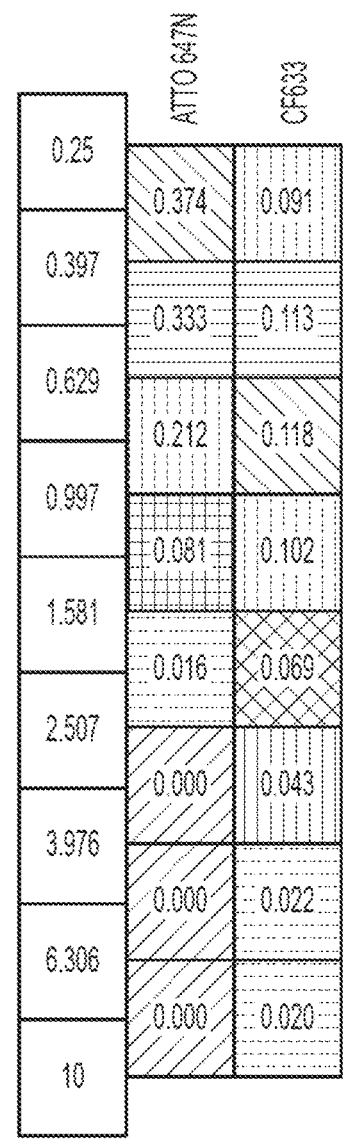

FIG. 37B depicts a signal profile for a marker across time bins for multiple sensors, according to some embodiments.

DETAILED DESCRIPTION

The inventors have developed new methods, compositions, and devices for identifying single molecules based on one or more luminescent properties of those molecules. In some embodiments, a molecule is identified based on its luminescent lifetime, absorption spectra, emission spectra, luminescent quantum yield, luminescent intensity, or a combination of two or more thereof. Identifying may mean assigning the exact molecular identity of a molecule, or may mean distinguishing or differentiating the particular molecule from a set of possible molecules. In some embodiments, a plurality of single molecules can be distinguished from each other based on different luminescent lifetimes, absorption spectra, emission spectra, luminescent quantum yields, luminescent intensities, or combinations of two or more thereof. In some embodiments, a single molecule is identified (e.g., distinguished from other molecules) by exposing the molecule to a series of separate light pulses and evaluating the timing or other properties of each photon that is emitted from the molecule. In some embodiments, information for a plurality of photons emitted sequentially from a single molecule is aggregated and evaluated to identify the molecule. In some embodiments, a luminescent lifetime of a molecule is determined from a plurality of photons that are emitted sequentially from the molecule, and the luminescent lifetime can be used to identify the molecule. In some embodiments, a luminescent intensity of a molecule is determined from a plurality of photons that are emitted sequentially from the molecule, and the luminescent intensity can be used to identify the molecule. In some embodiments, a luminescent lifetime and luminescent intensity of a molecule is determined from a plurality of photons that are emitted sequentially from the molecule, and the luminescent lifetime and luminescent intensity can be used to identify the molecule.

Aspects of the present application are useful for detecting and/or identifying one or more biological or chemical molecules. In some embodiments, chemical or biological reactions can be evaluated by determining the presence or absence of one or more reagents or products at one or more time points.

Aspects of the present application interrogate a molecule by exposing the molecule to light and determining one or more properties of one or more photons emitted from the molecule. In certain embodiments, the molecule is interrogated by exposing the molecule to a pulse of light and determining one or more properties of a photon emitted from the molecule. In some embodiments, the molecule is exposed to a plurality of separate light pulse events and one or more properties of separate photons emitted after separate light pulse events are determined. In some embodiments, the molecule does not emit a photon in response to each light pulse. However, a plurality of emitted photons can be evaluated by exposing the molecule to a series of separate light pulses and evaluating separate photons that are emitted after a subset of the light pulse events (e.g., photons emitted after about 10% of pulse events, or photons emitted after about 1% of pulse events).

Aspects of the present application are useful to monitor a chemical or biological reaction by determining the presence or absence of one or more reagents, intermediates, and/or products of the reaction at one or more time points. In some embodiments, the progression of a reaction over time can be analyzed by exposing a reaction sample to a series of separate light pulses and analyzing any emitted photon that is detected after each light pulse.

Accordingly, in some aspects of the application, a reaction sample is exposed to a plurality of separate light pulses and a series of emitted photons are detected and analyzed. In some embodiments, the series of emitted photons provides information about a single molecule that is present and that does not change in the reaction sample over the time of the experiment. However, in some embodiments, the series of emitted photons provides information about a series of different molecules that are present at different times in the reaction sample (e.g., as a reaction or process progresses).

In some embodiments, aspects of the present application can be used to assay biological samples, for example to determine the sequence of one or more nucleic acids or polypeptides in the sample and/or to determine the presence or absence of one or more nucleic acid or polypeptide variants (e.g., one or more mutations in a gene of interest) in the sample. In some embodiments, tests can be performed on patient samples (e.g., human patient samples) to provide nucleic acid sequence information or to determine the presence or absence of one or more nucleic acids of interest for diagnostic, prognostic, and/or therapeutic purposes. In some examples, diagnostic tests can include sequencing a nucleic acid molecule in a biological sample of a subject, for example by sequencing cell free deoxyribonucleic acid (DNA) molecules and/or expression products (e.g., ribonucleic acid (RNA)) in a biological sample of the subject.

In some embodiments, one or more molecules that are being analyzed (e.g., interrogated and/or identified) using luminescent lifetime and/or intensity can be labeled molecules (e.g., molecules that have been labeled with one or more luminescent markers). In some embodiments, individual subunits of biomolecules may be identified using markers. In some examples, luminescent markers are used to identify individual subunits of biomolecules. Some embodiments use luminescent markers (also referred to herein as "markers"), which may be exogenous or endogenous markers. Exogenous markers may be external luminescent markers used as a reporter and/or tag for luminescent labeling. Examples of exogenous markers may include, but are not limited to, fluorescent molecules, fluorophores, fluorescent dyes, fluorescent stains, organic dyes, fluorescent proteins, species that participate in fluorescence resonance energy transfer (FRET), enzymes, and/or quantum dots. Other exogenous markers are known in the art. Such exogenous markers may be conjugated to a probe or functional group (e.g., molecule, ion, and/or ligand) that specifically binds to a particular target or component. Attaching an exogenous tag or reporter to a probe allows identification of the target through detection of the presence of the exogenous tag or reporter. Examples of probes may include proteins, nucleic acid (e.g., DNA, RNA) molecules, lipids and antibody probes. The combination of an exogenous marker and a functional group may form any suitable probes, tags, and/or labels used for detection, including molecular probes, labeled probes, hybridization probes, antibody probes, protein probes (e.g., biotin-binding probes), enzyme labels, fluorescent probes, fluorescent tags, and/or enzyme reporters.

Although the present disclosure makes reference to luminescent markers, other types of markers may be used with devices, systems and methods provided herein. Such markers may be mass tags, electrostatic tags, electrochemical labels, or any combination thereof.

While exogenous markers may be added to a sample, endogenous markers may be already part of the sample. Endogenous markers may include any luminescent marker present that may luminesce or "autofluoresce" in the presence of excitation energy. Autofluorescence of endogenous fluorophores may provide for label-free and noninvasive labeling without requiring the introduction of exogenous fluorophores. Examples of such endogenous fluorophores may include hemoglobin, oxyhemoglobin, lipids, collagen and elastin crosslinks, reduced nicotinamide adenine dinucleotide (NADH), oxidized flavins (FAD and FMN), lipofuscin, keratin, and/or porphyrins, by way of example and not limitation.

Having recognized the need for simple, less complex apparatuses for performing single molecule detection and/or nucleic acid sequencing, the inventors have conceived of techniques for detecting single molecules using sets of luminescent tags (e.g., luminescent markers, luminescent labels) to label different molecules. Such single molecules may be nucleotides or amino acids having tags. Tags may be detected while bound to single molecules, upon release from the single molecules, or while bound to and upon release from the single molecules. In some examples, tags are luminescent tags. Each luminescent tag in a selected set is associated with a respective molecule. For example, a set of four tags may be used to "label" the nucleobases present in DNA—each tag of the set being associated with a different nucleobase, e.g., a first tag being associated with adenine (A), a second tag being associated with cytosine (C), a third tag being associated with guanine (G), and a fourth tag being associated with thymine (T). Moreover, each of the luminescent tags in the set of tags has different properties that may be used to distinguish a first tag of the set from the other tags in the set. In this way, each tag is uniquely identifiable using one or more of these distinguishing characteristics. By way of example and not limitation, the characteristics of the tags that may be used to distinguish one tag from another may include the emission energy and/or wavelength of the light that is emitted by the tag in response to excitation energy, the wavelength of the excitation light that is absorbed by a particular tag to place the tag in an excited state, and/or the emission lifetime of the tag.

Sequencing

Some aspects of the application are useful for sequencing biological polymers, such as nucleic acids and proteins. In some embodiments, methods, compositions, and devices described in the application can be used to identify a series of nucleotide or amino acid monomers that are incorporated into a nucleic acid or protein (e.g., by detecting a time-course of incorporation of a series of labeled nucleotide or amino acid monomers). In some embodiments, methods, compositions, and devices described in the application can be used to identify a series of nucleotides that are incorporated into a template-dependent nucleic acid sequencing reaction product synthesized by a polymerase enzyme.

In certain embodiments, the template-dependent nucleic acid sequencing product is carried out by naturally occurring nucleic acid polymerases. In some embodiments, the polymerase is a mutant or modified variant of a naturally occurring polymerase. In some embodiments, the template-dependent nucleic acid sequence product will comprise one or more nucleotide segments complementary to the template nucleic acid strand. In one aspect, the application provides a method of determining the sequence of a template (or target) nucleic acid strand by determining the sequence of its complementary nucleic acid strand.

In another aspect, the application provides methods of sequencing target nucleic acids by sequencing a plurality of nucleic acid fragments, wherein the target nucleic acid comprises the fragments. In certain embodiments, the method comprises combining a plurality of fragment sequences to provide a sequence or partial sequence for the parent target nucleic acid. In some embodiments, the step of combining is performed by computer hardware and software. The methods described herein may allow for a set of related target nucleic acids, such as an entire chromosome or genome to be sequenced.

During sequencing, a polymerizing enzyme may couple (e.g., attach) to a priming location of a target nucleic acid molecule. The priming location can be a primer that is complementary to a portion of the target nucleic acid molecule. As an alternative the priming location is a gap or nick that is provided within a double stranded segment of the target nucleic acid molecule. A gap or nick can be from 0 to at least 1, 2, 3, 4, 5, 6, 7, 8, 9, 10, 20, 30, or 40 nucleotides in length. A nick can provide a break in one strand of a double stranded sequence, which can provide a priming location for a polymerizing enzyme, such as, for example, a strand displacing polymerase enzyme.

In some cases, a sequencing primer can be annealed to a target nucleic acid molecule that may or may not be immobilized to a solid support. A solid support can comprise, for example, a sample well (e.g., a nanoaperture, a reaction chamber) on a chip used for nucleic acid sequencing. In some embodiments, a sequencing primer may be immobilized to a solid support and hybridization of the target nucleic acid molecule also immobilizes the target nucleic acid molecule to the solid support. In some embodiments, a polymerase is immobilized to a solid support and soluble primer and target nucleic acid are contacted to the polymerase. However, in some embodiments a complex comprising a polymerase, a target nucleic acid and a primer is formed in solution and the complex is immobilized to a solid support (e.g., via immobilization of the polymerase, primer, and/or target nucleic acid). In some embodiments, none of the components in a sample well (e.g., a nanoaperture, a reaction chamber) are immobilized to a solid support. For example, in some embodiments, a complex comprising a polymerase, a target nucleic acid, and a primer is formed in solution and the complex is not immobilized to a solid support.

Under appropriate conditions, a polymerase enzyme that is contacted to an annealed primer/target nucleic acid can add or incorporate one or more nucleotides onto the primer, and nucleotides can be added to the primer in a 5' to 3', template-dependent fashion. Such incorporation of nucleotides onto a primer (e.g., via the action of a polymerase) can generally be referred to as a primer extension reaction. Each nucleotide can be associated with a detectable tag that can be detected and identified (e.g., based on its luminescent lifetime and/or other characteristics) during the nucleic acid extension reaction and used to determine each nucleotide incorporated into the extended primer and, thus, a sequence of the newly synthesized nucleic acid molecule. Via sequence complementarity of the newly synthesized nucleic acid molecule, the sequence of the target nucleic acid molecule can also be determined. In some cases, annealing of a sequencing primer to a target nucleic acid molecule and incorporation of nucleotides to the sequencing primer can occur at similar reaction conditions (e.g., the same or similar reaction temperature) or at differing reaction conditions (e.g., different reaction temperatures). In some embodiments, sequencing by synthesis methods can include the presence of a population of target nucleic acid molecules (e.g., copies of a target nucleic acid) and/or a step of amplification of the target nucleic acid to achieve a population of target nucleic acids. However, in some embodiments sequencing by synthesis is used to determine the sequence of a single molecule in each reaction that is being evaluated (and nucleic acid amplification is not required to prepare the target template for sequencing). In some embodiments, a plurality of single molecule sequencing reactions are performed in parallel (e.g., on a single chip) according to aspects of the present application. For example, in some embodiments, a plurality of single molecule sequencing reactions are each performed in separate reaction chambers (e.g., nanoapertures, sample wells) on a single chip.

Embodiments are capable of sequencing single nucleic acid molecules with high accuracy and long read lengths, such as an accuracy of at least about 50%, 60%, 70%, 75%, 80%, 85%, 90%, 95%, 96%, 97%, 98%, 99%, 99.9%, 99.99%, 99.999%, or 99.9999%, and/or read lengths greater than or equal to about 10 base pairs (bp), 50 bp, 100 bp, 200 bp, 300 bp, 400 bp, 500 bp, 1000 bp, 10,000 bp, 20,000 bp, 30,000 bp, 40,000 bp, 50,000 bp, or 100,000 bp. In some embodiments, the target nucleic acid molecule used in single molecule sequencing is a single stranded target nucleic acid (e.g., deoxyribonucleic acid (DNA), DNA derivatives, ribonucleic acid (RNA), RNA derivatives) template that is added or immobilized to a sample well (e.g., nanoaperture) containing at least one additional component of a sequencing reaction (e.g., a polymerase such as, a DNA polymerase, a sequencing primer) immobilized or attached to a solid support such as the bottom or side walls of the sample well. The target nucleic acid molecule or the polymerase can be attached to a sample wall, such as at the bottom or side walls of the sample well directly or through a linker. The sample well (e.g., nanoaperture) also can contain any other reagents needed for nucleic acid synthesis via a primer extension reaction, such as, for example suitable buffers, co-factors, enzymes (e.g., a polymerase) and deoxyribonucleoside polyphosphates, such as, e.g., deoxyribonucleoside triphosphates, including deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include luminescent tags, such as fluorophores. In some embodiments, each class of dNTPs (e.g., adenine-containing dNTPs (e.g., dATP), cytosine-containing dNTPs (e.g., dCTP), guanine-containing dNTPs (e.g., dGTP), uracil-containing dNTPs (e.g., dUTPs) and thymine-containing dNTPs (e.g., dTTP)) is conjugated to a distinct luminescent tag such that detection of light emitted from the tag indicates the identity of the dNTP that was incorporated into the newly synthesized nucleic acid. Emitted light from the luminescent tag can be detected and attributed to its appropriate luminescent tag (and, thus, associated dNTP) via any suitable device and/or method, including such devices and methods for detection described elsewhere herein. The luminescent tag may be conjugated to the dNTP at any position such that the presence of the luminescent tag does not inhibit the incorporation of the dNTP into the newly synthesized nucleic acid strand or the activity of the polymerase. In some embodiments, the luminescent tag is conjugated to the terminal phosphate (e.g., the gamma phosphate) of the dNTP.

In some embodiments, the single-stranded target nucleic acid template can be contacted with a sequencing primer, dNTPs, polymerase and other reagents necessary for nucleic acid synthesis. In some embodiments, all appropriate dNTPs can be contacted with the single-stranded target nucleic acid template simultaneously (e.g., all dNTPs are simultaneously present) such that incorporation of dNTPs can occur continuously. In other embodiments, the dNTPs can be contacted with the single-stranded target nucleic acid template sequentially, where the single-stranded target nucleic acid template is contacted with each appropriate dNTP separately, with washing steps in between contact of the single-stranded target nucleic acid template with differing dNTPs. Such a cycle of contacting the single-stranded target nucleic acid template with each dNTP separately followed by washing can be repeated for each successive base position of the single-stranded target nucleic acid template to be identified.

In some embodiments, the sequencing primer anneals to the single-stranded target nucleic acid template and the polymerase consecutively incorporates the dNTPs (or other deoxyribonucleoside polyphosphate) to the primer based on the single-stranded target nucleic acid template. The unique luminescent tag associated with each incorporated dNTP can be excited with the appropriate excitation light during or after incorporation of the dNTP to the primer and its emission can be subsequently detected, using, any suitable device(s) and/or method(s), including devices and methods for detection described elsewhere herein. Detection of a particular emission of light (e.g., having a particular emission lifetime, intensity, spectrum and/or combination thereof) can be attributed to a particular dNTP incorporated. The sequence obtained from the collection of detected luminescent tags can then be used to determine the sequence of the single-stranded target nucleic acid template via sequence complementarity.

While the present disclosure makes reference to dNTPs, devices, systems and methods provided herein may be used with various types of nucleotides, such as ribonucleotides and deoxyribonucleotides (e.g., deoxyribonucleoside polyphosphates with at least 4, 5, 6, 7, 8, 9, or 10 phosphate groups). Such ribonucleotides and deoxyribonucleotides can include various types of tags (or markers) and linkers.

Example of Nucleic Acid Sequencing

The following example is meant to illustrate some of the methods, compositions and devices described herein. All aspects of the example are non-limiting. FIG. 1 schematically illustrates the setup of a single molecule nucleic acid sequencing method. 1-110 is a sample well (e.g., nanoaperture, reaction chamber) configured to contain a single complex comprising a nucleic acid polymerase 1-101, a target nucleic acid 1-102 to be sequenced, and a primer 1-104. In this example, a bottom region of sample well 1-110 is depicted as a target volume (e.g., the excitation region) 1-120.

As described elsewhere herein, the target volume is a volume towards which the excitation energy is directed. In some embodiments, the volume is a property of both the sample well volume and the coupling of excitation energy to the sample well. The target volume may be configured to limit the number of molecules or complexes confined in the target volume. In some embodiments, the target volume is configured to confine a single molecule or complex. In some embodiments, the target volume is configured to confine a single polymerase complex. In FIG. 1 the complex comprising polymerase 1-101 is confined in target volume 1-120. The complex may optionally be immobilized by attachment to a surface of the sample well. Exemplary processes for sample well surface preparation and functionalization are depicted in FIGS. 7-9 discussed in further detail elsewhere in the application. In this example the complex is immobilized by a linker 1-103 comprising one or more biomolecules (e.g., biotin) suitable for attaching the linker to the polymerase 1-101.

The volume of the aperture also contains a reaction mixture with suitable solvent, buffers, and other additives necessary for the polymerase complex to synthesize a nucleic acid strand. The reaction mixture also contains a plurality of types of luminescently labeled nucleotides. Each type of nucleotide is represented by the symbols *-A, @-T, $-G, #-C, wherein A, T, G, and C represent the nucleotide base, and the symbols *, @, $, and # represent a unique luminescent label attached to each nucleotide, through linker-. In FIG. 1, a #-C nucleotide is currently being incorporated into the complementary strand 1-102. The incorporated nucleotide is within the target volume 1-120.

FIG. 1 also indicates with arrows the concept of an excitation energy being delivered to a vicinity of the target volume, and a luminescence being emitted towards a detector. The arrows are schematic, and are not meant to indicate the particular orientation of excitation energy delivery or luminescence. In some embodiments, the excitation energy is a pulse of light from a light source. The excitation energy may travel through one or more device components, such as waveguides or filters, between the light source and the vicinity of the target volume. The emission energy may also travel through one or more device components, such as waveguides or filters, between the luminescent molecule and the detector. Some luminescences may emit on a vector which is not directed to the detector (e.g., towards the sidewall of the sample well) and may not be detected.

FIG. 2 schematically illustrates a sequencing process in a single sample well (e.g., a nanoaperture) over time. Stages A through D depict a sample well with a polymerase complex as in FIG. 1. Stage A depicts the initial state before any nucleotides have been added to the primer. Stage B depicts the incorporation event of a luminescently labeled nucleotide (#-C). Stage C depicts the period between incorporation events. In this example, nucleotide C has been added to the primer, and the label and linker previously attached to the luminescently labeled nucleotide (#-C) has been cleaved. Stage D depicts a second incorporation event of a luminescently labeled nucleotide (*-A). The complementary strand after Stage D consists of the primer, a C nucleotide, and an A nucleotide.

Stage A and C, both depict the periods before or between incorporation events, which are indicated in this example to last for about 10 milliseconds. In stages A and C, because there is no nucleotide being incorporated, there is no luminescently labeled nucleotide in the target volume (not drawn in FIG. 2), though background luminescence or spurious luminescence from luminescently labeled nucleotide which is not being incorporated may be detected. Stage B and D show incorporation events of different nucleotides (#-C, and *-A, respectively). In this example these events are also indicated to last for about 10 milliseconds.

The row labeled "Raw bin data" depicts the data generated during each Stage. Throughout the example experiment, a plurality of pulses of light are delivered to the vicinity of the target volume. For each pulse a detector is configured to record any emitted photon received by the detector. When an emitted photon is received by the detector it is separated into one of a plurality of time bins, of which there are 3 in this example. In some embodiments, the detector is configured with between 2 and 16 time bins. The "Raw bin data" records a value of 1 (shortest bars), 2 (medium bars), or 3 (longest bars), corresponding to the shortest, middle, and longest bins, respectively. Each bar indicates detection of an emitted photon.

Since there is no luminescently labeled nucleotide present in the target volume for Stage A or C, there are no photons detected. For each of Stage B and D a plurality of photon emission events (luminescent events or "luminescences" as used herein) is detected during the incorporation event. Luminescent label # has a shorter luminescence lifetime than luminescent label *. The Stage B data is thus depicted as having recorded lower average bin values, than Stage D where the bin values are higher.

The row labeled "Processed data" depicts raw data which has been processed to indicate the number (counts) of emitted photons at times relative to each pulse. Since each bar corresponds to the photon count of a particular time bin, the exemplary curves depicting processed data correspond to raw bin data comprising more time bins than the three time bins described in the figure. In this example, the data is only processed to determine luminescent lifetime, but the data may also be evaluated for other luminescent properties, such as luminescent intensity or the wavelength of the absorbed or emitted photons. The exemplary processed data approximates an exponential decay curve characteristic for the luminescence lifetime of the luminescent label in the target volume. Because luminescent label # has a shorter luminescence lifetime than luminescent label *, the processed data for Stage B has fewer counts at longer time durations, while the processed data for Stage D has relatively more counts at longer time durations.

The example experiment of FIG. 2 would identify the first two nucleotides added to the complementary strand as CA. For DNA, the sequence of the target strand immediately after the region annealed to the primer would thus be identified as GT. In this example the nucleotides C and A could be distinguished from amongst the plurality of C, G, T, and A, based on luminescent lifetime alone. In some embodiments, other properties, such as the luminescent intensity or the wavelength of the absorbed or emitted photons may be necessary to distinguish one or more particular nucleotide.

Signals emitted upon the incorporation of nucleotides can be stored in memory and processed at a later point in time to determine the sequence of the target nucleic acid template. This may include comparing the signals to a reference signals to determine the identities of the incorporated nucleotides as a function of time. Alternatively or in addition to, signal emitted upon the incorporation of nucleotide can be collected and processed in real time (e.g., upon nucleotide incorporation) to determine the sequence of the target nucleic acid template in real time.

The term "nucleic acid," as used herein, generally refers to a molecule comprising one or more nucleic acid subunits. A nucleic acid may include one or more subunits selected from adenine (A), cytosine (C), guanine (G), thymine (T), and uracil (U), or variants thereof. In some examples, a nucleic acid is deoxyribonucleic acid (DNA) or ribonucleic acid (RNA), or derivatives thereof. A nucleic acid may be single-stranded or double stranded. A nucleic acid may be circular.

The term "nucleotide," as used herein, generally refers to a nucleic acid subunit, which can include A, C, G, T or U, or variants or analogs thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (e.g., A or G, or variant or analogs thereof) or a pyrimidine (e.g., C, T or U, or variant or analogs thereof). A subunit can enable individual nucleic acid bases or groups of bases (e.g., AA, TA, AT, GC, CG, CT, TC, GT, TG, AC, CA, or uracil-counterparts thereof) to be resolved.

A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate, which can be selected from deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include detectable tags, such as luminescent tags or markers (e.g., fluorophores).

A nucleoside polyphosphate can have 'n' phosphate groups, where 'n' is a number that is greater than or equal to 2, 3, 4, 5, 6, 7, 8, 9, or 10. Examples of nucleoside polyphosphates include nucleoside diphosphate and nucleoside triphosphate. A nucleotide can be a terminal phosphate labeled nucleoside, such as a terminal phosphate labeled nucleoside polyphosphate. Such label can be a luminescent (e.g., fluorescent or chemiluminescent) label, a fluorogenic label, a colored label, a chromogenic label, a mass tag, an electrostatic label, or an electrochemical label. A label (or marker) can be coupled to a terminal phosphate through a linker. The linker can include, for example, at least one or a plurality of hydroxyl groups, sulfhydryl groups, amino groups or haloalkyl groups, which may be suitable for forming, for example, a phosphate ester, a thioester, a phosphoramidate or an alkyl phosphonate linkage at the terminal phosphate of a natural or modified nucleotide. A linker can be cleavable so as to separate a label from the terminal phosphate, such as with the aid of a polymerization enzyme. Examples of nucleotides and linkers are provided in U.S. Pat. No. 7,041,812, which is entirely incorporated herein by reference.

A nucleotide (e.g., a nucleotide polyphosphate) can comprise a methylated nucleobase. For example, a methylated nucleotide can be a nucleotide that comprises one or more methyl groups attached to the nucleobase (e.g., attached directly to a ring of the nucleobase, attached to a substituent of a ring of the nucleobase). Exemplary methylated nucleobases include 1-methylthymine, 1-methyluracil, 3-methyluracil, 3-methylcytosine, 5-methylcytosine, 1-methyladenine, 2-methyladenine, 7-methyladenine, N6-methyladenine, N6,N6-dimethyladenine, 1-methylguanine, 7-methylguanine, N2-methylguanine, and N2,N2-dimethylguanine.

The term "primer," as used herein, generally refers to a nucleic acid molecule (e.g., an oligonucleotide), which can include a sequence comprising A, C, G, T and/or U, or variants or analogs thereof. A primer can be a synthetic oligonucleotide comprising DNA, RNA, PNA, or variants or analogs thereof. A primer can be designed such that its nucleotide sequence is complementary to a target strand, or the primer can comprise a random nucleotide sequence. In some embodiments, a primer can comprise a tail (e.g., a poly-A tail, an index adaptor, a molecular barcode, etc.). In some embodiments, a primer can comprise 5 to 15 bases, 10 to 20 bases, 15 to 25 bases, 20 to 30 bases, 25 to 35 bases, 30 to 40 bases, 35 to 45 bases, 40 to 50 bases, 45 to 55 bases, 50 to 60 bases, 55 to 65 bases, 60 to 70 bases, 65 to 75 bases, 70 to 80 bases, 75 to 85 bases, 80 to 90 bases, 85 to 95 bases, 90 to 100 bases, 95 to 105 bases, 100 to 150 bases, 125 to 175 bases, 150 to 200 bases, or more than 200 bases.

Luminescent Properties

As described herein, a luminescent molecule is a molecule that absorbs one or more photons and may subsequently emit one or more photons after one or more time durations. The luminescence of the molecule is described by several parameters, including but not limited to luminescent lifetime, absorption spectra, emission spectra, luminescent quantum yield, and luminescent intensity. The terms absorption and excitation are used interchangeably throughout the application. A typical luminescent molecule may absorb, or undergo excitation by, light at multiple wavelengths. Excitation at certain wavelengths or within certain spectral ranges may relax by a luminescent emission event, while excitation at certain other wavelengths or spectral ranges may not relax by a luminescent emission event. In some embodiments, a luminescent molecule is only suitably excited for luminescence at a single wavelength or within a single spectral range. In some embodiments, a luminescent molecule is suitably excited for luminescence at two or more wavelengths or within two or more spectral ranges. In some embodiments, a molecule is identified by measuring the wavelength of the excitation photon or the absorption spectrum.

The emitted photon from a luminescent emission event will emit at a wavelength within a spectral range of possible wavelengths. Typically the emitted photon has a longer wavelength (e.g., has less energy or is red-shifted) compared to the wavelength of the excitation photon. In certain embodiments, a molecule is identified by measuring the wavelength of an emitted photon. In certain embodiments, a molecule is identified by measuring the wavelength of a plurality of emitted photon. In certain embodiments, a molecule is identified by measuring the emission spectrum.

Luminescent lifetime refers to the time duration between an excitation event and an emission event. In some embodiments, luminescent lifetime is expressed as the constant in an equation of exponential decay. In some embodiments, wherein there are one or more pulse events delivering excitation energy, the time duration is the time between the pulse and the subsequent emission event.

"Determining a luminescent lifetime" of a molecule can be performed using any suitable method (e.g., by measuring the lifetime using a suitable technique or by determining time-dependent characteristics of emission). In some embodiments, determining the luminescent lifetime of a molecule comprises determining the lifetime relative to one or more molecules (e.g., different luminescently labeled nucleotides in a sequencing reaction). In some embodiments, determining the luminescent lifetime of a molecule comprises determining the lifetime relative to a reference. In some embodiments, determining the luminescent lifetime of a molecule comprises measuring the lifetime (e.g., fluorescence lifetime). In some embodiments, determining the luminescent lifetime of a molecule comprises determining one or more temporal characteristics that are indicative of lifetime. In some embodiments, the luminescent lifetime of a molecule can be determined based on a distribution of a plurality of emission events (e.g., 1, 2, 3, 4, 5, 6, 7, 8, 9, 10, 11, 12, 13, 14, 15, 16, 17, 18, 19, 20, 30, 40, 50, 60, 70, 80, 90, 100, or more emission events) occurring across one or more time-gated windows relative to an excitation pulse. For example, a luminescent lifetime of a single molecule can be distinguished from a plurality of molecules having different luminescent lifetimes based on the distribution of photon arrival times measured with respect to an excitation pulse.

It should be appreciated that a luminescent lifetime of a single molecule is indicative of the timing of photons emitted after the single molecule reaches an excited state and the single molecule can be distinguished by information indicative of the timing of the photons. Some embodiments may include distinguishing a molecule from a plurality of molecules based on the molecule's luminescent lifetime by measuring times associated with photons emitted by the molecule. The distribution of times may provide an indication of the luminescent lifetime which may be determined from the distribution. In some embodiments, the single molecule is distinguishable from the plurality of molecules based on the distribution of times, such as by comparing the distribution of times to a reference distribution corresponding to a known molecule. In some embodiments, a value for the luminescent lifetime is determined from the distribution of times.

Luminescent quantum yield refers to the fraction of excitation events at a given wavelength or within a given spectral range that lead to an emission event, and is typically less than 1. In some embodiments, the luminescent quantum yield of a molecule described herein is between 0 and about 0.001, between about 0.001 and about 0.01, between about 0.01 and about 0.1, between about 0.1 and about 0.5, between about 0.5 and 0.9, or between about 0.9 and 1. In some embodiments, a molecule is identified by determining or estimating the luminescent quantum yield.

As used herein for single molecules, luminescent intensity refers to the number of emitted photons per unit time that are emitted by a molecule which is being excited by delivery of a pulsed excitation energy. In some embodiments, the luminescent intensity refers to the detected number of emitted photons per unit time that are emitted by a molecule which is being excited by delivery of a pulsed excitation energy, and are detected by a particular sensor or set of sensors.

The luminescent lifetime, luminescent quantum yield, and luminescent intensity may each vary for a given molecule under different conditions. In some embodiments, a single molecule will have a different observed luminescent lifetime, luminescent quantum yield, or luminescent intensity than for an ensemble of the molecules. In some embodiments, a molecule confined in a sample well (e.g., a nanoaperture) will have a different observed luminescent lifetime, luminescent quantum yield, or luminescent intensity than for molecules not confined in a sample well. In some embodiments, a luminescent label or luminescent molecule attached to another molecule will have a different luminescent lifetime, luminescent quantum yield, or luminescent intensity than the luminescent label or luminescent molecule not attached to another molecule. In some embodiments, a molecule interacting with a macromolecular complex (e.g., protein complex (e.g., nucleic acid polymerase)) will have different luminescent lifetime, luminescent quantum yield, or luminescent intensity than a molecule not interacting with a macromolecular complex.

In certain embodiments, a luminescent molecule described in the application absorbs one photon and emits one photon after a time duration. In some embodiments, the luminescent lifetime of a molecule can be determined or estimated by measuring the time duration. In some embodiments, the luminescent lifetime of a molecule can be determined or estimated by measuring a plurality of time durations for multiple pulse events and emission events. In some embodiments, the luminescent lifetime of a molecule can be differentiated amongst the luminescent lifetimes of a plurality of types of molecules by measuring the time duration. In some embodiments, the luminescent lifetime of a molecule can be differentiated amongst the luminescent lifetimes of a plurality of types of molecules by measuring a plurality of time durations for multiple pulse events and emission events. In certain embodiments, a molecule is identified or differentiated amongst a plurality of types of molecules by determining or estimating the luminescent lifetime of the molecule. In certain embodiments, a molecule is identified or differentiated amongst a plurality of types of molecules by differentiating the luminescent lifetime of the molecule amongst a plurality of the luminescent lifetimes of a plurality of types of molecules.

In certain embodiments, the luminescent emission event is a fluorescence. In certain embodiments, the luminescent emission event is a phosphorescence. As used herein, the term luminescence encompasses all luminescent events including both fluorescence and phosphorescence.

In one aspect, the application provides a method of determining the luminescent lifetime of a single luminescent molecule comprising: providing the luminescent molecule in a target volume; delivering a plurality of pulses of an excitation energy to a vicinity of the target volume; and detecting a plurality of luminescences from the luminescent molecule. In some embodiments, the method further comprises evaluating the distribution of the plurality of time durations between each pair of pulses and luminescences. In some embodiments, the method further comprises immobilizing the single luminescent molecule in the target volume.

In another aspect, the application provides a method of determining the luminescent lifetime of a plurality of molecules comprising: providing a plurality of luminescent molecules in a target volume; delivering a plurality of pulses of an excitation energy to a vicinity of the target volume; and detecting a plurality of luminescences from the luminescent molecules. In some embodiments, the method further comprises evaluating the distribution of the plurality of time durations between each pair of pulses and luminescences. In some embodiments, the method further comprises immobilizing the luminescent molecules in the target volume. In some embodiments, the plurality consists of between 2 and about 10 molecules, between about 10 and about 100 molecules, or between about 100 and about 1000 molecules. In some embodiments, the plurality consists of between about 1000 and about $10^6$ molecules, between about $10^6$ and about $10^9$ molecules, between about $10^9$ and about $10^{12}$ molecules, between about $10^{12}$ and about $10^{15}$ molecules, or between about $10^{15}$ and about $10^{18}$ molecules. In some embodiments, all molecules of the plurality are the same type of molecule.

FIG. 3 shows the exemplary decay profile 3-1 for four luminescent molecules with different luminescent lifetimes (longest to shortest, top to bottom). The amplitude can refer to the intensity of luminescence from a sample comprising many molecules, which decreases exponentially over time after the initial excitation based on the luminescent lifetime. The amplitude can alternatively refer to a number or count of emissions detected after a time duration after a plurality of pulses of excitation energy, for example, for a single molecule. The normalized cumulative distribution function 3-2 corresponds to 3-1, for four luminescent molecules with different luminescent lifetimes (shortest to longest, top to bottom). The CDF can represent the normalized probability of the luminescence amplitude of reaching zero (e.g., the cumulative probability of all excited molecules having luminesced) over time after the initial excitation based on the luminescent lifetime. The CDF can alternatively represent the normalized probability of a single molecule emitting luminescence at a certain time duration after a single pulse or after each of a plurality of pulses of excitation energy.

In one aspect, the application provides a method of determining the luminescent intensity of a single luminescent molecule comprising: providing the luminescent molecule in a target volume; delivering a plurality of pulses of an excitation energy to a vicinity of the target volume; and detecting a plurality of luminescences from the luminescent molecule. In some embodiments, the method further comprises determining the number of the plurality of detected luminescence per unit time. In some embodiments, the method further comprises immobilizing the single luminescent molecule in the target volume.

In another aspect, the application provides a method of determining the luminescent intensity of a plurality of molecules comprising: providing a plurality of luminescent molecules in a target volume; delivering a plurality of pulses of an excitation energy to a vicinity of the target volume; and detecting a plurality of luminescences from the luminescent molecules. In some embodiments, the method further comprises determining the number of the plurality of detected luminescence per unit time. In some embodiments, the method further comprises immobilizing the luminescent molecules in the target volume. In some embodiments, the plurality consists of between 2 and about 10 molecules, between about 10 and about 100 molecules, or between about 100 and about 1000 molecules. In some embodiments, the plurality consists of between about 1000 and about $10^6$ molecules, between about $10^6$ and about $10^9$ molecules, between about $10^9$ and about $10^{12}$ molecules, between about $10^{12}$ and about $10^{15}$ molecules, or between about $10^{15}$ and about $10^{18}$ molecules. In some embodiments, all molecules of the plurality are the same type of molecule.

Excitation Energy

In one aspect of methods described herein, one or more excitation energy is used to excite the luminescent labels of the molecules to be identified or distinguished. In some embodiments, an excitation energy is in the visible spectrum. In some embodiments, an excitation energy is in the ultraviolet spectrum. In some embodiments, an excitation energy is in the infrared spectrum. In some embodiments, one excitation energy is used to excite the luminescently labeled molecules. In some embodiments, two excitation energies are used to excite the luminescently labeled molecules. In some embodiments, three or more excitation energies are used to excite the luminescently labeled molecules. In some embodiments, each luminescently labeled molecule is excited by only one of the delivered excitation energies. In some embodiments, a luminescently labeled molecule is excited by two or more of the delivered excitation energies. In certain embodiments, an excitation energy may be monochromatic or confined to a spectral range. In some embodiments, a spectral range has a range of between about 0.1 nm and about 1 nm, between about 1 nm and about 2 nm, or between about 2 nm and about 5 nm. In some embodiments a spectral range has a range of between about 5 nm and about 10 nm, between about 10 nm and about 50 nm, or between about 50 nm and about 100 nm.

In certain embodiments, excitation energy is delivered as a pulse of light. In certain embodiments, excitation energy is delivered as a plurality of pulses of light. In certain embodiments, two or more excitation energies are used to excite the luminescently labeled molecules. In some embodiments, each excitation energy is delivered at the same time (e.g., in each pulse). In some embodiments, each excitation energy is delivered at different times (e.g., in separate pulses of each energy). The different excitation energies may be delivered in any pattern sufficient to allow detection of luminescence from the target molecules. In some embodiments, two excitation energies are delivered in each pulse. In some embodiments, a first excitation energy and a second excitation energy are delivered in alternating pulses. In some embodiments, a first excitation energy is delivered in a series of sequential pulses, and a second excitation energy is delivered in a subsequent series of sequential pulses, or an alternating pattern of such series.

In certain embodiments, the frequency of pulses of light is selected based on the luminescent properties of the luminescently labeled molecule. In certain embodiments, the frequency of pulses of light is selected based on the luminescent properties of a plurality of luminescently labeled nucleotides. In certain embodiments, the frequency of pulses of light is selected based on the luminescent lifetime of a plurality of luminescently labeled nucleotides. In some embodiments, the frequency is selected so that the gap between pulses is longer than the luminescent lifetimes of one or more luminescently labeled nucleotides. In some embodiments, the frequency is selected based on the longest luminescent lifetime of the plurality of luminescently labeled nucleotides. For example, if the luminescent lifetimes of the four luminescently labeled nucleotides are 0.25, 0.5, 1.0, and 1.5 ns, the frequency of pulses of light may be selected so that the gap between pulses exceeds 1.5 ns. In some embodiments, the gap is between about two times and about ten times, between about ten times and about 100 times, or between about 100 times and about 1000 times longer than the luminescent lifetime of one or more luminescently labeled molecules being excited. In some embodiments, the gap is about 10 times longer than the luminescent lifetime of one or more luminescently labeled molecules being excited. In some embodiments, the gap is between about 0.01 ns and about 0.1 ns, between about 1 ns and about 5 ns, between about 5 ns and about 15 ns, between about 15 ns and about 25 ns, or between about 25 ns and about 50 ns. In some embodiments, the gap is selected such that there is a 50%, 75%, 90%, 95%, or 99% probability that the molecules excited by the pulse will luminescently decay or that the excited state will relax by another mechanism.

In certain embodiments, wherein there are multiple excitation energies, the frequency of the pulses for each excitation energy is the same. In certain embodiments, wherein there are multiple excitation energies, the frequencies of the pulses for each excitation energy is different. For example, if a red laser is used to excite luminescent molecules with lifetimes of 0.2 and 0.5 ns, and a green laser is used to excite luminescent molecules with lifetimes of 5 ns and 7 ns, the gap after each red laser pulse may be shorter (e.g., 5 ns) than the gap after each green laser pulse (e.g., 20 ns).

In certain embodiments, the frequency of pulsed excitation energies is selected based on the chemical process being monitored. For a sequencing reaction the frequency may be selected such that a number of pulses are delivered sufficient to allow for detection of a sufficient number of emitted photons to be detected. A sufficient number, in the context of detected photons, refers to a number of photons necessary to identify or distinguish the luminescently labeled nucleotide from the plurality of luminescently labeled nucleotides. For example, a DNA polymerase may incorporate an additional nucleotide once every 20 milliseconds on average. The time that a luminescently labeled nucleotide interacts with the complex may be about 10 milliseconds, and the time between when the luminescent marker is cleaved and the next luminescently labeled nucleotide begins to interact may be about 10 milliseconds. The frequency of the pulsed excitation energy could then be selected to deliver sufficient pulses over 10 milliseconds such that a sufficient number of emitted photons are detected during the 10 millisecond when the luminescently labeled nucleotide is being incorporated. For example, at a frequency of 100 MHz, there will be 1 million pulses in 10 milliseconds (the approximate length of the incorporation event). If 0.1% of these pulses leads to a detected photon there will be 1,000 luminescent data points that can be analyzed to determine the identity of the luminescently labeled nucleotide being incorporated. Any of the above values are non-limiting. In some embodiments incorporation events may take between 1 ms and 20 ms, between 20 ms and 100 ms, or between 100 ms and 500 ms. In some embodiments, in which multiple excitation energies are delivered in separately timed pulses the luminescently labeled nucleotide may only be excited by a portion of the pulses. In some embodiments, the frequency and pattern of the pulses of multiple excitation energies is selected such that the number of pulses is sufficient to excite any one of the plurality of luminescently labeled nucleotides to allow for a sufficient number of emitted photons to be detected.

In some embodiments, the frequency of pulses is between about 1 MHz and about 10 MHz. In some embodiments, the frequency of pulses is between about 10 MHz and about 100 MHz. In some embodiments, the frequency of pulses is between about 100 MHz and about 1 GHz. In some embodiments, the frequency of pulses is between about 50 MHz and about 200 MHz. In some embodiments, the frequency of pulses is about 100 MHz. In some embodiments, the frequency is stochastic.

In certain embodiments, the excitation energy is between about 500 nm and about 700 nm. In some embodiments, the excitation energy is between about 500 nm and about 600 nm, or about 600 nm and about 700 nm. In some embodiments, the excitation energy is between about 500 nm and about 550 nm, between about 550 nm and about 600 nm, between about 600 nm and about 650 nm, or between about 650 nm and about 700 nm.

In certain embodiments, a method described herein comprises delivery of two excitation energies. In some embodiments, the two excitation energies are separated by between about 5 nm and about 20 nm, between about 20 nm and about 40 nm, between about 40 nm and about 60 nm, between about 60 nm and about 80 nm, between about 80 nm and about 100 nm, between about 100 nm and about 150 nm, between about 150 nm and about 200 nm, between about 200 nm and about 400 nm, or between at least about 400 nm. In some embodiments, the two excitation energies are separated by between about 20 nm and about 80 nm, or between about 80 nm and about 160 nm.

When an excitation energy is referred to as being in a specific range, the excitation energy may comprise a single wavelength, such that the wavelength is between or at the endpoints of the range, or the excitation energy may comprise a spectrum of wavelengths with a maximum intensity, such that the maximum intensity is between or at the endpoints of the range.

In certain embodiments, the first excitation energy is in the range of 450 nm to 500 nm and the second excitation energy is in the range of 500 nm to 550 nm, 550 nm to 600 nm, 600 nm to 650 nm, or 650 nm to 700 nm. In certain embodiments, the first excitation energy is in the range of 500 nm to 550 nm and the second excitation energy is in the range of 450 nm to 500 nm, 550 nm to 600 nm, 600 nm to 650 nm, or 650 nm to 700 nm. In certain embodiments, the first excitation energy is in the range of 550 nm to 600 nm and the second excitation energy is in the range of 450 nm to 500 nm, 500 nm to 550 nm, 600 nm to 650 nm, or 650 nm to 700 nm. In certain embodiments, the first excitation energy is in the range of 600 nm to 650 nm and the second excitation energy is in the range of 450 nm to 500 nm, 500 nm to 550 nm, 550 nm to 600 nm, or 650 nm to 700 nm. In certain embodiments, the first excitation energy is in the range of 650 nm to 700 nm and the second excitation energy is in the range of 450 nm to 500 nm, 500 nm to 550 nm, 550 nm to 600 nm, or 600 nm to 650 nm.

In certain embodiments, the first excitation energy is in the range of 450 nm to 500 nm and the second excitation energy is in the range of 500 nm to 550 nm. In certain embodiments, the first excitation energy is in the range of 450 nm to 500 nm and the second excitation energy is in the range of 550 nm to 600 nm. In certain embodiments, the first excitation energy is in the range of 450 nm to 500 nm and the second excitation energy is in the range of 600 nm to 670 nm. In certain embodiments, the first excitation energy is in the range of 500 nm to 550 nm and the second excitation energy is in the range of 550 nm to 600 nm. In certain embodiments, the first excitation energy is in the range of 500 nm to 550 nm and the second excitation energy is in the range of 600 nm to 670 nm. In certain embodiments, the first excitation energy is in the range of 550 nm to 600 nm and the second excitation energy is in the range of 600 nm to 670 nm. In certain embodiments, the first excitation energy is in the range of 470 nm to 510 nm and the second excitation energy is in the range of 510 nm to 550 nm. In certain embodiments, the first excitation energy is in the range of 470 nm to 510 nm and the second excitation energy is in the range of 550 nm to 580 nm. In certain embodiments, the first excitation energy is in the range of 470 nm to 510 nm and the second excitation energy is in the range of 580 nm to 620 nm. In certain embodiments, the first excitation energy is in the range of 470 nm to 510 nm and the second excitation energy is in the range of 620 nm to 670 nm. In certain embodiments, the first excitation energy is in the range of 510 nm to 550 nm and the second excitation energy is in the range of 550 nm to 580 nm. In certain embodiments, the first excitation energy is in the range of 510 nm to 550 nm and the second excitation energy is in the range of 580 nm to 620 nm. In certain embodiments, the first excitation energy is in the range of 510 nm to 550 nm and the second excitation energy is in the range of 620 nm to 670 nm. In certain embodiments, the first excitation energy is in the range of 550 nm to 580 nm and the second excitation energy is in the range of 580 nm to 620 nm. In certain embodiments, the first excitation energy is in the range of 550 nm to 580 nm and the second excitation energy is in the range of 620 nm to 670 nm. In certain embodiments, the first excitation energy is in the range of 580 nm to 620 nm and the second excitation energy is in the range of 620 nm to 670 nm.

Certain embodiments of excitation energy sources and devices for delivery of excitation energy pulses to a target volume are described elsewhere herein.

Luminescently Labeled Nucleotides

In one aspect, methods and compositions described herein comprises one or more luminescently labeled nucleotides. In certain embodiments, one or more nucleotides comprise deoxyribose nucleosides. In some embodiments, all nucleotides comprises deoxyribose nucleosides. In certain embodiments, one or more nucleotides comprise ribose nucleosides. In some embodiments, all nucleotides comprise ribose nucleosides. In some embodiments, one or more nucleotides comprise a modified ribose sugar or ribose analog (e.g., a locked nucleic acid). In some embodiments, one or more nucleotides comprise naturally occurring bases (e.g., cytosine, guanine, adenine, thymine, uracil). In some embodiments, one or more nucleotides comprise derivatives or analogs of cytosine, guanine, adenine, thymine, or uracil.

In certain embodiments, a method comprises the step of exposing a polymerase complex to a plurality of luminescently labeled nucleotides. In certain embodiments, a composition or device comprises a reaction mixture comprising a plurality of luminescently labeled nucleotides. In some embodiments, the plurality of nucleotides comprises four types of nucleotides. In some embodiments, the four types of nucleotides each comprise one of cytosine, guanine, adenine, and thymine. In some embodiments, the four types of nucleotides each comprise one of cytosine, guanine, adenine, and uracil.

In certain embodiments, the concentration of each type of luminescently labeled nucleotide in the reaction mixture is between about 50 nM and about 200 nM, about 200 nM and about 500 nM, about 500 nM and about 1 µM, about 1 µM and about 50 µM, or about 50 µM and 250 µM. In some embodiments, the concentration of each type of luminescently labeled nucleotide in the reaction mixture is between about 250 nM and about 2 µM. In some embodiments, the concentration of each type of luminescently labeled nucleotide in the reaction mixture is about 1 µM.

In certain embodiments, the reaction mixture contains additional reagents of use for sequencing reactions. In some embodiments, the reaction mixture comprises a buffer. In some embodiments, a buffer comprises 3-(N-morpholino) propanesulfonic acid (MOPS). In some embodiments, a buffer is present in a concentration of between about 1 mM and between about 100 mM. In some embodiments, the concentration of MOPS is about 50 mM. In some embodiments, the reaction mixture comprises one or more salt. In some embodiments, a salt comprises potassium acetate. In some embodiments, the concentration of potassium acetate is about 140 mM. In some embodiments, a salt is present in a concentration of between about 1 mM and about 200 mM. In some embodiments, the reaction mixture comprises a magnesium salt (e.g., magnesium acetate). In some embodiments, the concentration of magnesium acetate is about 20 mM. In some embodiments, a magnesium salt is present in a concentration of between about 1 mM and about 50 mM. In some embodiments, the reaction mixture comprises a reducing agent. In some embodiments, a reducing agent is dithiothreitol (DTT). In some embodiments, a reducing agent is present in a concentration of between about 1 mM and about 50 mM. In some embodiments, the concentration of DTT is about 5 mM. In some embodiments, the reaction mixture comprises one or photostabilizers. In some embodiments, the reaction mixture comprises an anti-oxidant, oxygen scavenger, or triplet state quencher. In some embodiments, a photostabilizer comprises protocatechuic acid (PCA). In some embodiments, a photostabilizer comprises 4-nitrobenzyl alcohol (NBA). In some embodiments, a photostabilizer is present in a concentration of between about 0.1 mM and about 20 mM. In some embodiments, the concentration of PCA is about 3 mM. In some embodiments, the concentration of NBA is about 3 mM. A mixture with a photostabilizer (e.g., PCA) may also comprise an enzyme to regenerate the photostabilizer (e.g., protocatechuic acid dioxygenase (PCD)). In some embodiments, the concentration of PCD is about 0.3 mM.

The application contemplates different methods for differentiating nucleotides amongst a plurality of nucleotides. In certain embodiments, each of the luminescently labeled nucleotides has a different luminescent lifetime. In certain embodiments, two or more of the luminescently labeled nucleotides have the same luminescent lifetimes or substantially the same luminescent lifetimes (e.g., lifetimes that cannot be distinguished by the method or device).

In certain embodiments, each of the luminescently labeled nucleotides absorbs excitation energy in a different spectral range. In certain embodiments, two of the luminescently labeled nucleotides absorb excitation energy in the same spectral range. In certain embodiments, three of the luminescently labeled nucleotides absorb excitation energy in the same spectral range. In certain embodiments, four or more of the luminescently labeled nucleotides absorb excitation energy in the same spectral range. In certain embodiments, two of the luminescently labeled nucleotides absorb excitation energy a different spectral range. In certain embodiments, three of the luminescently labeled nucleotides absorb excitation energy a different spectral range. In certain embodiments, four or more of the luminescently labeled nucleotides absorb excitation energy a different spectral range.

In certain embodiments, each of the luminescently labeled nucleotides emits photons in a different spectral range. In certain embodiments, two of the luminescently labeled nucleotides emits photons in the same spectral range. In certain embodiments, three of the luminescently labeled nucleotides emits photons in the same spectral range. In certain embodiments, four or more of the luminescently labeled nucleotides emits photons in the same spectral range. In certain embodiments, two of the luminescently labeled nucleotides emits photons in the different spectral range. In certain embodiments, three of the luminescently labeled nucleotides emits photons in the different spectral range. In certain embodiments, four or more of the luminescently labeled nucleotides emits photons in the different spectral range.

In certain embodiments, each of four luminescently labeled nucleotides has a different luminescent lifetime. In certain embodiments, two or more luminescently labeled nucleotides have different luminescent lifetimes and absorb and/or emit photons in a first spectral range, and one or more luminescently labeled nucleotides absorb and/or emit photons in a second spectral range. In some embodiments, each of three luminescently labeled nucleotides has a different luminescent lifetime and emit luminescence in a first spectral range, and a fourth luminescently labeled nucleotide absorbs and/or emits photons in a second spectral range. In some embodiments, each of two luminescently labeled nucleotides has a different luminescent lifetime and emit luminescence in a first spectral range, and a third and fourth luminescently labeled nucleotide each have different luminescent lifetimes and emit luminescence in a second spectral range.

In certain embodiments, each of four luminescently labeled nucleotides has a different luminescent intensity. In certain embodiments, two or more luminescently labeled nucleotides have different luminescent intensity and emit luminescence in a first spectral range, and one or more luminescently labeled nucleotides absorbs and/or emits photons in a second spectral range. In some embodiments, each of three luminescently labeled nucleotides has a different luminescent intensity and emit luminescence in a first spectral range, and a fourth luminescently labeled nucleotide absorbs and/or emits photons in a second spectral range. In some embodiments, each of two luminescently labeled nucleotides has a different luminescent intensity and emit luminescence in a first spectral range, and a third and fourth luminescently labeled nucleotide each have different luminescent intensity and emit luminescence in a second spectral range.

In certain embodiments, each of four luminescently labeled nucleotides has a different luminescent lifetime or luminescent intensity. In certain embodiments, two or more luminescently labeled nucleotides have different luminescent lifetime or luminescent intensity and emit luminescence in a first spectral range, and one or more luminescently labeled nucleotides absorbs and/or emits photons in a second spectral range. In some embodiments, each of three luminescently labeled nucleotides has a different luminescent lifetime or luminescent intensity and emit luminescence in a first spectral range, and a fourth luminescently labeled nucleotide absorbs and/or emits photons in a second spectral range. In some embodiments, each of two luminescently labeled nucleotides has a different luminescent lifetime or luminescent intensity and emit luminescence in a first spectral range, and a third and fourth luminescently labeled nucleotide each have different luminescent lifetime or luminescent intensity and emit luminescence in a second spectral range.

In certain embodiments, two or more luminescently labeled nucleotides have different luminescent lifetimes and absorb excitation energy in a first spectral range, and one or more luminescently labeled nucleotides absorbs excitation energy in a second spectral range. In some embodiments, each of three luminescently labeled nucleotides has a different luminescent lifetime and absorb excitation energy in a first spectral range, and a fourth luminescently labeled nucleotide absorbs excitation energy in a second spectral range. In some embodiments, each of two luminescently labeled nucleotides has a different luminescent lifetime and absorb excitation energy in a first spectral range, and a third and fourth luminescently labeled nucleotide each have different luminescent lifetimes and absorb excitation energy in a second spectral range.

In certain embodiments, two or more luminescently labeled nucleotides have different luminescent lifetime or luminescent intensity and absorb excitation energy in a first spectral range, and one or more luminescently labeled nucleotides absorbs excitation energy in a second spectral range. In some embodiments, each of three luminescently labeled nucleotides has a different luminescent lifetime or luminescent intensity and absorb excitation energy in a first spectral range, and a fourth luminescently labeled nucleotide absorbs excitation energy in a second spectral range. In some embodiments, each of two luminescently labeled nucleotides has a different luminescent lifetime or luminescent intensity and absorb excitation energy in a first spectral range, and a third and fourth luminescently labeled nucleotide each have different luminescent lifetime or luminescent intensity and absorb excitation energy in a second spectral range.

During sequencing the method of identifying a nucleotide may vary between various base pairs in the sequence. In certain embodiments, two types of nucleotides may be labeled to absorb at a first excitation energy, and those two types of nucleotides (e.g., A, G) are distinguished based on different luminescent intensity, whereas two additional types of nucleotides (e.g., C, T) may be labeled to absorb at a second excitation energy, and those two additional types of nucleotides are distinguished based on different luminescent lifetime. For such an embodiment, during sequencing certain segments of the sequence may be determined only based on luminescent intensity (e.g., segments incorporating only A and G), whereas other segments of the sequence may be determined only based on luminescent lifetime (e.g., segments incorporating only C and T). In some embodiments, between 2 and 4 luminescently labeled nucleotide are be differentiated based on luminescent lifetime. In some embodiments, between 2 and 4 luminescently labeled nucleotides are differentiated based on luminescent intensity. In some embodiments, between 2 and 4 luminescently labeled nucleotides are differentiated based on luminescent lifetime and luminescent intensity.

FIG. 4 shows the luminescent lifetime 4-1 of exemplary luminescently labeled nucleotides and the luminescent intensity 4-2 for the same exemplary nucleotides. For example, the fourth row shows data for a deoxythymidine hexaphosphate (dT6P) nucleotide linked to the fluorophore Alexa Fluor® 555 (AF555). This luminescently labeled nucleotide has a lifetime of approximately 0.25 ns and displays a luminescent intensity of approximately 20000 counts/s. The observed luminescent lifetime and luminescent intensity of any luminescently labeled nucleotide may, in general, differ for the nucleotide under incorporation conditions (e.g., in a single molecule complex, in a nanoaperture) versus other more typical conditions such as those for 4-1 and 4-2.

Luminescence Detection

In one aspect of methods described herein, an emitted photon (a luminescence) or a plurality of emitted photons is detected by one or more sensors. For a plurality of luminescently labeled molecules or nucleotides, each of the molecules may emit photons in a single spectral range, or a portion of the molecules may emit photons in a first spectral range and another portion of molecules may emit photons in a second spectral range. In certain embodiments, the emitted photons are detected by a single sensor. In certain embodiments, the emitted photons are detected by multiple sensors. In some embodiments, the photons emitted in a first spectral range are detected by a first sensor, and the photons emitted in a second spectral range are detected by a second sensor. In some embodiments, the photons emitted in each of a plurality of spectral ranges are detected by a different sensor.

In certain embodiments, each sensor is configured to assign a time bin to an emitted photon based on the time duration between the excitation energy and the emitted photon. In some embodiments, photons emitted after a shorter time duration will be assigned an earlier time bin, and photons emitted after a longer duration will be assigned a later time bin. In some embodiments, a plurality of pulses of excitation energy is delivered to vicinity of a target volume and a plurality of photons, which may include photon emission events, are detected. In some embodiments, the plurality of luminescences (e.g., photon emission events) correspond to incorporation of a luminescently labeled nucleotide into a nucleic acid product. In some embodiments, the incorporation of a luminescently labeled nucleotide lasts for between about 1 ms and about 5 ms, between about 5 ms and about 20 ms, between about 20 ms and about 100 ms, or between about 100 ms and about 500 ms. In some embodiments, between about 10 and about 100, between about 100 and about 1000, about 1000 and about 10000, or about 10000 and about 100000 luminescences are detected during incorporation of a luminescently labeled nucleotide.

In certain embodiments, there are no luminescences detected if a luminescently labeled nucleotide is not being incorporated. In some embodiments, there is a luminescence background. In some embodiments, spurious luminescences are detected when no luminescently labeled nucleotide is being incorporated. Such spurious luminescences may occur if one or more luminescently labeled nucleotides is in the target volume (e.g., diffuses into the target volume, or interacts with polymerase but is not incorporated) during a pulse of excitation energy, but is not being incorporated by the sequencing reaction. In some embodiments, the plurality of luminescences detected from a luminescently labeled nucleotide in the target volume but not being incorporated is smaller (e.g., ten times, 100 times, 1000 times, 10000 times) than the plurality of luminescences from a luminescently labeled nucleotide.

In some embodiments, for each plurality of detected luminescences corresponding to incorporation of a luminescently labeled nucleotide the luminescences are assigned a time bin based on the time duration between the pulse and the emitted photon. This plurality for an incorporation event is referred to herein as a "burst". In some embodiments, a burst refers to a series of signals (e.g., measurements) above a baseline (e.g., noise threshold value), wherein the signals correspond to a plurality of emission events that occur when the luminescently labeled nucleotide is within the excitation region. In some embodiments, a burst is separated from a preceding and/or subsequent burst by a time interval of signals representative of the baseline. In some embodiments, the burst is analyzed by determining the luminescent lifetime based on the plurality of time durations. In some embodiments, the burst is analyzed by determining the luminescent intensity based on the number of detected luminescences per a unit of time. In some embodiments, the burst is analyzed by determining the spectral range of the detected luminescences. In some embodiments, analyzing the burst data will allow assignment of the identity of the incorporated luminescently labeled nucleotide, or allow one or more luminescently labeled nucleotides to be differentiated from amongst a plurality of luminescently labeled nucleotides. The assignment or differentiation may rely on any one of luminescent lifetime, luminescent intensity, spectral range of the emitted photons, or any combination thereof.

FIG. 5 depicts the sequencing of an exemplary template nucleic acid. The sequencing experiment was run with 4 luminescently labeled nucleotides: deoxyadeno sine linked to Alexa Fluor® 647 (A-AF647), dexoythymidine linked to Alex Fluor 555 (T-AF555), deoxyguanidine linked to DyLight® 554-R1 (G-D554R1), and dexoycytidine linked to DyLight® 530-R2 (C-D530R2). The nucleotide A-AF647 is excited by excitation energy in the red spectral range, and T, G, and C nucleotides are excited by excitation in the green spectral range. The number of photons detected over ~200 s of a sequencing reaction are shown in an intensity trace 5-1. Each spike corresponds to a burst of detected luminescences and is marked with a dot. Each burst may correspond to the incorporation of a luminescently labeled nucleotide, and comprises thousands of detected luminescences. Different colored traces can be utilized to denote different excitation pulses. For example, a purple trace can be used for green excitation pulses, and a blue trace can be used for red excitation pulses. Bursts from the blue trace can be assigned to the incorporation of the nucleotide A-AF647 (the only nucleotide with red luminescent molecule in this example). FIG. 5 shows one way of reducing the raw data to differentiate bursts of the same color (e.g., bursts in the purple trace between T, G, and C) using an intensity versus lifetime plot 5-2. Each circle represents a burst from the purple trace. Each burst has been analyzed to determine the luminescent lifetime of the luminescently labeled nucleotide based on the time duration between pulse and emission of each detected photon. Additionally, each burst has been analyzed to determine the luminescent intensity of the luminescently labeled nucleotide based on the number of detected photons per second. The incorporation events are clustered in three groups corresponding to each of the three luminescently labeled nucleotides. The dark cluster in the lower portion of the plot (area of the plot below the dashed line) is assigned to C-D530R2 which has the longest luminescent lifetime and the lowest luminescent intensity. The light cluster in the lower portion of the plot (area of the plot below the dashed line) is assigned to G-D554R1 which has the intermediate lifetime and intensity. And the light cluster in the upper portion of the plot (area of the plot above the dashed line) is assigned to T-AF555 which has the shortest lifetime and highest intensity. FIG. 5 shows the alignment 5-3 between the sequence determined from the data and the known sequence of the template nucleic acid. Vertical bars indicate a match between the experimentally determined base and the target sequence. Dashes indicate a position in the template sequence for which no nucleotide was assigned in the determined sequence, or an extra position in the determined sequence which does not correspond to any position in the template sequence.

FIG. 6 depicts a second example for sequencing of a template nucleic acid. The sequencing experiment was run with 4 luminescently labeled nucleotides: deoxyadenosine linked to Alexa Fluor® 647 (A-AF647), dexoythymidine linked to Alex Fluor 555 (T-AF555), deoxyguanidine linked to Alexa Fluor® 647 (G-AF647), and a dexoycytidine linked to Alexa Fluor® 546 (C-AF546). The nucleotides A-AF647 and G-AF647 are excited by excitation energy in the red spectral range, and T and C nucleotides are excited by excitation in the green spectral range. In this experiment, A and G have the same luminescent marker, and are not discriminated. FIG. 6 shows the number of photons detected over ~300 s of a sequencing reaction in an intensity trace 6-1. Each spike corresponds to a burst of detected luminescences and is marked with a dot. Each burst may correspond to the incorporation of a luminescently labeled nucleotide, and comprises thousands of detected luminescences. The trace shows detected luminescences for green excitation pulses (corresponding to bases T and C). FIG. 6 shows one way of reducing the raw data to differentiate T and C using an intensity versus lifetime plot 6-2. Each circle represents a burst from the intensity trace 6-1. Each burst has been analyzed to determine the luminescent lifetime of the luminescently labeled nucleotide based on the time duration between pulse and emission of each detected photon. Additionally each burst has been analyzed to determine the luminescent intensity of the luminescently labeled nucleotide based on the number of detected photons per second. The incorporation events are clustered in two groups corresponding to each of the two luminescently labeled nucleotides. The dark cluster in the right portion of the plot (area of the plot to the right of the dashed line) is assigned to C-AF546 which has the longest luminescent lifetime and the lowest luminescent intensity. The light cluster in the right portion of the plot (area of the plot to the right of the dashed line) is assigned to T-AF555 which has the shortest lifetime and highest intensity. FIG. 6 shows the alignment 6-3 between the sequence determined from the data and the known sequence of the template nucleic acid. Vertical bars indicate a match between the experimentally determined base and the target sequence. Dashes indicate a position in the template sequence for which no nucleotide was assigned in the determined sequence, or an extra position in the determined sequence which does not correspond to any position in the template sequence.

In some embodiments, one or more components of a sequencing reaction can be prepared and used in a sample well, as depicted in the non-limiting embodiments shown in FIGS. 7-9, for example, for the analysis of luminescent labels in the context of a sequencing reaction.

Luminescent Labels

The terms luminescent tag, luminescent label and luminescent marker are used interchangeably throughout, and relate to molecules comprising one or more luminescent molecules. In certain embodiments, the incorporated molecule is a luminescent molecule, e.g., without attachment of a distinct luminescent label. Typical nucleotide and amino acids are not luminescent, or do not luminesce within suitable ranges of excitation and emission energies. In certain embodiments, the incorporated molecule comprises a luminescent label. In certain embodiments, the incorporated molecule is a luminescently labeled nucleotide. In certain embodiments, the incorporated molecule is a luminescently labeled amino acid or luminescently labeled tRNA. In some embodiments, a luminescently labeled nucleotide comprises a nucleotide and a luminescent label. In some embodiments, a luminescently labeled nucleotide comprises a nucleotide, a luminescent label, and a linker. In some embodiments, the luminescent label is a fluorophore.

In certain embodiments, the luminescent label, and optionally the linker, remain attached to the incorporated molecule. In certain embodiments, the luminescent label, and optionally the linker, are cleaved from the molecule during or after the process of incorporation.

In certain embodiments, the luminescent label is a cyanine dye, or an analog thereof. In some embodiments, the cyanine dye is of formula:

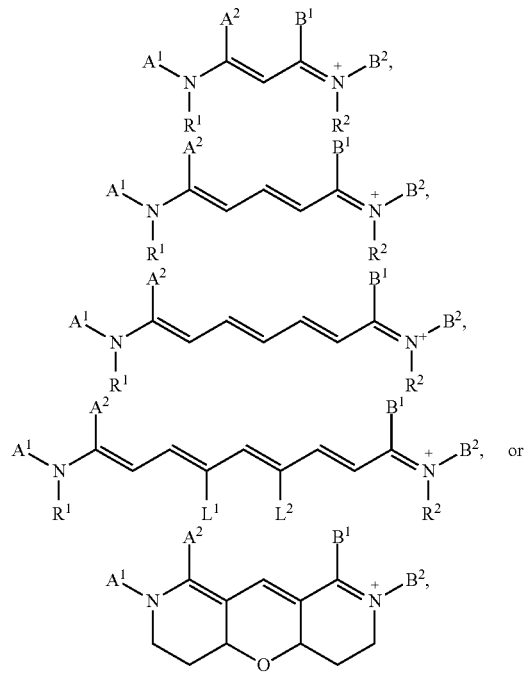

or a salt, stereoisomer, or tautomer thereof, wherein:

$A^1$ and $A^2$ are joined to form an optionally substituted, aromatic or non-aromatic, monocyclic or polycyclic, heterocyclic ring;

$B^1$ and $B^2$ are joined to form an optionally substituted, aromatic or non-aromatic, monocyclic or polycyclic, heterocyclic ring;

each of $R^1$ and $R^2$ is independently hydrogen, optionally substituted alkyl; and each of $L^1$ and $L^2$ is independently hydrogen, optionally substituted alkyl, or $L^1$ and $L^2$ are joined to form an optionally substituted, aromatic or non-aromatic, monocyclic or polycyclic, carbocyclic ring.

In certain embodiments, the luminescent label is a rhodamine dye, or an analog thereof. In some embodiments, the rhodamine dye is of formula:

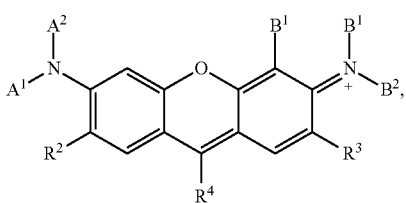

or a salt, stereoisomer, or tautomer thereof, wherein:
  each of $A^1$ and $A^2$ is independently hydrogen, optionally substituted alkyl, optionally substituted aromatic or non-aromatic heterocyclyl, optionally substituted aromatic or non-aromatic carbocyclyl, or optionally substituted carbonyl, or $A^1$ and $A^2$ are joined to form an optionally substituted, aromatic or non-aromatic, monocyclic or polycyclic, heterocyclic ring;
  each of $B^1$ and $B^2$ is independently hydrogen, optionally substituted alkyl, optionally substituted, aromatic or non-aromatic heterocyclyl, optionally substituted, aromatic or non-aromatic carbocyclyl, or optionally substituted carbonyl, or $B^1$ and $B^2$ are joined to form an optionally substituted, aromatic or non-aromatic, monocyclic or polycyclic, heterocyclic ring;
  each of $R^2$ and $R^3$ is independently hydrogen, optionally substituted alkyl, optionally substituted aryl, or optionally substituted acyl; and
  $R^4$ is hydrogen, optionally substituted alkyl, optionally substituted, optionally substituted aromatic or non-aromatic heterocyclyl, optionally substituted aromatic or non-aromatic carbocyclyl, or optionally substituted carbonyl.

In some embodiments, $R^4$ is optionally substituted phenyl. In some embodiments, $R^4$ is optionally substituted phenyl, wherein at least one substituent is optionally substituted carbonyl. In some embodiments, $R^4$ is optionally substituted phenyl, wherein at least one substituent is optionally substituted sulfonyl.

Typically, the luminescent label comprises an aromatic or heteroaromatic compound and can be a pyrene, anthracene, naphthalene, acridine, stilbene, indole, benzindole, oxazole, carbazole, thiazole, benzothiazole, phenanthridine, phenoxazine, porphyrin, quinoline, ethidium, benzamide, cyanine, carbocyanine, salicylate, anthranilate, coumarin, fluoroscein, rhodamine or other like compound. Exemplary dyes include xanthene dyes, such as fluorescein or rhodamine dyes, including 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N', N'-tetramethyl-6-carboxyrhodamine (TAMRA), 6-carboxy-X-rhodamine (ROX). Exemplary dyes also include naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS). Other exemplary dyes include coumarins, such as 3-phenyl-7-isocyanatocoumarin; acridines, such as 9-isothiocyanatoacridine and acridine orange; N-(p-(2-benzoxazolyl)phenyl)maleimide; cyanines, such as indodicarbocyanine 3 (Cy®3), (2Z)-2-[(E)-3-[3-(5-carboxypentyl)-1,1-dimethyl-6,8-disulfobenzo[e]indol-3-ium-2-yl]prop-2-enylidene]-3-ethyl-1,1-dimethyl-8-(trioxidanylsulfanyl)benzo[e]indole-6-sulfonate (Cy®3.5), 2-{2-[(2,5-dioxopyrrolidin-1-yl)oxy]-2-oxoethyl}-16,16,18,18-tetramethyl-6,7,7a,8a,9,10,16,18-octahydrobenzo[2'',3''] indolizino[8'',7'':5',6']pyrano[3',2':3,4]pyrido[1,2-a]indol-5-ium-14-sulfonate (Cy®3B), indodicarbocyanine 5 (Cy®5), indodicarbocyanine 5.5 (Cy®5.5), 3-(-carboxy-pentyl)-3'-ethyl-5,5'-dimethyloxacarbocyanine (CyA); 1H,5H,11H, 15H-Xantheno[2,3,4-ij:5,6,7-i'j']diquinolizin-18-ium, 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16,17-octahydro-inner salt (TR or Texas Red®); BODIPY® dyes; benzoxazoles; stilbenes; pyrenes; and the like.

For nucleotide sequencing, certain combinations of luminescently labeled nucleotides may be preferred. In some embodiments, at least one of the luminescently labeled nucleotides comprises a cyanine dye, or analog thereof. In some embodiments, at least one luminescently labeled nucleotides comprises a rhodamine dye, or analog thereof. In some embodiments, at least two luminescently labeled nucleotides each comprise a cyanine dye, or analog thereof. In some embodiments, at least two luminescently labeled nucleotides each comprise a rhodamine dye, or analog thereof. In some embodiments, at least three luminescently labeled nucleotides each comprise a cyanine dye, or analog thereof. In some embodiments, at least three luminescently labeled nucleotides each comprise a rhodamine dye, or analog thereof. In some embodiments, at least four luminescently labeled nucleotides each comprise a cyanine dye, or analog thereof. In some embodiments, at least four luminescently labeled nucleotides each comprise a rhodamine dye, or analog thereof. In some embodiments, three luminescently labeled nucleotides comprise a cyanine dye, or analog thereof, and a fourth luminescently labeled nucleotide comprises a rhodamine dye, or analog thereof. In some embodiments, two luminescently labeled nucleotides comprise a cyanine dye, or analog thereof, and a third, and optionally a fourth, luminescently labeled nucleotide comprises a rhodamine dye, or analog thereof. In some embodiments, three luminescently labeled nucleotides comprise a rhodamine dye, or analog thereof, and a third, and optionally a fourth, luminescently labeled nucleotide comprises a cyanine dye, or analog thereof.

In some embodiments, at least one labeled nucleotides is linked to two or more dyes (e.g., two or more copies of the same dye and/or two or more different dyes).

In some embodiments, at least two luminescently labeled nucleotides absorb a first excitation energy, wherein at least one of the luminescently labeled nucleotides comprises a cyanine dye, or analog thereof, and at least one of the luminescently labeled nucleotides comprises a rhodamine dye, or an analog thereof. In some embodiments, at least two luminescently labeled nucleotides absorb a second excitation energy, wherein at least one of the luminescently labeled nucleotides comprises a cyanine dye, or analog thereof, and at least one of the luminescently labeled nucleotides comprises a rhodamine dye, or an analog thereof. In some embodiments, at least two luminescently labeled nucleotides absorb a first excitation energy, wherein at least one of the luminescently labeled nucleotides comprises a cyanine dye, or analog thereof, and at least one of the luminescently labeled nucleotides comprises a rhodamine dye, or an analog thereof, and at least two additional luminescently labeled nucleotides absorb a second excitation energy, wherein at least one of the luminescently labeled nucleotides comprises a cyanine dye, or analog thereof, and at least one of the luminescently labeled nucleotides comprises a rhodamine dye, or an analog thereof.

In some embodiments, at least two luminescently labeled nucleotides absorb a first excitation energy, wherein at least one of the luminescently labeled nucleotides has a luminescent lifetime of less than about 1 ns, and at least one of the luminescently labeled nucleotides has a luminescent lifetime of greater than 1 ns. In some embodiments, at least two luminescently labeled nucleotides absorb a second excitation energy, wherein at least one of the luminescently labeled nucleotides has a luminescent lifetime of less than about 1 ns, and at least one of the luminescently labeled nucleotides has a luminescent lifetime of greater than 1 ns. In some embodiments, at least two luminescently labeled nucleotides absorb a first excitation energy, wherein at least one of the luminescently labeled nucleotides has a luminescent lifetime of less than about 1 ns, and at least one of the luminescently labeled nucleotides has a luminescent lifetime of greater than 1 ns, and at least additional two luminescently labeled nucleotides absorb a second excitation energy, wherein at least one of the luminescently labeled nucleotides has a luminescent lifetime of less than about 1 ns, and at least one of the luminescently labeled nucleotides has a luminescent lifetime of greater than 1 ns.

In certain embodiments, the luminescent label is a dye selected from Table 1. The dyes listed in Table 1 are non-limiting, and the luminescent labels of the application may include dyes not listed in Table 1. In certain embodiments, the luminescent labels of one or more luminescently labeled nucleotides is selected from Table 1. In certain embodiments, the luminescent labels of four or more luminescently labeled nucleotides is selected from Table 1.

TABLE 1

Exemplary fluorophores. Fluorophores

| | | |
|---|---|---|
| 5/6-Carboxyrhodamine 6G | Chromis 678C | DyLight ® 655-B1 |
| 5-Carboxyrhodamine 6G | Chromis 678Z | DyLight ® 655-B2 |
| 6-Carboxyrhodamine 6G | Chromis 770A | DyLight ® 655-B3 |
| 6-TAMRA | Chromis 770C | DyLight ® 655-B4 |
| Alexa Fluor ® 350 | Chromis 800A | DyLight ® 662Q |
| Alexa Fluor ® 405 | Chromis 800C | DyLight ® 675-B1 |
| Alexa Fluor ® 430 | Chromis 830A | DyLight ® 675-B2 |
| Alexa Fluor ® 480 | Chromis 830C | DyLight ® 675-B3 |
| Alexa Fluor ® 488 | Cy ® 3 | DyLight ® 675-B4 |
| Alexa Fluor ® 514 | Cy ® 3.5 | DyLight ® 679-C5 |
| Alexa Fluor ® 532 | Cy ® 3B | DyLight ® 680 |
| Alexa Fluor ® 546 | Cy ® 5 | DyLight ® 683Q |
| Alexa Fluor ® 555 | Dyomics-350 | DyLight ® 690-B1 |
| Alexa Fluor ® 568 | Dyomics-350XL | DyLight ® 690-B2 |
| Alexa Fluor ® 594 | Dyomics-360XL | DyLight ® 696Q |
| Alexa Fluor ® 610-X | Dyomics-370XL | DyLight ® 700-B1 |
| Alexa Fluor ® 633 | Dyomics-375XL | DyLight ® 700-B1 |
| Alexa Fluor ® 647 | Dyomics-380XL | DyLight ® 730-B1 |
| Alexa Fluor ® 660 | Dyomics-390XL | DyLight ® 730-B2 |
| Alexa Fluor ® 680 | Dyomics-405 | DyLight ® 730-B3 |
| Alexa Fluor ® 700 | Dyomics-415 | DyLight ® 730-B4 |
| Alexa Fluor ® 750 | Dyomics-430 | DyLight ® 747 |
| Alexa Fluor ® 790 | Dyomics-431 | DyLight ® 747-B1 |
| AMCA | Dyomics-478 | DyLight ® 747-B2 |
| ATTO 390 | Dyomics-480XL | DyLight ® 747-B3 |
| ATTO 425 | Dyomics-481XL | DyLight ® 747-B4 |
| ATTO 465 | Dyomics-485XL | DyLight ® 755 |
| ATTO 488 | Dyomics-490 | DyLight ® 766Q |
| ATTO 495 | Dyomics-495 | DyLight ® 775-B2 |
| ATTO 514 | Dyomics-505 | DyLight ® 775-B3 |
| ATTO 520 | Dyomics-510XL | DyLight ® 775-B4 |
| ATTO 532 | Dyomics-511XL | DyLight ® 780-B1 |
| ATTO 542 | Dyomics-520XL | DyLight ® 780-B2 |
| ATTO 550 | Dyomics-521XL | DyLight ® 780-B3 |
| ATTO 565 | Dyomics-530 | DyLight ® 800 |
| ATTO 590 | Dyomics-547 | DyLight ® 830-B2 |
| ATTO 610 | Dyomics-547P1 | eFluor ® 450 |
| ATTO 620 | Dyomics-548 | Eosin |
| ATTO 633 | Dyomics-549 | FITC |
| ATTO 647 | Dyomics-549P1 | Fluorescein |
| ATTO 647N | Dyomics-550 | HiLyte ™ Fluor 405 |

TABLE 1-continued

Exemplary fluorophores. Fluorophores

| | | |
|---|---|---|
| ATTO 655 | Dyomics-554 | HiLyte ™ Fluor 488 |
| ATTO 665 | Dyomics-555 | HiLyte ™ Fluor 532 |
| ATTO 680 | Dyomics-556 | HiLyte ™ Fluor 555 |
| ATTO 700 | Dyomics-560 | HiLyte ™ Fluor 594 |
| ATTO 725 | Dyomics-590 | HiLyte ™ Fluor 647 |
| ATTO 740 | Dyomics-591 | HiLyte ™ Fluor 680 |
| ATTO Oxa12 | Dyomics-594 | HiLyte ™ Fluor 750 |
| ATTO Rho101 | Dyomics-601XL | IRDye ® 680LT |
| ATTO Rho11 | Dyomics-605 | IRDye ® 750 |
| ATTO Rho12 | Dyomics-610 | IRDye ® 800CW |
| ATTO Rho13 | Dyomics-615 | JOE |
| ATTO Rho14 | Dyomics-630 | LightCycler ® 640R |
| ATTO Rho3B | Dyomics-631 | LightCycler ® Red 610 |
| ATTO Rho6G | Dyomics-632 | LightCycler ® Red 640 |
| ATTO Thio12 | Dyomics-633 | LightCycler ® Red 670 |
| BD Horizon ™ V450 | Dyomics-634 | LightCycler ® Red 705 |
| BODIPY ® 493/501 | Dyomics-635 | Lissamine Rhodamine B |
| BODIPY ® 530/550 | Dyomics-636 | Napthofluorescein |
| BODIPY ® 558/568 | Dyomics-647 | Oregon Green ® 488 |
| BODIPY ® 564/570 | Dyomics-647P1 | Oregon Green ® 514 |
| BODIPY ® 576/589 | Dyomics-648 | Pacific Blue ™ |
| BODIPY ® 581/591 | Dyomics-648P1 | Pacific Green ™ |
| BODIPY ® 630/650 | Dyomics-649 | Pacific Orange ™ |
| BODIPY ® 650/665 | Dyomics-649P1 | PET |
| BODIPY ® FL | Dyomics-650 | PF350 |
| BODIPY ® FL-X | Dyomics-651 | PF405 |
| BODIPY ® R6G | Dyomics-652 | PF415 |
| BODIPY ® TMR | Dyomics-654 | PF488 |
| BODIPY ® TR | Dyomics-675 | PF505 |
| C5.5 | Dyomics-676 | PF532 |
| C7 | Dyomics-677 | PF546 |
| CAL Fluor ® Gold 540 | Dyomics-678 | PF555P |
| CAL Fluor ® Green 510 | Dyomics-679P1 | PF568 |
| CAL Fluor ® Orange 560 | Dyomics-680 | PF594 |
| CAL Fluor ® Red 590 | Dyomics-681 | PF610 |
| CAL Fluor ® Red 610 | Dyomics-682 | PF633P |
| CAL Fluor ® Red 615 | Dyomics-700 | PF647P |
| CAL Fluor ® Red 635 | Dyomics-701 | Quasar ® 570 |
| Cascade ® Blue | Dyomics-703 | Quasar ® 670 |
| CF ™ 350 | Dyomics-704 | Quasar ® 705 |
| CF ™ 405M | Dyomics-730 | Rhoadmine 123 |
| CF ™ 405S | Dyomics-731 | Rhodamine 6G |
| CF ™ 488A | Dyomics-732 | Rhodamine B |
| CF ™ 514 | Dyomics-734 | Rhodamine Green |
| CF ™ 532 | Dyomics-749 | Rhodamine Green-X |
| CF ™ 543 | Dyomics-749P1 | Rhodamine Red |
| CF ™ 546 | Dyomics-750 | ROX |
| CF ™ 555 | Dyomics-751 | ROX |
| CF ™ 568 | Dyomics-752 | Seta ™ 375 |
| CF ™ 594 | Dyomics-754 | Seta ™ 470 |
| CF ™ 620R | Dyomics-776 | Seta ™ 555 |
| CF ™ 633 | Dyomics-777 | Seta ™ 632 |
| CF ™ 633-V1 | Dyomics-778 | Seta ™ 633 |
| CF ™ 640R | Dyomics-780 | Seta ™ 650 |
| CF ™ 640R-V1 | Dyomics-781 | Seta ™ 660 |
| CF ™ 640R-V2 | Dyomics-782 | Seta ™ 670 |
| CF ™ 660C | Dyomics-800 | Seta ™ 680 |
| CF ™ 660R | Dyomics-831 | Seta ™ 700 |
| CF ™ 680 | DyLight ® 350 | Seta ™ 750 |
| CF ™ 680R | DyLight ® 405 | Seta ™ 780 |
| CF ™ 680R-V1 | DyLight ® 415-Co1 | Seta ™ APC-780 |
| CF ™ 750 | DyLight ® 425Q | Seta ™ PerCP-680 |
| CF ™ 770 | DyLight ® 485-LS | Seta ™ R-PE-670 |
| CF ™ 790 | DyLight ® 488 | Seta ™ 646 |
| Chromeo ™ 642 | DyLight ® 504Q | Seta ™ u 380 |
| Chromis 425N | DyLight ® 510-LS | Seta ™ u 425 |
| Chromis 500N | DyLight ® 515-LS | Seta ™ u 647 |
| Chromis 515N | DyLight ® 521-LS | Seta ™ u 405 |
| Chromis 530N | DyLight ® 530-R2 | Sulforhodamine 101 |
| Chromis 550A | DyLight ® 543Q | TAMRA |
| Chromis 550C | DyLight ® 550 | TET |
| Chromis 550Z | DyLight ® 554-R0 | Texas Red ® |
| Chromis 560N | DyLight ® 554-R1 | TMR |
| Chromis 570N | DyLight ® 590-R2 | TRITC |
| Chromis 577N | DyLight ® 594 | Yakima Yellow ™ |

TABLE 1-continued

Exemplary fluorophores.
Fluorophores

| | | |
|---|---|---|
| Chromis 600N | DyLight ® 610-B1 | Zenon ® |
| Chromis 630N | DyLight ® 615-B2 | Zy3 |
| Chromis 645A | DyLight ® 633 | Zy5 |
| Chromis 645C | DyLight ® 633-B1 | Zy5.5 |
| Chromis 645Z | DyLight ® 633-B2 | Zy7 |
| Chromis 678A | DyLight ® 650 | Abberior ® ® Star 635 |
| Square 635 | Square 650 | Square 660 |
| Square 672 | Square 680 | Abberior ® Star 440SXP |
| Abberior ® Star 470SXP | Abberior ® Star 488 | Abberior ® Star 512 |
| Abberior ® Star 520SXP | Abberior ® Star 580 | Abberior ® Star 600 |
| Abberior ® Star 635 | Abberior ® Star 635P | Abberior ® Star RED |

Dyes may also be classified based on the wavelength of maximum absorbance or emitted luminescence. Table 2 provides exemplary fluorophores grouped into columns according to approximate wavelength of maximum absorbance. The dyes listed in Table 2 are non-limiting, and the luminescent labels of the application may include dyes not listed in Table 2. The exact maximum absorbance or emission wavelength may not correspond to the indicated spectral ranges. In certain, embodiments, the luminescent labels of one or more luminescently labeled nucleotides is selected from the "Red" group listed in Table 2. In certain embodiments, the luminescent labels of one or more luminescently labeled nucleotides is selected from the "Green" group listed in Table 2. In certain embodiments, the luminescent labels of one or more luminescently labeled nucleotides is selected from the "Yellow/Orange" group listed in Table 2. In certain embodiments, the luminescent labels of four nucleotides are selected such that all are selected from one of the "Red", "Yellow/Orange", or "Green" group listed in Table 2. In certain embodiments, the luminescent labels of four nucleotides are selected such that three are selected from a first group of the "Red", "Yellow/Orange", and "Green" groups listed in Table 2, and the fourth is selected from a second group of the "Red", "Yellow/Orange", and "Green" groups listed in Table 2. In certain embodiments, the luminescent labels of four nucleotides are selected such that two are selected from a first of the "Red", "Yellow/Orange", and "Green" group listed in Table 2, and the third and fourth are selected from a second group of the "Red", "Yellow/Orange", and "Green" groups listed in Table 2. In certain embodiments, the luminescent labels of four nucleotides are selected such that two are selected from a first of the "Red", "Yellow/Orange", and "Green" groups listed in Table 2, and a third is selected from a second group of the "Red", "Yellow/Orange", and "Green" groups listed in Table 2, and a fourth is selected from a third group of the "Red", "Yellow/Orange", and "Green" groups listed in Table 2.

TABLE 2

Exemplary fluorophores by spectral range.

| "Green" 520-570 nm | "Yellow/Orange" 570-620 nm | "Red" 620-670 nm |
|---|---|---|
| 5/6-Carboxyrhoadmine 6G | Alexa Fluor ® 594 | Alexa Fluor ® 633 |
| 6-TAMRA | Alexa Fluor ® 610-X | Alexa Fluor ® 647 |
| Alexa Fluor ® 532 | ATTO 590 | Alexa Fluor ® 660 |
| Alexa Fluor ® 546 | ATTO 610 | ATTO 633 |
| Alexa Fluor ® 555 | ATTO 620 | ATTO 647 |
| Alexa Fluor ® 568 | BODIPY ® 576/589 | ATTO 647N |
| ATTO 520 | BODIPY ® 581/591 | ATTO 655 |

TABLE 2-continued

Exemplary fluorophores by spectral range.

| "Green" 520-570 nm | "Yellow/Orange" 570-620 nm | "Red" 620-670 nm |
|---|---|---|
| ATTO 532 | CF ™ 594 | ATTO 665 |
| ATTO 542 | CF ™ 620R | ATTO 680 |
| ATTO 550 | Chromis 570N | ATTO Rho14 |
| ATTO 565 | Chromis 577N | BODIPY ® 630/650 |
| BODIPY ® 530/550 | Chromis 600N | BODIPY ® 650/665 |
| BODIPY ® 558/568 | Dyomics-590 | CAL Fluor ® Red 635 |
| BODIPY ® 564/570 | Dyomics-591 | CF ™ 633-V1 |
| CF ™ 514 | Dyomics-594 | CF ™ 640R-V1 |
| CF ™ 532 | Dyomics-601XL | CF ™ 633 |
| CF ™ 543 | Dyomics-605 | CF ™ 640R |
| CF ™ 546 | Dyomics-610 | CF ™ 640R-V2 |
| CF ™ 555 | Dyomics-615 | CF ™ 660C |
| CF ™ 568 | DyLight ® 590-R2 | CF ™ 660R |
| Chromis 530N | DyLight ® 594 | CF ™ 680 |
| Chromis 550A | DyLight ® 610-B1 | CF ™ 680R |
| Chromis 550C | DyLight ® 615-B2 | CF ™ 680R-V1 |
| Chromis 550Z | HiLyte ™ Fluor 594 | Chromeo ™ 642 |
| Chromis 560N | LightCycler ® ® Red 610 | Chromis 630N |
| Cy ® 3 | PF594 | Chromis 645A |
| Cy ® 3.5 | PF594 | Chromis 645A |
| Cy ® 3B | PF610 | Chromis 645C |
| Dyomics-530 | Quasar ® 570 | Chromis 645Z |
| Dyomics-547 | Abberior ® Star 580 | Cy ® 5 |
| Dyomics-547P1 | Abberior ® Star 600 | Cy ® 5.5 |
| Dyomics-548 | | Dyomics-630 |
| Dyomics-549P1 | | Dyomics-631 |
| Dyomics-550 | | Dyomics-632 |
| Dyomics-554 | | Dyomics-633 |
| Dyomics-555 | | Dyomics-634 |
| Dyomics-556 | | Dyomics-635 |
| Dyomics-560 | | Dyomics-636 |
| DyLight ® 521-LS | | Dyomics-647 |
| DyLight ® 530-R2 | | Dyomics-647P1 |
| DyLight ® 543Q | | Dyomics-648 |
| DyLight ® 550 | | Dyomics-648P1 |
| DyLight ® 554-R0 | | Dyomics-649 |
| DyLight ® 554-R1 | | Dyomics-649P1 |
| HiLyte ™ Fluor 532 | | Dyomics-650 |
| HiLyte ™ Fluor 555 | | Dyomics-651 |
| PF532 | | Dyomics-652 |
| PF546 | | Dyomics-654 |
| PF555P | | DyLight ® 633 |
| PF568 | | DyLight ® 633-B1 |
| Seta ™ 555 | | DyLight ® 633-B2 |
| Abberior ® Star 520SXP | | DyLight ® 650 |
| | | DyLight ® 655-B1 |
| | | DyLight ® 655-B2 |
| | | DyLight ® 655-B3 |
| | | DyLight ® 655-B4 |
| | | DyLight ® 662Q |
| | | DyLight ® 680 |
| | | DyLight ® 683Q |
| | | HiLyte ™ Fluor 647 |
| | | HiLyte ™ Fluor 680 |
| | | LightCycler ® ® 640R |
| | | LightCycler ® Red 640 |
| | | LightCycler ® Red 670 |
| | | PF633P |
| | | PF647P |
| | | Quasar ® 670 |
| | | Seta ™ 632 |
| | | Seta ™ 633 |
| | | Seta ™ 650 |
| | | Seta ™ 660 |
| | | Seta ™ 670 |
| | | Seta ™ Tau 647 |
| | | Square 635 |
| | | Square 650 |
| | | Square 660 |

TABLE 2-continued

Exemplary fluorophores by spectral range.

| "Green" 520-570 nm | "Yellow/Orange" 570-620 nm | "Red" 620-670 nm |
|---|---|---|
| | | Abberior ® Star 635 |
| | | Abberior ® Star 635P |
| | | Abberior ® Star RED |

In certain embodiments, the luminescent label may be (Dye 101), (Dye 102), (Dye 103), (Dye 104), (Dye 105), or (Dye 106), of formulae (in NHS ester form):

(Dye 101)
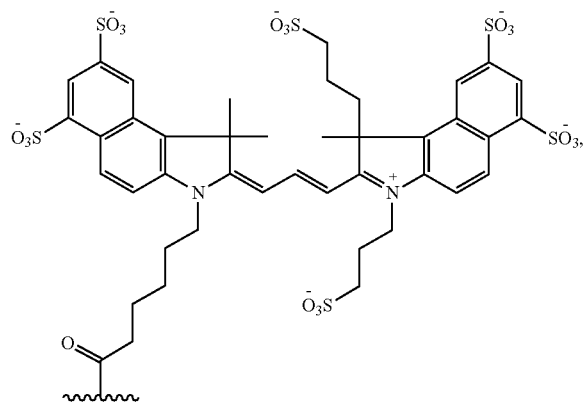

(Dye 102)
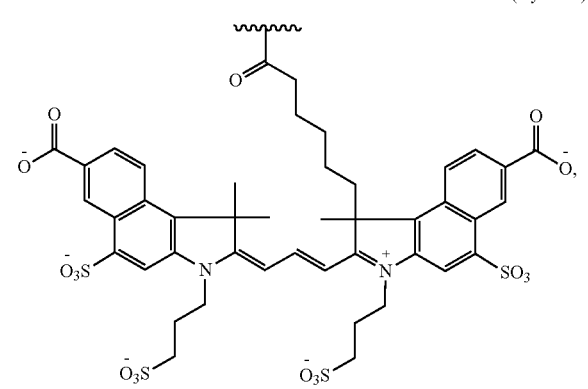

(Dye 103)
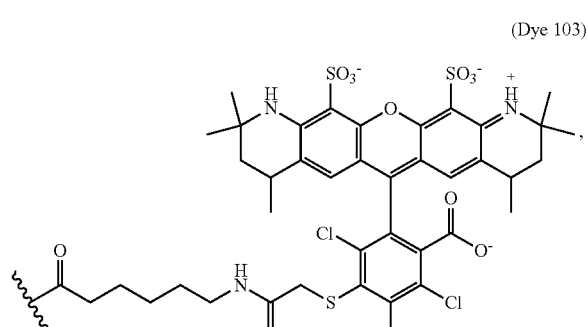

(Dye 104)
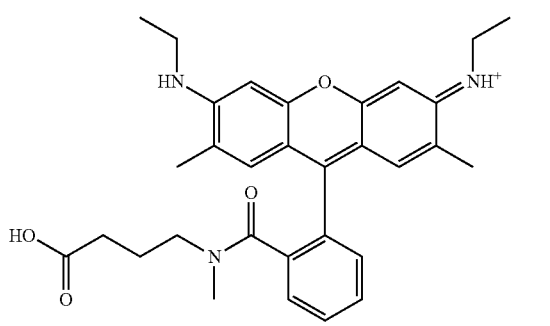

(Dye 105)
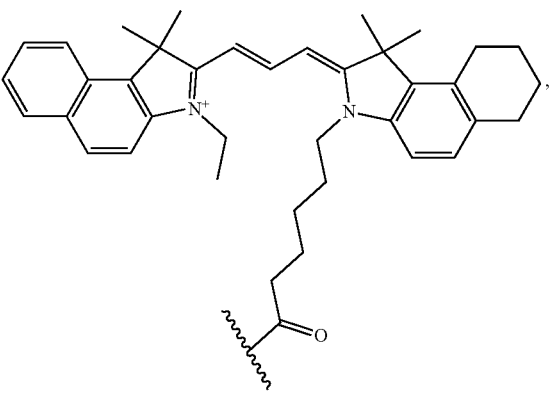

(Dye 106)
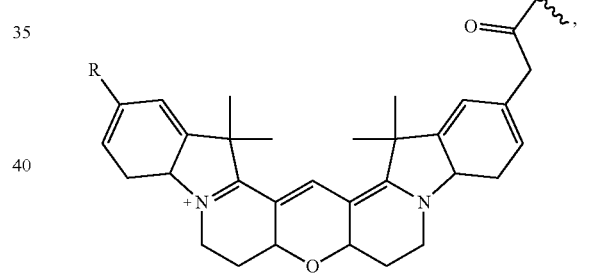

or an analog thereof. In some embodiments, each sulfonate or carboxylate is independently optionally protonated. In some embodiments, the dyes above are attached to the linker or nucleotide by formation of an amide bond at the indicated point of attachment.

In certain embodiments, the luminescent label may comprise a first and second chromophore. In some embodiments, an excited state of the first chromophore is capable of relaxation via an energy transfer to the second chromophore. In some embodiments, the energy transfer is a Förster resonance energy transfer (FRET). Such a FRET pair may be useful for providing a luminescent label with properties that make the label easier to differentiate from amongst a plurality of luminescent labels. In certain embodiments, the FRET pair may absorb excitation energy in a first spectral range and emit luminescence in a second spectral range.

For a set of luminescently labeled molecules (e.g., luminescently labeled nucleotides), the properties of a luminescently labeled FRET pair may allow for selection of a plurality of distinguishable molecules (e.g., nucleotides). In some embodiments, the second chromophore of a FRET pair has a luminescent lifetime distinct from a plurality of other luminescently labeled molecules. In some embodiments, the second chromophore of a FRET pair has a luminescent intensity distinct from a plurality of other luminescently labeled molecules. In some embodiments, the second chromophore of a FRET pair has a luminescent lifetime and luminescent intensity distinct from a plurality of other luminescently labeled molecules. In some embodiments, the second chromophore of a FRET pair emits photons in a spectral range distinct from a plurality of other luminescently labeled molecules. In some embodiments, the first chromophore of a FRET pair has a luminescent lifetime distinct from a plurality of luminescently labeled molecules. In certain embodiments, the FRET pair may absorb excitation energy in a spectral range distinct from a plurality of other luminescently labeled molecules. In certain embodiments, the FRET pair may absorb excitation energy in the same spectral range as one or more of a plurality of other luminescently labeled molecules.

In some embodiments, two or more nucleotides can be connected to a luminescent label, wherein the nucleotides are connected to distinct locations on the luminescent label. A non-limiting example could include a luminescent molecule that contains two independent reactive chemical moieties (e.g., azido group, acetylene group, carboxyl group, amino group) that are compatible with a reactive moiety on a nucleotide analog. In such an embodiment, a luminescent label could be connected to two nucleotide molecules via independent linkages. In some embodiments, a luminescent label can comprise two or more independent connections to two or more nucleotides.

In some embodiments, two or more nucleotides can be connected to a luminescent dye via a linker (e.g., a branched linker or a linker with two or more reactive sites onto which nucleotides and/or dyes can be attached). Accordingly, in some embodiments, two or more nucleotides (e.g., of the same type) can be linked to two or more dyes (e.g., of the same type).

In some embodiments, a luminescent label can comprise a quantum dot with luminescent properties. In some embodiments, one or more nucleotides are connected to a quantum dot. In some embodiments, one or more nucleotides are connected to a quantum dot via connections to distinct sites of the protein. In some embodiments, the surface of a quantum dot is coated with nucleotide molecules. In certain embodiments, a quantum dot is covalently connected to one or more nucleotides (e.g., via reactive moieties on each component). In certain embodiments, a quantum dot is non-covalently connected to one or more nucleotides (e.g., via compatible non-covalent binding partners on each component). In some embodiments, the surface of a quantum dot comprises one or more streptavidin molecules that are non-covalently bound to one or more biotinylated nucleotides.

In some embodiments, a luminescent label can comprise a protein with luminescent properties. In some embodiments, one or more nucleotides are connected to a luminescent protein. In some embodiments, one or more nucleotides are connected to a luminescent protein via connections to distinct sites of the protein. In certain embodiments, the luminescent labels of four nucleotides are selected such that one nucleotide is labeled with a fluorescent protein while the remaining three nucleotides are labeled with fluorescent dyes (e.g., the non-limiting examples in Tables 1 and 2). In certain embodiments, the luminescent labels of four nucleotides are selected such that two nucleotides are labeled with fluorescent proteins while the remaining two nucleotides are labeled with fluorescent dyes (e.g., the non-limiting examples in Tables 1 and 2). In certain embodiments, the luminescent labels of four nucleotides are selected such that three nucleotides are labeled with fluorescent proteins while the remaining nucleotide is labeled with a fluorescent dye (e.g., the non-limiting examples in Tables 1 and 2). In some embodiments, the luminescent labels of four nucleotides are selected such that all four nucleotides are labeled with fluorescent proteins.

According to some aspects of the application, luminescent labels (e.g., dyes, for example fluorophores) can damage polymerases in a sequencing reaction that is exposed to excitation light. In some aspects, this damage occurs during the incorporation of a luminescently labeled nucleotide, when the luminescent molecule is held in close proximity to the polymerase enzyme. Non-limiting examples of damaging reactions include the formation of a covalent bond between the polymerase and luminescent molecule and emission of radiative or non-radiative decay from the luminescent molecule to the enzyme. This can shorten the effectiveness of the polymerase and reduce the length of a sequencing run.

In some embodiments, a nucleotide and a luminescent label are connected by a relatively long linker or linker configuration to keep the luminescent label away from the polymerase during incorporation of the labeled nucleotide. The term "linker configuration" is used herein to refer to the entire structure connecting the luminescent molecule(s) to the nucleotide(s) and does not encompass the luminescent molecule(s) or the nucleotide(s).

In some embodiments, a single linker connects a luminescent molecule to a nucleotide. In some embodiments, a linker contains one or more points of divergence so that two or more (e.g., 2, 3, 4, 5, 6, 7, 8, 9, 10, or more) nucleotides are connected to each luminescent molecule, two or more (e.g., 2, 3, 4, 5, 6, 7, 8, 9, 10, or more) luminescent molecules are connected to each nucleotide, or two or more (e.g., 2, 3, 4, 5, 6, 7, 8, 9, 10, or more) nucleotides are connected to two or more (e.g., 2, 3, 4, 5, 6, 7, 8, 9, 10, or more) luminescent molecules.

In some embodiments, the linker configuration determines the distance between the luminescent label and the nucleotide. In some embodiments, the distance is about 1 nm or 2 nm to about 20 nm. For example, more than 2 nm, more than 5 nm, 5-10 nm, more than 10 nm, 10-15 nm, more than 15 nm, 15-20 nm, more than 20 nm. However, the distance between the luminescent label and the nucleotide cannot be too long since the luminescent label needs to be within the illumination volume to be excited when the nucleotide is held within the active site of the enzyme. Accordingly, in some embodiments, the overall linker length is less than 30 nm, less than 25 nm, around 20 nm, or less than 20 nm.

In some embodiments, a protecting molecule is included within a linker configuration. A protecting molecule can be a protein, protein homodimer, protein heterodimer, protein oligomer, a polymer, or other molecule that can protect the polymerase from the damaging reactions that can occur between the enzyme and the luminescent label. Non-limiting examples of protecting molecules include proteins (e.g., avidin, streptavidin, Traptavidin, NeutrAvidin, ubiquitin), protein complexes (e.g., Trypsin:BPTI, barnase:barstar, colicin E9 nuclease:Im9 immunity protein), nucleic acids (e.g., deoxyribonucleic acid, ribonucleic acid), polysaccharides, lipids, and carbon nanotubes.

In some embodiments, the protecting molecule is an oligonucleotide (e.g., a DNA oligonucleotide, an RNA oligonucleotide, or a variant thereof). In some embodiments, the oligonucleotide is single-stranded. In some embodiments, a luminescent label is attached directly or indirectly to one end of the single-stranded oligonucleotide (e.g., the 5' end or the 3' end) and one or more nucleotides are attached directly or indirectly to the other end of the single-stranded oligonucleotide (e.g., the 3' end or the 5' end). For example, the single-stranded oligonucleotide can comprise a luminescent label attached to the 5' end of the oligonucleotide and one or more nucleotides attached to the 3' end of the oligonucleotide. In some embodiments, the oligonucleotide is double-stranded (e.g., the oligonucleotide comprises two annealed, complementary oligonucleotide strands). In some embodiments, a luminescent label is attached directly or indirectly to one end of the double-stranded oligonucleotide and one or more nucleotides are attached directly or indirectly to the other end of the double-stranded nucleotide. In some embodiments, a luminescent label is attached directly or indirectly to one strand of the double-stranded oligonucleotide and one or more nucleotides are attached directly or indirectly to the other strand of the double-stranded nucleotide. For example, the double-stranded oligonucleotide can comprise a luminescent label attached to the 5' end of one strand of the oligonucleotide and one or more nucleotides attached to the 5' end of the other strand.

In some embodiments, a protecting molecule is connected to one or more luminescent molecules and to one or more nucleotide molecules. In some embodiments, the luminescent molecule(s) are not adjacent to the nucleotide(s). For example, one or more luminescent molecules can be connected on a first side of the protecting molecule and one or more nucleotides can be connected to a second side of the protecting molecule, wherein the first and second sides of the protecting molecule are distant from each other. In some embodiments, they are on approximately opposite sides of the protecting molecule.

The distance between the point at which a protecting molecule is connected to a luminescent label and the point at which the protecting molecule is connected to a nucleotide can be a linear measurement through space or a non-linear measurement across the surface of the protecting molecule. The distance between the luminescent label and nucleotide connection points on a protecting molecule can be measured by modeling the three-dimensional structure of the protecting molecule. In some embodiments, this distance can be 2, 4, 6, 8, 10, 12, 14, 16, 18, 20 nm or more. Alternatively, the relative positions of the luminescent label and nucleotide on a protecting molecule can be described by treating the structure of the protecting molecule as a quadratic surface (e.g., ellipsoid, elliptic cylinder). In some embodiments, the luminescent label and the nucleotide are separated by a distance that is at least one eighth of the distance around an ellipsoidal shape representing the protecting molecule. In some embodiments, the luminescent label and the nucleotide are separated by a distance that is at least one quarter of the distance around an ellipsoidal shape representing the protecting molecule. In some embodiments, the luminescent label and the nucleotide are separated by a distance that is at least one third of the distance around an ellipsoidal shape representing the protecting molecule. In some embodiments, the luminescent label and the nucleotide are separated by a distance that is one half of the distance around an ellipsoidal shape representing the protecting molecule.

FIG. 10 illustrates a non-limiting example 10-1 of a luminescent molecule (200) separated from a nucleotide (250) by a protecting molecule (100). The luminescent molecule (200) is connected to the protecting molecule (100) via a linker (300), wherein the linker (300) is attached to the protecting molecule (100). The nucleotide (250) is connected to the protecting molecule (100) via a linker (350), wherein the linker (350) is attached to the protecting molecule (100). Protecting molecules can be useful to provide a steric barrier that prevents a luminescent label from getting near the polymerase. Protecting molecules can be useful to absorb, or protect the polymerase from, radiative and non-radiative decay emitted by a luminescent molecule. Protecting molecules can be useful to provide both a steric barrier and a decay barrier between the luminescent label and the polymerase.

The size of a protecting molecule should be such that a luminescent label is unable or unlikely to directly contact the polymerase when a nucleotide is held within the active site of the enzyme. The size of a protecting molecule should also be such that an attached luminescent label is within the illumination volume to be excited when a nucleotide is held within the active site of the enzyme. The size of a protecting molecule should be chosen with consideration to the linker that is selected to connect a luminescent label to the protecting molecule and the linker that is selected to connect a nucleotide to the protecting molecule. The protecting molecule and the linkers used to connect the luminescent label and nucleotide (e.g., nucleoside polyphosphate) comprise the linker configuration, wherein the size of the linker configuration should be such that the luminescent label is unable to directly contact the polymerase when the nucleotide is held within the active site of the enzyme.

The protecting molecule (and/or the linker configuration comprising the protecting molecule) is preferably water soluble. In some embodiments, it is preferable that the protecting molecule (and/or the linker configuration comprising the protecting molecule) has an net negative charge.

In some embodiments, the label (e.g., the luminescent molecule) is not covalently linked to the nucleotide due to one or more non-covalent linkages connecting the label to the nucleotide. In some embodiments, one or more linkers are non-covalently attached to the protecting molecule and/or the luminescent molecule(s). In some embodiments, one or more linkers are non-covalently attached to the protecting molecule and/or the nucleotides. In some embodiments, a luminescent label is covalently attached to a linker, wherein the linker is non-covalently attached to the protecting molecule (e.g., via one or more binding partners). In some embodiments, a nucleotide is covalently attached to a linker, wherein the linker is non-covalently attached to the protecting molecule (e.g., via one or more binding partners).

FIGS. 10-15 illustrate non-limiting examples of one or more luminescent molecules and one or more nucleotides connected via a protecting molecule, wherein one or more luminescent molecules and one or more nucleotides are non-covalently attached to the protecting molecule.

FIG. 10 illustrates a non-limiting example 10-2 that comprises the elements of 10-1, wherein a linker comprises a non-covalent binding ligand (400) that non-covalently attaches a luminescent molecule to a non-covalent binding site (110) of a protecting molecule (shaded shape) and a second linker comprises a non-covalent binding ligand (450) that non-covalently attaches a nucleotide to a second non-covalent binding site (120) of the protecting molecule.

FIG. 10 illustrates a non-limiting example 10-3 that comprises the elements of 10-2, wherein a protecting molecule (shaded shape) comprises four independent non-covalent binding sites. A second independent luminescent molecule can be non-covalently attached to a non-covalent binding site (111) of the protecting molecule via a non-covalent binding ligand (401). A second independent nucleotide molecule can be non-covalently attached to a non-covalent binding site (121) of the protecting molecule via a non-covalent binding ligand (451). In this embodiment depicting two independent luminescent molecules and two independent nucleotides non-covalently bound at four independent non-covalent binding sites of a protecting molecule, the number of luminescent molecules and nucleotides were arbitrarily chosen. In some embodiments, the four independent non-covalent binding sites of a protecting molecule comprise one luminescent molecule at one site and one nucleotide in each of the remaining three sites. In some embodiments, the four independent non-covalent binding sites of a protecting molecule comprise one nucleotide at one site and one luminescent molecule in each of the remaining three sites.

FIG. 10 illustrates a non-limiting example 10-4 that comprises the elements of 10-3, wherein a linker (301) comprises two independent non-covalent binding ligands (400, 401) that non-covalently attach a single luminescent molecule via two independent non-covalent binding sites of a protecting molecule (shaded shape) and a linker (351) comprises two independent non-covalent binding ligands (450, 451) that non-covalently attach a single nucleotide via the remaining two independent non-covalent binding sites of the protecting molecule.

FIG. 11 illustrates a non-limiting example 11-1 that comprises the elements of 10-4, wherein the linker (301) comprises a point of divergence (302) that permits the attachment of two luminescent molecules.

FIG. 11 illustrates a non-limiting example 11-2 that comprises the elements of 11-1, wherein the linker (351) comprises a point of divergence (352) that permits the attachment of two nucleotides.

FIG. 11 illustrates a non-limiting example 11-3 that comprises the elements of 11-2, wherein the linker (302) comprises two additional points of divergence (304) that permit the attachment of four luminescent molecules and the linker (352) comprises two additional points of divergence (354) that permit the attachment of four nucleotides.

FIG. 11 illustrates a non-limiting example 11-4 that comprises the elements of 11-3, wherein each point of divergence depicted in (304) comprises an additional attachment moiety that permits the attachment of an additional luminescent molecule for a total of six luminescent molecules and each point of divergence depicted in (354) comprises an additional attachment moiety that permits the attachment of an additional nucleotide for a total of six nucleotides.

FIG. 12 illustrates a non-limiting example of a set of labeled nucleotide molecules that can be used in a sequencing reaction: thymine 12-1, adenine 12-2, cytosine 12-3, and guanine 12-4. In this embodiment, a protecting molecule comprising four non-covalent binding sites is used to connect six of the same type of nucleotide to one or more luminescent molecules. In this embodiment, six of the same type of nucleotide are attached to the protecting molecule via two separate linkers, each linker comprising an independent non-covalent binding ligand that is covalently linked to three of the same type of nucleotide. As depicted by 12-1, 12-2, and 12-3, a single luminescent molecule is non-covalently attached to the protecting molecule via a linker comprising two independent non-covalent binding ligands that non-covalently attach to two independent binding sites of the protecting molecule. As depicted in 12-4, a point of divergence in the luminescent linker permits the addition of a second luminescent molecule.

In a sequencing experiment comprising the four exemplary nucleotides, the luminescent labels of 12-1, 12-2, and 12-3 can comprise three unique luminescent molecules (e.g., three different fluorophores). Since these exemplary molecules each contain only a single fluorophore, the properties (e.g., luminescent lifetime, luminescent intensity, emission wavelength) used to distinguish amongst thymine, adenine, or cytosine incorporation would be highly similar or indistinguishable if unique fluorophores are not used. Guanine 12-4 is connected to two luminescent molecules. In some embodiments, the luminescent label of 12-4 can comprise two of the same luminescent molecule, wherein the selected molecule is different from the fluorophores used in 12-1, 12-2, and 12-3. In a sequencing reaction comprising four unique nucleotides connected to four unique fluorophores, each fluorophore should have one or more unique luminescent properties (e.g., luminescent lifetime, intensity, emission wavelength, or a combination of two or more thereof) that allow each one to be distinguished among the plurality. In some embodiments, the two fluorophores of 12-4 can comprise two of the same fluorophore, wherein the selected fluorophore is identical to one of the fluorophores of 12-1, 12-2, and 12-3. In a sequencing reaction comprising unique nucleotides connected to a differing number of the same luminescent molecule, the differing number of fluorophores should confer unique properties (e.g., increased luminescent intensity) to allow one nucleotide to be distinguished from among the plurality. The two fluorophores of 12-4 can alternatively comprise a FRET pair.

FIG. 12 further illustrates a non-limiting example of a sequencing experiment and how unique luminescent properties can be used to distinguish among a plurality of luminescently labeled nucleotides 12-5. The luminescent label connected to each base (thymine, adenine, cytosine, guanine) has luminescent properties (e.g., luminescent lifetime, luminescent intensity, and/or emission wavelength) that allow each labeled nucleotide to be distinguished from the plurality of labeled nucleotides. The inclusion of multiple nucleotides of the same type functions to accelerate incorporation rates in a sequencing reaction.

A sequencing experiment utilizing the luminescently labeled nucleotides 12-5 can be conducted in exemplary reaction vessel 12-6. The reaction takes place in a chamber above the waveguide, which serves as a conduit for excitation energy, delivering the excitation energy to the sample in the bottom of the reaction chamber by the evanescent wave from the waveguide. The aperture blocks light radiating from the waveguide to bulk sample and ambient and/or stray light from the sensor, as well as providing a fabrication path for the reaction chamber. The reaction chamber is an etched structure that places the sample on the bottom and within a region of high excitation from the evanescent wave of the waveguide. Selective surface chemistry is used to provide the bottom and sidewall of the reaction chamber with different composition, so that the sample can be selectively localized to the bottom of the reaction chamber. An exemplary workflow for surface preparation is shown in FIG. 7, which depicts a process comprising, inter alia, processes related to achieving selective surface chemistry. For example, passivation of surfaces (e.g., as depicted in the non-limiting embodiment shown in FIG. 8) can provide a selective surface substrate that will be useful during functionalization of the surface (e.g., as depicted in the non-limiting embodiment shown in FIG. 9).

The incorporation of a specific nucleotide can be distinguished from among four luminescently labeled nucleotides during a sequencing reaction per the exemplary workflow 12-7. Throughout the course of an experiment, there are two distinct periods: a pulse period and a detection period. During the pulse period, lasting 20 picoseconds, no emission light is collected. Following the pulse period is the detection period, lasting 10 nanoseconds, wherein four time bins capture emission events occurring over the detection period (i). A pulse and detection period comprise one cycle. Emission events are continuously binned and accumulated over the course of 1 million cycles (ii). The overall distribution of emission events across time bins are representative of luminescent lifetime and can be used to match a particular set of a data to a known lifetime distribution (iii). In some embodiments, the distribution of emission events (e.g., luminescent lifetime) does not distinguish one luminescently labeled base from a plurality of other labeled molecules. In addition to the distribution of emission events, the quantity of emission events (e.g., luminescent intensity) can be used to identify a single molecule from a plurality of others.

FIG. 13 illustrates a non-limiting example 13-1 that comprises the elements of 10-4, wherein a non-covalent binding site of the protecting molecule is engineered to be a non-functioning binding site (461). In some embodiments, the protecting molecule of 13-1 can comprise streptavidin. In some embodiments, the binding site is non-functional due to an inability to non-covalently bind a biotin molecule. The non-limiting embodiment 13-1 depicts a single luminescent molecule attached to a protecting molecule via two independent non-covalent binding interactions and six nucleotides attached to the protecting molecule via a single non-covalent binding interaction. In some embodiments, a protecting molecule with three functional non-covalent binding sites can comprise one or more luminescent molecules attached via a single non-covalent interaction and one or more nucleotides attached via two independent non-covalent interactions. In some embodiments, a protecting molecule with three functional non-covalent binding sites can comprise one or more luminescent molecules attached via two independent non-covalent interactions and one or more nucleotides attached via a single non-covalent interaction.

FIG. 13 illustrates a non-limiting example 13-2 that comprises the elements of 10-3, wherein two non-covalent binding sites of the protecting molecule are engineered to be non-functioning binding sites (411, 461). In some embodiments, the protecting molecule of 13-2 can comprise streptavidin. In some embodiments, the binding sites are non-functional due to an inability to non-covalently bind a biotin molecule. The non-limiting embodiment 13-2 depicts a single luminescent molecule attached to the protecting molecule via a single independent non-covalent binding interaction and six nucleotides attached to the protecting molecule via a single non-covalent binding interaction. In some embodiments, a protecting molecule with two functional non-covalent binding sites can comprise one or more luminescent molecules attached via a single non-covalent interaction and one or more nucleotides attached via a single non-covalent interaction. In some embodiments, the two non-functional non-covalent binding sites are cis binding sites or trans binding sites, wherein "cis binding sites" are defined as being in closer proximity than "trans binding sites." FIG. 13 further depicts a non-limiting example 13-3 of the generation of a streptavidin molecule with two non-functional trans binding sites.

In some embodiments, a linker can be comprised of nucleotides. FIG. 14 illustrates a non-limiting exemplary reaction scheme in which a luminescent molecule and a nucleotide are connected via a protecting molecule, wherein the linkers attaching the luminescent molecule and the nucleotide to the protecting molecule comprise oligonucleotides (e.g., oligonucleotides comprising DNA, RNA, PNA, or modified forms thereof) attached via divalent linkers. A divalent linker (360) that is comprised of an oligonucleotide is non-covalently bound to two independent non-covalent binding sites of a protecting molecule (a). A luminescent molecule (201) fused to an oligonucleotide complementary to the linker (360) is introduced to generate a luminescently labeled protecting molecule (b). A second divalent linker (361) that is comprised of an oligonucleotide is introduced to form (c). A nucleotide (251) fused to an oligonucleotide complementary to the linker (361) is introduced to generate the final product (d).

FIG. 15 illustrates a non-limiting exemplary reaction scheme in which a luminescent molecule is attached to a protecting molecule via annealed complementary oligonucleotides, wherein each oligonucleotide strand contains one non-covalent binding ligand compatible with a binding site on the protecting molecule. A first oligonucleotide (362) that is fused to a luminescent molecule and non-covalent binding ligand is annealed (i) to a complementary oligonucleotide (363) that is fused to a non-covalent binding ligand. The annealed product (364) is bound to a protecting molecule (ii) and purified. The purified luminescently labeled protecting molecule is bound with nucleotides (iii) using any techniques or configurations disclosed herein. FIG. 15 also depicts an exemplary sequencing experiment performed using a nucleotide that was labeled with a Cy®3 dye using a duplex DNA linker analogous to the non-limiting example in the reaction scheme.

In some embodiments, one or more linkers are covalently attached to the protecting molecule and/or the luminescent molecule(s). In some embodiments, one or more linkers are covalently attached to the protecting molecule and/or the nucleotide(s).

FIGS. 16-20 illustrate non-limiting examples of a luminescent molecule and a nucleotide connected via a protecting molecule, wherein the luminescent molecule and the nucleotide are covalently attached to the protecting molecule.

FIG. 16 depicts a reaction scheme 16-1 for generating a generic protecting molecule (shaded shape), wherein the protecting molecule comprises two genetically-encoded tags. A genetically-encoded tag (325) is designed to form a covalent attachment to a specific reactive group fused to a luminescent molecule (i) and a separate genetically-encoded tag (375) is designed to form a covalent attachment to a specific reactive group fused to a nucleotide (ii) to form the final product (c). FIG. 16 further depicts a non-limiting embodiment of a scheme 16-2 for the covalent attachment of a generic substrate comprising a bioorthogonal functional group (star shape) such as an azide, aldehyde, or alkyne, via a genetically-encoded tag (curved line), along with non-limiting examples 16-3 of genetically-encoded tags and kinetic rate constants.

FIG. 17 depicts a non-limiting example of a reaction scheme 17-1 for generating a generic protecting molecule (shaded shape), wherein the protecting molecule is a protein that comprises a reactive group at the N-terminus and a reactive group at the C-terminus. A first reactive group at a first terminus of the protein (326) is designed to form a covalent attachment to a specific reactive group fused to a luminescent molecule. A second reactive group of the remaining terminus of the protein (376) is designed to form a covalent attachment to a specific reactive group fused to a nucleotide. Non-limiting examples 17-2 of reactive N-terminus and C-terminus groups and the corresponding reactive groups are further depicted.

FIG. 18 depicts a non-limiting example of a reaction scheme 18-1 for generating a generic protecting molecule (shaded shape), wherein the protecting molecule is a protein that comprises a reactive unnatural amino acid at one part of the protein and a reactive unnatural amino acid at another part of the protein. A first reactive unnatural amino acid at a first part of the protein (327) is designed to form a covalent attachment to a specific reactive group fused to a luminescent molecule. A second reactive unnatural amino acid at a second part of the protein (377) is designed to form a covalent attachment to a specific reactive group fused to a nucleotide. FIG. 18 further depicts a generic and non-limiting scheme 18-2 for the chemical labeling of a target protein. In this example, an unnatural amino acid (e.g., an unnatural amino acid selected from non-limiting examples 18-3) bearing a unique biorthogonal functionality is introduced site-specifically into a protein via genetic code expansion and then chemoselectively labeled with an externally added probe.

FIG. 19A is a non-limiting example of a luminescent molecule and a nucleotide separated by a non-protein protecting molecule (101). Non-limiting examples of non-protein protecting molecules can include nucleic acid molecules (deoxyribonucleic acid, ribonucleic acid), lipids, and carbon nanotubes. As shown, the luminescent molecule and the nucleotide are attached directly to the non-protein protecting molecule (e.g., covalently attached). In some embodiments, the luminescent molecule and the nucleotide are attached directly to a contiguous part of the non-protein protecting molecule. For example, in some embodiments, the non-protein protecting molecule is a nucleic acid molecule, and the luminescent molecule and/or nucleotide are bound directly to a nucleotide of the nucleic acid molecule. In some embodiments, the luminescent molecule and/or nucleotide are attached to the non-protein protecting molecule via a linker that is not a contiguous part of the non-protein protecting molecule. For example, in some embodiments, the non-protein protecting molecule is a nucleic acid molecule, and the luminescent molecule and/or nucleotide are attached to the nucleic acid via a linker.

In some embodiments, the luminescent molecule and the nucleotide can be attached to the non-protein protecting molecule via reactive moieties, as depicted in FIG. 19B. In this example, a reactive moiety (550) on the luminescent molecule is covalently attached to the non-protein protecting molecule via a corresponding reactive moiety (500) on the non-protein protecting molecule. A reactive moiety (551) on the nucleotide is covalently attached to the non-protein protecting molecule (101) via a corresponding reactive moiety (501) on the non-protein protecting molecule. In some embodiments, the reactive moiety 500 and/or the reactive moiety 501 are attached directly to a contiguous part of the non-protein protecting molecule. In some embodiments, the reactive moiety 500 and/or the reactive moiety 501 are attached to the non-protein protecting molecule via a linker that is not a contiguous part of the non-protein protecting molecule.

In some embodiments, a protecting molecule is comprised of a protein-protein pair. A protein-protein pair can comprise any set of polypeptide binding partners (e.g., protein-receptor, enzyme-inhibitor, antibody-antigen). FIG. 20 depicts a non-limiting embodiment of a protecting molecule comprised of a protein-protein binding pair. In this non-limiting example, one polypeptide (102) of the binding pair is orthogonally labeled with luminescent molecules and a second polypeptide (103) is orthogonally linked to nucleotides. Non-limiting examples of protein-protein binding pairs include Trypsin-BPTI, barnase-barstar, and colicin E9 nuclease-Im9 immunity protein.

FIG. 21 depicts non-limiting examples of linker configurations comprising one or more luminescent molecules attached to a non-covalent binding ligand. In an embodiment 21-1, a first linker layer comprising a non-covalent binding ligand (410), spacer linker (310), and reactive moiety (510) is attached to a luminescent molecule (210) comprising a compatible reactive moiety (211). The reactive moiety of the first linker layer can be used to attach directly to a luminescent molecule or nucleotide via a compatible reactive moiety. The reactive moiety of the first linker layer can be used to attach a second linker layer via a compatible reactive moiety. In an embodiment 21-2, two luminescent molecules are attached to the first linker layer via a second linker layer, wherein the second linker layer comprises a reactive moiety compatible with the reactive moiety of the first layer, a spacer linker comprising a point of divergence (312), and two reactive moieties (522) compatible with the reactive moiety of the luminescent molecule. The two reactive moieties of the second linker layer can be used to attach directly to luminescent or nucleotide molecules. The two reactive moieties of the second linker layer can be used to attach a third linker layer to further increase the number of luminescent molecules or nucleotides comprising a linker configuration. In an embodiment 21-3, six luminescent molecules are attached to the second linker layer via a third linker layer bound at each reactive moiety (522), wherein each third linker layer comprises a compatible reactive moiety (513), a spacer linker that is tri-functionalized (313), and three reactive moieties (523) compatible with the reactive moieties of the luminescent molecules.

Accordingly, a luminescent label may be attached to the molecule directly, e.g., by a bond, or may be attached via a linker or a linker configuration. In certain embodiments, the linker comprises one or more phosphates. In some embodiments, a nucleotide is connected to a luminescent label by a linker comprising one or more phosphates. As used herein, a linker described as having one or more phosphates refers to a linker that comprises one or more phosphates present within the linker structure and not directly attached to the one or more phosphates of a nucleotide. In some embodiments, a nucleotide is connected to a luminescent label by a linker comprising three or more phosphates. In some embodiments, a nucleotide is connected to a luminescent label by a linker comprising four or more phosphates.

In certain embodiments, a linker comprises an aliphatic chain. In some embodiments a linker comprises $-(CH_2)_n-$, wherein n is an integer from 1 to 20, inclusive. In some embodiments, n is an integer from 1 to 10, inclusive. In certain embodiments, a linker comprises a heteroaliphatic chain. In some embodiments, a linker comprises a polyethylene glycol moiety. In some embodiments, a linker comprises a polypropylene glycol moiety. In some embodiments, a linker comprises $-(CH_2CH_2O)_n-$, wherein n is an integer from 1 to 20, inclusive. In some embodiments, a linker comprises —(CH$_2$CH$_2$O)$_n$—, wherein n is an integer from 1 to 10, inclusive. In certain embodiments, a linker comprises —(CH$_2$CH$_2$O)$_4$—. In certain embodiments, a linker comprises one or more arylenes. In some embodiments, a linker comprises one or more phenylenes (e.g., para-substituted phenylene). In certain embodiments, a linker comprises a chiral center. In some embodiments, a linker comprises proline, or a derivative thereof. In some embodiments, a linker comprises a proline hexamer, or a derivative thereof. In some embodiments, a linker comprises coumarin, or a derivative thereof. In some embodiments, a linker comprises naphthalene, or a derivative thereof. In some embodiments, a linker comprises anthracene, or a derivative thereof. In some embodiments, a linker comprises a polyphenylamide, or a derivative thereof. In some embodiments, a linker comprises chromanone, or a derivative thereof. In some embodiments, a linker comprises 4-aminopropargyl-L-phenylalanine, or a derivative thereof. In certain embodiments, a linker comprises a polypeptide.

In some embodiments, a linker comprises an oligonucleotide. In some embodiments, a linker comprises two annealed oligonucleotides. In some embodiments, the oligonucleotide or oligonucleotides comprise deoxyribose nucleotides, ribose nucleotide, or locked ribose nucleotides.

In certain embodiments, a linker comprises a photostabilizer. In some embodiments, the linker is of formula:

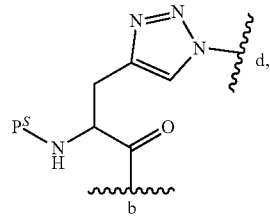

wherein P$^S$ is a photostabilizer, the position labeled d is attached to a luminescent label, and the position labeled b is attached to a nucleotide. In some embodiments, the position labeled d is attached to a luminescent label by a linker as described herein. In some embodiments, the position labeled b is attached to a nucleotide by a linker as described herein.

In certain embodiments, a linker comprises one or more phosphates, an aliphatic chain, a heteroaliphatic chain, and one or more amides (e.g., —C(=O)NH—). In certain embodiments, a linker comprising one or more phosphates and an aliphatic chain can be synthesized via the exemplary reaction scheme 22-1 depicted in FIG. 22. Exemplary linker structures are further depicted in 22-2 and 22-3. In certain embodiments, a linker is selected from linkers depicted in Table 3. Certain exemplary linker structures in Table 3 are shown linked to nucleotides (e.g., nucleoside hexaphosphate) and/or dyes.

TABLE 3
Exemplary linkers or linker/dye combination.
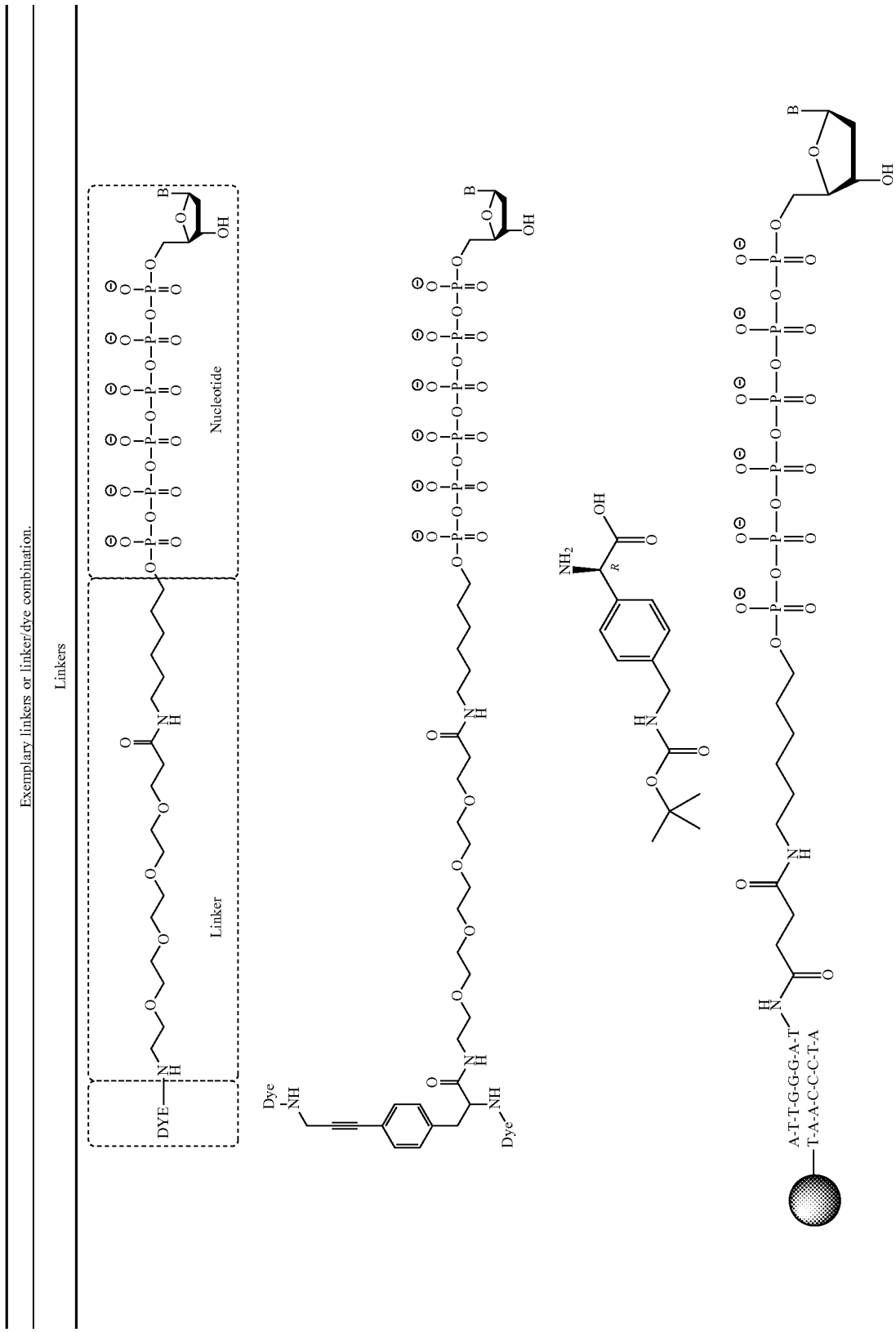

TABLE 3-continued
Exemplary linkers or linker/dye combination.
Linkers
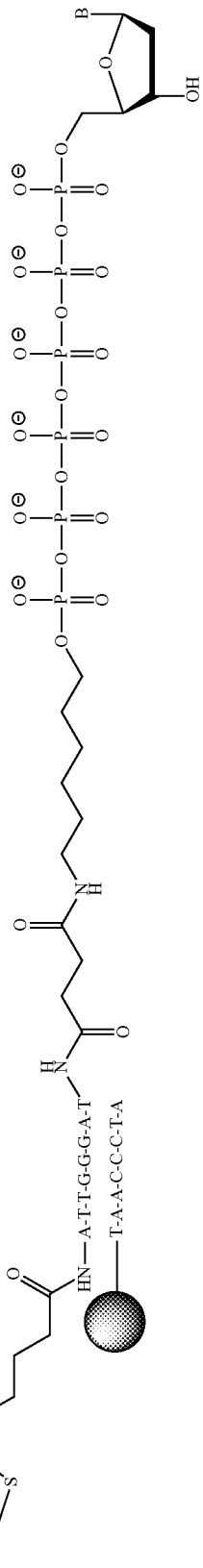
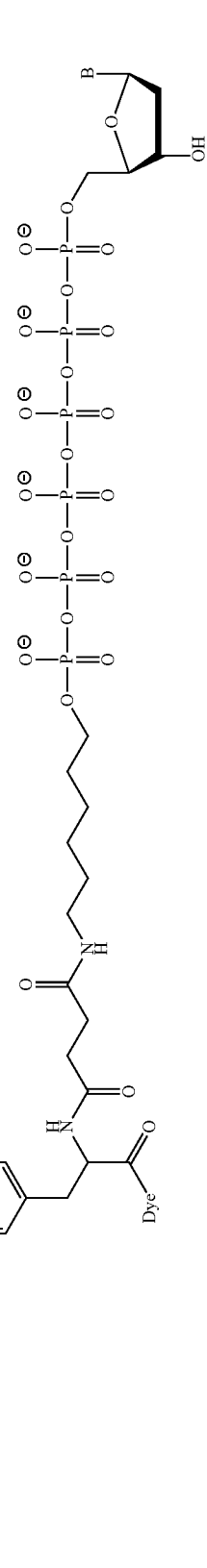

TABLE 3-continued
Exemplary linkers or linker/dye combination.
Linkers
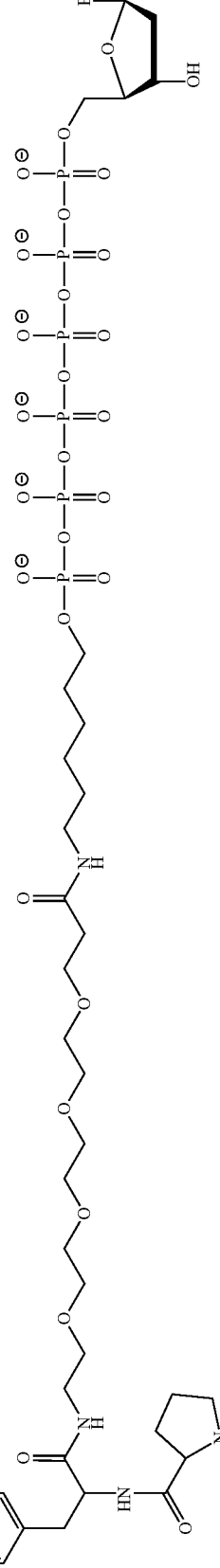

In certain embodiments, a linker comprises one or more phosphates, an aliphatic chain, a heteroaliphatic chain, one or more amides (e.g., —C(═O)NH—), and one or more biotin moieties. In certain embodiments, a biotinylated linker contains one or more functionalizable, reactive moieties (e.g., acetylene group, azido group). In certain embodiments, a linker is selected from the non-limiting linkers depicted in Table 4. Certain exemplary linker structures in Table 4 are shown linked to nucleotides (e.g., nucleoside hexaphosphate).

TABLE 4
Exemplary biotinylated linkers.
Biotinylated Linkers
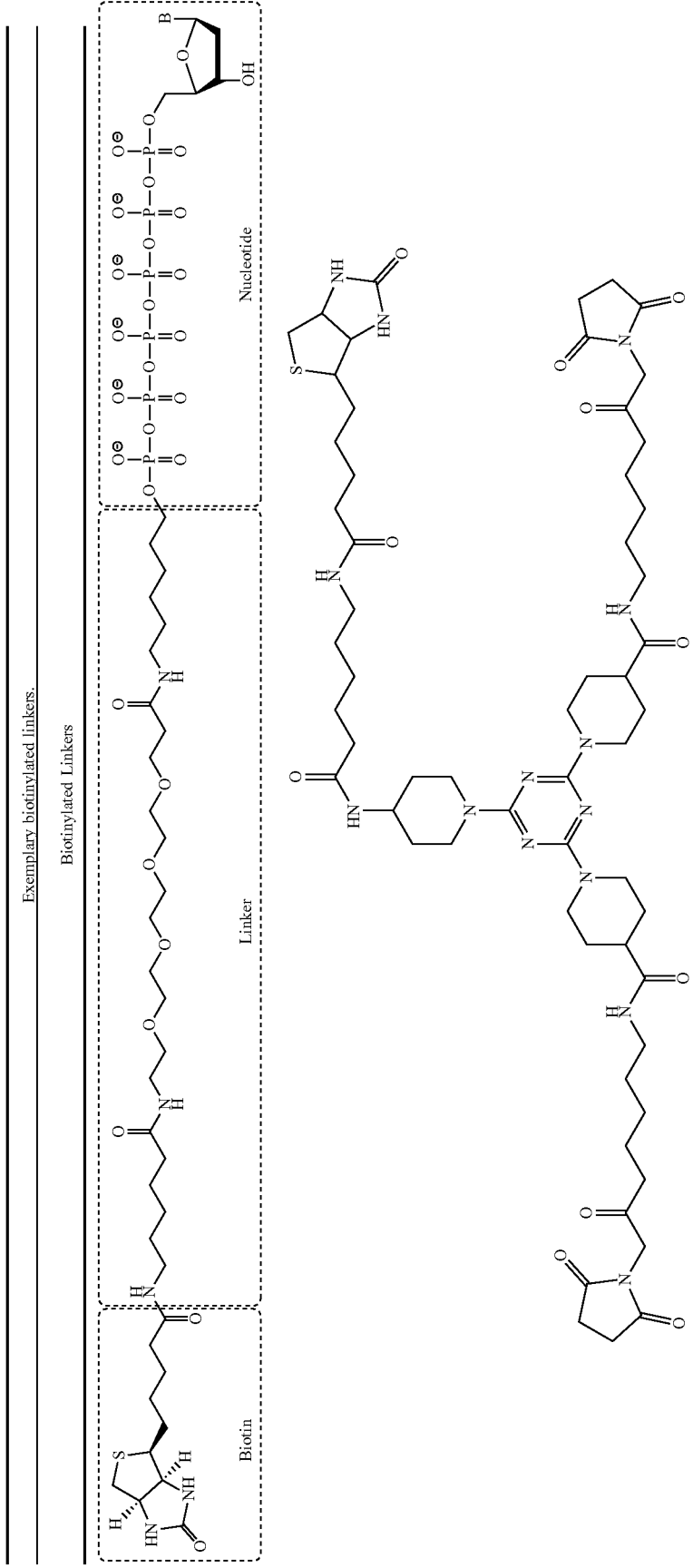

TABLE 4-continued
Exemplary biotinylated linkers.
Biotinylated Linkers
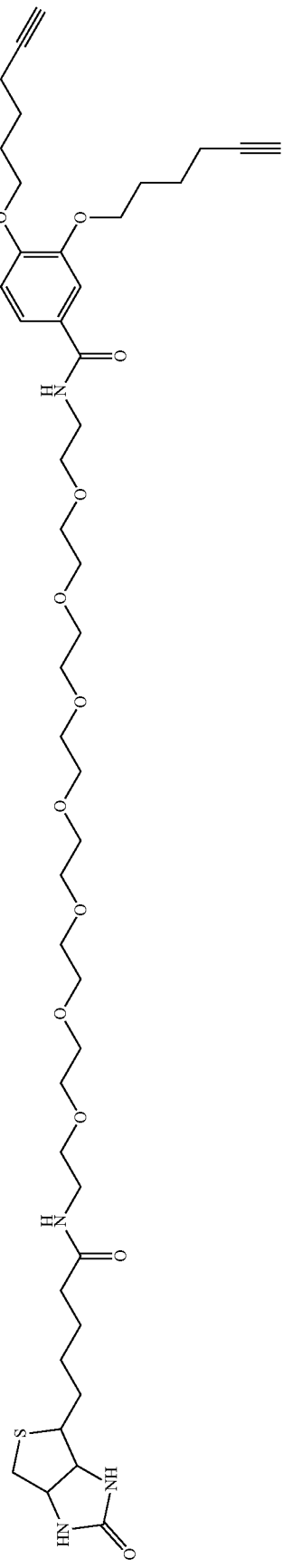

TABLE 4-continued
Exemplary biotinylated linkers.
Biotinylated Linkers
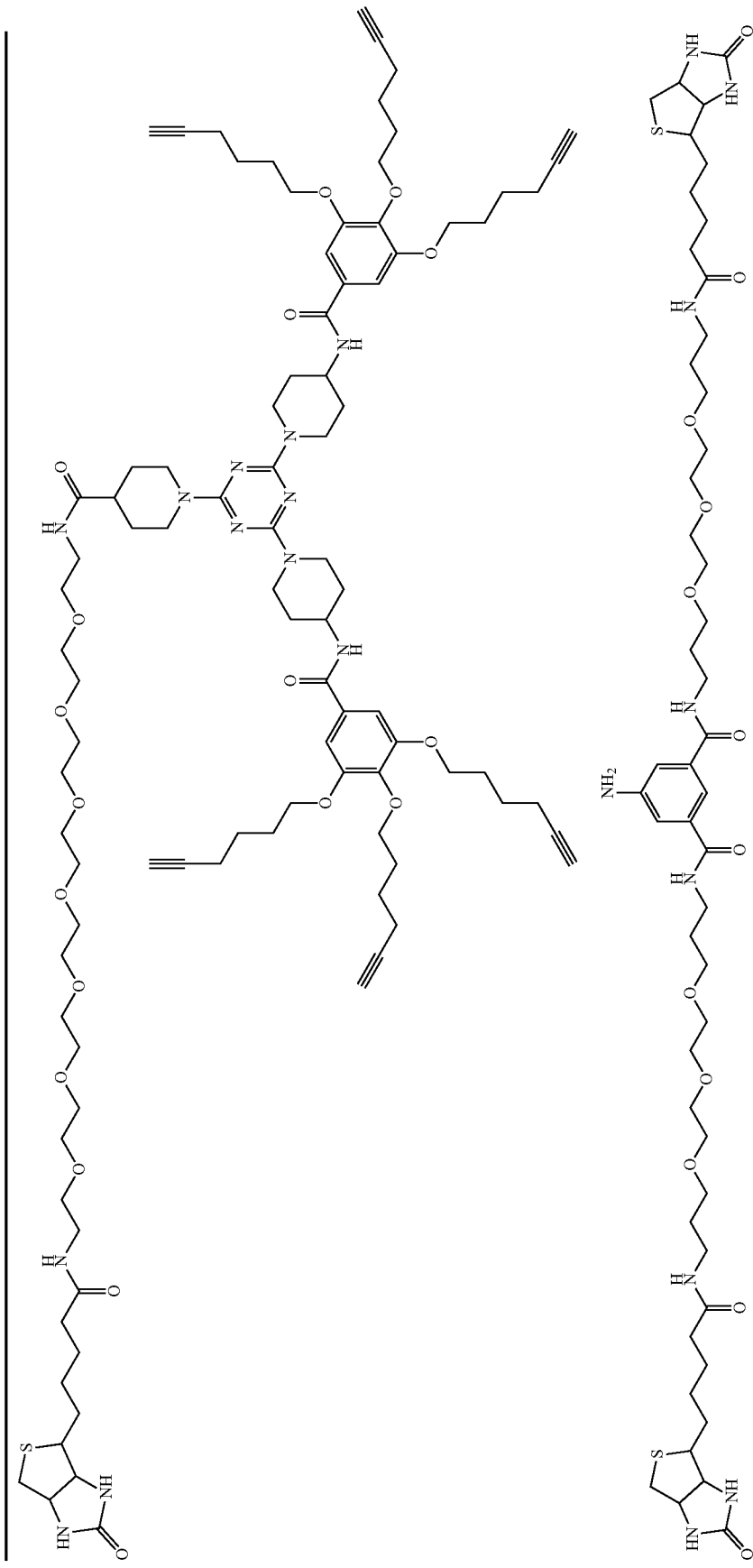

TABLE 4-continued
Exemplary biotinylated linkers.
Biotinylated Linkers
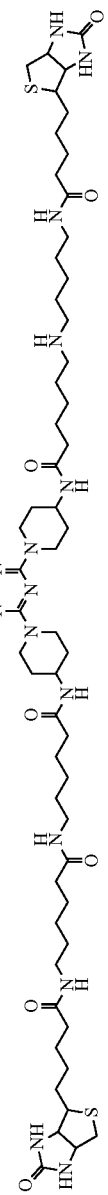
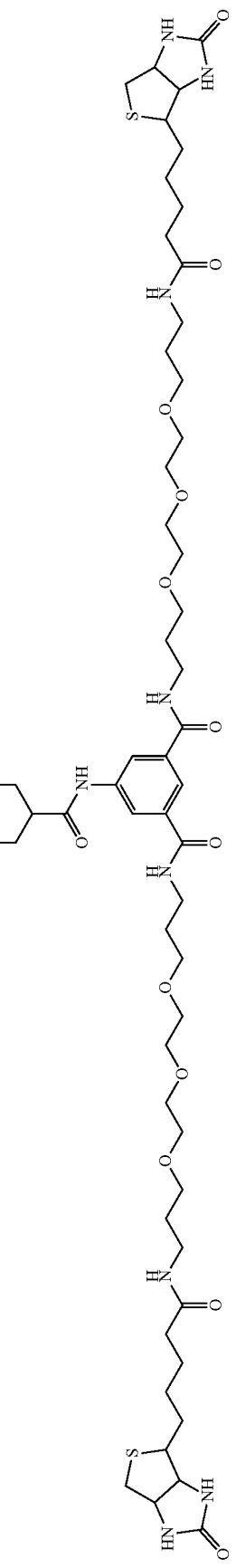

TABLE 4-continued
Exemplary biotinylated linkers.
Biotinylated Linkers
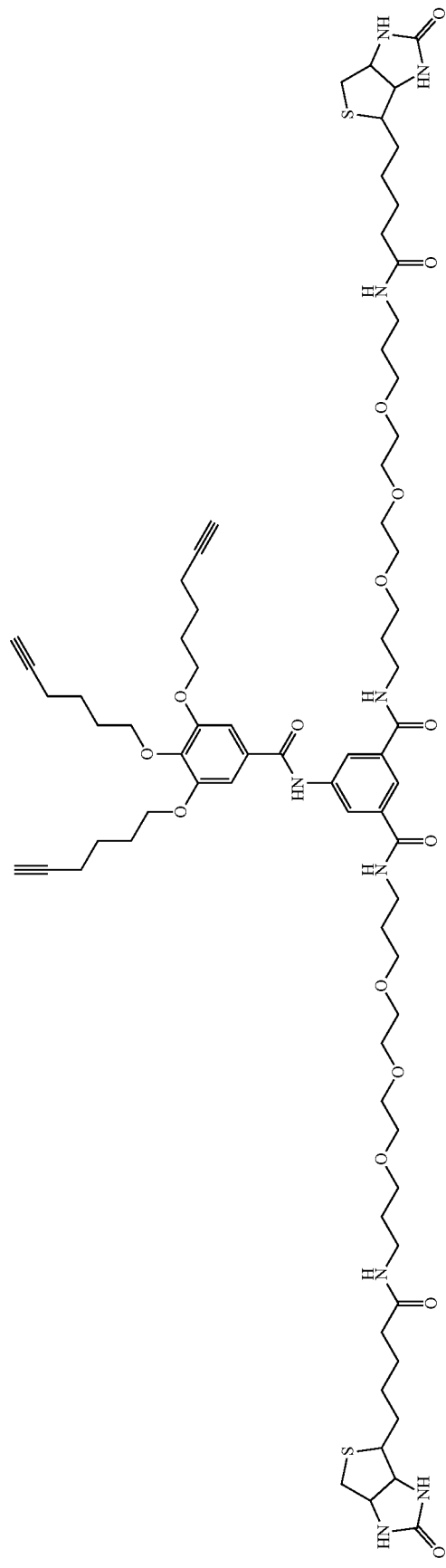

TABLE 4-continued
Exemplary biotinylated linkers.
Biotinylated Linkers
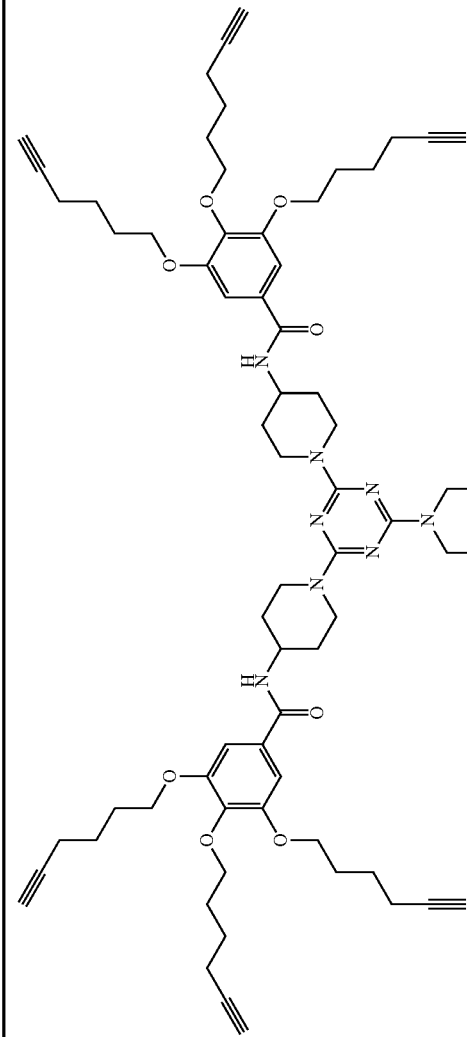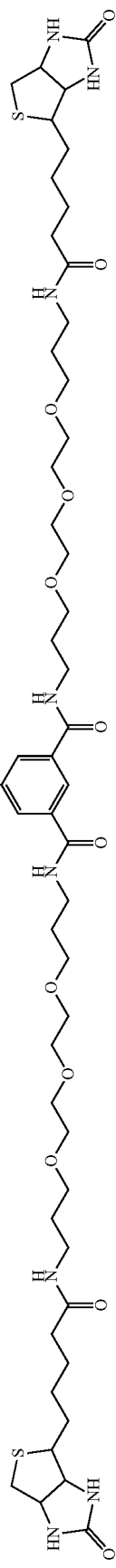

TABLE 4-continued

Exemplary biotinylated linkers.

Biotinylated Linkers

TABLE 4-continued

Exemplary biotinylated linkers.

Biotinylated Linkers

In some embodiments, a linker is synthesized from precursors comprising a first layer, and optionally a second and/or third layer. In some embodiments, a "first layer" contains one or more biotin moieties. In certain embodiments, the first layer of a linker contains a single biotin moiety. In certain embodiments, the first layer of a linker contains two biotin moieties. In some embodiments, a first layer contains one or more reactive moieties (e.g., azido group, acetylene group, carboxyl group, amino group). In some embodiments, the first layer of a linker is selected from the structures depicted in Table 5.

TABLE 5

Exemplary first linker layers.

First Layers

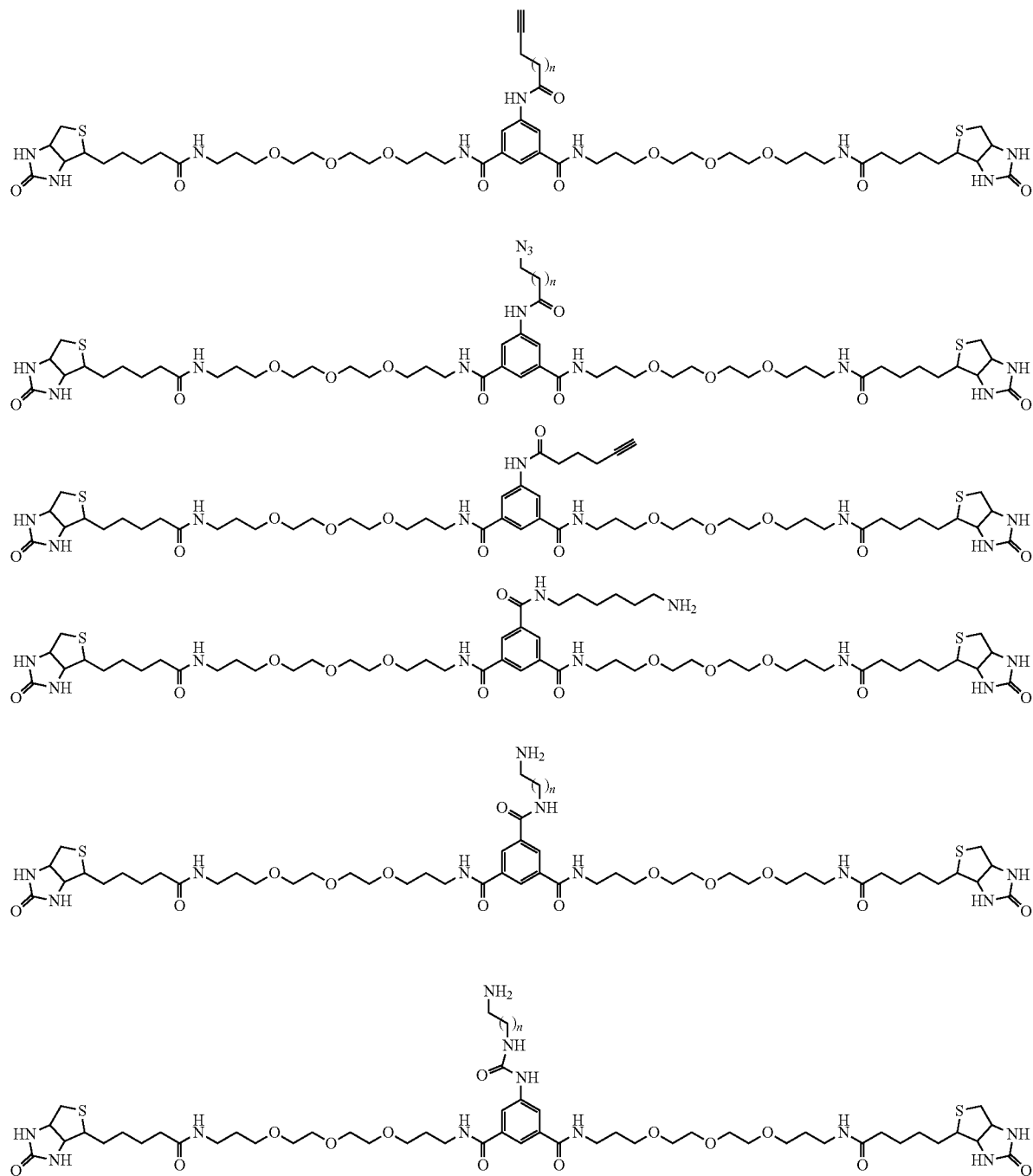

TABLE 5-continued

Exemplary first linker layers.

First Layers

In some embodiments, the first layer of a linker can be synthesized according to the following exemplary reaction scheme:

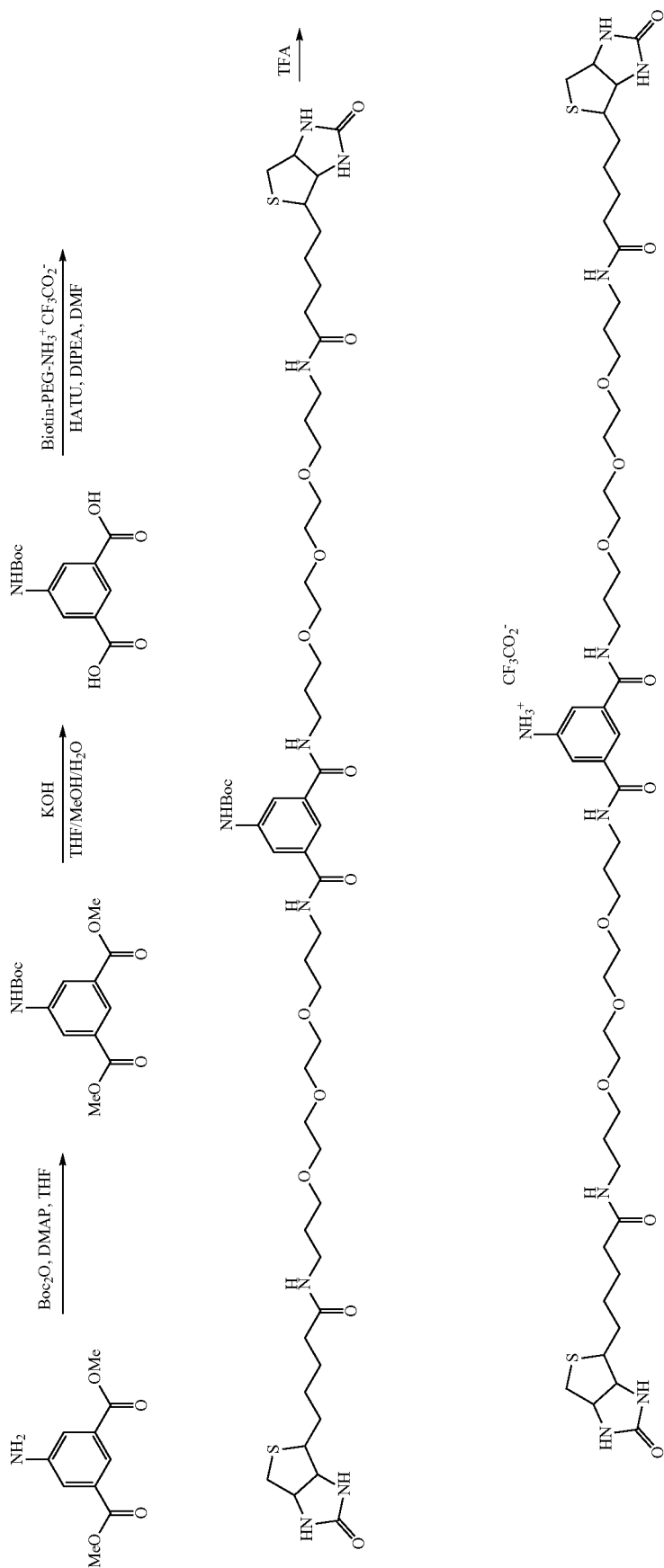

In further embodiments, the first layer of a linker can be synthesized according to the following exemplary reaction scheme:

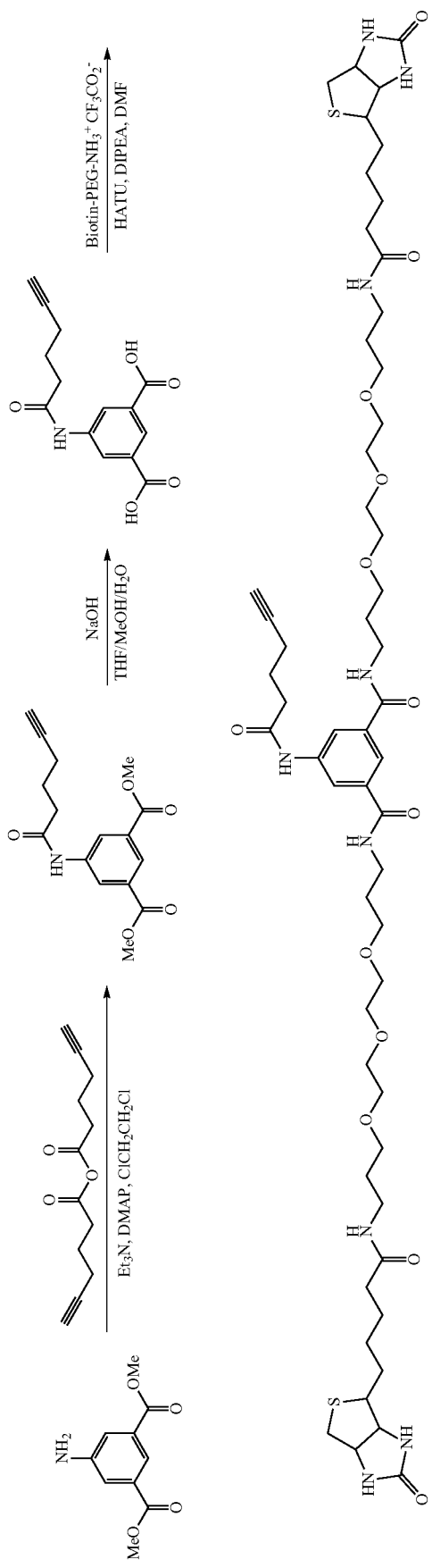

In yet further embodiments, the first layer of a linker can be synthesized according to the following exemplary reaction scheme:

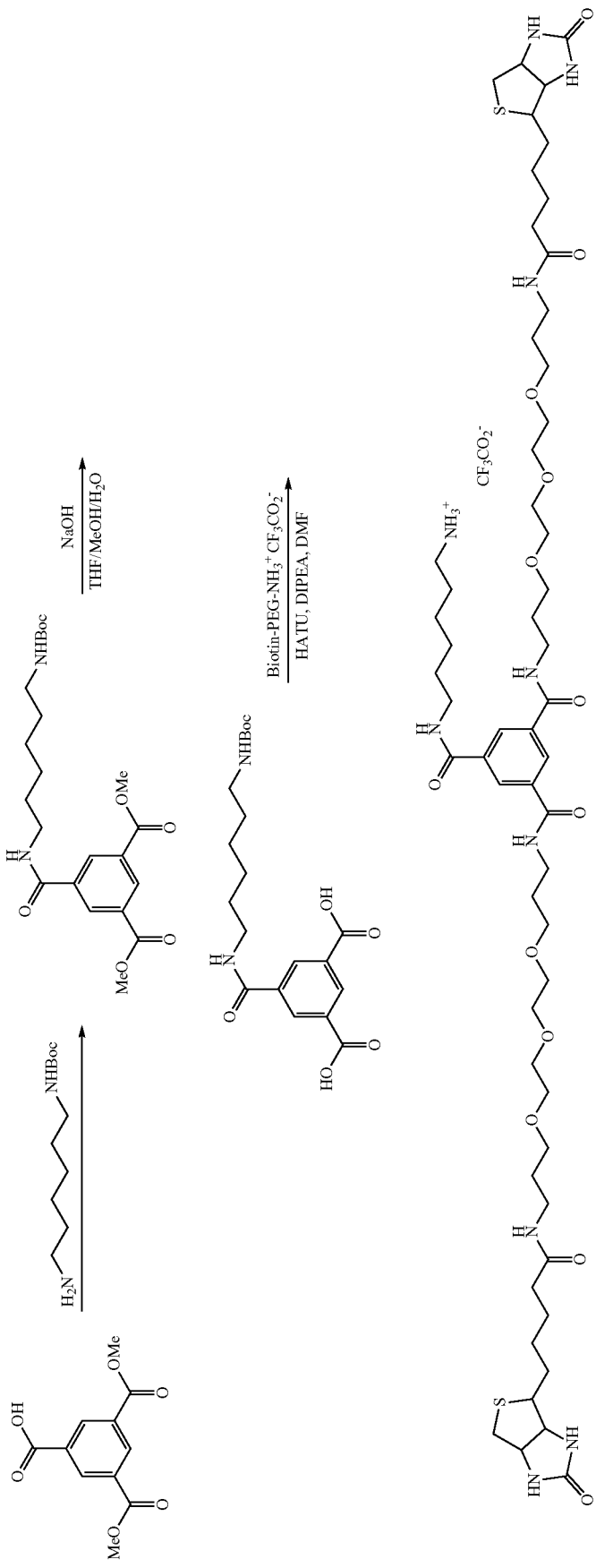

In some embodiments, a "second layer" contains one or more reactive moieties (e.g., azido group, acetylene group, carboxyl group, amino group). In some embodiments, a second layer is covalently attached to a first layer of a linker. In some embodiments, a second layer covalently connects a first layer to a third layer. In some embodiments, a "third layer" contains one or more reactive moieties (e.g., azido group, acetylene group, carboxyl group, amino group). In some embodiments, a third layer is covalently attached to a first layer of a linker. In some embodiments, a third layer is covalently connected to a first layer via a second layer. In some embodiments, a linker comprises a first and second layer. In some embodiments, a linker comprises a first and third layer. In some embodiments, a linker comprises a first, second, and third layer. In certain embodiments, a second and/or third linker layer is selected from the structures depicted in Table 6.

TABLE 6
Exemplary second and third linker layers.
Second and Third Layers
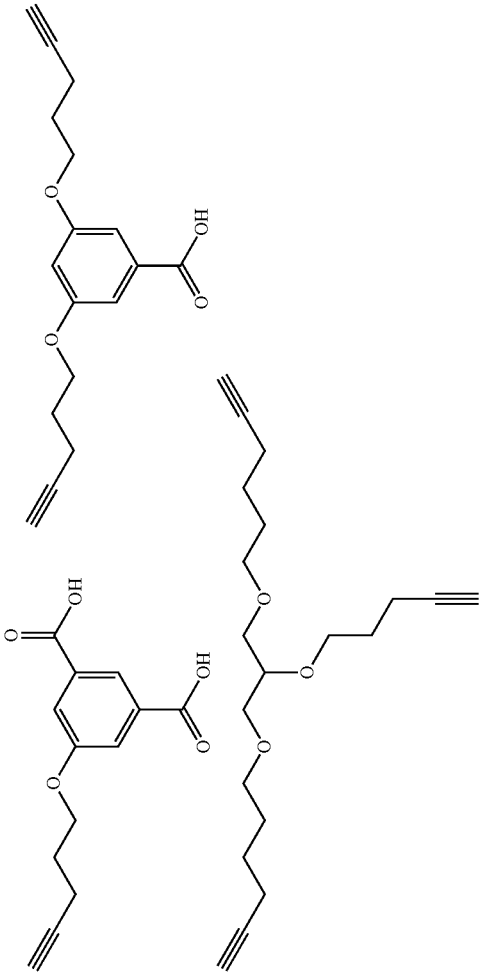

TABLE 6-continued
Exemplary second and third linker layers.
Second and Third Layers
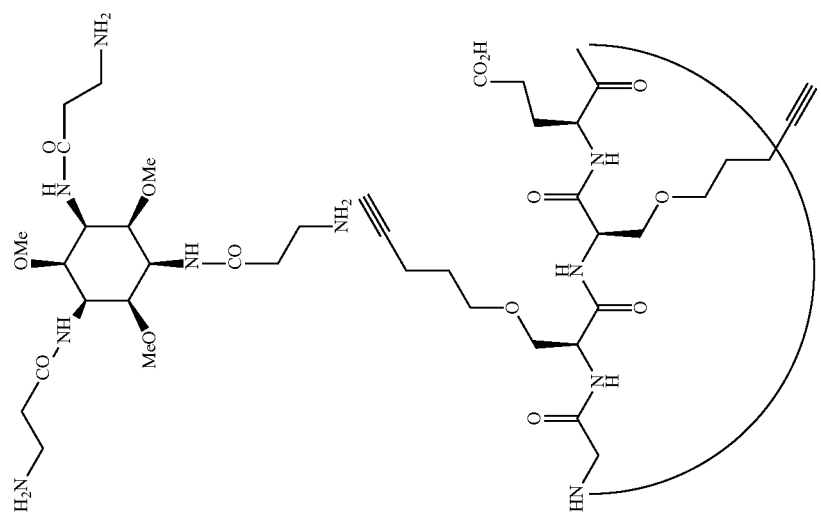

TABLE 6-continued
Exemplary second and third linker layers.
Second and Third Layers
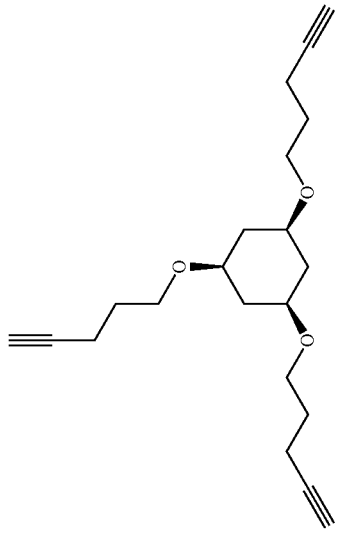

In some embodiments, a linker comprising more than a first layer (e.g., a second layer and/or a third layer) can be synthesized according to the following exemplary reaction scheme:

103                                    104
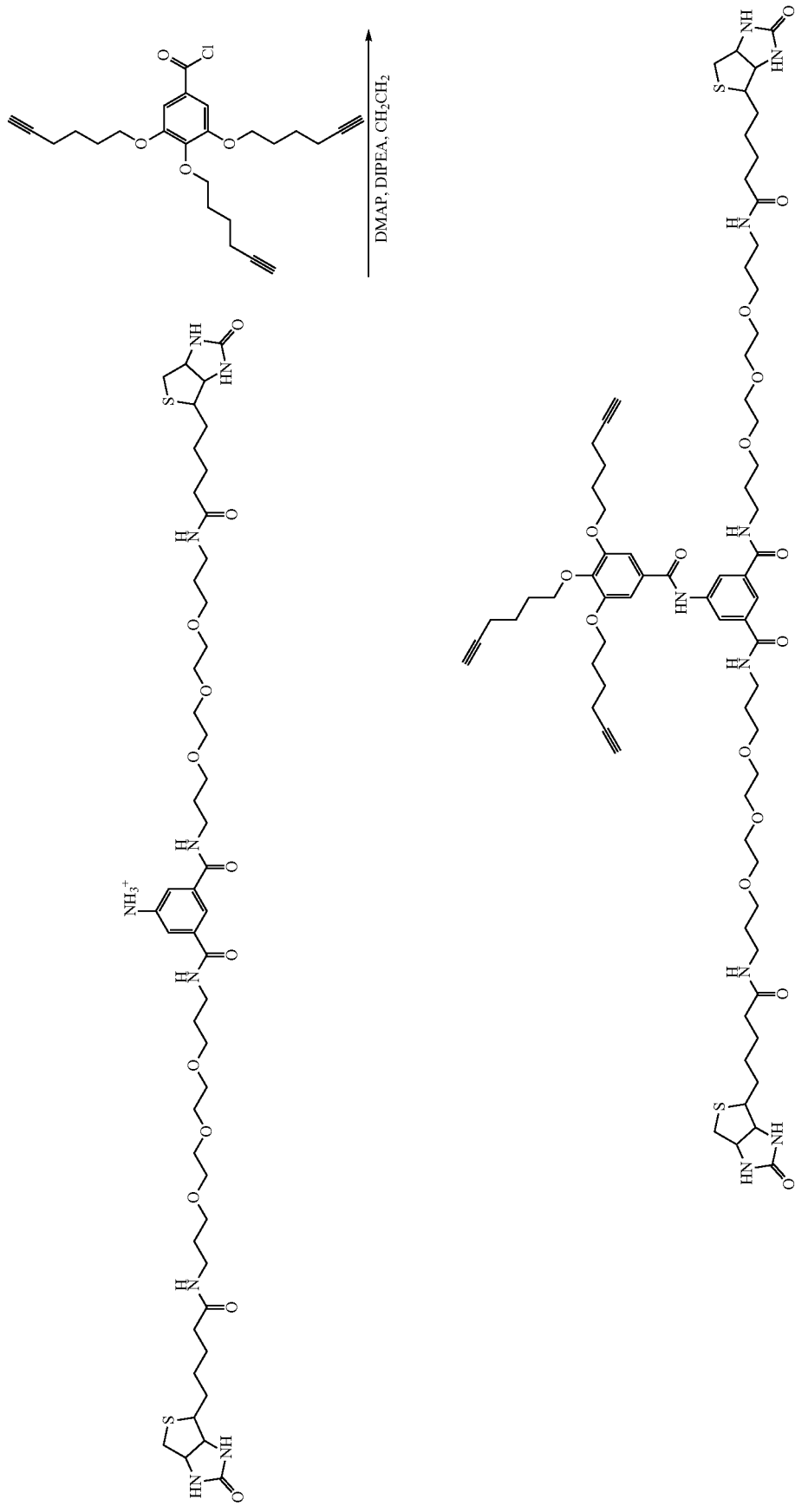

In some embodiments, a linker comprising at least a second and a third layer can be synthesized according to the following exemplary reaction scheme:

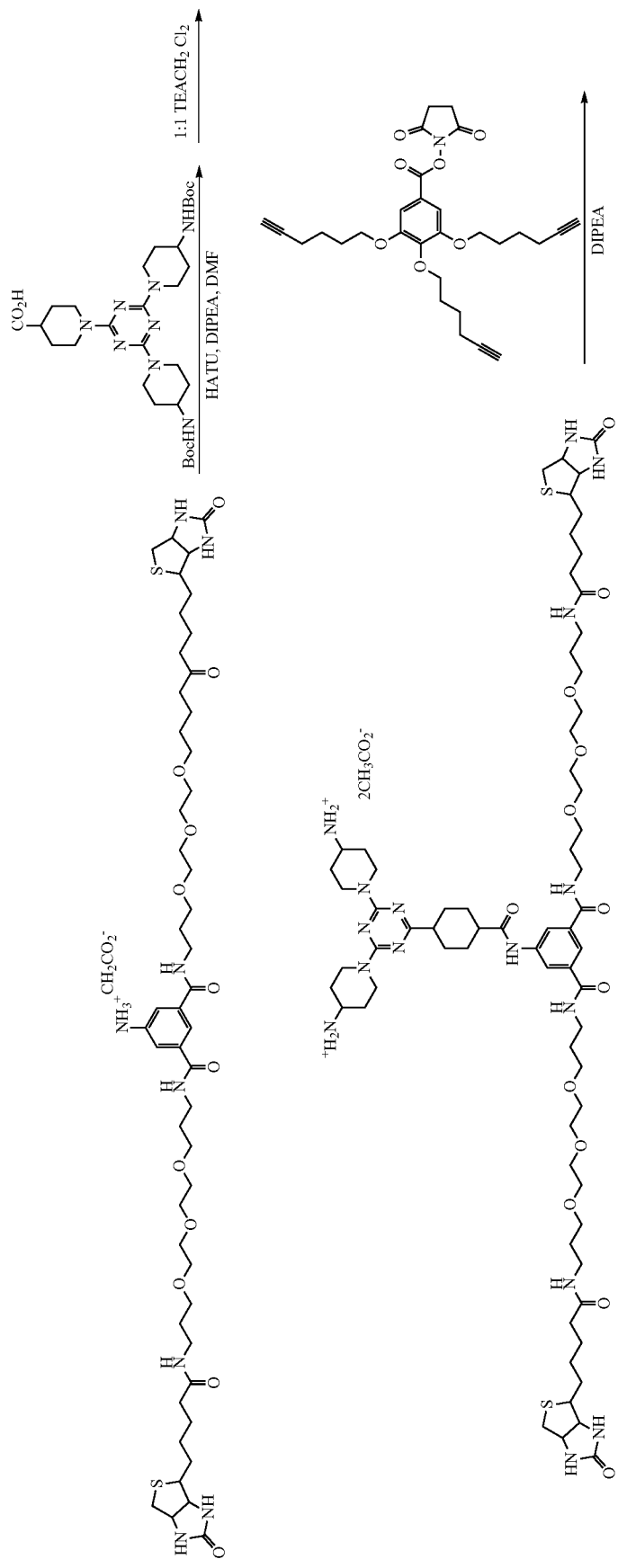

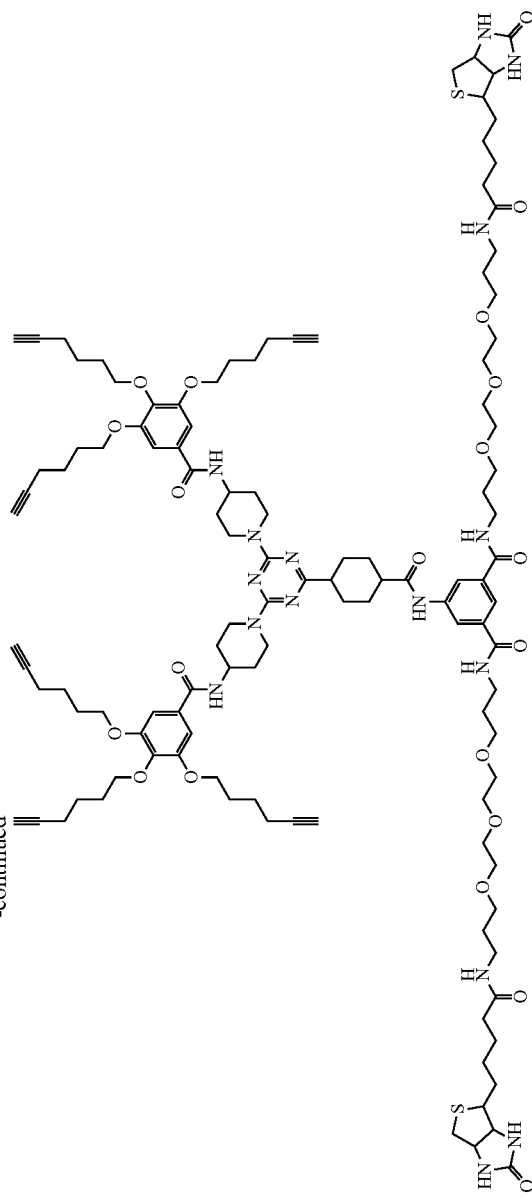
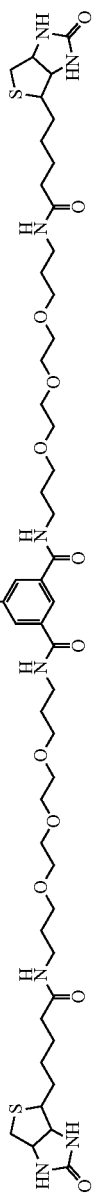

Exemplary luminescent labels with biotinylated linkers are shown in Table 7. It should be appreciated that different luminescent labels can be substituted in place of the dyes depicted in Table 7.

or metal oxide layers. In some embodiments, the first material is a transparent material or glass. In some embodiments, the bottom surface is flat. In some embodiments, the bottom surface is a curved well. In some embodiments, the

TABLE 7

Exemplary luminescent labels with biotinylated linkers.

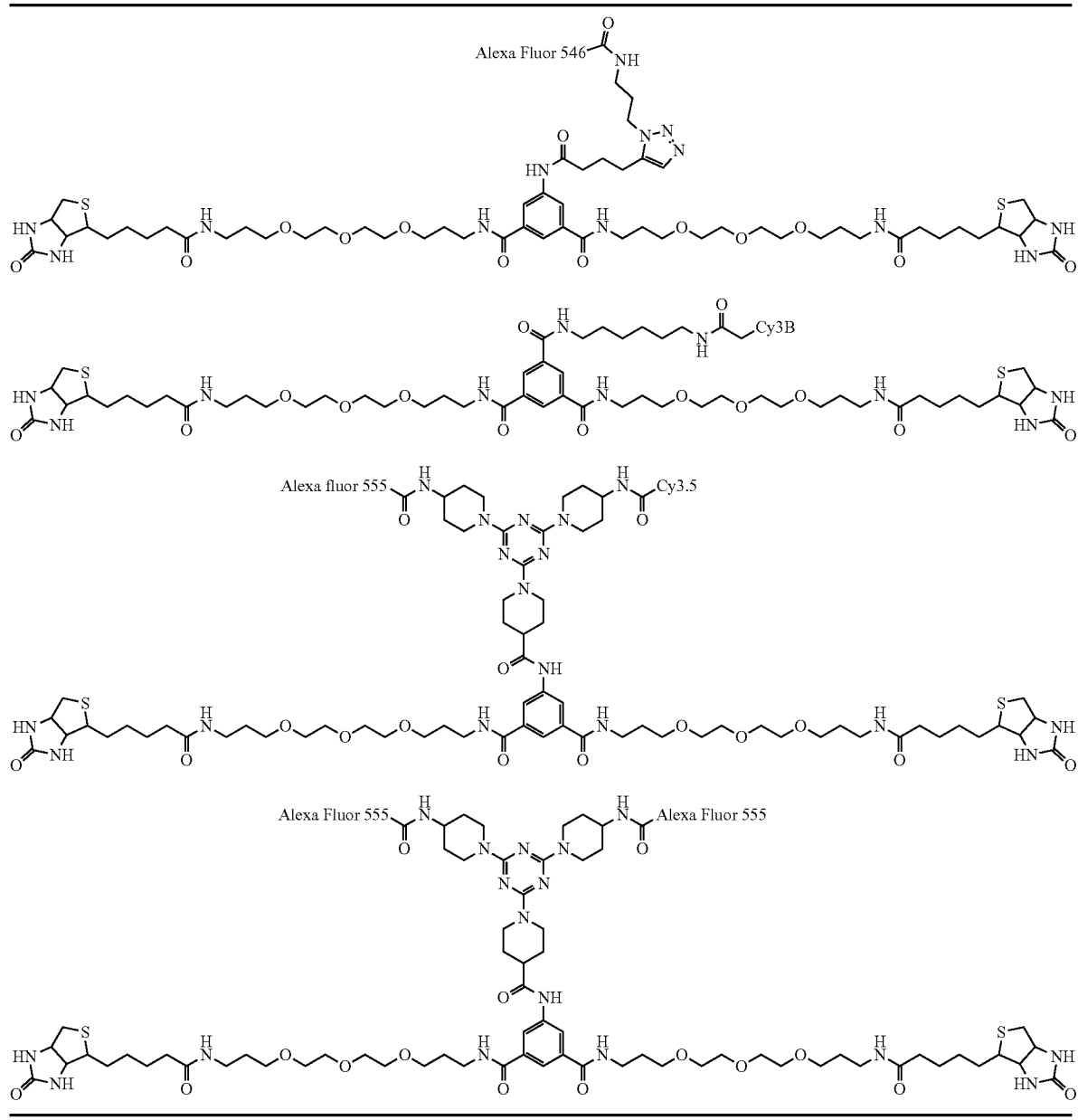

Sample Well (e.g., Nanoaperture) Surface Preparation

In certain embodiments, a method of detecting one or more luminescently labeled molecules is performed with the molecules confined in a target volume (e.g., a reaction volume). In some embodiments, the target volume is a region within a sample well (e.g., a nanoaperture). Embodiments of sample wells (e.g., nanoapertures) and the fabrication of sample wells (e.g., nanoapertures) are described elsewhere herein. In certain embodiments, the sample well (e.g., nanoaperture) comprises a bottom surface comprising a first material and sidewalls formed by a plurality of metal bottom surface includes a portion of the sidewalls below the sidewalls formed by a plurality of metal or metal oxide layers. In some embodiments, the first material is fused silica or silicon dioxide. In some embodiments, the plurality of layers each comprise a metal (e.g., Al, Ti) or metal oxide (e.g., $Al_2O_3$, $TiO_2$, TiN).

Passivation

In embodiments when one or more molecule or complex is immobilized on the bottom surface it may be desirable to passivate the sidewalls to prevent immobilization on the sidewall surfaces. In some embodiments, the sidewalls are passivated by the steps of: depositing a metal or metal oxide barrier layer on the sidewall surfaces; and applying a coating to the barrier layer. In some embodiments, the metal oxide barrier layer comprises aluminum oxide. In some embodiments, the step of depositing comprises depositing the metal or metal oxide barrier layer on the sidewall surfaces and the bottom surface. In some embodiments, the step of depositing further comprises etching metal or metal oxide barrier layer off of the bottom surface.

In some embodiments, the barrier layer coating comprises phosphonate groups. In some embodiments, the barrier layer coating comprises phosphonate groups with an alkyl chain. In some embodiments, the alkyl chain comprises a straight-chain saturated hydrocarbon group having 1 to 20 carbon atoms. In some embodiments, the barrier layer coating comprises hexylphosphonic acid (HPA). In some embodiments, the barrier layer coating comprises a polymeric phosphonate. In some embodiments, the barrier layer coating comprises polyvinylphosphonic acid (PVPA). In some embodiments, the barrier layer coating comprises phosphonate groups with a substituted alkyl chain. In some embodiments, the alkyl chain comprises one or more amides. In some embodiments, the alkyl chain comprises one or more poly(ethylene glycol) chains. In some embodiments, the coating comprises phosphonate groups of formula:

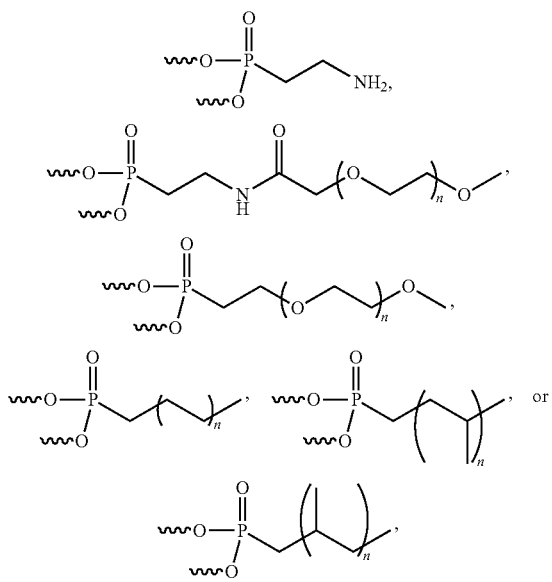

wherein n is an integer between 0 and 100, inclusive, and ⋯ is hydrogen or a point of attachment to the surface. In some embodiments n is an integer between 3 and 20, inclusive. In some embodiments, the barrier layer coating comprises a mixture of different types of phosphonate groups. In some embodiments, the barrier layer coating comprises a mixture of phosphonate groups comprising poly(ethylene glycol) chains of different PEG weight.

In certain embodiments, the barrier layer comprises nitrodopa groups. In certain embodiments, the barrier layer coating comprises groups of formula:

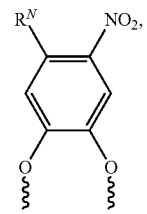

wherein $R^N$ is an optionally substituted alkyl chain and ⋯ is hydrogen or a point of attachment to the surface. In some embodiments, $R^N$ comprises a polymer. In some embodiments, $R^N$ comprises a poly(lysine) or a poly(ethylene glycol). In some embodiments, the barrier layer comprises a co-polymer of poly(lysine) comprising lysine monomers, wherein the lysine monomers independently comprise PEG, nitrodopa groups, phosphonate groups, or primary amines. In certain embodiments, the barrier layer comprises a polymer of formula (P):

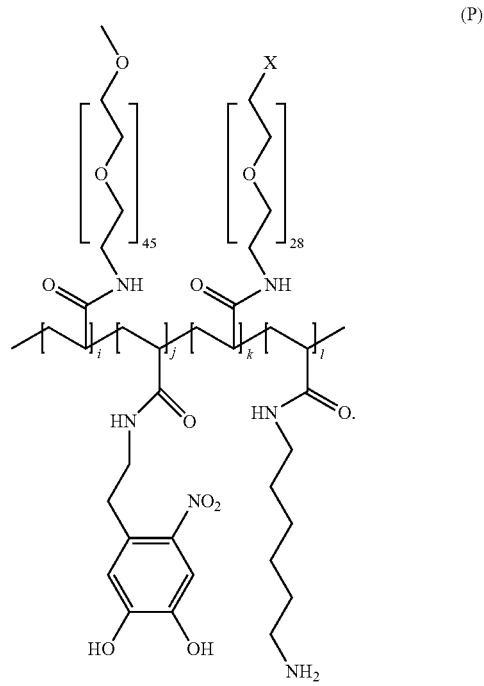

In some embodiments, X is —OMe, a biotin group, phosphonate, or silane. In some embodiments, each of i, j, k, and l is independently an integer between 0 and 100, inclusive.

FIG. 8 depicts two methods of passivating a metal oxide surface. In 8-1 a metal oxide surface is treated with (2-aminoethyl)phosphonic acid, providing a surface coated with (2-aminoethyl)phosphonate groups. In a second passivation step, the surface is treated with a poly(ethylene glycol) NHS ester. Reaction of the NHS esters with the amine groups of the surface phosphonate groups forms amide bonds to form a surface coated with PEG functionalized phosphonate groups. In 8-2 the metal oxide surface is treated with a PEG functionalized phosphonic acid, to provide in one step a surface coated with PEG functionalized phosphonate groups. The exemplary embodiment 8-2 further depicts the addition of a second PEG functionalized phosphonic acid, to provide a surface coated with two types of PEG functionalized phosphonate groups. In this example, the first PEG phosphonic acid with average molecular weight of 550, and the second PEG phosphonic acid with average molecular weight of 180. As depicted, the shorter PEG chain phosphonic acids may help fill in gaps in the surface coating that remain after treatment with the initial PEG phosphonic acid with longer PEG chains.

Polymerase Immobilization

In embodiments when one or more molecule or complex is immobilized on the bottom surface it may be desirable to functionalize the bottom surface to allow for attachment of one or more molecule or complex. In certain embodiments, the bottom surface comprises a transparent glass. In certain embodiments, the bottom surface comprises fused silica or silicon dioxide. In some embodiments, the bottom surface is functionalized with a silane. In some embodiments, the bottom surface is functionalized with an ionically charged polymer. In some embodiments, the ionically charged polymer comprises poly(lysine). In some embodiments, the bottom surface is functionalized with poly(lysine)-graft-poly(ethylene glycol). In some embodiments, the bottom surface is functionalized with biotinlyated bovine serum albumin (BSA).

In certain embodiments, the bottom surface is functionalized with a coating comprising nitrodopa groups. In certain embodiments, the coating comprises groups of formula:

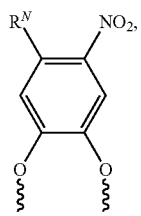

wherein $R^N$ is an optionally substituted alkyl chain and ⌇ is hydrogen or a point of attachment to the surface. In some embodiments, $R^N$ comprises a polymer. In some embodiments, $R^N$ comprises a poly(lysine) or a poly(ethylene glycol). In some embodiments, $R^N$ comprises a biotinylated poly(ethylene glycol). In some embodiments, the coating comprises a co-polymer of poly(lysine) comprising lysine monomers, wherein the lysine monomers independently comprise PEG, biotinylated PEG, nitrodopa groups, phosphonate groups, or silanes. In certain embodiments, the coating comprises a polymer of formula (P):

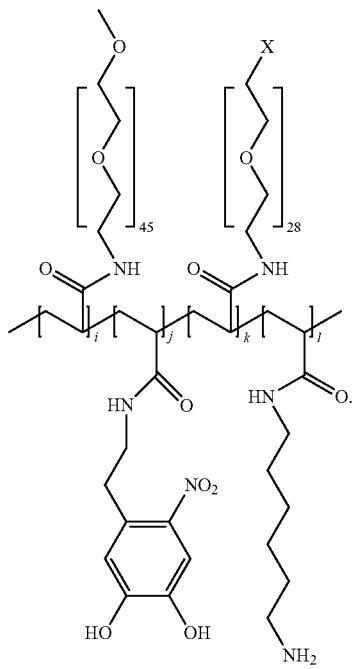

In some embodiments, X is —OMe, a biotin group, phosphonate, or silane. In some embodiments, each of i, j, k, and l is independently an integer between 0 and 100, inclusive.

In some embodiments, the bottom surface is functionalized with a silane comprising an alkyl chain. In some embodiments, the bottom surface is functionalized with a silane comprising an optionally substituted alkyl chain. In some embodiments, the bottom surface is functionalized with a silane comprising a poly(ethylene glycol) chain. In some embodiments, the bottom surface is functionalized with a silane comprising a coupling group. For example the coupling group may comprise chemical moieties, such as amine groups, carboxyl groups, hydroxyl groups, sulfhydryl groups, metals, chelators, and the like. Alternatively, they may include specific binding elements, such as biotin, avidin, streptavidin, neutravidin, lectins, SNAP-Tags™ or substrates therefore, associative or binding peptides or proteins, antibodies or antibody fragments, nucleic acids or nucleic acid analogs, or the like. Additionally, or alternatively, the coupling group may be used to couple an additional group that is used to couple or bind with the molecule of interest, which may, in some cases include both chemical functional groups and specific binding elements. By way of example, a coupling group, e.g., biotin, may be deposited upon a substrate surface and selectively activated in a given area. An intermediate binding agent, e.g., streptavidin, may then be coupled to the first coupling group. The molecule of interest, which in this particular example would be biotinylated, is then coupled to the streptavidin In some embodiments, the bottom surface is functionalized with a silane comprising biotin, or an analog thereof. In some embodiments, the bottom surface is functionalized with a silane comprising a poly(ethylene) glycol chain, wherein the poly(ethylene glycol) chain comprises biotin. In certain embodiments, the bottom surface is functionalized with a mixture of silanes, wherein at least one type of silane comprises biotin and at least one type of silane does not comprise biotin. In some embodiments, the mixture comprises about 10 fold less, about 25 fold less, about 50 fold less, about 100 fold less, about 250 fold less, about 500 fold less, or about 1000 fold less of the biotinylated silane than the silane not comprising biotin.

FIG. 9 depicts two exemplary routes to generating a functionalized glass bottom surface. In the top route the glass surface is exposed to a mixture of a PEG-silane and a biotinylated-PEG-silane in a ratio of 250:1. In the bottom route, the glass surface is first exposed to isocyanato-propyl-triethoxysilane (IPTES). Reaction of the isocyanate groups with a mixture of a PEG-amine and biotinylated-PEG-amine forms urea bonds and yields a surface with PEG and biotinylated-PEG chains attached to the surface via silane groups.

FIG. 7 depicts a non-limiting exemplary process for preparing the sample well surface from the fabricated chip to initiation of a sequencing reaction. The sample well is depicted with a bottom surface (unshaded rectangle) and sidewalls (shaded vertical rectangles). The sidewalls may be comprised of multiple layers (e.g., Al, $Al_2O_3$, Ti, $TiO_2$, TiN). In step (a) the sidewalls are deposited with a barrier layer of $Al_2O_3$. The $Al_2O_3$ barrier layer is then coated, in step (b), with a PEG phosphonate groups, for example, by treating the surface with one or more PEG-phosphonic acids. In step (c), the bottom surface is functionalized, for example, with a mixture of PEG-silane and biotinylated-PEG-silane. The ovals represent individual biotin groups which may provide sites for an attachment of a single molecule or complex, such as a polymerase complex. In step (d), a polymerase complex is attached to a biotin group on the bottom surface. The polymerase may be attached by way of a binding agent, such as streptavidin, and a biotin tag on the polymerase complex. The polymerase complex may further comprise a template nucleic acid and primer (not shown). Step (e) depicts the initiation of a sequencing reaction by exposure of the immobilized polymerase complex to luminescently labeled nucleotides.

The polymerase complex may be immobilized on the surface by exposing the complex to the functionalized surface in a binding mixture. In some embodiments, the binding mixture comprises one or more salts. In some embodiments, a salt comprises potassium acetate. In some embodiments, a salt comprises calcium chloride. In some embodiments, a salt is present in a concentration of between about 1 mM and about 10 mM. In some embodiments, a salt is present in a concentration of between about 10 mM and about 50 mM. In some embodiments, a salt is present in a concentration of between about 50 mM and about 100 mM. In some embodiments, a salt is present in a concentration of between about 100 mM and about 250 mM. In some embodiments, the concentration of potassium acetate is about 75 mM. In some embodiments, the concentration of calcium chloride is about 10 mM. In some embodiments, the binding mixture comprises a reducing agent. In some embodiments, a reducing agent comprises dithiothreitol (DTT). In some embodiments, the reducing agent is present in a concentration of between about 1 mM and about 20 mM. In some embodiments, the concentration of dithiothreitol is about 5 mM. In some embodiments, the binding mixture comprises a buffer. In some embodiments, a buffer comprises MOPS. In some embodiments, a buffer is present in a concentration of between about 10 mM and about 100 mM. In some embodiments, the concentration of MOPS is about 50 mM. In some embodiments, a buffer is present at a pH of between about 5.5 and about 6.5. In some embodiments, a buffer is present at a pH of between about 6.5. and about 7.5 In some embodiments, a buffer is present at a pH of between about 7.5. and about 8.5 In some embodiments, the binding mixture comprises deoxynucleotide triphosphates (dNTPs). In some embodiments, the deoxynucleotide triphosphates are present in a concentration of between 250 nM and 10 μM. In some embodiments, the concentration of dNTPs is about 2 μM. In some embodiments, the binding mixture comprises a surfactant. In some embodiments, the surfactant is a Tween surfactant (e.g., Tween 20). In some embodiments, the surfactant is present in a volume percent of between about 0.01% and about 0.1%. In some embodiments, the volume percent of Tween is about 0.03%.

Polymerases

The term "polymerase," as used herein, generally refers to any enzyme (or polymerizing enzyme) capable of catalyzing a polymerization reaction. Examples of polymerases include, without limitation, a nucleic acid polymerase, a transcriptase or a ligase. A polymerase can be a polymerization enzyme.

Embodiments directed towards single molecule nucleic acid extension (e.g., for nucleic acid sequencing) may use any polymerase that is capable of synthesizing a nucleic acid complementary to a target nucleic acid molecule. In some embodiments, a polymerase may be a DNA polymerase, an RNA polymerase, a reverse transcriptase, and/or a mutant or altered form of one or more thereof.

Examples of polymerases include, but are not limited to, a DNA polymerase, an RNA polymerase, a thermostable polymerase, a wild-type polymerase, a modified polymerase, *E. coli* DNA polymerase I, T7 DNA polymerase, bacteriophage T4 DNA polymerase φ29 (psi29) DNA polymerase, Taq polymerase, Tth polymerase, Tli polymerase, Pfu polymerase, Pwo polymerase, Vent® polymerase, Deep Vent™ polymerase, Ex Taq™ polymerase, LA Taq™ polymerase, Sso polymerase, Poc polymerase, Pab polymerase, Mth polymerase, ES4 polymerase, Tru polymerase, Tac polymerase, Tne polymerase, Tma polymerase, Tca polymerase, Tih polymerase, Tfi polymerase, Platinum® Taq polymerases, Tbr polymerase, Tfl polymerase, Tth polymerase, Pfuturbo® polymerase, Pyrobest™ polymerase, Pwo polymerase, KOD polymerase, Bst polymerase, Sac polymerase, Klenow fragment, polymerase with 3' to 5' exonuclease activity, and variants, modified products and derivatives thereof. In some embodiments, the polymerase is a single subunit polymerase. Non-limiting examples of DNA polymerases and their properties are described in detail in, among other places, DNA Replication 2nd edition, Kornberg and Baker, W. H. Freeman, New York, N.Y. (1991).

Upon base pairing between a nucleobase of a target nucleic acid and the complementary dNTP, the polymerase incorporates the dNTP into the newly synthesized nucleic acid strand by forming a phosphodiester bond between the 3' hydroxyl end of the newly synthesized strand and the alpha phosphate of the dNTP. In examples in which the luminescent tag conjugated to the dNTP is a fluorophore, its presence is signaled by excitation and a pulse of emission is detected during or after the step of incorporation. For detection labels that are conjugated to the terminal (gamma) phosphate of the dNTP, incorporation of the dNTP into the newly synthesized strand results in release the beta and gamma phosphates and the detection label, which is free to diffuse in the sample well, resulting in a decrease in emission detected from the fluorophore.

In some embodiments, the polymerase is a polymerase with high processivity. However, in some embodiments, the polymerase is a polymerase with reduced processivity. Polymerase processivity generally refers to the capability of a polymerase to consecutively incorporate dNTPs into a nucleic acid template without releasing the nucleic acid template.

In some embodiments, the polymerase is a polymerase with low 5'-3' exonuclease activity and/or 3'-5' exonuclease. In some embodiments, the polymerase is modified (e.g., by amino acid substitution) to have reduced 5'-3' exonuclease activity and/or 3'-5' activity relative to a corresponding wild-type polymerase. Further non-limiting examples of DNA polymerases include 9° Nm™ DNA polymerase (New England Biolabs), and a P680G mutant of the Klenow exo-polymerase (Tuske et al. (2000) JBC 275(31):23759-23768). In some embodiments, a polymerase having reduced processivity provides increased accuracy for sequencing templates containing one or more stretches of nucleotide repeats (e.g., two or more sequential bases of the same type).

In some embodiments, the polymerase is a polymerase that has a higher affinity for a labeled nucleotide than for a non-labeled nucleic acid.

Embodiments directed toward single molecule RNA extension (e.g., for RNA sequencing) may use any reverse transcriptase that is capable of synthesizing complementary DNA (cDNA) from an RNA template. In such embodiments, a reverse transcriptase can function in a manner similar to a polymerase in that cDNA can be synthesized from an RNA template via the incorporation of dNTPs to a reverse transcription primer annealed to an RNA template. The cDNA can then participate in a sequencing reaction and its sequence determined as described above and elsewhere herein. The determined sequence of the cDNA can then be used, via sequence complementarity, to determine the sequence of the original RNA template. Examples of reverse transcriptases include Moloney Murine Leukemia Virus reverse transcriptase (M-MLV), avian myeloblastosis virus (AMV) reverse transcriptase, human immunodeficiency virus reverse transcriptase (HIV-1) and telomerase reverse transcriptase.

The processivity, exonuclease activity, relative affinity for different types of nucleic acid, or other property of a nucleic acid polymerase can be increased or decreased by one of skill in the art by mutation or other modification relative to a corresponding wild-type polymerase.

Templates

The present disclosure provides devices, systems and methods for detecting biomolecules or subunits thereof, such as nucleic acid molecules. Such detection can include sequencing. A biomolecule may be extracted from a biological sample obtained from a subject (e.g., a human or other subject). In some embodiments, the subject may be a patient. In some embodiments, a target nucleic acid may be detected and/or sequenced for diagnostic, prognostic, and/or therapeutic purposes. In some embodiments, information for a sequencing assay may be useful to assist in the diagnosis, prognosis, and/or treatment of a disease or condition. In some embodiments, the subject may be suspected of having a health condition, such as a disease (e.g., cancer). In some embodiments, the subject may be undergoing treatment for a disease.

In some embodiments, a biological sample may be extracted from a bodily fluid or tissue of a subject, such as breath, saliva, urine, blood (e.g., whole blood or plasma), stool, or other bodily fluid or biopsy sample. In some examples, one or more nucleic acid molecules are extracted from the bodily fluid or tissue of the subject. The one or more nucleic acids may be extracted from one or more cells obtained from the subject, such as part of a tissue of the subject, or obtained from a cell-free bodily fluid of the subject, such as whole blood.

A biological sample may be processed in preparation for detection (e.g., sequencing). Such processing can include isolation and/or purification of the biomolecule (e.g., nucleic acid molecule) from the biological sample, and generation of more copies of the biomolecule. In some examples, one or more nucleic acid molecules are isolated and purified from a bodily fluid or tissue of the subject, and amplified through nucleic acid amplification, such as polymerase chain reaction (PCR). Then, the one or more nucleic acid molecules or subunits thereof can be identified, such as through sequencing. However, in some embodiments nucleic acid samples can be evaluated (e.g., sequenced) as described in this application without requiring amplification.

As described in this application, sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (e.g., sequencing by synthesis). As an alternative, sequencing can include the direct identification of individual subunits of the biomolecule.

During sequencing, signals indicative of individual subunits of a biomolecule may be collected in memory and processed in real time or at a later point in time to determine a sequence of the biomolecule. Such processing can include a comparison of the signals to reference signals that enable the identification of the individual subunits, which in some cases yields reads. Reads may be sequences of sufficient length (e.g., at least about 30, 50, 100 base pairs (bp) or more) that can be used to identify a larger sequence or region, e.g., that can be aligned to a location on a chromosome or genomic region or gene.

Sequence reads can be used to reconstruct a longer region of a genome of a subject (e.g., by alignment). Reads can be used to reconstruct chromosomal regions, whole chromosomes, or the whole genome. Sequence reads or a larger sequence generated from such reads can be used to analyze a genome of a subject, such as to identify variants or polymorphisms. Examples of variants include, but are not limited to, single nucleotide polymorphisms (SNPs) including tandem SNPs, small-scale multi-base deletions or insertions, also referred to as indels or deletion insertion polymorphisms (DIPs), Multi-Nucleotide Polymorphisms (MNPs), Short Tandem Repeats (STRs), deletions, including microdeletions, insertions, including microinsertions, structural variations, including duplications, inversions, translocations, multiplications, complex multi-site variants, copy number variations (CNV). Genomic sequences can comprise combinations of variants. For example, genomic sequences can encompass the combination of one or more SNPs and one or more CNVs.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes the human genome. In some embodiments, the sequence of an entire genome is determined. However, in some embodiments, sequence information for a subset of a genome (e.g., one or a few chromosomes, or regions thereof) or for one or a few genes (or fragments thereof) is sufficient for diagnostic, prognostic, and/or therapeutic applications.

Nucleic acid sequencing of a plurality of single-stranded target nucleic acid templates may be completed where multiple sample wells (e.g., nanoapertures) are available, as is the case in devices described elsewhere herein. Each sample well can be provided with a single-stranded target nucleic acid template and a sequencing reaction can be completed in each sample well. Each of the sample wells may be contacted with the appropriate reagents (e.g., dNTPs, sequencing primers, polymerase, co-factors, appropriate buffers, etc.) necessary for nucleic acid synthesis during a primer extension reaction and the sequencing reaction can proceed in each sample well. In some embodiments, the multiple sample wells are contacted with all appropriate dNTPs simultaneously. In other embodiments, the multiple sample wells are contacted with each appropriate dNTP separately and each washed in between contact with different dNTPs. Incorporated dNTPs can be detected in each sample well and a sequence determined for the single-stranded target nucleic acid in each sample well as is described elsewhere herein.

While some embodiments may be directed to diagnostic testing by detecting single molecules in a specimen, the inventors have also recognized that the single molecule detection capabilities of the present disclosure may be used to perform polypeptide (e.g., protein) sequencing or nucleic acid (e.g., DNA, RNA) sequencing of one or more nucleic acid segments of, for example, genes.

In some aspects, methods described herein can be performed using one or more devices or apparatuses described in more detail below.

Overview of the Apparatus

The inventors have further recognized and appreciated that a compact, high-speed apparatus for performing detection and quantitation of single molecules or particles could reduce the cost of performing complex quantitative measurements of biological and/or chemical samples and rapidly advance the rate of biochemical technological discoveries. Moreover, a cost-effective device that is readily transportable could transform not only the way bioassays are performed in the developed world, but provide people in developing regions, for the first time, access to essential diagnostic tests that could dramatically improve their health and well-being. For example, embodiments described herein may be used for diagnostic tests of blood, urine and/or saliva that may be used by individuals in their home, or by a doctor in a remote clinic in a developing country.

A pixelated sensor device with a large number of pixels (e.g., hundreds, thousands, millions or more) allows for the detection of a plurality of individual molecules or particles in parallel. The molecules may be, by way of example and not limitation, proteins and/or DNA. Moreover, a high-speed device that can acquire data at more than one hundred frames per second allows for the detection and analysis of dynamic processes or changes that occur over time within the sample being analyzed.

The inventors have recognized and appreciated that one hurdle preventing bioassay equipment from being made more compact was the need to filter the excitation light from causing undesirable detection events at the sensor. Optical filters used to transmit the desired signal light (the luminescence) and sufficiently block the excitation light can be thick, bulky, expensive, and intolerant to variations in the incidence angle of light, preventing miniaturization. The inventors, however, recognized and appreciated that using a pulsed excitation source can reduce the need for such filtering or, in some cases, remove the need for such filters altogether. By using sensors capable of determining the time a photon is detected relative to the excitation light pulse, the signal light can be separated from the excitation light based on the time that the photon is received, rather than the spectrum of the light received. Accordingly, the need for a bulky optical filter is reduced and/or removed in some embodiments.

The inventors have recognized and appreciated that luminescence lifetime measurements may also be used to identify the molecules present in a sample. An optical sensor capable of detecting when a photon is detected is capable of measuring, using the statistics gathered from many events, the luminescence lifetime of the molecule being excited by the excitation light. In some embodiments, the luminescence lifetime measurement may be made in addition to a spectral measurement of the luminescence. Alternatively, a spectral measurement of the luminescence may be completely omitted in identifying the sample molecule. Luminescence lifetime measurements may be made with a pulsed excitation source. Additionally, luminescence lifetime measurements may be made using an integrated device that includes the sensor, or a device where the light source is located in a system separate from the integrated device.

The inventors have also recognized and appreciated that integrating a sample well (e.g., a nanoaperture) and a sensor in a single integrated device capable of measuring luminescent light emitted from biological samples reduces the cost of producing such a device such that disposable bioanalytical chips may be formed. Disposable, single-use integrated devices that interface with a base instrument may be used anywhere in the world, without the constraint of requiring high-cost biological laboratories for sample analyses. Thus, automated bioanalytics may be brought to regions of the world that previously could not perform quantitative analysis of biological samples. For example, blood tests for infants may be performed by placing a blood sample on a disposable integrated device, placing the disposable integrated device into a small, portable base instrument for analysis, and processing the results by a computer for immediate review by a user. The data may also be transmitted over a data network to a remote location to be analyzed, and/or archived for subsequent clinical analyses.

The inventors have also recognized and appreciated that a disposable, single-use device may be made more simply and for lower cost by not including the light source on the chip. Instead, the light source may be reusable components incorporated into a system that interfaces with the disposable chip to analyze a sample.

The inventors have also recognized and appreciated that, when a sample is tagged with a plurality of different types of luminescent markers, any suitable characteristic of luminescent markers may be used to identify the type of marker that is present in a particular pixel of the chip. For example, characteristics of the luminescence emitted by the markers and/or characteristics of the excitation absorption may be used to identify the markers. In some embodiments, the emission energy of the luminescence (which is directly related to the wavelength of the light) may be used to distinguish a first type of marker from a second type of marker. Additionally, or alternatively, luminescence lifetime measurements may also be used to identify the type of marker present at a particular pixel. In some embodiments, luminescence lifetime measurements may be made with a pulsed excitation source using a sensor capable of distinguishing a time when a photon is detected with sufficient resolution to obtain lifetime information. Additionally, or alternatively, the energy of the excitation light absorbed by the different types of markers may be used to identify the type of marker present at a particular pixel. For example, a first marker may absorb light of a first wavelength, but not equally absorb light of a second wavelength, while a second marker may absorb light of the second wavelength, but not equally absorb light of the first wavelength. In this way, when more than one excitation light source, each with a different excitation energy, may be used to illuminate the sample in an interleaved manner, the absorption energy of the markers can be used to identify which type of marker is present in a sample. Different markers may also have different luminescent intensities. Accordingly, the detected intensity of the luminescence may also be used to identify the type of marker present at a particular pixel.

I. Overview of the System

The system includes an integrated device and an instrument configured to interface with the integrated device. The integrated device includes an array of pixels, where a pixel includes a sample well and at least one sensor. A surface of the integrated device has a plurality of sample wells, where a sample well is configured to receive a sample from a specimen placed on the surface of the integrated device. A specimen may contain multiple samples, and in some embodiments, different types of samples. The plurality of sample wells may have a suitable size and shape such that at least a portion of the sample wells receive one sample from a specimen. In some embodiments, the number of samples within a sample well may be distributed among the sample wells such that some sample wells contain one sample with others contain zero, two or more samples.

In some embodiments, a specimen may contain multiple single-stranded DNA templates, and individual sample wells on a surface of an integrated device may be sized and shaped to receive a single-stranded DNA template. Single-stranded DNA templates may be distributed among the sample wells of the integrated device such that at least a portion of the sample wells of the integrated device contain a single-stranded DNA template. The specimen may also contain tagged dNTPs which then enter in the sample well and may allow for identification of a nucleotide as it is incorporated into a strand of DNA complementary to the single-stranded DNA template in the sample well. In such an example, the "sample" may refer to both the single-stranded DNA and the tagged dNTP currently being incorporated by a polymerase. In some embodiments, the specimen may contain single-stranded DNA templates and tagged dNTPS may be subsequently introduced to a sample well as nucleotides are incorporated into a complementary strand of DNA within the sample well. In this manner, timing of incorporation of nucleotides may be controlled by when tagged dNTPs are introduced to the sample wells of an integrated device.

Excitation energy is provided from an excitation source located separate from the pixel array of the integrated device. The excitation energy is directed at least in part by elements of the integrated device towards one or more pixels to illuminate an illumination region within the sample well. A marker or tag may then emit emission energy when located within the illumination region and in response to being illuminated by excitation energy. In some embodiments, one or more excitation sources are part of the instrument of the system where components of the instrument and the integrated device are configured to direct the excitation energy towards one or more pixels.

Emission energy emitted by a sample may then be detected by one or more sensors within a pixel of the integrated device. Characteristics of the detected emission energy may provide an indication for identifying the marked associated with the emission energy. Such characteristics may include any suitable type of characteristic, including an arrival time of photons detected by a sensor, an amount of photons accumulated over time by a sensor, and/or a distribution of photons across two or more sensors. In some embodiments, a sensor may have a configuration that allows for the detection of one or more timing characteristics associated with a sample's emission energy (e.g., fluorescence lifetime). The sensor may detect a distribution of photon arrival times after a pulse of excitation energy propagates through the integrated device, and the distribution of arrival times may provide an indication of a timing characteristic of the sample's emission energy (e.g., a proxy for fluorescence lifetime). In some embodiments, the one or more sensors provide an indication of the probability of emission energy emitted by the marker or tag (e.g., fluorescence intensity). In some embodiments, a plurality of sensors may be sized and arranged to capture a spatial distribution of the emission energy. Output signals from the one or more sensors may then be used to distinguish a marker from among a plurality of markers, where the plurality of markers may be used to identify a sample within the specimen. In some embodiments, the In some embodiments, a sample may be excited by multiple excitation energies, and emission energy and/or timing characteristics of the emission energy emitted by the sample in response to the multiple excitation energies may distinguish a marker from a plurality of markers.

A schematic overview of the system 23-100 is illustrated in FIGS. 23A and 23B. The system comprises both an integrated device 23-102 that interfaces with an instrument 23-104. In some embodiments, instrument 23-104 may include one or more excitation sources 23-106 integrated as part of instrument 23-104. In some embodiments, an excitation source may be external to both instrument 23-104 and integrated device 23-102, and instrument 23-104 may be configured to receive excitation energy from the excitation source and direct it to the integrated device. The integrated device may interface with the instrument using any suitable socket for receiving the integrated device and holding it in precise optical alignment with the excitation source. The excitation source 23-106 may be configured to provide excitation energy to the integrated device 23-102. As illustrated schematically in FIG. 23B, the integrated device 23-102 has multiple pixels, where at least a portion of pixels 23-112 may perform independent analysis of a sample. Such pixels 23-112 may be referred to as "passive source pixels" since a pixel receives excitation energy from a source 23-106 separate from the pixel, where the source excites a plurality of pixels. A pixel 23-112 has a sample well 23-108 configured to receive a sample and a sensor 23-110 for detecting emission energy emitted by the sample in response to illuminating the sample with excitation energy provided by the excitation source 23-106. Sample well 23-108 may retain the sample in proximity to a surface of integrated device 23-102 to provide ease in delivery of excitation energy to the sample and detection of emission energy from the sample.

Optical elements for guiding and coupling excitation energy to the sample well 23-108 are located both on integrated device 23-102 and the instrument 23-104. Such source-to-well elements may comprise one or more grating couplers located on integrated device 23-102 to couple excitation energy to the integrated device and waveguides to deliver excitation energy from instrument 23-104 to sample wells in pixels 23-112. In some embodiments, elements located on the integrated device may act to direct emission energy from the sample well towards the sensor. Sample well 23-108, a portion of the excitation source-to-well optics, and the sample well-to-sensor optics are located on integrated device 23-102. Excitation source 23-106 and a portion of the source-to-well components are located in instrument 23-104. In some embodiments, a single component may play a role in both coupling excitation energy to sample well 23-108 and delivering emission energy from sample well 23-108 to sensor 23-110. Examples of suitable components, for coupling excitation energy to a sample well and/or directing emission energy to a sensor, to include in an integrated device are described in U.S. patent application Ser. No. 14/821,688 entitled "INTEGRATED DEVICE FOR PROBING, DETECTING AND ANALYZING MOLECULES," and U.S. patent application Ser. No. 14/543,865 entitled "INTEGRATED DEVICE WITH EXTERNAL LIGHT SOURCE FOR PROBING, DETECTING, AND ANALYZING MOLECULES," both of which are incorporated by reference in their entirety.

As illustrated in FIG. 23B, the integrated device comprises a plurality of pixels where a pixel 23-112 is associated with its own individual sample well 23-108 and at least one sensor 23-110. The plurality of pixels may be arranged in an array, and there may be any suitable number of pixels in the array. The number of pixels in integrated device 23-102 may be in the range of approximately 10,000 pixels to 1,000,000 pixels or any value or range of values within that range. In some embodiments, the pixels may be arranged in an array of 512 pixels by 512 pixels. Integrated device 23-102 and instrument 23-104 may include multi-channel, high-speed communication links for handling data associated with large pixel arrays (e.g., more than 10,000 pixels).

Instrument 23-104 interfaces with integrated device 23-102 through integrated device interface 23-114. Integrated device interface 23-114 may include components to position and/or align integrated device 23-102 to instrument 23-104 to improve coupling of excitation energy from excitation source 23-106 to integrated device 23-102. Excitation source 23-106 may be any suitable light source that is arranged to deliver excitation energy to at least one sample well. Examples of suitable excitation sources are described in U.S. patent application Ser. No. 14/821,688 entitled "INTEGRATED DEVICE FOR PROBING, DETECTING AND ANALYZING MOLECULES," which is incorporated by reference in its entirety. In some embodiments, excitation source 23-106 includes multiple excitation sources that are combined to deliver excitation energy to integrated device 23-102. The multiple excitation sources may be configured to produce multiple excitation energies or wavelengths. The integrated device interface 23-114 may receive readout signals from the sensors in the pixels located on the integrated device. The integrated device interface 23-114 may be designed such that the integrated device attaches to the instrument by securing the integrated device to the integrated device interface 23-114.

The instrument 23-104 includes a user interface 23-116 for controlling the operation of instrument 23-104. The user interface 23-116 is configured to allow a user to input information into the instrument, such as commands and/or settings used to control the functioning of the instrument. In some embodiments, the user interface 23-116 may include buttons, switches, dials, and a microphone for voice commands. Additionally, the user interface 23-116 may allow a user to receive feedback on the performance of the instrument and/or integrated device, such as proper alignment and/or information obtained by readout signals from the sensors on the integrated device. In some embodiments, the user interface 23-116 may provide feedback using a speaker to provide audible feedback, and indicator lights and/or display screen for providing visual feedback. In some embodiments, the instrument 23-104 includes a computer interface 23-118 used to connect with a computing device 23-120. Any suitable computer interface 23-118 and computing device 23-120 may be used. For example, the computer interface 23-118 may be a USB interface or a FireWire interface. The computing device 23-120 may be any general purpose computer, such as a laptop or desktop computer. The computer interface 23-118 facilitates communication of information between the instrument 23-104 and the computing device 23-120. Input information for controlling and/or configuring the instrument 23-104 may be provided through the computing device 23-120 connected to the computer interface 23-118 of the instrument. Output information may be received by the computing device 23-120 through the computer interface 23-118. Such output information may include feedback about performance of the instrument 23-104 and/or integrated device 23-112 and information from the readout signals of the sensor 23-110. The instrument 23-104 may also include a processing device 23-122 for analyzing data received from the sensor 23-110 and/or sending control signals to the excitation source 23-106. In some embodiments, the processing device 23-122 may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) In some embodiments, the processing of data from the sensor 23-110 may be performed by both the processing device 23-122 and the external computing device 23-120. In other embodiments, the computing device 23-120 may be omitted and processing of data from the sensor 23-110 may be performed solely by processing device 23-122.

A cross-sectional schematic of the integrated device 24-102 illustrating a row of pixels is shown in FIG. 24A. Each pixel 24-112 includes a sample well 24-108 and a sensor 24-110. The sensor 24-110 may be aligned and positioned to sample well 24-112 such that sensor 24-110 receives emission energy emitted by a sample within sample well 24-112. Examples of suitable sensors are described in U.S. patent application Ser. No. 14/821,656 entitled "INTEGRATED DEVICE FOR TEMPORAL BINNING OF RECEIVED PHOTONS," which is incorporated by reference in its entirety.

An excitation source coupled to the integrated device may provide excitation energy to one or more pixels of integrated device 24-102. FIG. 24B is a schematic illustrating coupling of excitation source 24-106 to integrated device 24-102 to provide excitation energy 24-130 (shown in dashed lines) to integrated device 24-102. FIG. 24B illustrates the path of excitation energy from excitation energy source 24-106 to a sample well 24-108 in pixel 24-112. Components located off of the integrated device may be used to position and align the excitation source 24-106 to the integrated device. Such components may include optical components including lenses, mirrors, prisms, apertures, attenuators, and/or optical fibers. Additional mechanical components may be included in the instrument to allow for control of one or more alignment components. Such mechanical components may include actuators, stepper motors, and/or knobs.

The integrated device includes components that direct the excitation energy 24-130 towards pixels in the integrated device. Within each pixel 24-112, excitation energy is coupled to the sample well 24-108 associated with the pixel. Although FIG. 24B illustrates excitation energy coupling to each sample well in a row of pixels, in some embodiments, excitation energy may not couple to all of the pixels in a row. In some embodiments, excitation energy may couple to a portion of pixels or sample wells in a row of pixels of the integrated device. Excitation energy may illuminate a sample located within a sample well. The sample may reach an excited state in response to being illuminated by the excitation energy. When a sample is in an excited state, the sample may emit emission energy and the emission energy may be detected by a sensor. FIG. 24B schematically illustrates the path of emission energy 24-140 (shown as solid lines) from sample well 24-108 to sensor 24-110 of pixel 24-112. Sensor 24-110 in pixel 24-112 may be configured and positioned to detect emission energy from sample well 24-108.

In some embodiments, sensor 24-110 may include multiple sub-sensors. A sample to be analyzed may be introduced into sample well 24-108 of pixel 24-112. The sample may be a biological sample or any other suitable sample, such as a chemical sample. The sample may include multiple molecules and the sample well may be configured to isolate a single molecule. In some instances, the dimensions of the sample well may act to confine a single molecule within the sample well, allowing measurements to be performed on the single molecule. An excitation source 24-106 may be configured to deliver excitation energy into the sample well 24-108, so as to excite the sample or at least one luminescent marker attached to the sample or otherwise associated with the sample while it is within an illumination area within the sample well 24-108.

When an excitation source delivers excitation energy to a sample well, at least one sample within the well may luminesce, and the resulting emission may be detected by a sensor. As used herein, the phrases "a sample may luminesce" or "a sample may emit radiation" or "emission from a sample" mean that a luminescent tag, marker, or reporter, the sample itself, or a reaction product associated with the sample may produce the emitted radiation.

One or more components of an integrated device may direct emission energy towards a sensor. The emission energy or energies may be detected by the sensor and converted to at least one electrical signal. The electrical signals may be transmitted along conducting lines in the circuitry of the integrated device connected to the instrument through the integrated device interface, such as integrated device interface 23-114 of instrument 23-104 shown in FIG. 23B. The electrical signals may be subsequently processed and/or analyzed. Processing or analyzing of electrical signals may occur on a suitable computing device either located on the instrument 23-104 or off instrument, such as computing device 23-120 shown in FIG. 23B.

In operation, parallel analyses of samples within the sample wells are carried out by exciting the samples within the wells using the excitation source and detecting signals from sample emission with the sensors. Emission energy from a sample may be detected by a corresponding sensor and converted to at least one electrical signal. The resulting signal, or signals, may be processed on the integrated device in some embodiments, or transmitted to the instrument for processing by the processing device and/or computing device. Signals from a sample well may be received and processed independently from signals associated with the other pixels.

In some embodiments, a sample may be labeled with one or more markers, and emission associated with the markers is discernable by the instrument. For example the sensor may be configured to convert photons from the emission energy into electrons to form an electrical signal that may be used to discern a lifetime that is dependent on the emission energy from a specific marker. By using markers with different lifetimes to label samples, specific samples may be identified based on the resulting electrical signal detected by the sensor.

A sample may contain multiple types of molecules and different luminescent markers may uniquely associate with a molecule type. During or after excitation, the luminescent marker may emit emission energy. One or more properties of the emission energy may be used to identify one or more types of molecules in the sample. Properties of the emission energy used to distinguish among types of molecules may include a fluorescence lifetime value, intensity, and/or emission wavelength. A sensor may detect photons, including photons of emission energy, and provide electrical signals indicative of one or more of these properties. In some embodiments, electrical signals from a sensor may provide information about a distribution of photon arrival times across one or more time intervals. The distribution of photon arrival times may correspond to when a photon is detected after a pulse of excitation energy is emitted by an excitation source. A value for a time interval may correspond to a number of photons detected during the time interval. Relative values across multiple time intervals may provide an indication of a temporal characteristic of the emission energy (e.g., lifetime). Analyzing a sample may include distinguishing among markers by comparing values for two or more different time intervals within a distribution. In some embodiments, an indication of the intensity may be provided by determining a number of photons across all time bins in a distribution.

II. Integrated Device

The integrated device may be configured to receive excitation energy from an external excitation energy source. In some embodiments, a region of the device may be used to couple to an excitation energy source located off the integrated device. Components of the integrated device may guide excitation energy from the excitation source coupling region to at least one pixel. In some embodiments, at least one waveguide may be configured to deliver excitation energy to at least one pixel having a sample well. A sample located within the sample well may emit emission energy in response to being illuminated with excitation energy. One or more sensors located within the pixel are configured to receive the emission energy.

Components and/or layers of integrated device 25-200 according to some embodiments shown in FIG. 25 include a sample well 25-203, waveguide 25-220, and sensor 25-275 integrated into one device. Sample well 25-203 may be formed in sample well layer 25-201 of integrated device 25-200. In some embodiments, the sample well layer 25-201 may be metal. Sample well 25-203 may have a dimension $D_{rv}$ which may indicate a cross-sectional dimension of the sample well. Sample well 25-203 may act as a nanoaperture and have one or more sub-wavelength dimensions that create a field enhancement effect that increases the intensity of the excitation of the sample in sample well 25-203. Waveguide 25-220 is configured to deliver excitation energy from excitation source 25-230 located off device 25-200 to sample well 25-203. The waveguide 25-220 may be formed in a layer between sample well layer 25-201 and sensor 25-275. The design of integrated device 25-200 allows for sensor 25-275 to collect luminescence emitted from a sample in sample well 25-203. At least some of the time, the sample absorbs excitation energy and emits a photon with an energy less than that of the excitation energy, referred to as emission energy or luminescence.

Having sample well 25-203 and sensor 25-275 on integrated device 25-200 may reduce the optical distance that light travels from the sample well 25-203 to sensor 25-215. Dimensions of integrated device 25-200 or components within the device may be configured for a certain optical distance. Optical properties of the materials of components and/or one or more layers of the device may determine an optical distance between a sample well and a sensor. In some embodiments, the thicknesses of one or more layers may determine the optical distance between the sample well and sensor in a pixel. Additionally or alternatively, the index of refraction of materials that form one or more layers of integrated device 25-200 may determine the optical distance between sample well 25-203 and sensor 25-275 in a pixel. Such an optical distance between the sample well and sensor in a pixel may be less than 1 mm, less than 100 microns, less than 25 microns, and/or less than 10 microns. One or more layers may be present between sample well layer 25-201 and waveguide layer 25-220 to improve coupling of excitation energy from waveguide 25-220 to sample well 25-203. Although integrated device 25-200 shown in FIG. 25 illustrates only a single layer 25-210, multiple layers may be formed between sample well 25-203 and waveguide 25-220. Layer 25-210 may be formed with optical properties to improve coupling of excitation energy from waveguide 25-220 to sample well 25-203. Layer 25-210 may be configured to reduce scattering and/or absorption of excitation energy and/or increase luminescence from a sample in sample well 25-203. Layer 25-210 may be optically transparent, according to some embodiments, so that light may travel to and from the sample well 25-203 with little attenuation. In some embodiments, dielectric materials may be used to form layer 25-210. In some embodiments, excitation energy coupling components within layer 25-210 and/or at the interface between layer 25-210 and sample well layer 25-201 may be provided to improve coupling of excitation energy from waveguide 25-220 to sample well 25-203. As an example, energy-collection components 25-215 formed at the interface between sample well layer 25-201 and layer 25-210 may be configured to improve coupling of excitation energy from waveguide 25-220 to sample well 25-203. Energy-collection components 25-215 are optional and, in some embodiments, the configuration of waveguide 25-220 and sample well 25-203 may allow for adequate coupling excitation energy without the presence of excitation energy collection components 25-215.

Luminescent light or energy emitted from a sample in the sample well 25-203 may be transmitted to the sensor 25-275 in a variety of ways, some examples of which are described in detail below. Some embodiments may use optical components to increase the likelihood that light of a particular wavelength is directed to an area or portion of the sensor 25-275 that is dedicated to detecting light of that particular wavelength. The sensor 25-275 may include multiple portions for detecting simultaneously light of different wavelengths that may correspond to emissions from different luminescent markers.

One or more layers may be present between sample well 25-203 and sensor 25-275 that may be configured to improve collection of luminescence from sample well 25-203 to sensor 25-275. Luminescence directing components may be located at the interface between sample well layer 25-201 and layer 25-210. The energy-collection components 25-215 may focus emission energy toward the sensor 25-275, and may additionally or alternatively spatially separate emission energies that have different characteristic energies or wavelengths. Such energy-collection components 25-215 may include a grating structure for directing luminescence towards sensor 25-275. In some embodiments, the grating structure may be a series of concentric rings or "bullseye" grating structure configuration. The concentric circular gratings may protrude from a bottom surface of the sample well layer 25-201. The circular gratings may act as plasmonic elements which may be used to decrease the spread of the signal light and direct the signal light towards associated sensor 25-275. Such a bullseye grating may direct luminescence more efficiently towards sensor 25-275.

Layer 25-225 may be formed adjacent to the waveguide. The optical properties of layer 25-225 may be selected to improve collection of luminescence from the sample well to sensor 25-275. In some embodiments, layer 25-225 may be a dielectric material. A baffle may be formed between sample well layer 25-201 and sensor 25-275. Baffle 25-240 may be configured such that the sensor 25-275 receives luminescence corresponding to sample well 25-203 and reduces luminescence, and reflected/scattered excitation from other sample wells. Filtering elements 25-260 may be positioned and configured to reduce excitation energy from reaching sensor 25-275. In some embodiments, filtering elements 25-260 may include a filter that selectively transmits emission energy of one or more markers used to label a sample. In embodiments with an array of sample wells and an array of sensors where each sample well has a corresponding sensor, a baffle corresponding to each sample well may be formed to reduce luminescence from other sample wells and reflected and/or scattered excitation light from being collected by a sensor corresponding to the sample well.

One or more layers may be formed between waveguide 25-220 and sensor 25-275 to reduce transmission of excitation energy to sensor. In some embodiments, filtering elements may be formed between waveguide 25-220 and sensor 25-275. Such filtering elements may be configured to reduce transmission of excitation energy to sensor 25-275 while allowing luminescence from the sample well to be collected by sensor 25-275.

The emission energy or energies may be detected by the sensor 25-275 and converted to at least one electrical signal. The electrical signal or signals may be transmitted along one or more row or column conducting lines (not shown) to the integrated electronic circuitry on the substrate 25-200 for subsequent signal processing.

The above description of FIG. 25 is an overview of some of the components of the apparatus according to some embodiments. In some embodiments, one or more elements of FIG. 25 may be absent or in a different location. The components of the integrated device 25-200 and excitation source 25-230 are described in more detail below.

A. Excitation Source Coupling Region

The integrated device may have an excitation source coupling region configured to couple with an external excitation energy source and guide excitation towards at least one pixel in a pixel area of the integrated device. The excitation source coupling region may include one or more structures configured to couple light into at least one waveguide. Any suitable mechanism for coupling excitation energy into a waveguide may be used.

The excitation source coupling region of an integrated device may include structural components configured to couple with an external excitation source. An integrated device may include a grating coupler configured to couple with an external excitation source positioned proximate a surface of the integrated device and direct light towards at least one waveguide of the integrated device. Features of the grating coupler, such as the size, shape, and/or grating configurations may be formed to improve coupling of the excitation energy from the excitation source to the waveguide. The grating coupler may include one or more structural components where the spacing between the structural components may act to propagate light. One or more dimensions of the grating coupler may provide desirable coupling of light having a certain characteristic wavelength.

An integrated device may also include a waveguide having a tapered region at an end of the waveguide. One or more dimensions of the waveguide perpendicular to a direction of light propagation in the waveguide may be larger at an end of the waveguide, forming a tapered region of the waveguide. In some embodiments, the tapered region of a waveguide may have a dimension perpendicular to the propagation of light and parallel to a surface of the integrated device that is larger at an end of the waveguide and becomes smaller along the length of the waveguide. In embodiments that include a grating coupler, the tapered region can be positioned proximate to the grating coupler such that the larger end of the tapered region is located closest to the grating coupler. The tapered region may be sized and shaped to improve coupling of light between the grating coupler and the waveguide by expanding one or more dimensions of the waveguide to allow for improved mode overlap of the waveguide with the grating coupler. In this manner, an excitation source positioned proximate the surface of an integrated device may couple light into the waveguide via the grating coupler. Such a combination of grating coupler and waveguide taper may allow for more tolerance in the alignment and positioning of the excitation source to the integrated device.

A grating coupler may be positioned in a region of the integrated device external to the pixels of the integrated device. On a surface of the integrated device, the sample wells of the pixels may occupy a region of the surface separate from the excitation source coupling region. An excitation source positioned proximate to the surface of the excitation source coupling region may couple with the grating coupler. The sample wells may be positioned separate from the excitation source coupling region to reduce interference of light from the excitation source on performance of the pixels. A grating coupler of an integrated device may be formed within one or more layers of the integrated device that include a waveguide. In this manner, an excitation source coupling region of an integrated device may include a grating coupler within the same plane of the integrated device as a waveguide. The grating coupler may be configured for a particular set of beam parameters, including beam width, angle of incidence, and/or polarization of the incident excitation energy.

A cross-sectional view of integrated device 26-200 is shown in FIG. 26. Integrated device 26-200 includes at least one sample well 26-222 formed in layer 26-223 of integrated device 26-200. Integrated device 26-200 includes grating coupler 26-216 and waveguide 26-220 formed in substantially the same plane of integrated device 26-200. In some embodiments, grating coupler 26-216 and waveguide 26-220 are formed from the same layer of integrated device 26-200 and may include the same material. Excitation source coupling region 26-201 of integrated device 26-200 includes grating coupler 26-216. As shown in FIG. 26, sample well 26-222 is positioned on a surface of integrated device 26-200 external to excitation source coupling region 26-201. Excitation source 26-214 positioned relative to integrated device 26-200 may provide excitation energy incident on surface 26-215 of integrated device 26-200 within excitation source coupling region 26-201. By positioning grating coupler 26-216 within excitation source coupling region 26-201, grating coupler 26-216 may couple with the excitation energy from excitation source 26-214 and couple excitation energy to waveguide 26-220. Waveguide 26-220 is configured to propagate excitation energy to the proximity of one or more sample wells 26-222.

A grating coupler may be formed from one or more materials. In some embodiments, a grating coupler may include alternating regions of different materials along a direction parallel to propagation of light in the waveguide. As shown in FIG. 26, grating coupler 26-216 includes structures that are surrounded by material 26-224. The one or more materials that form a grating coupler may have one or more indices of refraction suitable for coupling and propagating light. In some embodiments, a grating coupler may include structures formed from one material surrounded by a material having a larger index of refraction. As an example, a grating coupler may include structures formed of silicon nitride and surrounded by silicon dioxide.

Any suitable dimensions and/or inter-grating spacing may be used to form a grating coupler. Grating coupler 26-216 may have a dimension perpendicular to the propagation of light through the waveguide, such as along the y-direction as shown in FIG. 26, of approximately 50 nm, approximately 100 nm, approximately 150 nm, or approximately 200 nm. Spacing between structures of the grating coupler along a direction parallel to light propagation in the waveguide, such as along the z-direction as shown in FIG. 26, may have any suitable distance. The inter-spacing grating may be approximately 300 nm, approximately, 350 nm, approximately, 400 nm, approximately 420 nm, approximately 450 nm, or approximately 500 nm. In some embodiments, the inter-grating spacing may be variable within a grating coupler. Grating coupler 26-216 may have one or more dimensions substantially parallel to surface 26-215 of integrated device 26-200 that provide a suitable area for coupling with external excitation source 26-214. The area of grating coupler 26-216 may coincide with one or more dimensions of a beam of light from excitation source 26-214 such that the beam overlaps with grating coupler 26-215. A grating coupler may have an area configured for a beam diameter of approximately 10 microns, approximately 20 microns, approximately 30 microns, or approximately 40 microns. An integrated device may include a layer formed on a side of a grating coupler opposite to the excitation source configured reflect light. The layer may reflect excitation energy that passes through the grating coupler towards the grating coupler. By including the layer in an integrated device, coupling efficiency of the excitation energy to the waveguide may be improved. An example of a reflective layer is layer 26-218 of integrated device 26-200 shown in FIG. 26. Layer 26-218 is positioned within excitation source coupling region 26-201 of integrated device 26-200 and is configured to reflect light towards grating coupler 26-216. Layer 26-218 is formed proximate to the side of grating coupler 26-216 opposite to the incident excitation energy from excitation source 26-214. Positioning layer 26-218 external to pixels of integrated device 26-200 may reduce interference of layer 26-218 on the performance capabilities of the pixels. Layer may 26-218 may include any suitable material. Layer 26-218 may be substantially reflective for one or more excitation energies. In some embodiments, this layer may include Al, AlCu, and/or TiN.

B. Waveguide

An integrated device may include one or more waveguides arranged to deliver a desired amount of excitation energy to one or more sample wells of the integrated device. A waveguide positioned in the vicinity of one or more sample wells such that as excitation energy propagates along the waveguide a portion of excitation energy couples to the one or more sample wells. A waveguide may couple excitation energy to a plurality of pixels and act as a bus waveguide. For example, a single waveguide may deliver excitation energy to a row or a column of pixels of an integrated device. In some embodiments, a waveguide may be configured to propagate excitation energy having a plurality of characteristic wavelengths. A pixel of an integrated device may include additional structures (e.g., microcavity) configured to direct excitation energy from the waveguide toward the vicinity of the sample well. In some embodiments, a waveguide may carry an optical mode having an evanescent tail configured to extend into a sample well and/or in a region in the vicinity of the sample well. Additional energy-coupling structures located near the sample well may couple energy from the evanescent tail into the sample well.

One or more dimensions of a waveguide of an integrated device may provide desired propagation of excitation energy along the waveguide and/or into one or more sample wells. A waveguide may have a dimension perpendicular to the propagation of light and parallel to a plane of the waveguide, which may be considered as a cross-sectional width. A waveguide may have a cross-sectional width of approximately 0.4 microns, approximately 0.5 microns, approximately 0.6 microns, approximately 0.65 microns, approximately 0.8 microns, approximately 1 micron, or approximately 1.2 microns. A waveguide may have a dimension perpendicular to the propagation of light and perpendicular to a plane of the waveguide, which may be considered as a cross-sectional height. A waveguide may have a cross-sectional height of approximately 0.05 microns, approximately 0.1 microns, approximately 0.15 microns, approximately 0.16 microns, approximately 0.17 microns, approximately 0.2 microns, or approximately 0.3 microns. In some embodiments, a waveguide has a larger cross-sectional width than cross-sectional height. A waveguide may be positioned a certain distance from one or more sample wells within in integrated device, such as distance D shown in FIG. 26 between sample well 26-222 and waveguide 26-220, that is approximately 0.3 microns, 0.5 microns, or approximately 0.7 microns.

In an exemplary embodiment, a waveguide may have a cross-sectional width of approximately 0.5 μm and a cross-sectional height of approximately 0.1 μm, and be positioned approximately 0.5 μm below the sample well layer. In another exemplary embodiment, a waveguide may have a cross-sectional width of approximately 1 μm and a cross-sectional height of 0.18 μm, and be positioned 0.3 μm below the sample well layer.

A waveguide may be dimensioned to support a single transverse radiation mode or may be dimensioned to support multi-transverse radiation modes. In some embodiments, one or more dimensions of a waveguide may act such that the waveguide sustains only a single transverse mode and may selectively propagate TE or TM polarization modes. In some implementations, a waveguide may have highly reflective sections formed on its ends, so that it supports a longitudinal standing mode within the waveguide. By supporting one mode, the waveguide may have reduced modal interference effects from cross coupling of modes having different propagation constants. In some embodiments, the highly reflective sections comprise a single, highly reflective surface. In other embodiments, the highly reflective sections comprise multiple reflective structures that, in aggregate, result in a high reflectance. Waveguides may be configured to split excitation energy from a single excitation source having a higher output intensity using waveguide beam splitters to create a plurality of excitation energy beams from a single excitation source. Such beam splitters may include evanescent coupling mechanisms. Additionally or alternatively, photonic crystals may be used in the waveguide structure to improve propagation of excitation energy and/or in the material surrounding the waveguide to reduce scattering of excitation energy.

The position and arrangement of the waveguide with respect to other components in a pixel of the integrated devices may be configured to improve coupling of excitation energy towards a sample well, improve collection of emission energy by the sensor, and/or reduce signal noise introduced by excitation energy. A waveguide may be sized and/or positioned relative to a sample well so as to reduce interference of excitation energy propagating in the waveguide with emission energy emitted from the sample well. Positioning and arrangement of a waveguide in an integrated device may depend on the refractive indices of the waveguide and material surrounding the waveguide. For example, a dimension of the waveguide perpendicular to a direction of light propagation along the waveguide and within a plane of the waveguide may be increased so that a substantial amount of emission energy from a sample well passes through the waveguide as it propagates to the sensor of the pixel. In some implementations, a distance between a sample well and waveguide and/or waveguide thickness may be selected to reduce reflections from one or more interfaces between the waveguide and a surrounding material. According to some embodiments, reflection of emission energy by a waveguide may be reduced to less than about 5% in some embodiments, less than about 2% in some embodiments, and yet less than about 1% in some embodiments.

The capability of a waveguide to propagate excitation energy may depend both on the material for the waveguide and material surrounding the waveguide. In this manner, the waveguide structure may include a core material, such as waveguide 26-220, and a cladding material, such as region 26-224 as illustrated in FIG. 26. The material of both the waveguide and surrounding material may allow for propagation of excitation energy having a characteristic wavelength through the waveguide. Material for either the waveguide or the surrounding material may be selected for particular indices of refraction or combination of indices of refraction. The waveguide material may have a lower refractive index than the waveguide surrounding material. Example waveguide materials include silicon nitride ($Si_xN_y$), silicon oxynitride, silicon carbide, tantalum oxide ($TaO_2$), aluminum dioxide. Example waveguide surrounding materials include silicon dioxide ($SiO_2$) and silicon oxide. The waveguide and/or the surrounding material may include one or more materials. In some instances, a desired refractive index for a waveguide and/or surrounding material can be obtained by forming the waveguide and/or surrounding material to include more than one material. In some embodiments, a waveguide comprises silicon nitride and a surrounding material comprises silicon dioxide.

Splitting waveguides from a single waveguide to multiple waveguides may allow for excitation energy to reach multiple rows or columns of sample wells of an integrated device. An excitation source may be coupled to an input waveguide and the input waveguide may be split into multiple output waveguides, where each output waveguide delivers excitation energy to a row or column of sample wells. Any suitable techniques for splitting and/or combining waveguides may be used. Such waveguide splitting and/or combining techniques may include a star splitter or coupler, a Y splitter, and/or an evanescent coupler. Additionally or alternatively, a multi-mode interference splitter (MMI) may be used for splitting and/or combining waveguides. One or more of these waveguide splitting and/or combining techniques may be used for directing excitation energy to a sample well.

C. Sample Well

According to some embodiments, a sample well 27-210 may be formed at one or more pixels of an integrated device. A sample well may comprise a small volume or region formed at a surface of a substrate 27-105 and arranged such that samples 27-101 may diffuse into and out of the sample well from a specimen deposited on the surface of the substrate, as depicted in FIG. 27A and FIG. 27B, which illustrate a single pixel 27-100 of an integrated device. In various embodiments, a sample well 27-210 may be arranged to receive excitation energy from a waveguide 27-240. Samples 27-101 that diffuse into the sample well may be retained, temporarily or permanently, within an excitation region 27-215 of the sample well by an adherent 27-211. In the excitation region, a sample may be excited by excitation energy (e.g., excitation radiation 27-247), and subsequently emit radiation that may be observed and evaluated to characterize the sample.

In further detail of operation, at least one sample 27-101 to be analyzed may be introduced into a sample well 27-210, e.g., from a specimen (not shown) containing a fluid suspension of samples. Excitation energy from a waveguide 27-240 may excite the sample or at least one marker attached to the sample or included in a tag associated with the sample while it is within an excitation region 27-215 within the sample well. According to some embodiments, a marker may be a luminescent molecule (e.g., fluorophore) or quantum dot. In some implementations, there may be more than one marker that is used to analyze a sample (e.g., distinct markers and tags that are used for single-molecule genetic sequencing as described in "Real-Time DNA Sequencing from Single Polymerase Molecules," by J. Eid, et al., *Science* 323, p. 133 (2009), which is incorporated by reference in its entirety). During and/or after excitation, the sample or marker may emit emission energy. When multiple markers are used, they may emit at different characteristic energies and/or emit with different temporal characteristics including different lifetimes. The emission energy from the sample well may radiate or otherwise travel to a sensor 27-260 where the emission energy is detected and converted into electrical signals that can be used to characterize the sample.

According to some embodiments, a sample well 27-210 may be a partially enclosed structure, as depicted in FIG. 27B. In some implementations, a sample well 27-210 comprises a sub-micron-sized hole or opening (characterized by at least one transverse dimension $D_{sw}$) formed in at least one layer of material 27-230. In some cases, the hole may be referred to as a "nanoaperture." The transverse dimension of the sample well may be between approximately 20 nanometers and approximately 1 micron, according to some embodiments, though larger and smaller sizes may be used in some implementations. A volume of the sample well 27-210 may be between about $10^{-21}$ liters and about $10^{-15}$ liters, in some implementations. A sample well may be formed as a waveguide that may, or may not, support a propagating mode. A sample well may be formed as a waveguide that may, or may not, support a propagating mode. In some embodiments, a sample well may be formed as a zero-mode waveguide (ZMW) having a cylindrical shape (or similar shape) with a diameter (or largest transverse dimension) $D_{sw}$. A ZMW may be formed in a single metal layer as a nano-scale hole that does not support a propagating optical mode through the hole.

Because the sample well 27-210 has a small volume, detection of single-sample events (e.g., single-molecule events) at each pixel may be possible even though samples may be concentrated in an examined specimen at concentrations that are similar to those found in natural environments. For example, micromolar concentrations of the sample may be present in a specimen that is placed in contact with the integrated device, but at the pixel level only about one sample (or single molecule event) may be within a sample well at any given time. Statistically, some sample wells may contain no samples and some may contain more than one sample. However, an appreciable number of sample wells may contain a single sample (e.g., at least 30% in some embodiments), so that single-molecule analysis can be carried out in parallel for a large number of pixels. Because single-molecule or single-sample events may be analyzed at each pixel, the integrated device makes it possible to detect rare events that may otherwise go unnoticed in ensemble averages.

A transverse dimension $D_{sw}$ of a sample well may be between about 500 nanometers (nm) and about one micron in some embodiments, between about 250 nm and about 500 nm in some embodiments, between about 100 nm and about 250 nm in some embodiments, and yet between about 20 nm and about 100 nm in some embodiments. According to some implementations, a transverse dimension of a sample well is between approximately 80 nm and approximately 180 nm, or between approximately one-quarter and one-eighth of the excitation wavelength or emission wavelength. According to other implementations, a transverse dimension of a sample well is between approximately 120 nm and approximately 170 nm. In some embodiments, the depth or height of the sample well 27-210 may be between about 50 nm and about 500 nm. In some implementations, the depth or height of the sample well 27-210 may be between about 80 nm and about 250 nm.

A sample well 27-210 having a sub-wavelength, transverse dimension can improve operation of a pixel 27-100 of an integrated device in at least two ways. For example, excitation energy incident on the sample well from a side opposite the specimen may couple into the excitation region 27-215 with an exponentially decreasing power, and not propagate through the sample well to the specimen. As a result, excitation energy is increased in the excitation region where it excites a sample of interest, and is reduced in the specimen where it would excite other samples that would contribute to background noise. Also, emission from a sample retained at a base of the well (e.g., nearer to the sensor 27-260) is preferably directed toward the sensor, since emission propagating up through the sample well is highly suppressed. Both of these effects can improve signal-to-noise ratio at the pixel. The inventors have recognized several aspects of the sample well that can be improved to further boost signal-to-noise levels at the pixel. These aspects relate to sample well shape and structure, and also to adjacent optical and plasmonic structures (described below) that aid in coupling excitation energy to the sample well and emitted radiation from the sample well.

According to some embodiments, a sample well 27-210 may be formed as a nanoaperture configured to not support a propagating mode for particular wavelengths of interest. In some instances, the nanoaperture is configured where all modes are below a threshold wavelength and the aperture may be a sub-cutoff nanoaperture (SCN). For example, the sample well 27-210 may comprise a cylindrically-shaped hole or bore in a conductive layer. The cross-section of a sample well need not be round, and may be elliptical, square, rectangular, or polygonal in some embodiments. Excitation energy 27-247 (e.g., visible or near infrared radiation) may enter the sample well through an entrance aperture 27-212 that may be defined by walls 27-214 of the sample well at a first end of the well, as depicted in FIG. 27B. When formed as a SCN, the excitation energy may decay exponentially along a length of the nanoaperture (e.g. in the direction of the specimen). In some implementations, the waveguide may comprise a SCN for emitted radiation from the sample, but may not be a SCN for excitation energy. For example, the aperture and waveguide formed by the sample well may be large enough to support a propagating mode for the excitation energy, since it may have a shorter wavelength than the emitted radiation. The emission, at a longer wavelength, may be beyond a cut-off wavelength for a propagating mode in the waveguide. According to some embodiments, the sample well 27-210 may comprise a SCN for the excitation energy, such that the greatest intensity of excitation energy is localized to an excitation region 27-215 of the sample well at an entrance to the sample well 27-210 (e.g., localized near the interface between layer 27-235 and layer 27-230 as depicted in the drawing). Such localization of the excitation energy can improve localization of emission energy from the sample, and limit the observed emission that emitted from a single sample (e.g., a single molecule).

According to some embodiments, a pixel 27-100 may include additional structures. For example, a pixel 27-100 may include one or more excitation-coupling structure 27-220 that affects coupling of excitation energy to a sample within the sample well. A pixel may also include an emission-directing structure 27-250 that affects directing emission energy from a sample within the sample well to sensor 27-260.

To improve the intensity of excitation energy that is localized at the sample well, other sample well structures were developed and studied by the inventors. FIG. 27C depicts an embodiment of a sample well that includes a cavity or divot 27-216 at an excitation end of the sample well. Adding a divot 27-216 to the sample well allows a sample to move into a region of higher excitation intensity, according to some embodiments. In some implementations, the shape and structure of the divot alters the local excitation field (e.g., because of a difference in refractive index between the layer 27-235 and fluid in the sample well), and can further increase the intensity of the excitation energy in the divot. Divot 27-216 may be formed within layer 27-235 such that a portion of the sample volume that occupies sample well 27-214 and divot 27-216 is surrounded by the material that forms layer 27-216.

The divot may have any suitable shape. The divot may have a transverse shape that is substantially equivalent to a transverse shape of the sample well, e.g., round, elliptical, square, rectangular, polygonal, etc. In some embodiments, the sidewalls of the divot may be substantially straight and vertical, like the walls of the sample well. In some implementations, the sidewalls of the divot may be sloped and/or curved, as depicted in the drawing. The transverse dimension of the divot may be approximately the same size as the transverse dimension of the sample well in some embodiments, may be smaller than the transverse dimension of the sample well in some embodiments, or may be larger than the transverse dimension of the sample well in some embodiments. The divot 27-216 may extend between approximately 10 nm and approximately 200 nm beyond sample well layer 27-230. In some implementations, the divot may extend between approximately 50 nm and approximately 150 nm beyond sample well layer 27-230. In some embodiments, the divot may extend between approximately 150 nm and approximately 250 nm beyond sample well layer 27-230. By forming the divot, the excitation region 27-215 may extend outside the sample well, as depicted in FIG. 27C.

Some embodiments relate to an integrated device having a sample well with a divot positioned proximate to a waveguide. FIG. 28 shows an integrated device having sample well 28-632 formed in layer 28-630 and layer 28-636. Layer 28-630 may be a metal layer and include one or more metals (e.g., Al). Layer 28-636 may act as a dielectric layer and include one or more dielectric materials (e.g., silicon dioxide). Sample well 28-632 may have a variable dimension in a direction parallel to layer 28-630 and/or layer 28-636. Sample well 28-632 may have a dimension D2 along the z-direction at least within layer 28-630 of the integrated device, and in some embodiments, dimension D2 may be considered a diameter of sample well 28-632. Dimension D2 of sample well 28-632 may be approximately 700 nm, approximately 800 nm, approximately 900 nm, approximately 1 micron, or approximately 1.1 microns. Sample well 28-632 may have a dimension D1 along the z-direction within layer 28-636 of the integrated device and in some embodiments, may be consider a diameter at a surface of sample well 28-632. Dimension D1 may be approximately 100 nm, approximately 150 nm, approximately 200 nm, or approximately 250 nm. The surface of sample well 28-632 having dimension D1 is positioned a dimension d1 along the x-direction from waveguide 28-634. Positioning sample well 28-632 proximate to waveguide 28-634 by distance d1 may allow for improved coupling of excitation energy from waveguide 28-634 to sample well 28-632. Dimension d1 may be approximately 50 nm, approximately 100 nm, approximately 150 nm, approximately 200 nm, or approximately 250 nm.

D. Coupling Excitation Energy to Sample Well

Coupling of excitation energy to one or more sample wells of the integrated device may occur through one or more techniques. As previously discussed, in some embodiments, a waveguide is positioned to couple with an excitation source to one or more sample wells. As excitation energy propagates along the waveguide, a portion of the excitation energy may be couple to one or more sample wells through a variety of light coupling techniques. For example, the waveguide may guide excitation energy substantially in one direction, and an evanescent wave or tail may form perpendicular to this one direction and, in some instances, be located outside the waveguide structure. Such an evanescent tail may direct a portion of excitation energy towards one or more sample wells. In some embodiments, the sample well layer may be designed and configured to direct excitation energy to a localized region within the sample well. The sample well may be configured to retain a sample within the localized region of the sample well such that excitation energy is directed towards the sample.

Additionally, one or more components may be formed in an integrated device to improve or enhance coupling of excitation energy into a sample well. These additional components may be formed in a pixel and provide coupling of excitation energy from a waveguide into the pixel and towards the sample well. One or more components located in a pixel may act to tap a portion of the excitation energy from a waveguide into the pixel. Such components may include optical structures such as, grating structures, scattering structures, microcavities and/or nano-antennas. Features or configurations of one or more of these components may be selected for coupling a certain amount of excitation energy to each sample well within a row or column of sample wells. A waveguide configured to provide excitation energy to a row of pixels may couple to a component in each pixel region to provide a portion of the excitation energy to each pixel in the row of pixels. When a waveguide is configured to direct excitation energy from an excitation source towards one or more pixels, the waveguide may be referred to as a bus waveguide.

Components positioned adjacent to a sample well may improve coupling of excitation energy from waveguide to sample well. Such components may be called taps and/or microcavities. A microcavity may deflect a portion of the excitation energy from the waveguide such that excitation energy reaches the sample well. One or more microcavities may be used to couple excitation energy to a sample well. The one or more microcavities may reduce loss of excitation energy from the waveguide, including metallic loss. One or more microcavities may act as a lens to focus excitation energy to the sample well. In some embodiments, one or more microcavities may improve directing luminescence from a marker in the sample well towards the sensor. The microcavities may have a cylindrical, convex, concave, rectangular, spherical, or elliptical configuration or any other suitable shape. A microcavity may be formed from any suitable material. In some embodiments, a microcavity may include silicon nitride.

One or more microcavities may overlap with at least a portion of a waveguide to direct excitation energy towards the sample well when viewed from the top of the integrated device where the sample wells are present. The thickness of a waveguide may be configured to reduce loss of excitation energy and improve coupling of excitation energy to one or more microcavities. In some embodiments, microcavities along a row of sample wells may vary in strength of coupling between the waveguide to each sample well. The microcavities may increase coupling along the propagation direction of the excitation energy in order to accommodate a reduced power in the waveguide as excitation energy is directed out of the waveguide to each sample well. In some embodiments, one or more microcavities are adjacent to the sample well. There may be an offset distance between the location of the center of a sample well and the center of a microcavity. In other embodiments, one microcavity is located below a sample well such that at least a portion of the sample well and a portion of the microcavity overlap when viewed from the top of the integrated device where the sample wells are present.

One or more dimensions of a waveguide of an integrated device may vary along the length of the waveguide in the direction of light propagation through the waveguide. Varying one or more dimensions along the waveguide may improve coupling efficiency and substantial uniformity in the amount of excitation energy provided by the waveguide to a plurality of sample wells. In some embodiments, the cross-sectional width of a waveguide may vary along a row or column of pixels. The waveguide may include a taper such that the cross-sectional width of the waveguide decreases along the direction of propagation of excitation energy through the waveguide. In some embodiments, a tapered waveguide may be configured for a similar coupling efficiency for a row of pixels where pixels in the row include a microcavity and a sample well. A combination of varying one or more dimensions of the tapered waveguide and/or the microcavity may accommodate reduction in power of excitation energy along the length of a waveguide as excitation energy is coupled to each sample well in the row.

In some embodiments, a waveguide may couple to a sample well by an evanescent field. In some embodiments, a bullseye grating structure having concentric grating rings positioned proximate to a sample well may improve coupling of excitation energy from the waveguide to the sample well. In some embodiments, the waveguide may include a region having a reduced cross-sectional width in the vicinity of a sample well such that an evanescent field from the excitation energy propagating in the waveguide couples to the sample well. For a row of pixels, a waveguide may include multiple regions having a reduced cross-sectional width along the length of the waveguide to improve coupling uniformity and efficiency among sample wells in the row. In this manner, the waveguide may be considered to have pinched sections at certain locations along the waveguide.

The layer of an integrated device having one or more sample wells may interfere with propagation of light through a waveguide. In some embodiments, the sample well layer is formed of a metal (e.g., aluminum). It may be desirable to position the sample well layer at a certain distance from the waveguide to reduce loss and improve performance of the device. These techniques may allow for a desired performance achieved by positioning the sample well layer at a certain distance from the waveguide while allowing a sample well in the layer to receive a sufficient amount of excitation energy.

E. Directing Emission Energy to Sensor

An integrated device may include one or more components positioned between a sample well and a sensor of a pixel to improve collection of luminescence by the sensor from a sample in the sample well. Such components may improve the signal-to-noise ratio of the luminescence signal to a background signal to provide improved detection of a luminescent marker. Some components may direct luminescence from a sample well to a corresponding sensor in a pixel. In some embodiments, a component may provide both suitable coupling of excitation energy to a sample well and coupling of luminescence out of the sample well. Other components (e.g., filters) may reduce excitation energy and other light not associated with the sample and/or marker from contributing to a signal acquired by the sensor.

A bullseye grating may be formed from concentric grating rings around a sample well. A bullseye grating may couple with a sample well to improve propagation of luminescence out of the sample well. The bullseye grating structure may direct luminescence towards a sensor in a pixel having the sample well. In some embodiments, an effective diameter of the luminescence directed by a bullseye grating is approximately 5 microns.

In some embodiments, one or more microcavities provided for coupling of a waveguide and a sample well to allow propagation of excitation energy to the sample well may also direct luminescence from the sample well to a sensor.

A baffle having an opening centered on a sensor may be formed between a sample well and the sensor. As shown in FIG. 26, baffle layer 26-226 is positioned between sample well 26-22 and sensor layer 26-230. A baffle in a pixel may be designed to suppress collection of energy besides luminescence for the pixel. A baffle associated with a sample well and a sensor may allow for luminescence from the sample well to reach the sensor while reducing luminescence from neighboring pixels, excitation energy, and other energy not associated with the luminescence from the sample well associated with the sensor. A dimension of the opening of the baffle may be configured to allow luminescence directed by a bullseye on the same pixel. As shown in FIG. 26, baffle 26-226 has openings along the z-direction to allow luminescence to pass through to sensors positioned in layer 26-230. The material of a baffle may be selected for certain optical properties, such as reducing transmission of certain light wavelengths or energies at certain incident angles. In some embodiments, a baffle may be formed by multiple layers of materials having different refractive indices. A baffle may include one or more layers of silicon, silicon nitride (Si3N4), silicon, titanium nitride (TiN), and aluminum (Al). A layer configured to form a baffle may have a cross-sectional height of approximately 20 nm, approximately 20 nm, approximately 50 nm, approximately 60 nm, approximately 70 nm, approximately 80 nm, or approximately 90 nm.

Filtering components may be formed between a waveguide and a sensor for reducing collection of excitation energy by the sensor. Any suitable manner for filtering excitation energy may be provided. Techniques for filtering the excitation energy may include filtering based on one or more characteristics of light. Such characteristics may include wavelength and/or polarization. Filtering components may selectively suppress scattered excitation energy while allowing luminescence to pass through to the sensor. Layer 26-228 shown in FIG. 26 may include one or more filtering components described herein.

An integrated device may include a wavelength filter configured to reflect light of one or more characteristic wavelengths and allow transmission of light having a different characteristic wavelength. In some embodiments, light reflected by a wavelength filter may have a shorter characteristic wavelength than the light transmitted by the wavelength filter. Such a wavelength filter may reflect excitation energy and allow transmission of luminesce since excitation energy used to excite a marker typically has a shorter characteristic wavelength than luminesce emitted by the marker in response reaching an excitation state by the excitation energy.

F. Sensor

Any suitable sensor capable of acquiring time bin information may be used for measurements to detect lifetimes of luminescent markers. For example, U.S. patent application Ser. No. 14/821,656 entitled "INTEGRATED DEVICE FOR TEMPORAL BINNING OF RECEIVED PHOTONS," describes a sensor capable of determining an arrival time of a photon, and is incorporated by reference in its entirety. The sensors are aligned such that each sample well has at least one sensor region to detect luminescence from the sample well. In some embodiments, the integrated device may include Geiger mode avalanche photodiode arrays and/or single photon avalanche diode arrays (SPADs).

Described herein is an integrated photodetector that can accurately measure, or "time-bin," the timing of arrival of incident photons, and which may be used in a variety of applications, such as sequencing of nucleic acids (e.g., DNA sequencing), for example. In some embodiments, the integrated photodetector can measure the arrival of photons with nanosecond or picosecond resolution, which can facilitate time-domain analysis of the arrival of incident photons.

Some embodiments relate to an integrated circuit having a photodetector that produces charge carriers in response to incident photons and which is capable of discriminating the timing at which the charge carriers are generated by the arrival of incident photons with respect to a reference time (e.g., a trigger event). In some embodiments, a charge carrier segregation structure segregates charge carriers generated at different times and directs the charge carriers into one or more charge carrier storage regions (termed "bins") that aggregate charge carriers produced within different time periods. Each bin stores charge carriers produced within a selected time interval. Reading out the charge stored in each bin can provide information about the number of photons that arrived within each time interval. Such an integrated circuit can be used in any of a variety of applications, such as those described herein.

An example of an integrated circuit having a photodetection region and a charge carrier segregation structure will be described. In some embodiments, the integrated circuit may include an array of pixels, and each pixel may include one or more photodetection regions and one or more charge carrier segregation structures, as discussed below.

FIG. 29A shows a diagram of a pixel 29-900, according to some embodiments. Pixel 29-900 includes a photon absorption/carrier generation region 29-902 (also referred to as a photodetection region), a carrier travel/capture region 29-906, a carrier storage region 29-908 having one or more charge carrier storage regions, also referred to herein as "charge carrier storage bins" or simply "bins," and readout circuitry 29-910 for reading out signals from the charge carrier storage bins.

The photon absorption/carrier generation region 29-902 may be a region of semiconductor material (e.g., silicon) that can convert incident photons into photogenerated charge carriers. The photon absorption/carrier generation region 29-902 may be exposed to light, and may receive incident photons. When a photon is absorbed by the photon absorption/carrier generation region 29-902 it may generate photogenerated charge carriers, such as an electron/hole pair. Photogenerated charge carriers are also referred to herein simply as "charge carriers."

An electric field may be established in the photon absorption/carrier generation region 29-902. In some embodiments, the electric field may be "static," as distinguished from the changing electric field in the carrier travel/capture region 29-906. The electric field in the photon absorption/carrier generation region 29-902 may include a lateral component, a vertical component, or both a lateral and a vertical component. The lateral component of the electric field may be in the downward direction of FIG. 29A, as indicated by the arrows, which induces a force on photogenerated charge carriers that drives them toward the carrier travel/capture region 106. The electric field may be formed in a variety of ways.

In some embodiments, one or more electrodes may be formed over the photon absorption/carrier generation region 29-902. The electrodes(s) may have voltages applied thereto to establish an electric field in the photon absorption/carrier generation region 29-902. Such electrode(s) may be termed "photogate(s)." In some embodiments, photon absorption/carrier generation region 29-902 may be a region of silicon that is fully depleted of charge carriers.

In some embodiments, the electric field in the photon absorption/carrier generation region 29-902 may be established by a junction, such as a PN junction. The semiconductor material of the photon absorption/carrier generation region 29-902 may be doped to form the PN junction with an orientation and/or shape that produces an electric field that induces a force on photogenerated charge carriers that drives them toward the carrier travel/capture region 29-906. In some embodiments, the P terminal of the PN junction diode may connected to a terminal that sets its voltage. Such a diode may be referred to as a "pinned" photodiode. A pinned photodiode may promote carrier recombination at the surface, due to the terminal that sets its voltage and attracts carriers, which can reduce dark current. Photogenerated charge carriers that are desired to be captured may pass underneath the recombination area at the surface. In some embodiments, the lateral electric field may be established using a graded doping concentration in the semiconductor material.

As illustrated in FIG. 29A, a photon may be captured and a charge carrier 29-901A (e.g., an electron) may be produced at time t1. In some embodiments, an electrical potential gradient may be established along the photon absorption/carrier generation region 29-902 and the carrier travel/capture region 29-906 that causes the charge carrier 29-901A to travel in the downward direction of FIG. 29A (as illustrated by the arrows shown in FIG. 29A). In response to the potential gradient, the charge carrier 29-901A may move from its position at time t1 to a second position at time t2, a third position at time t3, a fourth position at time t4, and a fifth position at time t5. The charge carrier 29-901A thus moves into the carrier travel/capture region 29-906 in response to the potential gradient.

The carrier travel/capture region 29-906 may be a semiconductor region. In some embodiments, the carrier travel/capture region 29-906 may be a semiconductor region of the same material as photon absorption/carrier generation region 29-902 (e.g., silicon) with the exception that carrier travel/capture region 29-906 may be shielded from incident light (e.g., by an overlying opaque material, such as a metal layer).

In some embodiments, and as discussed further below, a potential gradient may be established in the photon absorption/carrier generation region 29-902 and the carrier travel/capture region 29-906 by electrodes positioned above these regions. However, the techniques described herein are not limited as to particular positions of electrodes used for producing an electric potential gradient. Nor are the techniques described herein limited to establishing an electric potential gradient using electrodes. In some embodiments, an electric potential gradient may be established using a spatially graded doping profile. Any suitable technique may be used for establishing an electric potential gradient that causes charge carriers to travel along the photon absorption/carrier generation region 29-902 and carrier travel/capture region 29-906.

A charge carrier segregation structure may be formed in the pixel to enable segregating charge carriers produced at different times. In some embodiments, at least a portion of the charge carrier segregation structure may be formed over the carrier travel/capture region 29-906. As will be described below, the charge carrier segregation structure may include one or more electrodes formed over the carrier travel/capture region 29-906, the voltage of which may be controlled by control circuitry to change the electric potential in the carrier travel/capture region 29-906.

The electric potential in the carrier travel/capture region 29-906 may be changed to enable capturing a charge carrier. The potential gradient may be changed by changing the voltage on one or more electrodes overlying the carrier travel/capture region 29-906 to produce a potential barrier that can confine a carrier within a predetermined spatial region. For example, the voltage on an electrode overlying the dashed line in the carrier travel/capture region 29-906 of FIG. 29A may be changed at time t5 to raise a potential barrier along the dashed line in the carrier travel/capture region 29-906 of FIG. 29A, thereby capturing charge carrier 29-901A. As shown in FIG. 29A, the carrier captured at time t5 may be transferred to a bin "bin0" of carrier storage region 29-908. The transfer of the carrier to the charge carrier storage bin may be performed by changing the potential in the carrier travel/capture region 29-906 and/or carrier storage region 29-908 (e.g., by changing the voltage of electrode(s) overlying these regions) to cause the carrier to travel into the charge carrier storage bin.

Changing the potential at a certain point in time within a predetermined spatial region of the carrier travel/capture region 29-906 may enable trapping a carrier that was generated by photon absorption that occurred within a specific time interval. By trapping photogenerated charge carriers at different times and/or locations, the times at which the charge carriers were generated by photon absorption may be discriminated. In this sense, a charge carrier may be "time binned" by trapping the charge carrier at a certain point in time and/or space after the occurrence of a trigger event. The time binning of a charge carrier within a particular bin provides information about the time at which the photogenerated charge carrier was generated by absorption of an incident photon, and thus likewise "time bins," with respect to the trigger event, the arrival of the incident photon that produced the photogenerated charge carrier. FIG. 29B illustrates capturing a charge carrier at a different point in time and space. As shown in FIG. 29B, the voltage on an electrode overlying the dashed line in the carrier travel/capture region 29-906 may be changed at time t9 to raise a potential barrier along the dashed line in the carrier travel/capture region 106 of FIG. 29B, thereby capturing carrier 29-901B. As shown in FIG. 29B, the carrier captured at time t9 may be transferred to a bin "bin1" of carrier storage region 29-908. Since charge carrier 29-901B is trapped at time t9, it represents a photon absorption event that occurred at a different time (i.e., time t6) than the photon absorption event (i.e., at t1) for carrier 29-901A, which is captured at time t5.

Performing multiple measurements and aggregating charge carriers in the charge carrier storage bins of carrier storage region 29-908 based on the times at which the charge carriers are captured can provide information about the times at which photons are captured in the photon absorption/carrier generation area 29-902. Such information can be useful in a variety of applications, as discussed above.

In some embodiments, the duration of time each time bin captures after an excitation pulse may vary. For example, shorter time bins may be used to detect luminescence shortly after the excitation pulse, while longer time bins may be used at times further from an excitation pulse. By varying the time bin intervals, the signal to noise ratio for measurements of the electrical signal associated with each time bin may be improved for a given sensor. Since the probability of a photon emission event is higher shortly after an excitation pulse, a time bin within this time may have a shorter time interval to account for the potential of more photons to detect. While at longer times, the probability of photon emission may be less and a time bin detecting within this time may be longer to account for a potential fewer number of photons. In some embodiments, a time bin with a significantly longer time duration may be used to distinguish among multiple lifetimes. For example, the majority of time bins may capture a time interval in the range of approximately 0.1-0.5 ns, while a time bin may capture a time interval in the range of approximately 2-5 ns. The number of time bins and/or the time interval of each bin may depend on the sensor used to detect the photons emitted from the sample object.

Determining the time interval for each bin may include identifying the time intervals needed for the number of time bins provided by the sensor to distinguish among luminescent markers used for analysis of a sample. The distribution of the recorded histogram may be compared to known histograms of markers under similar conditions and time bins to identify the type of marker in the sample well. Different embodiments of the present application may measure lifetimes of markers but vary in the excitation energies used to excite a marker, the number of sensor regions in each pixel, and/or the wavelength detected by the sensors.

III. Excitation Source

According to some embodiments, one or more excitation sources may be located external to the integrated device, and may be arranged to deliver pulses of light to an integrated device having sample wells. For example, U.S. Provisional Patent Application 62/164,485, entitled "PULSED LASER," filed May 20, 2015 and U.S. Provisional Patent Application 62/310,398, entitled "PULSED LASER," filed Mar. 18, 2016 describe examples of pulsed laser sources that may be used as an excitation source, each of which is incorporated by reference in its entirety. The pulses of light may be coupled to a plurality of sample wells and used to excite one or more markers within the wells, for example. The one or more excitation sources may deliver pulses of light at one or more characteristic wavelengths, according to some implementations. In some cases, an excitation source may be packaged as an exchangeable module that mounts in or couples to a base instrument, into which the integrated device may be loaded. Energy from an excitation source may be delivered radiatively or non-radiatively to at least one sample well or to at least one sample in at least one sample well. In some implementations, an excitation source having a controllable intensity may be arranged to deliver excitation energy to a plurality of pixels of an integrated device. The pixels may be arranged in a linear array (e.g., row or column), or in a 2D array (e.g., a sub-area of the array of pixels or the full array of pixels).

Any suitable light source may be used for an excitation source. Some embodiments may use incoherent light sources and other embodiments may use coherent light sources. By way of non-limiting examples, incoherent light sources according to some embodiments may include different types of light emitting diodes (LEDs) such as organic LEDs (OLEDs), quantum dots (QLEDs), nanowire LEDs, and (in)organic semiconductor LEDs. By way of non-limiting examples, coherent light sources according to some embodiments may include different types of lasers such as semiconductor lasers (e.g., vertical cavity surface emitting lasers (VCSELs), edge emitting lasers, and distributed-feedback (DFB) laser diodes). Additionally or alternatively, slab-coupled optical waveguide laser (SCOWLs) or other asymmetric single-mode waveguide structures may be used. In some implementations, coherent light sources may comprise organic lasers, quantum dot lasers, and solid state lasers (e.g., a Nd:YAG or ND:Glass laser, pumped by laser diodes or flashlamps). In some embodiments, a laser-diode-pumped fiber laser may be used. A coherent light source may be passively mode locked to produce ultrashort pulses. There may be more than one type of excitation source for an array of pixels on an integrated device. In some embodiments, different types of excitation sources may be combined. An excitation source may be fabricated according to conventional technologies that are used to fabricate a selected type of excitation source.

By way of introduction and without limiting the invention, an example arrangement of a coherent light source is depicted in FIG. 30A. The drawing illustrates an analytical instrument 30-100 that may include an ultrashort-pulsed laser excitation source 30-110 as the excitation source. The ultrashort pulsed laser 30-110 may comprise a gain medium 30-105 (which may be a solid-state material is some embodiments), a pump source for exciting the gain medium (not shown), and at least two cavity mirrors 30-102, 30-104 that define ends of an optical laser cavity. In some embodiments, there may be one or more additional optical elements in the laser cavity for purposes of beam shaping, wavelength selection, and/or pulse forming. When operating, the pulsed-laser excitation source 30-110 may produce an ultrashort optical pulse 30-120 that circulates back-and-forth in the laser cavity between the cavity's end mirrors 30-102, 30-104 and through the gain medium 30-105. One of the cavity mirrors 30-104 may partially transmit a portion of the circulating pulse, so that a train of optical pulses 30-122 is emitted from the pulsed laser 30-110 to subsequent component 30-160, such as an optical component and integrated device. The emitted pulses may sweep out a beam (indicated by the dashed lines) that is characterized by a beam waist w. Measured temporal intensity profiles of the emitted pulses 30-122 may appear as depicted in FIG. 30B. In some embodiments, the peak intensity values of the emitted pulses may be approximately equal, and the profiles may have a Gaussian temporal profile, though other profiles such as a sech profile may be possible. In some cases, the pulses may not have symmetric temporal profiles and may have other temporal shapes. In some embodiments, gain and/or loss dynamics may yield pulses having asymmetric profiles. The duration of each pulse may be characterized by a full-width-half-maximum (FWHM) value, as indicated in FIG. 30B. Ultrashort optical pulses may have FWHM values less than 100 picoseconds.

The pulses emitting from a laser excitation source may be separated by regular intervals T. In some embodiments, T may be determined by active gain and/or loss modulation rates in the laser. For mode-locked lasers, T may be determined by a round-trip travel time between the cavity end mirrors 30-102, 30-104. According to some embodiments, the pulse separation time T may be between about 1 ns and about 100 ns. In some cases, the pulse separation time T may be between about 0.1 ns and about 1 ns. In some implementations, the pulse separation time T may be between about 100 ns and about 2 μs.

In some embodiments, an optical system 30-140 may operate on a beam of pulses 30-122 from a laser excitation source 30-110. For example, the optical system may include one or more lenses to reshape the beam and/or change the divergence of the beam. Reshaping of the beam may include increasing or decreasing the value of the beam waist and/or changing a cross-sectional shape of the beam (e.g., elliptical to circular, circular to elliptical, etc.). Changing the divergence of the beam may comprise converging or diverging the beam flux. In some implementations, the optical system 30-140 may include an attenuator or amplifier to change the amount of beam energy. In some cases, the optical system may include wavelength filtering elements. In some implementations, the optical system may include pulse shaping elements, e.g., a pulse stretcher and/or pulse compressor. In some embodiments, the optical system may include one or more nonlinear optical elements, such as a saturable absorber for reducing a pulse length. According to some embodiments, the optical system 30-140 may include one or more elements that alter the polarization of pulses from a laser excitation source 30-110. In some implementations, an optical system 30-140 may include a nonlinear crystal for converting the output wavelength from an excitation source 30-110 to a shorter wavelength via frequency doubling or to a longer wavelength via parametric amplification. For example, an output of the laser may be frequency-doubled in a nonlinear crystal (e.g., in periodically-poled lithium niobate (PPLN)) or other non-poled nonlinear crystal. Such a frequency-doubling process may allow more efficient lasers to generate wavelengths more suitable for excitation of selected fluorophores.

The phrase "characteristic wavelength" or "wavelength" may refer to a central or predominant wavelength within a limited bandwidth of radiation produced by an excitation source. In some cases, it may refer to a peak wavelength within a bandwidth of radiation produced by an excitation source. A characteristic wavelength of an excitation source may be selected based upon a choice of luminescent markers or probes that are used in a bioanalysis device, for example. In some implementations, the characteristic wavelength of a source of excitation energy is selected for direct excitation (e.g., single photon excitation) of a chosen fluorophore. In some implementations, the characteristic wavelength of an excitation source is selected for indirect excitation (e.g., multi-photon excitation or harmonic conversion to a wavelength that will provide direct excitation). In some embodiments, excitation radiation may be generated by a light source that is configured to generate excitation energy at a particular wavelength for application to a sample well. In some embodiments, a characteristic wavelength of the excitation source may be less than a characteristic wavelength of corresponding emission from the sample. For example, an excitation source may emit radiation having a characteristic wavelength between 500 nm and 700 nm (e.g., 515 nm, 532 nm, 563 nm, 594 nm, 612 nm, 632 nm, 647 nm). In some embodiments, an excitation source may provide excitation energy centered at two different wavelengths, such as 532 nm and 593 nm for example.

In some embodiments, a pulsed excitation source may be used to excite a luminescent marker in order to measure an emission lifetime of the luminescent marker. This can be useful for distinguishing luminescent markers based on emission lifetime rather than emission color or wavelength. As an example, a pulsed excitation source may periodically excite a luminescent marker in order to generate and detect subsequent photon emission events that are used to determine a lifetime for the marker. Lifetime measurements of luminescent markers may be possible when the excitation pulse from an excitation source transitions from a peak pulse power or intensity to a lower (e.g., nearly extinguished) power or intensity over a duration of time that is less than the lifetime of the luminescent marker. It may be beneficial if the excitation pulse terminates quickly, so that it does not re-excite the luminescent marker during a post-excitation phase when a lifetime of the luminescent marker is being evaluated. By way of example and not limitation, the pulse power may drop to approximately 20 dB, approximately 40 dB, approximately 80 dB, or approximately 120 dB less than the peak power after 250 picoseconds. In some implementations, the pulse power may drop to approximately 20 dB, approximately 40 dB, approximately 80 dB, or approximately 120 dB less than the peak power after 100 picoseconds.

An additional advantage of using ultrashort excitation pulses to excite luminescent markers is to reduce photobleaching of the markers. Applying continuous excitation energy to a marker may bleach and/or damage a luminescent marker over time. Even though a peak pulse power of the excitation source may be considerably higher than a level that would rapidly damage a marker at continuous exposure, the use of ultrashort pulses may increase the amount of time and number of useful measurements before the marker becomes damaged by the excitation energy.

When using a pulsed excitation source to discern lifetimes of luminescent markers, the time between pulses of excitation energy may be as long as or longer than a longest lifetime of the markers in order to observe and evaluate emission events after each excitation pulse. For example, the time interval T (see FIG. 30B) between excitation pulses may be longer than any emission lifetime of the examined fluorophores. In this case, a subsequent pulse may not arrive before an excited fluorophore from a previous pulse has had a reasonable amount of time to fluoresce. In some embodiments, the interval T needs to be long enough to determine a time between an excitation pulse that excites a fluorophore and a subsequent photon emitted by the fluorophore after termination of excitation pulse and before the next excitation pulse.

Although the interval between excitation pulses T should be long enough to observe decay properties of the fluorophores, it is also desirable that T is short enough to allow many measurements to be made in a short period of time. By way of example and not limitation, emission lifetimes of fluorophores used in some applications may be in the range of about 100 picoseconds to about 10 nanoseconds. Accordingly, excitation pulses used to detect and/or discern such lifetimes may have durations (FWHM) ranging from about 25 picoseconds to about 2 nanoseconds, and may be provided at pulse repetition rates ranging from about 20 MHz to about 1 GHz.

In further detail, any suitable techniques for modulating the excitation energy to create a pulsed excitation source for lifetime measurements may be used. Direct modulation of an excitation source, such as a laser, may involve modulating the electrical drive signal of the excitation source so the emitted power is in the form of pulses. The input power for a light source, including the optical pumping power, and excited-state carrier injection and/or carrier removal from a portion of the gain region, may be modulated to affect the gain of the gain medium, allowing the formation of pulses of excitation energy through dynamic gain shaping. Additionally, the quality (Q) factor of the optical resonator may be modulated by various means to form pulses using Q-switching techniques. Such Q-switching techniques may be active and/or passive. The longitudinal modes of a resonant cavity of a laser may be phase-locked to produce a series of pulses of emitted light through mode-locking. Such mode-locking techniques may be active and/or passive. A laser cavity may include a separate absorbing section to allow for modulation of the carrier density and control of the absorption loss of that section, thus providing additional mechanisms for shaping the excitation pulse. In some embodiments, an optical modulator may be used to modulate a beam of continuous wave (CW) light to be in the form of a pulse of excitation energy. In other embodiments, a signal sent to an acoustic optic modulator (AOM) coupled to an excitation source may be used to change the deflection, intensity, frequency, phase, and/or polarization of the outputted light to produce a pulsed excitation energy. AOMs may also be used for continuous wave beam scanning, Q-switching, and/or mode-locking. Although the above techniques are described for creating a pulsed excitation source, any suitable way to produce a pulsed excitation source may be used for measuring lifetimes of luminescent markers.

In some embodiments, techniques for forming a pulsed excitation source suitable for lifetime measurements may include modulation of an input electrical signal that drives photon emission. Some excitation sources (e.g., diode lasers and LEDs) convert an electrical signal, such as an input current, into a light signal. The characteristics of the light signal may depend on characteristics of the electrical signal. In producing a pulsed light signal, the electrical signal may vary over time in order to produce a variable light signal. Modulating the electrical signal to have a specific waveform may produce an optical signal with a specific waveform. The electrical signal may have a sinusoidal waveform with a certain frequency and the resulting pulses of light may occur within time intervals related to the frequency. For example, an electrical signal with a 500 MHz frequency may produce a light signal with pulses every 2 nanoseconds. Combined beams produced by distinct pulsed excitation sources, whether similar or different from each other, may have a relative path difference below 1 mm.

In some excitation sources, such as laser diodes, the electrical signal changes the carrier density and photons are produced through the recombination of electron and hole pairs. The carrier density is related to the light signal such that when the carrier density is above a threshold, a substantial number of coherent photons are generated via stimulated emission. Current supplied to a laser diode may inject electrons or carriers into the device, and thereby increase the carrier density. When the carrier density is above a threshold, photons may be generated at a faster rate than the current supplying the carriers, and thus the carrier density may decrease below the threshold and photon generation reduces. With the photon generation reduced, the carrier density begins to increase again, due to continued current injection and the absorption of photons, and eventually increases above the threshold again. This cycle leads to oscillations of the carrier density around the threshold value for photon generation, resulting in an oscillating light signal. These dynamics, known as relaxation oscillations, can lead to artifacts in the light signal due to oscillations of the carrier density. When current is initially supplied to a laser, there may be oscillations before the light signal reaches a stable power due to oscillations in the carrier density. When forming a pulsed excitation source, oscillations of the carrier density may introduce artifacts for a pulsed light signal. Artifacts from such relaxation oscillations may broaden a pulsed light signal and/or produce a tail in the light signal, limiting the lifetimes that can be detected by such a pulsed light source since the excitation signal may overlap with emitted photons by a luminescent marker.

In some embodiments, techniques for shortening the time duration of an excitation pulse may be used to reduce the excitation energy required to detect luminescent markers and thereby reduce or delay bleaching and other damage to the luminescent markers. Techniques for shortening the time duration of the excitation pulse may be used to reduce the power and/or intensity of the excitation energy after a maximum value or peak of the excitation pulse, allowing the detection of shorter lifetimes. Such techniques may electrically drive the excitation source in order to reduce the excitation power after the peak power. An electrical driving signal may be tailored to drive the intensity of the pulse of excitation energy to zero as quickly as possible after the peak pulse. Such a technique may involve reversing the sign of an electrical driving signal after the peak power is produced. The electrical signal may be tailored to quickly reduce the carrier density after the first relaxation oscillation or first oscillation of the optical signal. By reducing the carrier density after the first oscillation, a light pulse of just the first oscillation may be generated. The electrical signal may be configured to generate a short pulse that turns the light signal off quickly by reducing the number of photons emitted after a peak in the signal. A picosecond laser diode system may be designed to emit light pulses, according to some embodiments. In some embodiments, saturable absorbers, including semiconductor saturable absorbers (SESAMs) may be used to suppress the optical tail. In such embodiments, using the saturable absorbers may suppress the optical tail by 3-5 dB or, in some instances, greater than 5 dB. Reducing the effects of a tail in the excitation pulse may reduce and/or eliminate any requirements on additional filtering of the excitation energy, increase the range of lifetimes that can be measured, and/or enable faster pulse rates. Increasing the excitation pulse rate may enable more experiments to be conducted in a given time, which may decrease the time needed to acquire enough statistics to identify a lifetime for a marker labeling a sample object.

Additionally, two or more of these techniques may be used together to generate pulsed excitation energy. For example, pulsed excitation energy emitted from a directly modulated source may be further modified using optical modulation techniques. Techniques for modulating the excitation pulse and tailoring the electrical pulse driving signal may be combined in any suitable way to optimize a pulsed excitation energy for performing lifetime measurements. A tailored electrical drive signal may be applied to a pulsed excitation energy from a directly modulated source.

In some embodiments, a laser diode having a certain number of wire bonds may be used as a pulsed excitation source. Laser diodes with more wire bonds may reduce the inductance of the excitation source. Laser diodes having a lower inductance may enable the current into the laser to operate at a higher frequency. Selecting a packaging method to minimize inductance may improve the power supplied to the excitation source at higher frequencies, enabling shorter excitation pulses, faster reductions of optical power after the peak, and/or increased pulse repetition rate for detecting luminescent markers.

In some embodiments, a transmission line in combination with an excitation source may be used for generating light pulses. The transmission line may match the impedance of a laser diode in order to improve performance and/or quality of light pulses. In some embodiments, the transmission line impedance may be 50 ohms. In some instances, the terminating resistance may be similar to the resistance of the line in order to avoid reflections. Alternatively or additionally, the terminating impedance may be similar to the impedance of the line in order to avoid reflections. The terminating impedance may less than the impedance of the line in order to reflect a negative pulse. In other embodiments, the terminating impedance may have a capacitive or inductive component in order to control the shape of the negative reflection pulse. In other embodiments, the transmission line may allow for a higher frequency of pulses. Using a transmission line may produce electrical pulses having a frequency within a range of 40 MHz to 500 MHz. A transmission line may be used in combination with a tailored electrical signal described above in order to produce a pulsed light source with light pulses having a certain time duration and a specific time interval.

Techniques for tailoring the electrical signal to improve the production of light pulses may include connecting the excitation source to a circuit with a negative bias capability. In some embodiments, a negative bias may be provided on an excitation source after a light pulse emits to reduce emission of a tail in the light pulse. An exemplary circuit may include a current source, diode laser, resistor, capacitor, and switch that may be implemented to reduce the presence of a tail in a light pulse. Such a circuit may create a constant current that bypasses the diode laser when the switch is closed, or in a conducting state. When the switch is open, the switch may have a high resistance and current may flow through the diode laser. Light pulses may be generated by opening and closing the switch to provide intermittent current to the diode laser. In some instances, the resistor may be sufficiently high and the capacitor sufficiently small such that there is a voltage across the capacitor when the switch is open and the diode laser emits light. When the switch is closed, the voltage across the capacitor will reverse bias the diode laser. Such a reverse bias may reduce or eliminate the presence of a tail in the light pulse. In such instances, the switch may be configured to close after the peak of the light pulse in order to reduce the laser power shortly after the peak light pulse. The value of the resistor in the circuit may be selected such that the charge on the capacitor will discharge before the switch is subsequently opened and/or a subsequent light pulse is generated by the laser diode.

Additional circuit components may be provided to tailor an electrical signal of a laser diode in order to produce light pulses. In some embodiments, multiple capacitors, resistors, and voltages may be connected as a network circuit to control the waveform of an electrical signal supplied to a laser diode. A controlled waveform may be created by switching a number of voltages, $V1, V2, \ldots, VN$ with corresponding signals $S1, S2, \ldots, SN$ when there are N capacitor sub-circuits.

In some embodiments, an electrical signal for generating light pulses may use a circuit having discrete components, including radio frequency (RF) and/or microwave components. Discrete components that may be included in such a circuit are DC blocks, adaptors, logic gates, terminators, phase shifters, delays, attenuators, combiners, and/or RF amplifiers. Such components may be used to create a positive electrical signal having a certain amplitude followed by a negative electrical signal with another amplitude. There may be a delay between the positive and negative electrical signals. In other embodiments, a circuit may produce multiple electrical signals combined to form an electrical pulse signal configured to drive an excitation source. Such a circuit may produce a differential output which may be used to increase the power of the light pulse. By adjusting the discrete components of the circuit, the electrical output signal may be adjusted to produce a light pulse suitable for lifetime measurements.

In some embodiments, excitation sources may be combined to generate light pulses for lifetime measurements. Synchronized pulsed sources may be coupled to a circuit or load over a certain distance. In some embodiments, excitation sources may be coupled in parallel to a circuit. The excitation sources may be from the same source or from multiple sources. In some embodiments with multiple sources, the multiple sources may vary in type of excitation source. When combining sources, it may be important to consider the impedance of the circuit and the excitation sources in order to have sufficient power supplied to the excitation sources. Combination of sources may be achieved by using one or more of the above-described techniques for producing a pulsed excitation source.

An excitation source may include a battery or any other power supply arranged to provide power to the excitation source. For example, an excitation source may be located in a base instrument and its operating power may be received through an integrated bioanalysis device to which it is coupled (e.g., via conducting power leads). An excitation source may be controlled independently of or in collaboration with control of an integrated bioanalysis device. As just one example, control signals for an excitation source may be provided to the excitation source wirelessly or via a wired interconnection (e.g., a USB interconnect) with a personal computer and/or the integrated bioanalysis device.

In some implementations, an excitation source may be operated in a time-gated and/or synchronized manner with one or more sensors of an integrated device. For example, an excitation source may be turned on to excite a luminescent marker, and then turned off. The sensor may be turned off while the excitation source is turned on, and then may be turned on for a sampling interval after the excitation source is turned off. In some embodiments, the sensor may be turned on for a sampling interval while the excitation source is turned on.

IV. Example Measurements with the Integrated Device and Excitation Source

Measurements for detecting, analyzing, and/or probing molecules in a sample may be obtained using any combination of the integrated device or integrated device and an excitation source described in the present application. The excitation source may be a pulsed excitation source or, in some instances, a continuous wave source. A luminescent marker tagged to a specific sample may indicate the presence of the sample. Luminescent markers may be distinguished by an excitation energy, luminescence emission wavelength, and/or the lifetime of emission energy emitted by a marker. Markers with similar luminescence emission wavelength may be identified by determining the lifetime for each marker. Additionally, markers with similar lifetimes may be identified by the luminescence emission wavelength for each marker. By using markers, where markers are identified by a combination of the temporal and/or spectral properties of the emitted luminescence, a quantitative analysis and/or identification of markers and associated samples may be performed.

Lifetime measurements may be used to determine that a marker is present in a sample well. The lifetime of a luminescent marker may be identified by performing multiple experiments where the luminescent marker is excited into an excited state and then the time when a photon emits is measured. The excitation source is pulsed to produce a pulse of excitation energy and directed at the marker. The time between the excitation pulse and a subsequent photon emission event from a luminescent marker is measured. By repeating such experiments with a plurality of excitation pulses, the number of instances a photon emits within a particular time interval may be determined. Such results may populate a histogram representing the number of photon emission events that occur within a series of discrete time intervals or time bins. The number of time bins and/or the time interval of each bin may be adjusted to identify a particular set of lifetimes and/or markers.

What follows is a description of example measurements that may be made to identify luminescent markers in some embodiments. Specifically, examples of distinguishing luminescent markers using only a luminescent lifetime measurement, a joint spectral and luminescent lifetime measurement, and only a luminescent lifetime measurement, but using two different excitation energies are discussed. Embodiments are not limited to the examples detailed below. For example, some embodiments may identify the luminescent markers using only spectral measurements.

Any suitable luminescent markers may be used. In some embodiments, commercially available fluorophores may be used. By way of example and not limitation, the following fluorophores may be used: Atto Rho14 ("ATRho14"), DyLight® 650 ("D650"), SetaTMTau 647 ("ST647"), CF™ 633 ("C633"), CF™ 647 ("C647"), Alexa Fluor® 647 ("AF647"), BODIPY® 630/650 ("B630"), CF™ 640R ("C640R") and/or Atto 647N ("AT647N").

Additionally and/or optionally, luminescent markers may be modified in any suitable way to increase the speed and accuracy of the sample analysis process. For example, a photostabilizer may be conjugated to a luminescent marker. Examples of photostabilizers include but are not limited to oxygen scavengers or triplet-state quenchers. Conjugating photostabilizers to the luminescent marker may increase the rate of photons emitted and may also reduce a "blinking" effect where the luminescent marker does not emit photons. In some embodiments, when a biological event occurs on the millisecond scale, an increased rate of photon emission may increase the probability of detection of the biological event. Increased rates of photon events may subsequently increase the signal-to-noise ratio of luminescence signal and increase the rate at which lifetime measurements are made, leading to a faster and more accurate sample analysis.

Furthermore, the environment in a sample well of an integrated device may be tuned to engineer the lifetime of the markers as needed. This can be achieved by recognizing that the lifetime of a marker is effected by the density of state of the marker, which can be tuned using the environment. For example, the farther a marker is from the bottom metal layer of the sample well, the longer the lifetime. Accordingly, to increase the lifetime of a marker, the depth of a bottom surface of a sample well, such as a divot, may extend a certain distance from a metal layer. Also, the materials used to form the sample well can affect the lifetime of the markers. While different markers typically have their lifetimes shifted in the same direction (e.g., either longer or shorter), the affect may scale differently for different markers. Accordingly, two markers that cannot be distinguished via lifetime measurements in free-space may be engineered to be distinguishable by fabricating the sample well environment to adjust the lifetimes of the various markers.

A. Lifetime Measurements

Lifetime measurements may be performed using one excitation energy wavelength to excite a marker in a sample well. A combination of markers having distinct lifetimes are selected to distinguish among the individual markers based on the lifetime measurements. Additionally, the combination of markers are able to reach an excited state when illuminated by the excitation source used. An integrated device configured for lifetime measurements using one excitation may include multiple pixels positioned along a row where each sample well is configured to couple with the same waveguide. A pixel includes a sample well and a sensor. One or more microcavities or a bullseye grating may be used to couple the waveguide to the sample well for each pixel.

A pulsed excitation source may be one of the pulsed excitation sources using the techniques described above. In some instances, the pulsed excitation source may be a semiconductor laser diode configured to emit pulses through direct modulated electrical pumping of the laser diode. The power of the pulses is less than 20 dB of the pulse peak power at approximately 250 picoseconds after the peak. The time interval for each excitation pulse is in the range of 20-200 picoseconds. The time duration between each excitation pulse is in the range of 1-50 nanoseconds. A schematic of how example measurements may be performed is shown in FIG. 31A. Since one excitation energy is used, an excitation filter suitable for reducing transmission of the excitation energy to the sensor may be formed in the integrated device, such as the wavelength excitation filter discussed above.

The sensor for each pixel has at least one photosensitive region per a pixel. Photons are detected within time intervals of when they reach the sensor. Increasing the number of time bins may improve resolution of the recorded histogram of photons collected over a series of time bins and improve differentiation among different luminescent markers. When the sensor is configured to detect a particular wavelength, the four luminescent markers may emit luminescence similar to the particular wavelength. Alternatively, the four luminescent markers may emit luminescence at different wavelengths.

An example set of four luminescent markers that are distinguishable based on lifetime measurements are ATRho14, Cy®5, AT647N, and CF™633 as shown by the plot in FIG. 31B. These four markers have varying lifetimes and produce distinguishing histograms when at least four time bins are used. FIG. 31C outlines a signal profile for each of these markers across 16 time bins. The signal profile is normalized for each marker. The time bins vary in time interval in order to provide a unique signal profile for each of the markers. FIGS. 32A and 32B illustrates signal profiles, both continuous and discrete, respectively, of another exemplary set of markers, ATTO Rho14, D650, ST647, and CF™633, that are distinguishable based on lifetime measurements. Other sets of markers include ATTO Rho14, C647, ST647, CF™633; Alexa Fluor® 647, B630, C640R, CF™633; and ATTO Rho14, ATTO 647N, AlexaFluor647, CF™633.

B. Spectral-Lifetime Measurements

Lifetime measurements may be combined with spectral measurements of one or more luminescent markers. Spectral measurements may depend on the wavelength of luminescence for individual markers and are captured using at least two sensor regions per pixel. An exemplary structure of the integrated device includes pixels that each have a sensor with two distinct regions, each region configured to detect a different wavelength. A multi-wavelength filter may be used to selectively transmit light of different wavelength to each sensor region. For example, one sensor region and filter combination may be configured to detect red light while another sensor region and filter combination may be configured to detect green light.

Combining both lifetime measurements with spectral measurements may be performed using one excitation energy wavelength to excite a marker in a sample well. A combination of markers is selected having at least two distinct luminescence wavelengths where the markers emitting at a wavelength have distinct lifetimes are selected to distinguish among the individual markers based on the lifetime and spectral measurements. Additionally, the combination of markers is selected to be able to reach an excited state when illuminated by the excitation source used.

The excitation source is a pulsed excitation source, and may be one of the excitation sources using the techniques described above. In some instances, the pulsed excitation source may be a semiconductor laser diode configured to emit pulses through direct modulated electrical pumping of the laser diode. The power of the pulses are less than 20 dB the peak power after 250 picoseconds after the peak. The time duration for each excitation pulse is in the range of 20-200 picoseconds. The time interval between each excitation pulse is in the range of 1-50 nanoseconds. A schematic of how example measurements may be performed is shown in FIG. 33A. Since one excitation energy is used, an excitation filter suitable for reducing transmission of the excitation energy to the sensor may be used.

The sensor for each pixel has at least two photosensitive regions per pixel. In some embodiments there are two photosensitive regions per a pixel. In other embodiments, there are four photosensitive regions per a pixel. Each photosensitive region is configured to detect a different wavelength or range of wavelengths. Photons are detected within time intervals of when they reach the sensor. Increasing the number of time bins may improve resolution of the recorded histogram of photons collected over a series of time bins and improve differentiation among different luminescent markers by their individual lifetimes. In some embodiments, there are two time bins per a region of the sensor. In other embodiments, there are four time bins per a region of the sensor.

An example set of four luminescent markers that are distinguishable based on lifetime measurements are ATTO Rho14, AS635, Alexa Fluor® 647, and ATTO 647N. These four markers have two that emit at one similar wavelength and another similar wavelength. Within each pair of markers that emit at a similar wavelength, the pair of markers have different lifetimes and produce distinguishing histograms when at least four time bins are used. In this example, ATTO Rho14 and AS635 emit similar luminescence wavelengths and have distinct lifetimes. Alexa Fluor® 647 and ATTO 647N emit similar luminescence wavelengths, different from the wavelengths emitted by ATTO Rho 14 and AS635, and have distinct lifetimes. FIG. 33B shows a plot lifetime as a function of emission wavelength for this set of markers to illustrate how each of these markers is distinguishable based on a combination of lifetime and emission wavelength. FIG. 34A shows a plot of power as a function of wavelength for ATT Rho14, Alexa Fluor® 647, and ATT) 647N. FIG. 34B shows plots of fluorescence signal over time for each one of these markers when present in a sample well with a diameter of 135 nm. FIG. 35A illustrates the signal profile for these markers across four photosensitive regions and each region captures four time bins. The signal profiles are normalized and are used to distinguish among the different markers by the relative number of photons captured by a photosensitive region for each of the four time bins. Other sets of four fluorophores for such spectral-lifetime measurements are ATRho14, D650, ST647, CF™633; ATTO Rho14, C647, ST647, CF™633; Alexa Fluor® 647, B630, C640R, CF™633; and ATTO Rho 14, ATTO 647N, Alexa Fluor® 647, CF™633. FIG. 35B shows a plot of the signal profile of intensity over time for ATRho14, D650, ST647, and C633. FIG. 35C illustrates the signal profile for ATRho14.

C. Lifetime-Excitation Energy Measurements

Lifetime measurements combined with using at least two excitation energy wavelengths may be used to distinguish among multiple markers. Some markers may excite when one excitation wavelength is used and not another. A combination of markers having distinct lifetimes is selected for each excitation wavelength to distinguish among the individual markers based on the lifetime measurements. In this embodiment, an integrated device may be configured to have each pixel with a sensor having one region and the external excitation source may be configured to provide two excitation energy wavelengths are electrically modulated pulsed diode lasers with temporal interleaving.

The excitation source is a combination of at least two excitation energies. The excitation source is a pulsed excitation source and may be one or more of the excitation sources using the techniques described above. In some instances, the pulsed excitation source may be two semiconductor laser diode configured to emit pulses through direct modulated electrical pumping of the laser diode. The power of the pulses are 20 dB less than the pulse peak power at 250 picoseconds after the peak. The time interval for each excitation pulse is in the range of 20-200 picoseconds. The time interval between each excitation pulse is in the range of 1-50 nanoseconds. One excitation wavelength is emitted per a pulse and by knowing the excitation wavelength a subset of markers with distinct lifetimes is uniquely identified. In some embodiments, pulses of excitation alternate among the different wavelengths. For example, when two excitation wavelengths are used subsequent pulses alternate between one wavelength and the other wavelength. A schematic of how example measurements may be performed is shown in FIG. 36A. Any suitable technique for combining multiple excitation sources and interleaving pulses having different wavelengths may be used. Examples of some techniques for delivering pulses of more than one excitation wavelength to a row of sample wells are illustrated are described herein. In some embodiments, there is a single waveguide per a row of sample wells and there are two excitation sources that are combined such that pulses of excitation energy alternate between the two excitation wavelengths. In some embodiments, there are two waveguides per a row of sample wells and each waveguide is configured to carry one of two excitation wavelengths. In other embodiments, there is a single waveguide per a row of pixels and one wavelength couples to one end of the waveguide and another wavelength couples to the other end.

The sensor for each pixel has at least one photosensitive region per a pixel. The photosensitive region may have dimensions of 5 microns by 5 microns. Photons are detected within time intervals of when they reach the sensor. Increasing the number of time bins may improve resolution of the recorded histogram of photons collected over a series of time bins and improve differentiation among different luminescent markers. The sensor has at least two time bins.

An example set of four luminescent markers that are distinguishable based on lifetime measurements are Alexa Fluor® 546, Cy®3B, Alexa Fluor® 647, and ATTO 647N. As shown in FIG. 36B, Alexa Fluor® 546 and Cy®3B excite at one wavelength, such as 532 nm, and have distinct lifetimes. Alexa Fluor® 647 and ATTO 647N excite at another wavelength, 640 nm, and have distinct lifetimes as shown in FIG. 37A. Distinguishable normalized signal profiles across 16 time bins for ATTO647N and CF™633, which are both excited at 640 nm, are shown in FIG. 37B. By detecting a photon after a known excitation wavelength, one of these two pairs of markers may be determined based on the previous excitation wavelength and each marker for a pair is identified based on lifetime measurements.

EQUIVALENTS AND SCOPE

Various aspects of the present application may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of determining the sequence of a template nucleic acid comprising:
   (i) exposing a complex in a target volume, the complex comprising the template nucleic acid, a primer, and a polymerizing enzyme, to a plurality of types of luminescently labeled nucleotides, wherein each type of luminescently labeled nucleotide has a different luminescent lifetime and/or luminescent intensity;
   (ii) directing a series of pulses of one or more excitation energies towards a vicinity of the target volume;
   (iii) detecting a plurality of emitted photons from luminescently labeled nucleotides during sequential incorporation into a nucleic acid comprising the primer; and
   (iv) identifying the sequence of incorporated nucleotides by determining the lifetime and intensity of the luminescently labeled nucleotides.

2. The method of claim 1, wherein detecting further comprises recording for each detected emitted photon a time duration between detection of the emitted photon and a prior pulse of excitation energy.

3. The method of claim 1, wherein each type of luminescently labeled nucleotide emits photons after being illuminated by a single excitation energy.

4. The method of claim 3, wherein the single excitation energy is in a spectral range of about 470 to about 510 nm, about 510 to about 550 nm, about 550 to about 580 nm, about 580 nm to about 620 nm, or about 620 nm to about 670 nm.

5. The method of claim 1, wherein one or more type of luminescently labeled nucleotide emits photons after being illuminated by a first excitation energy, and one or more type of luminescently labeled nucleotide emits photons after being illuminated by a second excitation energy.

6. The method of claim 5, wherein the first excitation energy is in a spectral range of about 470 nm to about 510 nm, about 510 to about 550 nm, about 550 to about 580 nm, about 580 nm to about 620 nm, or about 620 nm to about 670 nm, and the second excitation energy is in a spectral range of about 470 to about 510 nm, about 510 to about 550 nm, about 550 to about 580 nm, about 580 nm to about 620 nm, or about 620 nm to about 670 nm.

7. The method of claim 1, wherein each type of luminescently labeled nucleotide emits photons in a single spectral range.

8. The method of claim 1, wherein one or more type of luminescently labeled nucleotide emits photons in a first spectral range, and one or more type of luminescently labeled nucleotide emits photons in a second spectral range.

9. The method of claim 1, wherein at least one type, at least two types, at least three types, or at least four of the types of luminescently labeled nucleotides each comprise a luminescent label selected from the group consisting of 6-TAMRA, 6G, Alex Fluor 546, Alexa Fluor® 555, Alexa Fluor® 568, Alexa Fluor® 610, Alexa Fluor® 647, Aberrior Star 635, ATTO 425, ATTO 465, ATTO 488, ATTO 495, ATTO 514, ATTO 520, ATTO Rho6G, ATTO 542, ATTO 647N, ATTO Rho 14, Chromis 630, Chromis 654A, Chromeo™ 642, CF™514, CF™532, CF™543, CF™546, CF™546, CF™555, CF™568, CF™633, CF™640R, CF™660C, CF™660R, CF™680R, Cy®3, Cy®3B, Cy®3.5, Cy®5, Cy®5.5, Dyomics-530, Dyomics-547P1, Dyomics-549P1, Dyomics-550, Dyomics-554, Dyomics-555, Dyomics-556, Dyomics-560, Dyomics-650, Dyomics-680, DyLight® 554-R1, DyLight® 530-R2, DyLight® 594, DyLight® 635-B2, DyLight® 650, DyLight® 655-B4, DyLight® 675-B2, DyLight® 675-B4, DyLight® 680, HiLyte™ Fluor 532, HiLyte™ Fluor 555, HiLyte™ Fluor 594, LightCycler® 640R, Seta™ 555, Seta™ 670, Seta™700, Seta™u 647, and Seta™u 665, or are of formulae (Dye 101), (Dye 102), (Dye 103), (Dye 104), (Dye 105), or (Dye 106):

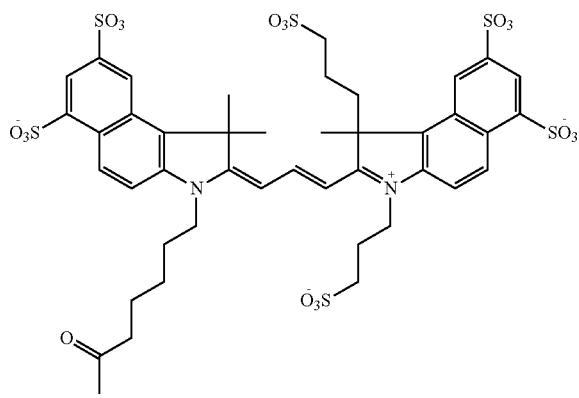

(Dye 101),

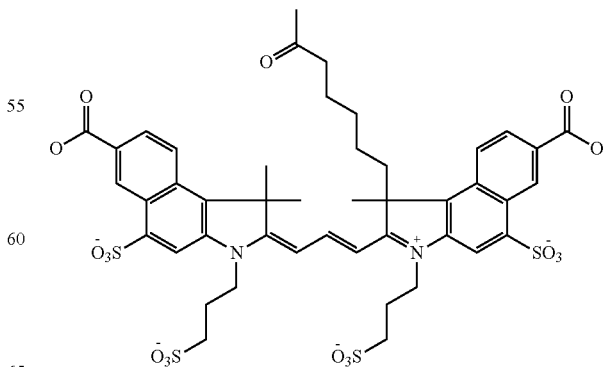

(Dye 102),

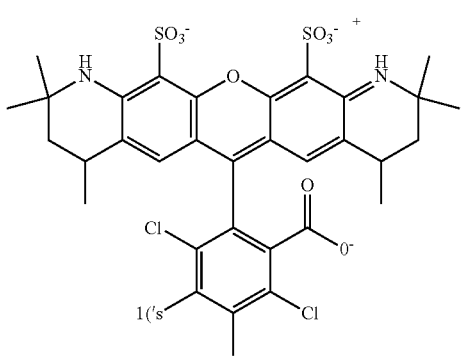

(Dye 103),

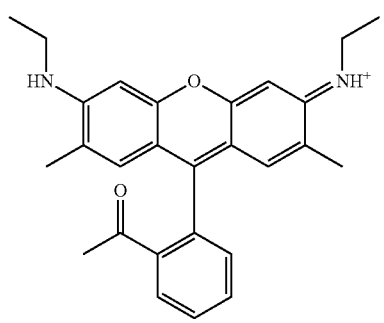 [SMILES: CCNc1cc2oc3c/c(=[NH+]\CC)c(C)cc-3c(-c3ccccc3C(C)=O)c2cc1C]

(Dye 104),

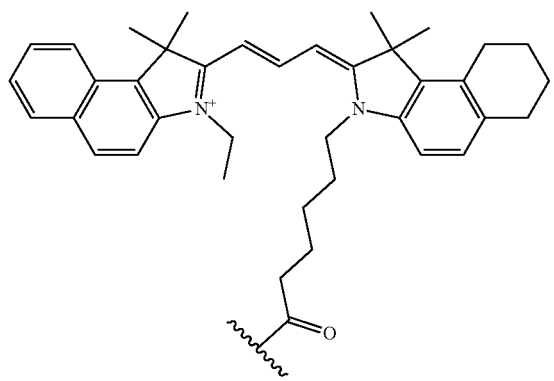 [SMILES: *C(=O)CCCCCN1/C(=C\C=C\C2=[N+](CC)c3ccc4ccccc4c3C2(C)C)C(C)(C)c2c1ccc1c2CCCC1]

(Dye 105),

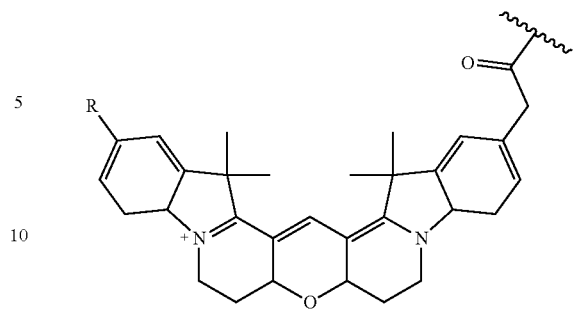

(Dye 106), wherein each sulfonate or carboxylate is independently optionally protonated.

10. The method of claim 1, wherein the series of pulses is delivered at an average frequency of between about 10 MHz and about 100 MHz or between about 100 MHz and about 1 GHz.

11. The method of claim 10, wherein the average frequency is between about 50 MHz and about 200 MHz.

12. The method of claim 1, wherein for each incorporated luminescently labeled nucleotide, the number of detected emitted photons is between about 10 and about 100, or between about 100 and about 1,000.

13. The method of claim 1, wherein the complex comprises a DNA polymerase.

14. The method of claim 1, wherein the complex is immobilized on a solid support.

15. The method of claim 14, wherein the solid support is a bottom surface of a sample well.

16. The method of claim 1, wherein a single complex is confined in the target volume.

17. The method of claim 1, wherein the plurality of types of luminescently labeled nucleotides comprises a first nucleotide comprising deoxyadenosine, a second nucleotide comprising deoxyguanosine, a third nucleotide comprising deoxycytidine, and a fourth nucleotide comprising deoxythymidine.

18. The method of claim 1, wherein the plurality of types of luminescently labeled nucleotides each comprise a luminescent label and a nucleotide connected by a linker.

19. The method of claim 18, wherein the linker comprises a protecting molecule that minimizes the extent of interactions between the luminescent label and the polymerizing enzyme.

20. The method of claim 19, wherein the protecting molecule comprises a protein or a nucleic acid.

21. The method of claim 1, wherein at least one type of luminescently labeled nucleotide comprises a first and second chromophore of a FRET pair.

22. The method of claim 21, wherein the FRET pair absorbs excitation energy in the same spectral range as one or more of the plurality of other types of luminescently labeled nucleotides.

23. The method of claim 1, wherein the lifetime and intensity of the luminescently labeled nucleotides are determined based on the timing of the emitted photons and optionally the total number of emitted photons detected within a time period.

* * * * *